US012591780B2

(12) United States Patent
Vessere et al.

(10) Patent No.: US 12,591,780 B2
(45) Date of Patent: Mar. 31, 2026

(54) DATA COMPRESSION FOR ARTIFICIAL INTELLIGENCE-BASED BASE CALLING

(71) Applicant: Illumina, Inc., San Diego, CA (US)

(72) Inventors: Gery Vessere, Oakland, CA (US); Gavin Derek Parnaby, Laguna Niguel, CA (US); Anindita Dutta, San Francisco, CA (US); Dorna Kashefhaghighi, Menlo Park, CA (US); Kishore Jaganathan, San Francisco, CA (US); Amirali Kia, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 1217 days.

(21) Appl. No.: 17/179,395

(22) Filed: Feb. 18, 2021

(65) Prior Publication Data

US 2021/0265016 A1 Aug. 26, 2021

Related U.S. Application Data

(60) Provisional application No. 62/979,399, filed on Feb. 20, 2020, provisional application No. 62/979,411, filed on Feb. 20, 2020.

(51) Int. Cl.
G06N 3/084 (2023.01)
C12Q 1/6869 (2018.01)
(Continued)

(52) U.S. Cl.
CPC ............ G06N 3/084 (2013.01); G06F 18/23 (2023.01); G06N 3/063 (2013.01); G06V 10/454 (2022.01);
(Continued)

(58) Field of Classification Search
None
See application file for complete search history.

(56) References Cited

U.S. PATENT DOCUMENTS

| | | | |
|---|---|---|---|
| 5,641,658 A | 6/1997 | Adams et al. | |
| 6,090,592 A | 7/2000 | Adams et al. | |
| (Continued) | | | |

FOREIGN PATENT DOCUMENTS

| | | |
|---|---|---|
| CA | 2894317 A1 | 12/2016 |
| CA | 3104851 A1 | 11/2020 |
| (Continued) | | |

OTHER PUBLICATIONS

Shujian Liu. (Dec. 9, 2018). Temporal Convolutional Network. Kaggle.com; Kaggle. https://www.kaggle.com/code/christofhenkel/temporal-convolutional-network (Year: 2018).*

(Continued)

*Primary Examiner* — Kaitlyn L Minchella
*Assistant Examiner* — Noah A. Auger
(74) *Attorney, Agent, or Firm* — Keller Preece PLLC

(57) ABSTRACT

The technology disclosed relates to an artificial intelligence-based method of base calling. In particular, it relates to processing, through a spatial network of a neural network-based base caller, a first window of per-cycle analyte channel sets in for a first window of sequencing cycles of a sequencing run, and generating respective sequences of spatial output sets for respective sequencing cycles in the first window of sequencing cycles, processing, through a compression network of the neural network-based base caller, respective final spatial output sets in the respective sequences of spatial output sets, and generating respective compressed spatial output sets for the respective sequencing cycles in the first window of sequencing cycles, and generating, based on the respective compressed spatial output (Continued)

Neural Network-Based Base Caller 100 sets, base call predictions for one or more sequencing cycles in the first window of sequencing cycles.

20 Claims, 62 Drawing Sheets

(51) Int. Cl.

| | |
|---|---|
| G06F 18/23 | (2023.01) |
| G06N 3/063 | (2023.01) |
| G06V 10/44 | (2022.01) |
| G06V 10/762 | (2022.01) |
| G06V 10/764 | (2022.01) |
| G06V 10/77 | (2022.01) |
| G06V 10/82 | (2022.01) |
| G16B 30/20 | (2019.01) |

(52) U.S. Cl.
CPC .......... *G06V 10/762* (2022.01); *G06V 10/764* (2022.01); *G06V 10/7715* (2022.01); *G06V 10/82* (2022.01); *G16B 30/20* (2019.02); *C12Q 1/6869* (2013.01)

(56) References Cited

U.S. PATENT DOCUMENTS

| | | | |
|---|---|---|---|
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,427,673 | B2 | 9/2008 | Balasubramanian et al. |
| 7,541,444 | B2 | 6/2009 | Milton et al. |
| 7,566,537 | B2 | 7/2009 | Balasubramanian et al. |
| 7,592,435 | B2 | 9/2009 | Milton et al. |
| 8,182,993 | B2 | 5/2012 | Tomaney et al. |
| 8,241,573 | B2 | 8/2012 | Banerjee et al. |
| 8,392,126 | B2 | 3/2013 | Mann |
| 8,401,258 | B2 | 3/2013 | Hargrove et al. |
| 8,407,012 | B2 | 3/2013 | Erlich et al. |
| 8,594,439 | B2 | 11/2013 | Staelin et al. |
| 8,725,425 | B2 | 5/2014 | Heiner et al. |
| 8,795,971 | B2 | 8/2014 | Kersey et al. |
| 8,965,076 | B2 | 2/2015 | Garcia et al. |
| 9,279,154 | B2 | 3/2016 | Previte et al. |
| 9,453,258 | B2 | 9/2016 | Kain et al. |
| 9,708,656 | B2 | 7/2017 | Turner et al. |
| 10,023,911 | B2 | 7/2018 | Tomaney et al. |
| 10,068,053 | B2 * | 9/2018 | Kermani ................ G16B 40/20 |
| 10,068,054 | B2 | 9/2018 | Van Rooyen et al. |
| 10,152,776 | B2 | 12/2018 | Langlois et al. |
| 10,168,438 | B2 | 1/2019 | Dennis et al. |
| 10,241,075 | B2 | 3/2019 | Davey et al. |
| 10,354,747 | B1 | 7/2019 | DePristo et al. |
| 10,423,861 | B2 | 9/2019 | Gao et al. |
| 10,527,549 | B2 | 1/2020 | Rebetez et al. |
| 10,540,591 | B2 | 1/2020 | Gao et al. |
| 10,619,195 | B2 | 4/2020 | Lamb et al. |
| 10,648,027 | B2 | 5/2020 | Mannion et al. |
| 10,711,299 | B2 | 7/2020 | Rothberg et al. |
| 10,713,794 | B1 | 7/2020 | He et al. |
| 10,740,880 | B2 | 8/2020 | Paik et al. |
| 10,740,883 | B2 | 8/2020 | Zerfass et al. |
| 10,755,810 | B2 | 8/2020 | Buckler et al. |
| 10,963,673 | B2 | 3/2021 | Schaumberg et al. |
| 11,138,496 | B2 | 10/2021 | Seth |
| 2002/0055100 | A1 | 5/2002 | Kawashima et al. |
| 2003/0062485 | A1 | 4/2003 | Fernandez et al. |
| 2004/0002090 | A1 | 1/2004 | Mayer et al. |
| 2004/0096853 | A1 | 5/2004 | Mayer |
| 2006/0014151 | A1 | 1/2006 | Ogura et al. |
| 2006/0040297 | A1 | 2/2006 | Leamon et al. |
| 2006/0064248 | A1 | 3/2006 | Saidi et al. |
| 2006/0188901 | A1 | 8/2006 | Barnes et al. |
| 2006/0240439 | A1 | 10/2006 | Smith et al. |
| 2006/0269130 | A1 | 11/2006 | Maroy et al. |
| 2007/0128624 | A1 | 6/2007 | Gormley et al. |
| 2007/0166705 | A1 | 7/2007 | Milton et al. |
| 2008/0009420 | A1 | 1/2008 | Schroth et al. |
| 2008/0234136 | A1 | 9/2008 | Drmanac et al. |
| 2008/0242560 | A1 | 10/2008 | Gunderson et al. |
| 2009/0081775 | A1 | 3/2009 | Hodneland et al. |
| 2010/0046830 | A1 | 2/2010 | Wang et al. |
| 2010/0111370 | A1 | 5/2010 | Black et al. |
| 2010/0157086 | A1 | 6/2010 | Segale et al. |
| 2011/0059865 | A1 | 3/2011 | Smith et al. |
| 2011/0065607 | A1 | 3/2011 | Kersey et al. |
| 2011/0281736 | A1 | 11/2011 | Drmanac et al. |
| 2011/0286628 | A1 | 11/2011 | Goncalves et al. |
| 2011/0295902 | A1 | 12/2011 | Mande et al. |
| 2012/0015825 | A1 | 1/2012 | Zhong et al. |
| 2012/0020537 | A1 | 1/2012 | Garcia et al. |
| 2013/0059740 | A1 | 3/2013 | Drmanac et al. |
| 2013/0079232 | A1 | 3/2013 | Kain et al. |
| 2013/0124100 | A1 | 5/2013 | Drmanac et al. |
| 2013/0188866 | A1 | 7/2013 | Obrador et al. |
| 2013/0250407 | A1 | 9/2013 | Schaffer et al. |
| 2014/0051588 | A9 | 2/2014 | Drmanac et al. |
| 2014/0152801 | A1 | 6/2014 | Fine et al. |
| 2015/0079596 | A1 | 3/2015 | Eltoukhy et al. |
| 2015/0117784 | A1 | 4/2015 | Lin et al. |
| 2015/0169824 | A1 | 6/2015 | Kermani et al. |
| 2016/0042511 | A1 | 2/2016 | Chukka et al. |
| 2016/0078272 | A1 | 3/2016 | Hammoud |
| 2016/0110498 | A1 | 4/2016 | Bruand et al. |
| 2016/0196479 | A1 | 7/2016 | Chertok et al. |
| 2016/0350914 | A1 | 12/2016 | Champlin et al. |
| 2016/0356715 | A1 | 12/2016 | Zhong et al. |
| 2016/0357903 | A1 | 12/2016 | Shendure et al. |
| 2016/0371431 | A1 | 12/2016 | Haque et al. |
| 2017/0044601 | A1 | 2/2017 | Crnogorac et al. |
| 2017/0098032 | A1 | 4/2017 | Desai et al. |
| 2017/0116520 | A1 | 4/2017 | Min et al. |
| 2017/0161545 | A1 | 6/2017 | Champlin et al. |
| 2017/0169313 | A1 | 6/2017 | Choi et al. |
| 2017/0249421 | A1 | 8/2017 | Eberle et al. |
| 2017/0249744 | A1 | 8/2017 | Wang et al. |
| 2017/0362634 | A1 | 12/2017 | Ota et al. |
| 2018/0075279 | A1 | 3/2018 | Gertych et al. |
| 2018/0107927 | A1 | 4/2018 | Frey |
| 2018/0114337 | A1 | 4/2018 | Li et al. |
| 2018/0189613 | A1 | 7/2018 | Wolf et al. |
| 2018/0195953 | A1 | 7/2018 | Langlois et al. |
| 2018/0201992 | A1 | 7/2018 | Wu et al. |
| 2018/0211001 | A1 | 7/2018 | Gopalan et al. |
| 2018/0274023 | A1 | 9/2018 | Belitz et al. |
| 2018/0305751 | A1 | 10/2018 | Vermaas et al. |
| 2018/0322327 | A1 | 11/2018 | Smith et al. |
| 2018/0330824 | A1 | 11/2018 | Athey |
| 2018/0334711 | A1 | 11/2018 | Kelley et al. |
| 2018/0334712 | A1 | 11/2018 | Singer et al. |
| 2018/0340234 | A1 | 11/2018 | Scafe et al. |
| 2019/0034586 | A1 | 1/2019 | Pirrotte et al. |
| 2019/0080450 | A1 | 3/2019 | Arar et al. |
| 2019/0107642 | A1 | 4/2019 | Farhadi Nia et al. |
| 2019/0114544 | A1 | 4/2019 | Sundaram et al. |
| 2019/0156915 | A1 | 5/2019 | Zhang et al. |
| 2019/0164010 | A1 | 5/2019 | Ma et al. |
| 2019/0170680 | A1 | 6/2019 | Sikora et al. |
| 2019/0180153 | A1 | 6/2019 | Buckler et al. |
| 2019/0213473 | A1 | 7/2019 | Dutta et al. |
| 2019/0236454 | A1 | 8/2019 | Fok et al. |
| 2019/0237160 | A1 | 8/2019 | Rothberg et al. |
| 2019/0237163 | A1 | 8/2019 | Wang et al. |
| 2019/0244348 | A1 | 8/2019 | Buckler et al. |
| 2019/0266491 | A1 | 8/2019 | Gao et al. |
| 2019/0272638 | A1 | 9/2019 | Mouton et al. |
| 2019/0332118 | A1 | 10/2019 | Wang et al. |
| 2019/0377930 | A1 | 12/2019 | Chen et al. |
| 2019/0392578 | A1 | 12/2019 | Chukka et al. |
| 2020/0027002 | A1 | 1/2020 | Hickson et al. |
| 2020/0054306 | A1 | 2/2020 | Mehanian et al. |

(56) References Cited

U.S. PATENT DOCUMENTS

| | | |
|---|---|---|
| 2020/0057838 A1 | 2/2020 | Yekhanin et al. |
| 2020/0065675 A1 | 2/2020 | Sundaram et al. |
| 2020/0176082 A1 | 6/2020 | Massingham |
| 2020/0193597 A1 | 6/2020 | Fan et al. |
| 2020/0226368 A1 | 7/2020 | Bakalo et al. |
| 2020/0256856 A1 | 8/2020 | Chou et al. |
| 2020/0302223 A1 | 9/2020 | Dutta et al. |
| 2020/0302224 A1 | 9/2020 | Jaganathan et al. |
| 2020/0302297 A1 | 9/2020 | Jaganathan et al. |
| 2020/0302603 A1 | 9/2020 | Barnes et al. |
| 2020/0320294 A1 | 10/2020 | Mangal et al. |
| 2020/0342955 A1 | 10/2020 | Guo et al. |
| 2020/0364565 A1 | 11/2020 | Kostem |
| 2020/0388029 A1 | 12/2020 | Saltz et al. |
| 2021/0027462 A1 | 1/2021 | Bredno et al. |
| 2021/0056287 A1 | 2/2021 | Schaumburg et al. |
| 2021/0072391 A1 | 3/2021 | Li et al. |
| 2021/0089827 A1 | 3/2021 | Kumagai et al. |
| 2021/0115490 A1 | 4/2021 | Embree et al. |
| 2021/0390278 A1 | 12/2021 | Van Leeuwen et al. |

FOREIGN PATENT DOCUMENTS

| | | |
|---|---|---|
| CN | 110245685 A | 9/2019 |
| EP | 3130681 A1 | 2/2017 |
| EP | 3373238 A1 | 9/2018 |
| JP | 2007199397 A | 8/2007 |
| JP | 6712344 B2 | 6/2020 |
| RU | 2428734 C2 | 9/2011 |
| RU | 2688485 C2 | 5/2019 |
| WO | 9106678 A1 | 5/1991 |
| WO | 2004018497 A2 | 3/2004 |
| WO | 2005065814 A1 | 7/2005 |
| WO | 2006064199 A1 | 6/2006 |
| WO | 2007010251 A2 | 1/2007 |
| WO | 2007123744 A2 | 11/2007 |
| WO | 2008154317 A1 | 12/2008 |
| WO | 2012058096 A1 | 5/2012 |
| WO | 2014077276 A1 | 5/2014 |
| WO | 2014142921 A1 | 9/2014 |
| WO | 2015084985 A2 | 6/2015 |
| WO | 2016145516 A1 | 9/2016 |
| WO | 2016201564 A1 | 12/2016 |
| WO | 2017184997 A1 | 10/2017 |
| WO | 2018129314 A1 | 7/2018 |
| WO | 2018165099 A1 | 9/2018 |
| WO | 2018203084 A1 | 11/2018 |
| WO | 2019027767 A1 | 2/2019 |
| WO | 2019028047 A1 | 2/2019 |
| WO | 2019055856 A1 | 3/2019 |
| WO | 2019079182 A1 | 4/2019 |
| WO | 2019079202 A1 | 4/2019 |
| WO | 2019090251 A2 | 5/2019 |
| WO | 2019136284 A1 | 7/2019 |
| WO | 2019136388 A1 | 7/2019 |
| WO | 2019140402 A1 | 7/2019 |
| WO | 2019147904 A1 | 8/2019 |
| WO | 2020014280 A1 | 1/2020 |
| WO | 2020123552 A1 | 6/2020 |

OTHER PUBLICATIONS

Jason Brownlee. (Jul. 5, 2019). A Gentle Introduction to 1x1 Convolutions to Manage Model Complexity. Machine Learning Mastery. https://machinelearningmastery.com/introduction-to-1x1-convolutions-to-reduce-the-complexity-of-convolutional-neural-networks/ (Year: 2019).*

LaPierre, N., Egan, R., Wang, W., & Wang, Z. (2019). De novo Nanopore read quality improvement using deep learning. BMC bioinformatics, 20, 1-9. (Year: 2019).*

NL 2023311 NL Search Report, dated Mar. 24, 2020, 15 pages.

NL 2023312, NL Search Report, dated Mar. 24, 2020, 22 pages.

NL 2023317, NL Search Report, dated Mar. 24, 2020, 16 pages.

NL 2023316, NL Search Report, dated Mar. 23, 2020, 15 pages.

U.S. Appl. No. 16/825,991—Notice of Allowance dated Aug. 5, 2021, 10 pages.

Krishnakumar et. al., Systematic and stochastic influences on the performance of the MinION nanopore sequencer across a range of nucleotide bias, Scientific Reports, published Feb. 16, 2018, 13 pages.

Tegfalk, Application of Machine Learning techniques to perform base-calling in next-generation DNA sequencing, KTH Royal Institue of Technology, dated 2020, 53 pages.

U.S. Appl. No. 16/826,168—Office Action dated Aug. 31, 2021, 55 pages.

Kircher-etal_Improved-base-calling-for-the-Illumina-Genome-Analyzer-using-machine-learning-strategies_Aug. 14, 2009_10pages.

Albrecht et al., Deep learning for single molecule science, Nano-technology, dated Sep. 18, 2017, 11 pages.

U.S. Appl. No. 16/825,987—Office Action (Quayle) dated Oct. 19, 2021, 85 pages.

PCT/US2021047763—International Search Report and Written Opinion, dated Dec. 20, 2021, 11 pages.

PCT/US2021/018422 Second Written Opinion, dated Feb. 4, 2022, 8 pages.

Adriana Romero et. al., FitNets: Hints for Thin Deep Nets, published Mar. 27, 2015, 13 pages.

U.S. Appl. No. 16/874,599—Notice of Allowance dated Dec. 3, 2021, 12 pages.

U.S. Appl. No. 16/825,987—Response to Office Action (Quayle) dated Oct. 19, 2021, filed Jan. 13, 2022, 11 pages .

U.S. Appl. No. 16/825,987—Notice of Allowance, dated Jan. 28, 2022, 12 pages.

U.S. Appl. No. 16/825,987—Supplemental Notice of Allowance, dated Feb. 7, 2022, 8 pages.

U.S. Appl. No. 16/826,168—Response to Office Action dated Aug. 31, 2021, filed Jan. 31, 2022, 15 pages.

CN 2020800036223—Voluntary Amendments, filed May 20, 2021, 26 pages.

EP 20719053.9—Rules 161(2) and 162 Communication, dated Oct. 28, 2021, 3 pages.

IL 279522—Response to Notice Before Acceptance dated Aug. 1, 2021, filed Nov. 28, 2021, 3 pages.

KR 10-2020-7037712—Voluntary Amendments with translation, dated Nov. 9, 2021, 7 pages.

EP 20719052.1—Rules 161(1) and 162 Communication, dated Oct. 28, 2021. 3 pages.

IL 279525—Response to Notice Before Acceptance dated Aug. 1, 2021, filed Nov. 28, 2021, 4 pages.

KR 10-2020-7037713—Voluntary Amendments with translation, dated Nov. 9, 2021, 26 pages.

ZA 2020/07998—Notice of Allowance, dated Aug. 12, 2021, 2 pages.

EP 20718112.4—Rules 161(2) and 162 Communication, dated Oct. 28, 2021, 3 pages.

IL 279527—Response to Notice Before Examination dated Aug. 1, 2021, filed Nov. 28, 2021, 3 pages.

KR 10-2021-7003269—Voluntary Amendments with translation, dated Nov. 9, 2021, 7 pages.

ZA 2020/07999—Notice of Allowance, dated Aug. 12, 2021, 2 pages.

EP 20719294.9—Rules 161(1) and 162 Communication, dated Oct. 28, 2021, 3 pages.

IL 281668—Response to Notice Before Examination dated Oct. 10, 2021, filed Feb. 8, 2022, 4 pages.

KR 10-2021-7009877—Voluntary Amendments with translation, dated Nov. 9, 2021, 21 pages.

EP 20757979.8—Rules 161(2) and 162 Communication, dated Oct. 28, 2021, 3 pages.

IL 279533—Response to Notice Before Examination dated Aug. 1, 2021, filed Nov. 29, 2021, 3 pages.

KR 10-2021-7003270—Voluntary Amendments with translation, dated Nov. 9, 2021, 29 pages.

ZA 2020/08000—Notice of Acceptance, dated Aug. 12, 2021, 2 pages.

(56) References Cited

OTHER PUBLICATIONS

Robinson et al., Computational Exome and Genome Analysis—Chapter 3 Illumina Technology, dated 2018, 25 pages.

Wang et. al., An adaptive decorrelation method removes Illumina DNA base-calling errors caused by crosstalk between adjacent clusters—with Supplemental Materials, Scientific Reports, published Feb. 20, 2017, 17 pages.

PCT/US2020/033280—International Preliminary Report on Patentability, dated Jul. 23, 2021, 11 pages.

Pfeiffer et. al., Systematic evaluation of error rates and causes in short samples in next-generation sequencing, Scientific Reports, published Jul. 19, 2018, 14 pages.

PCT/US2020/033281—International Preliminary Report on Patentability, dated Aug. 31, 2021, 10 pages.

Bell, C. J. et al. Comprehensive carrier testing for severe childhood recessive diseases by next generation sequencing. Sci. Transl. Med. 3, Jan. 12, 2011, 28 pages.

Smedley, D. et al. A whole-genome analysis framework for effective identification of pathogenic regulatory variants in mendelian disease. Am. J. Hum. Genet. 99, 595-606 (2016).

Jagadeesh, K. A. et al. M-CAP eliminates a majority of variants of uncertain significance in clinical exomes at high sensitivity. Nat. Genet. 48, 1581-1586 (2016).

Grimm, D. G. The evaluation of tools used to predict the impact of missense variants is hindered by two types of circularity. Human. Mutat. 36, 513-523 (2015).

Hefferman, R. et al. Improving prediction of secondary structure, local backbone angles, and solvent accessible surface area of proteins by iterative deep learning. Sci. Rep. 5, 11476 (2015) 11 pages.

Wang, S., Peng, J., Ma, J. & Xu, J. Protein secondary structure prediction using deep convolutional neural fields. Sci. Rep. 6, 18962-18962 (2016).

Harpak, A., Bhaskar, A., & Pritchard, J. K. Mutation rate variation is a primary determinant of the distribution of allele frequencies in humans. PLoS Genet. Dec. 15, 2016, 22pgs.

Payandeh, J., Scheuer, T., Zheng, N. & Catterall, W. A. The crystal structure of a voltage-gated sodium channel. Nature 475, 353-358 (2011).

Shen, H. et al. Structure of a eukaryotic voltage-gated sodium channel at near-atomic resolution. Science 355, eaal4326 (2017), 19 pages.

Nakamura, K. et al. Clinical spectrum of SCN2A mutations expanding to Ohtahara syndrome. Neurology 81, 992-998 (2013).

Ioannidis, Nilah M., et al., "REVEL—An Ensemble Method for Predicting the Pathogenicity of Rare Missense Variants", Oct. 5, 2016, 9 pages.

Quang Daniel, et. al., "DANN—a deep learning approach for annotating the pathogenicity of genetic variants", Oct. 22, 2014, 3 pages.

Sundaram, et. al., "Predicting the clinical impact of human mutation with deep neural networks", Aug. 2018, 15pgs.

Xiong, et. al., "The human splicing code reveals new insights into the genetic determinants of disease", Jan. 9, 2015, 20pgs.

Yue, et. al., "Deep Learning for Genomics—A Concise Overview from internet", May 8, 2018, 40pgs.

Yuen, et. al., "Genome wide characteristics of de novo mutations in autism", Jun. 1, 2016, 10pgs.

Libbrecht, et. al., "Machine learning in genetics and genomics", Jan. 2, 2017, 30pgs.

Min, et. al., "Deep Learning in Bioinformatics", Jul. 25, 2016, 19 pgs.

Torng, Wen, et al., "3D deep convolutional neural networks for amino acid environment similarity analysis", 2017, 23pages.

Chen, Kathleen M., et. al., "Selene—a PyTorch based deep learning library for sequence level data", Oct. 10, 2018, 15pages.

Grob, C., et. al., "Predicting variant deleteriousness in non human species Applying the CADD approach in mouse", 2018, 11 pages.

Li, et. al., "FoldingZero—Protein Folding from Scratch in Hydrophobic Polar Model", Dec. 3, 2018, 10 pages.

Rentzsch, et. al., "CADD—predicting the deleteriousness of variants throughout the human genome", Oct. 11, 2018, 9 pages.

Zou, etal, "A primer on deep learning in genomics", Nov. 26, 2018, 7pages.

Alberts, Bruce, et al., "Molecular biology of the cell", Sixth Edition, 2015, 3 pages.

PCT/US2018/055840—International Search Report and Written Opinion dated Jan. 25, 2019, 18 pages.

Wei etal_The Role of Balanced Training and Testing Data Sets for Binary Classifiers in Bioinformatics dated Jul. 9, 2013 12 pages.

PCT/US2018/055878—International Search Report and Written Opinion dated Jan. 22, 2019, 20 pages.

PCT/US2018/055881—International Search Report and Written Opinion dated Jan. 25, 2019, 17 pages.

Duggirala, Ravindranath, et.al., "Genome Mapping and Genomics in Human and Non Human Primate", 2015, 306pgs.

Brookes, Anthony J., "The essence of SNPs", 1999, pp. 177-186.

UniProtKB P04217 A1BG Human [retrieved on Mar. 13, 2019 from (www.uniprot.org/uniprot/P04217), 12pages.

Bahar, Protein Actions Principles and Modeling, Chapter 7, 2017 pp. 165-166.

Dunbrack, Roland L., Re Question about your Paper titled "The Role of Balanced Training and Testing Data Sets for Binary Classifiers in Bioinformatics", Message to Sikander Mohammed Khan, Feb. 3, 2019, E-mailm, 3pgs.

DbSNP rs2241788 [Retrieved on Mar. 13, 2019], Retrieved from the Internet<www.ncbi.nlm.nih.gov/snp/rs2241788>, 5 pages.

Wei, et. al., "Prediction of phenotypes of missense mutations in human proteins from biological assemblies", Feb. 2013, 28 pages.

Zhang, Jun, and Bin Liu. "PSFM-DBT—identifying DNA-binding proteins by combing position specific frequency matrix and distance-bigram transformation." International journal of molecular sciences 18.9 (2017) 1856.

Gao, Tingting, et al. "Identifying translation initiation sites in prokaryotes using support vector machine." Journal of theoretical biology 262.4 (2010) 644-649. (Year 2010).

Bi, Yingtao, et al. "Tree-based position weight matrix approach to model transcription factor binding site profiles." PloS one6.9 (2011) e24210.

Korhonen, Janne H., et al. "Fast motif matching revisited—high-order PWMs, SNPs and indels." Bioinformatics 33.4 (2016) 514-521.

Wong, Sebastien C., et al. "Understanding data augmentation for classification—when to warp?. " 2016 international conference on digital image computing—techniques and applications (DICTA). IEEE, 2016.

Chang, Chia-Yun, et al. "Oversampling to overcome overfitting—exploring the relationship between data set composition, molecular descriptors, and predictive modeling methods." Journal of chemical information and modeling 53.4 (2013) 958-971.

Li, Gangmin, and Bei Yao. "Classification of Genetic Mutations for Cancer Treatment with Machine Learning Approaches." International Journal of Design, Analysis and Tools for Integrated Circuits and Systems 7.1 (2018) pp. 63-67.

Martin-Navarro, Antonio, et al. "Machine learning classifier for identification of damaging missense mutations exclusive to human mitochondrial DNA-encoded polypeptides." BMC bioinformatics 18.1 (2017) p. 158.

Krizhevsky, Alex, et al, ImageNet Classification with Deep Convolutional Neural Networks, 2012, 9 Pages.

Geeks for Geeks, "Underfitting and Overfilling in Machine Learning", [retrieved on Aug. 26, 2019]. Retrieved from the Internet <www.geeksforgeeks.org/underfitting-and-overfitting-in-machine-learning/>, 2 pages.

Despois, Julien, "Memorizing is not learning!—6 tricks to prevent overfitting in machine learning", Mar. 20, 2018, 17 pages.

Bhande, Anup What is underfitting and overfitting in machine learning and how to deal with it, Mar. 11, 2018, 10pages.

PCT/US2019031621—International Search Report and Written Opinion dated Aug. 7, 2019, 17 pages.

Carter et al., "Cancer-specific high-throughput annotation of somatic mutations—computational prediction of driver missense mutations," Cancer research 69, No. 16 (2009) pp. 6660-6667.

(56) References Cited

OTHER PUBLICATIONS

PCT/US2021/018258—Second Written Opinion, dated Jan. 25, 2022, 11 pages.
PCT/US2021/018910—International Search Report and Written Opinion, dated Aug. 25, 2021, 24 pages.
Puckelwartz et al., Supercomputing for the parallelization of whole genome analysis, Bioinformatics, dated Feb. 12, 2014, pp. 1508-1513, 6 pages.
Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.
PCT/US2021/018910—Article 34 Amendment, filed Dec. 19, 2021, 9 pages.
PCT/US2021/018910—Second Written Opinion, dated Feb. 21, 2022, 17 pages.
PCT/US2021/018422—Article 34 Amendment, dated Dec. 20, 2021, 7 pages.
PCT/US/2021/018427—Second Written Opinion, dated Feb. 4, 2022, 9 pages.
PCT/US/2021/018427—Article 34 Amendment, filed Dec. 19, 2021, 7 pages.
PCT/US2021/018913—Second Written Opinion, dated Feb. 4, 2022, 8 pages.
Ye et al., BlindCall: ultra-fast base-calling of high-throughput sequencing data by blind deconvolution, Bioinformatics, vol. 30, No. 9, dated Jan. 4, 2014, pp. 1214-1219, 6 pages.
Wang et al., Achieving Accurate and Fast Base-calling by a Block model of the Illumina Sequencing Data, Science Direct, vol. 48, No. 28, dated Jan. 1, 2015, pp. 1462-1465, 4 pages.
PCT/US2021/018913—Article 34 Amendment, filed Dec. 19, 2021, 18 pages.
PCT/US2021/018915—Second Written Opinion, dated Feb. 4, 2022, 9 pages.
PCT/US2021/018915—Article 34 Amendment, filed Dec. 19, 2021, 7 pages.
PCT/US2021/018917—Second Written Opinion, dated Feb. 4, 2022, 7 pages.
PCT/US2021/018917—Article 34 Amendment, filed Dec. 19, 2021, 6 pages.
U.S. Appl. No. 17/468,411—Office Action, dated Feb. 24, 2022, 36 pages.
Gao et al., Deep Learning in Protein Structural Modeling and Design, Patterns—CelPress, dated Dec. 11, 2020, 23 pages.
Pejaver et al., Inferring the molecular and phenotypic impact of amino acid variants with MutPred2—with Supplementary Information, Nature Communications, dated 2020, 59 pages.
Pakhrin et al., Deep learning based advances in protein structure prediction, International Journal of Molecular sciences, published May 24, 2021, 30 pages.
Wang et al. Predicting the impacts of mutations on protein-ligand binding affinity based on molecular dynamics simulations and machine learning methods, Computational and Structural Biotechnology Journal 18, dated Feb. 20, 2022, pp. 439-454, 16 pages.
Iqbal et al., Comprehensive characterization of amino acid positions in protein structures reveals molecular effects of missense variants, and supplemental information, PNAS, vol. 117, No. 45, dated Nov. 10, 2020, 35 pages.
Forghani et al., Convolutional Neural Network Based Approach to In Silica Non-Anticipating Prediction of Antigenic Distance for Influenza Virus, Viruses, published Sep. 12, 2020, vol. 12, 20 pages.
Jing et al., Learning from protein structure with geometric vector perceptrons, Arxiv: 2009: 01411v2, dated Dec. 31, 2020, 18 pages.
Stenson, P. D. et al. The Human Gene Mutation Database—building a comprehensive mutation repository for clinical and molecular genetics, diagnostic testing and personalized genomic medicine. Hum. Genet. 133, 1-9 (2014).
Alipanahi, et. al., "Predicting the Sequence Specificities of DNA and RNA Binding Proteins by Deep Learning", Aug. 2015, 9pgs.

Angermueller, et. al., "Accurate Prediction of Single Cell DNA Methylation States Using Deep Learning", Apr. 11, 2017, 13pgs.
Ching, et. al., "Opportunities and Obstacles for Deep Learning in Biology and Medicine", Jan. 19, 2018, 123pgs.
Ching, et. al., "Opportunities and Obstacles for Deep Learning in Biology and Medicine", May 26, 2017, 47pgs.
Gu, et. al., "Recent Advances in Convolutional Neural Networks", Jan. 5, 2017, 37pgs.
Leung, et. al., "Deep learning of the tissue regulated splicing code", 2014, 9pgs.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
MacArthur, D. G. et al. Guidelines for investigating causality of sequence variants in human disease. Nature 508, 469-476 (2014).
Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755 (2011).
Rehm, H. L. Evolving health care through personal genomics. Nat. Rev. Genet. 18, 259-267 (2017).
Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project—300 genomes from 142 diverse populations. Nature 538, 201-206 (2016).
Genomes Project Consortium. et al. A global reference for human genetic variation. Nature 526, 68-74 (2015).
Liu, X., Jian, X. & Boerwinkle, E. dbNSFP—a lightweight database of human nonsynonymous SNPs and their functional predictions. Human. Mutat. 32, 894-899 (2011).
Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).
Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158(2017).
Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
De Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP—the NCBI database of genetic variation. Nucleic Acids Res. 29, 308-211 (2001).

(56) References Cited

OTHER PUBLICATIONS

Schrago, C. G., & Russo, C. A. Timing the origin of New World monkeys. Mol. Biol. Evol. 20, 1620-1625 (2003).

Landrum, M. J. et al. ClinVar—public archive of interpretations of clinically relevant variants. Nucleic Acids Res. 44, D862-868 (2016).

Brandon, E. P., Idzerda, R. L. & McKnight, G. S. Targeting the mouse genome—a compendium of knockouts (Part II). Curr. Biol. 5, 758-765 (1995).

Jeschke, J. G. & Currie, P. D. Animal models of human disease—zebrafish swim into view. Nat. Rev. Genet. 8, 353-367 (2007).

Sittig, L. J. et al. Genetic background limits generalizability of genotype—phenotype relationships. Neuron 91, 1253-1259 (2016).

Bazykin, G. A. et al. Extensive parallelism in protein evolution. Biol. Direct 2, 20, 13 pages (2007).

Ng, P. C., & Henikoff, S. Predicting deleterious amino acid substitutions. Genome Res. 11, 863-874 (2001).

Adzhubei, I. A. et al. A method and server for predicting damaging missense mutations. Nat. Methods 7, 248-249 (2010).

Chun, S. & Fay, J. C. Identification of deleterious mutations within three human genomes. Genome Res. 19, 1553-1561 (2009).

Schwarz, J. M., Rodelsperger, C., Schuelke, M. & Seelow, D. MutationTaster evaluates disease-causing potential of sequence alterations. Nat. Methods 7, 575-576 (2010).

Reva, B., Antipin, Y., & Sander, C. Predicting the functional impact of protein mutations—application to cancer genomics. Nucleic Acids Res. 39, e118 (2011), 14pgs.

Dong, C. et al. Comparison and integration of deleteriousness prediction methods for nonsynonymous SNVs in whole exome sequencing studies. Hum. Mol. Genet. 24, 2125-2137 (2015).

Carter, H., Douville, C., Stenson, P. D., Cooper, D. N., & Karchin, R. Identifying Mendelian disease genes with the variant effect scoring tool. BMC Genom, (2013), 13 pages.

Choi, Y., Sims, G. E., Murphy, S., Miller, J. R., & Chan, A. P. Predicting the functional effect of amino acid substitutions and indels. PLoS One 7, e46688 (2012).

Gulko, B., Hubisz, M. J., Gronau, I., & Siepel, A. A method for calculating probabilities of fitness consequences for point mutations across the human genome. Nat. Genet. 47, 276-283 (2015).

Shihab, H. A. et al. An integrative approach to predicting the functional effects of non-coding and coding sequence variation. Bioinformatics 31, 1536-1543 (2015).

PCT/US2021/018422 International Search Report and Written Opinion, dated Jun. 10, 2021, 12 pages.

Aggarwal, Neural Networks and Deep Learning: A Textbook, Springer, dated Aug. 26, 2018, 512 pages.

Wang et. al., Deep Neural Network Approximation for Custom Hardware: Where We've Been, Where We're Going, Cornell University, dated Jan. 21, 2019, 37 pages.

Lavin et. al., Fast Algorithms for Convolutional Neural Networks, dated Nov. 10, 2015, 9 pages.

Liu et. al., A Uniform Architecture Design for Accelerating 2D and 3D CNNs on FPGAs, published Jan. 7, 2019, 19 pages.

PCT/US2021/018427 International Search Report and Written Opinion, dated Jun. 1, 2021, 15 pages.

PCT/US2021/018913 International Search Report and Written Opinion, dated Jun. 10, 2021, 11 pages.

Zeng et. al., Causalcall: Nanopore Basecalling Using a Temporal Convolutional Network, dated Jan. 20, 2020, 11 pages.

PCT/US2021/018915 International Search Report and Written Opinion, dated Jun. 15, 2021, 13 pages.

Kwon et. al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.

Sze et. al., Efficient Processing of Deep Neural Networks: A Tutorial and Survey, Cornell University Library, dated Mar. 27, 2017, 21 pages.

Sundaram, L et. al., "Predicitng the clinical impact of human mutation with deep neural networks", Nat. Genet. 50, 1161-1170 (2018).

Jaganathan, K. et. al., "Predicting splicing from primary sequence with deep learning", Cell 176, 535-548, (2019).

Kircher, Martin, et al. "A general framework for estimating the relative pathogenicity of human genetic variants." Nature genetics 46.3 (2014): 310. (Year:2014).

Henikoff, S. & Henikoff, J. G. Amino acid substitution matrices from protein blocks. Proc. Natl. Acad. Sci. USA 89, 10915-10919 (1992).

Li, W. H., Wu, C. I. & Luo, C. C. Nonrandomness of point mutation as reflected in nucleotide substitutions in pseudogenes and its evolutionary implications. J. Molec. Evol. 21, 58-71 (1984).

Grantham, R. Amino acid difference formula to help explain protein evolution. Science 185, 862-864 (1974).

LeCun, Y., Botlou, L., Bengio, Y., & Haffner, P. Gradient based learning applied to document recognition. Proc. IEEE 36, 2278-2324 (1998).

Vissers, L. E., Gilissen, C., & Veltman, J. A. Genetic studies in intellectual disability and related disorders. Nat. Rev. Genet. 17, 9-18 (2016).

Neale, B. M. et al. Patterns and rates of exonic de novo mutations in autism spectrum disorders. Nature 485, 242-245 (2012).

Sanders, S. J. et al. De novo mutations revealed by whole-exome sequencing are strongly associated with autism. Nature 485, 237-241 (2012).

De Rubeis, S. et al. Synaptic, transcriptional and chromatin genes disrupted in autism. Nature 515, 209-215 (2014).

Deciphering Developmental Disorders Study. Large-scale discovery of novel genetic causes of developmental disorders. Nature 519, 223-228 (2015).

Deciphering Developmental Disorders Study. Prevalence and architecture of de novo mutations in developmental disorders. Nature 542, 433-438 (2017).

Iossifov, I. et al. The contribution of de novo coding mutations to autism spectrum disorder. Nature 515, 216-221 (2014).

Zhu, X. Need, A. C., Petrovski, S. & Goldstein, D. B. One gene, many neuropsychiatric disorders: lessons from Mendelian diseases. Nat. Neurosci. 17, 773-781, (2014).

Leffler, E. M. et al. Revisiting an old riddle: what determines genetic diversity levels within species? PLoS Biol. 10, e1001388 (2012), 9pages.

Estrada, A. et al. Impending extinction crisis of the world's primates—why primates matter. Sc. Adv. 3, e1600946 (2017), 17 pages.

Kent, W. J. et al. The human genome browser at UCSC. Genome Res. 12, 996-1006 (2002).

Tyner, C. et al. The UCSC Genome Browser database—2017 update. Nucleic Acids Res. 45, D626-D634 (2017).

Kabsch, W., & Sander, C. Dictionary of protein secondary structure—pattern recognition of hydrogen-bonded and geometrical features. Biopolymers 22, 2577-2637 (1983).

Joosten, R. P. et al. A series of PDB related databases for everyday needs. Nucleic Acids Res. 39, 411-419 (2011).

He, K, Zhang, X., Ren, S., & Sun, J. Identity mappings in deep residual networks. in 14th European Conference on Computer Vision—ECCV 2016. ECCV 2016. Lecture Notes in Computer Science, vol. 9908; 630 6, 15 (Springer, Cham, Switzerland; 2016).

Ionita-Laza, I., McCallum, K., Xu, B., & Buxbaum, J. D. A spectral approach integrating functional genomic annotations for coding and noncoding variants. Nat. Genet. 48, 214-220 (2016).

Li, B. et al. Automated inference of molecular mechanisms of disease from amino acid substitutions. Bioinformatics 25, 2744-2750 (2009).

Lu, Q. et al. A statistical framework to predict functional non-coding regions in the human genome through integrated analysis of annotation data. Sci. Rep. 5, 10576 (2015), 13pgs.

Shihab, H. A. et al. Predicting the functional, molecular, and phenotypic consequences of amino acid substitutions using hidden Markov models. Human. Mutat. 34, 57-65 (2013).

Davydov, E. V. et al. Identifying a high fraction of the human genome to be under selective constraint using GERP++. PLoS Comput. Biol. 6, Dec. 2, 2010, 13 pages.

(56)　　　　　References Cited

OTHER PUBLICATIONS

Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).

Jain, S., White, M., Radivojac, P. Recovering true classifier performance in positive-unlabeled learning. in Proceedings Thirty-First AAAI Conference on Artificial Intelligence. 2066-2072 (AAAI Press, San Francisco; 2017).

De Ligt, J. et al. Diagnostic exome sequencing in persons with severe intellectual disability. N. Engl. J. Med. 367, 1921-1929 (2012).

Iossifov, I. et al. De novo gene disruptions in children on the autistic spectrum. Neuron 74, 285-299 (2012).

O'Roak, B. J. et al. Sporadic autism exomes reveal a highly interconnected protein network of de novo mutations. Nature 485, 246-250 (2012).

Rauch, A. et al. Range of genetic mutations associated with severe non-syndromic sporadic intellectual disability—an exome sequencing study. Lancet 380, 1674-1682 (2012).

Epi, K. C. et al. De novo mutations in epileptic encephalopathies. Nature 501, 217-221 (2013).

EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).

Gilissen, C. et al. Genome sequencing identifies major causes of severe intellectual disability. Nature 511, 344-347 (2014).

Lelieveld, S. H. et al. Meta-analysis of 2,104 trios provides support for 10 new genes for intellectual disability. Nat. Neurosci. 19, 1194-1196 (2016).

Famiglietti, M. L. et al. Genetic variations and diseases in UniProtKB Swiss-Prot—the ins and outs of expert manual curation. Human. Mutat. 35, 927-935 (2014).

Horaitis, O., Talbot, C. C.Jr., Phommarinh, M., Phillips, K. M., & Cotton, R. G. A database of locus-specific databases. Nat. Genet. 39, 425 (2007).

Min, et. al., "Deep Learning in Bioinformatics", Jun. 19, 2016, 46pgs.

Jiminez et. al., DeepSite—protein binding site predictor using 3D CNNs, dated Oct. 1, 2017, 7 pages.

Pu et. al., "DeepDrug3D: Classification of ligand-binding pockets in proteins with a convolutional neural network", dated Feb. 4, 2019, 23 pages.

Adam, "Deep learning, 3D technology to improve structure modeling for protein interactions, create better drugs", dated Jan. 9, 2020, 4 pages.

Varela, "Ligvoxel: A Deep Learning Pharmacore-Field Predictor", dated Mar. 19, 2019, 5 pages.

Li et. al., "Predicting changes in protein thermostability upon mutation with deep 3D convolutional neural networks", dated Feb. 28, 2020, 21 pages.

Raschka et. al., "Machine Learning and AI-based approaches for bioactive ligand discovery and GPCR-ligand recognition", dated Jun. 6, 2020, 33 pages.

Morrone et. al., "Combining docking pose rank and structure with deep learning improves protein-ligand binding mode prediction", dated Oct. 7, 2019, 13 pages.

Li, "Machine Learning Methods for Medical and Biological Image Computing", dated Summer 2016, 113 pages.

Rivera et. al., "A Deep Learning Approach to Protein Structure Prediction", dated Apr. 24, 2019, 22 pages.

Aritake et. al., "Single-molecule localization by voxel-wise regression using convolutional neural network", dated Nov. 3, 2020, 11 pages.

Townshend et. al., "End-to-End Learning on 3D Protein Structure for Interface Prediction", dated 2019, 10 pages.

Amidi et. al., "EnzyNet: enzyme classification using 3D convolutional neural networks on spatial representation", dated Jul. 25, 2017, 18 pages.

Luna, "Machine Learning in structural biology and chemoinformatics", dated 2019, 106 pages.

Anonymous, "Transferrable end-to-end learning for protein interface prediction", dated 2019, 12 pages.

Dias et. al., "Artificial intelligence in clinical and genomic diagnostics", dated 2019, 12 pages.

Luna et. al., "A Deep-Learning Approach toward Rational Molecular Docking Protocol Selection", dated May 27, 2020, 12 pages.

Li et. al., "DeepAtom: A Framework for Protein-Ligand Binding Affinity Prediction", dated 2019, 8 pages.

Zhang et. al., "Template-based prediction of protein structure with deep learning", dated Jun. 2, 2020, 16 pages.

Wallach et. al., AtomNet: A Deep Convolutional Neural Network for Bioactivity Prediction in Structure-based Drug Discovery, dated Oct. 10, 2015, 11 pages.

Illumina, Two-Channel SBS Sequencing Technology, 2016, 2 pages.

Illumina, Low-diversity sequencing on the Illumina HiSeq Platform, 2014, 2 pages.

Hedegaard, An introduction to "Next Generation" DNA Sequencing, dated Nov. 26, 2017, 63 pages.

Jordan , An overview of semantic image segmentation, dated May 21, 2018, 28 pages retrieved on Jul. 21, 2021. Retrieved from the internet [URL: https://www.jeremyjordan.me/semantic-segmentation/ ].

Lanchantin, Deep Motif Dashboard: Visualizing and Understanding Genomic Sequences Using Deep Neural Networks, Oct. 18, 2016, 11 pages.

Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/ ].

James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].

Townley, Illumina Primary and Secondary Analysis, Illumina UK, 2010, 33 pages.

Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa ].

Bowen, Nanotechnology for a Genomic Revolution, Illumina, dated Dec. 14, 2016, 40 pages.

Han, Deconvolutions in Convolutional Neural Networks, Postech Computer Vision Lab, 2015, 20 pages.

Illumina, Illumina's Genotyping Data Normalization Methods, 2006, 6 pages.

Illumina, Quality Scores for Next-Generation Sequencing—Assessing sequencing accuracy using Phred quality scoring, 2011, 2 pages.

Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].

Illumina, An Introduction to Next-Generation Sequencing Technology, 2017, 16 pages.

Belanovic, Library of Parameterized Hardware Modules for Floating-Point Arithmetic with an Example Application, Northeastern University, Boston, MA, May 2002, 83 pages.

Massingham, Base Calling: methods, problems and alternatives, EMBL Advanced Course in Analysis of Short Read Sequencing Data, Jun. 8, 2009-Jun. 10, 2009, 84 pages.

Thoma, A Survey of Semantic Segmentation, dated May 11, 2016, 16 pages.

Rodriguez-Ezpeleta, Bioinformatics for High Throughput Sequencing, Springer, 2012, 266 pages.

Illumina, Optimizing Cluster Density on Illumina Sequencing Systems, 2016, 12 pages.

Boza et. al., DeepNano: Deep recurrent neural networks for base calling in MinION nanopore reads, PLOS ONE, dated Jun. 5, 2017, 13 pages.

Kircher, Understanding and Improving high-throughput sequencing data production and analysis, Leipzig University, 2011, 216 pages.

(56) References Cited

OTHER PUBLICATIONS

Lutteropp, Error-Profile-Aware Correction of Next Generation Sequencing Reads, Karlsruhe Institute of Technology, dated Mar. 31, 2017, 96 pages.

Illumina, HCS 1.4/RTA 1.12 Theory of Operation, 2010, 32 pages.

Cacho, Base-Calling of High-throughput Sequencing Data Using a Random Effects Mixture Model, UC Riverside, Dec. 2016, 102 pages.

Zhou et. al., Incorporating Side-Channel Information into Convolutional Neural Networks for Robotic Tasks, 2017, 7 pages.

Linder, Modeling the intronic regulation of Alternative Splicing using Deep Convolutional Neural Nets, KTH Institute of Technology, dated Jun. 14, 2015, 53 pages.

Bentley et. al., Accurate Whole Human Genome Sequencing using Reversible Terminator Chemistry, Nature, Nov. 2008, 21 pages.

Ilumina, Calculating Percent Passing Filter for Patterned and Nonpatterned Flow Cells, 2017, 2 pages.

Fritzilas, An Overview of Illumina's Sequencing Technology and its Applications, University of Primorska, dated Mar. 4, 2011, 47 pages.

Albrecht et al., Deep learning for single-molecule science, Nanotechnology (28), dated 2017, 423001, 11 pages.

MiSEQ: Imaging and Base Calling: Illumina, Inc. Online Training Course, dated Jan. 1, 2013 [retrieved on Jul. 13, 2020], Retrieved from <URL: https://support.illumina.com/training.html >, 13 pages.

MiSEQ: Imaging and Base Calling Script, retrieved on [Jun. 14, 2021], Retrieved from the internet <URL: https://support.illumina.com/content/dam/illumina-support/courses/MiSeq_Imaging_and_Base_Calling/story_content/external_files/MiSeq%20Imaging%20and%20Base%20Calling%20Script.pdf >.

PCT/US2020/024087 PCT Direct Letter, dated Mar. 21, 2020, 5 pages.

PCT/US2020/024087 International Search Report and Written Opinion, dated Aug. 28, 2020, 24 pages.

PCT/US2020/024087 Article 34 Amendment, filed Mar. 21, 2020, 7 pages.

PCT/US2020/024087 Second Written Opinion, dated Apr. 7, 2021, 12 pages.

PCT/US2020/024087 Article 34 Letter Response to Second Written Opinion, dated May 7, 2021, 7 pages.

Zhao et. al., Object detection with Deep Learning: A Review, dated Jul. 15, 2018, 22 pages.

Lee et. al., Fast Object Localization Using a CNN Feature Map Based Multi-Scale Search, dated Apr. 12, 2016, 16 pages.

PCT/US2020/24088 PCT Direct Letter, filed Mar. 21, 2020, 4 pages.

PCT/US2020/024088 Article 34 Letter in response to Second Written Opinion, dated May 28, 2021, 9 pages.

PCT/US2020/024088 Second Written Opinion, dated Apr. 20, 2021, 17 pages.

PCT/US2020/024088 International Search Report and Written Opinion, dated Sep. 7, 2020, 29 pages.

PCT/US2020/024088 Article 34 Letter in Response to Written Opinion, dated Mar. 9, 2021, 11 pages.

PCT/US2020/024088 Partial Search Report and Invitation to Pay Fees, dated Jul. 8, 2020, 22 pages.

Misiunas et. al., QuipuNet: convolutional neural network for single-molecule nanopore sensing, dated May 30, 2018, 7 pages.

Boza et. al., Deep Recurrent Neural Networks for Base Calling in MinION Nanopore Reads, dated Mar. 30, 2016, 12 pages.

Kao et. al., BayesCall: A model-based base-calling algorithm for high-throughput short-read sequencing, Genome Research (19), pp. 1884-1895, dated 2009.

Rang et. al., From squiggle to basepair: computational approaches for improving nanopore sequencing read accuracy, Genome Biology 2018, (19), 30.

Wang et. al., An adaptive decorrelation method removes Illumina DNA base-calling errors caused by crosstalk between adjacent clusters, Scientific Reports, published Feb. 20, 2017, 11 pages.

Cacho et. al., A comparison of Base Calling Algorithms for Illumina Sequencing Technology, dated Oct. 5, 2015, Briefings in Bioinformatics 2016 (17), 786-795.

PCT/US2020/024091 PCT Direct Letter, dated Mar. 21, 2020, 5 pages.

PCT/US2020/024091 Partial Search Report and Invitation to Pay Fee, dated Jul. 3, 2020, 17 pages.

PCT/US2020/024091 International Search Report and Written Opinion, dated Oct. 23, 2020, 24 pages.

PCT/US2020/024091 Article 34 Letter in Reponse to International Search Report and Written Opinion, filed Mar. 8, 2021, 10 pages.

PCT/US2020/024091 Second Article 34 Amendment Letter, dated Mar. 22, 2021, 10 pages.

PCT/US2020/024091 Written Opinion of the International Preliminary Examining Authority (Second Written Opinon), dated Apr. 20, 2021, 14 pages.

PCT/US2020/024091 Second Article 34 Amendment in response to Second Written Opinion, dated May 30, 2021, 9 pages.

Luo et. al., G-softmax: Improving Intra-class Compactness and Inter-class Separability of Features, dated Apr. 8, 2019, 15 pages.

Luo et. al., A multi-task convolutional deep neural network for variant calling in single molecule sequencing, Nature Communications (10), No. 1, dated Mar. 1, 2019.

Kingma et. al., Adam: A method for Stochastic Optimization, ICLR 2015, dated Jul. 23, 2015.

Luo et. al., Skyhawk: An Artificial Neural Network-based discriminator for reviewing clinically significant genomic variants, dated Jan. 28, 2019, 8 pages.

MiSEQ: Imaging and Base Calling: Illumina, Inc. Online Training Course, colored version, [retrieved on Oct. 11, 2020], Retrieved from <URL: https://support.illumina.com/training.html >, 9 pages.

PCT/US2020/024092 PCT Direct Letter, dated Mar. 21, 2020, 5 pages.

PCT/US2020/024092 Partial Search Report and Invitation to Pay Fees, dated Sep. 11, 2020, 22 pages.

PCT/US2020/024092 International Search Report and Written Opinion, dated Nov. 2, 2020, 24 pages.

PCT/US2020/024092 Article 34 Amendment in Response to International Search Report and Written Opinion, dated Mar. 2, 20221, 7 pages.

PCT/US2020/024092 Second Written Opinion dated Apr. 7, 2021, 13 pages.

PCT/US2020/024092 Article 34 Amendment Response to Second Written Opinion, dated May 7, 2021, 10 pages.

PCT/US2021/018910—Partial Search Report and Invitation to Pay Fees dated May 31, 2021, 14 pgs.

PCT/US2020/033280 International Search Report and Written Opinion, dated Jul. 22, 2020, 18 pages.

PCT/US2020/033280 Article 34 Amendment, dated Apr. 19, 2021, 10 pages.

PCT/US2020/033281 International Search Report and Written Opinion, dated Aug. 14, 2020, 15 pages.

Kircher et. al., Improved base-calling for the Illumina Genome Analyzer using Machine Learning Strategies, Genome Biology, published Aug. 14, 2009, 9 pages.

PCT/US2020/033281 Second Written Opinion, dated May 10, 2021, 8 pages.

Angermueller, Christof, et. al., Deep learning for computational biology, Molecular Systems Biology, dated Jun. 6, 2016, 16 pages.

PCT/US2021/018258 International Search Report and Written Opinion, dated May 26, 2021, 17 pages.

Smith et. al., Barcoding and demultiplexing Oxford nanopore native RNA sequencing reads with deep residual learning, bioRxiv, dated Dec. 5, 2019, 18 pages.

PCT/US2021/018910 Partial Search Report and Invitation to pay fee, dated May 31, 2021, 14 pages.

Hacteria Wiki, HiSeq2000—Next Level Hacking—Hackteria Wiki, retrieved on Apr. 12, 2021, retrieved from the internet [URL: https://www.hackteria.org/wiki/HiSeq2000_-_Next_Level_Hacking ], 42 pages.

Pei et al., A Topological Measurement for Weighted Protein Interaction Network, IEEE Computational Systems Bioinformatics Conference dated 2005, 11 pages.

(56)     References Cited

OTHER PUBLICATIONS

Assfalg et. al., "3DString, A Feature String Kernel for 3D Object Classification on Voxelized Data", dated Nov. 6, 2006, 10 pages.

Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].

Illumina, Reducing Whole-Genome Data Storage Footprint, Illumina Whitepaper, 2010-2014, 4 pages.

Badrinarayanan et. al., SegNet: A Deep Convolutional Encoder-Decoder Architecture for Image Segmentation, dated Oct. 10, 2016, 14 pages.

Li et. al., CS231 Lecture 13 Segmentation and Attention, Stanford University, dated Feb. 24, 2016, 133 pages.

Whiteford et. al., Swift: Primary data analysis for the Illumina Solexa sequencing platform, Bioinformatics, vol. 25, No. 17, 2009, pp. 2194-2199, 7 pages.

Schilling, The Effect of Batch Normalization on Deep Convolutional Neural Networks, KTH Royal Institute of Technology, 2016, 113 pages.

Tutorial Image Segmentation, BoofCV, 6 pages, retrieved on Jul. 23, 2021. Retrieved from [URL: https://boofcv.org/index.php?title=Tutorial_Image_Segmentation ].

Illumina, Understanding Illumina Quality Scores, dated Apr. 23, 2014, 2 pages.

Yue et. al., Deep Learning for Genomics: A Concise Overview, dated May 8, 2018, 40 pages.

Zhang et. al., Estimating Phred scores of Illumina base calls by logistic regression and sparse modeling, Bio Med Central Bioinformatics, 2017, 14 pages.

Renaud et. al., freelbis: an efficient base caller with calibrated quality scores for Illumina sequencers, dated Mar. 6, 2013, 2 pages.

Kircher, Improving data quality of the Illumina Genome Analyzer platform, Max Planck Institute for Evolutionary Anthropology, dated Oct. 24, 2009, 46 pages.

Mitra et. al., Strategies for Achieving High Sequencing Accuracy for Low Diversity Samples and Avoiding Sample Bleeding Using Illumina Platform, PLOS One, published Apr. 10, 2015, 21 pages.

Datta et. al., Statistical Analyses of Next Generation Sequence Data: A Partial Overview, Journal of Proteomics and Bioinformatics, vol. 3, Issue 6, 2010, 8 pages.

Erlich et. al., Alta-Cyclic: a self-optimizing base-caller for next generation sequencing, Nature Methods, Aug. 2008, 7 pages.

Kao et. al., Algorithms for Next-Generation High-Throughput Sequencing Technologies, University of California, Berkeley, 2011, 106 pages.

Kircher et. al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].

Teng et. al., Chiron: translating nanopore raw signal directly into nucleotide sequence using deep learning, GigaScience, 7, 2018, 9 pages.

Ratkovic, Deep Learning Model for Base Calling of MinION Nanopore Reads, dated Jun. 2017, 48 pages.

Teng et. al., Chiron: translating nanopore raw signal directly into nucleotide sequence using deep learning, dated Aug. 23, 2017, 10 pages.

Stoiber et. al., BasecRAWller: Streaming Nanopore Basecalling Directly from Raw Signal, dated May 1, 2017, 15 pages.

Li et. al., DeepSimulator: a deep simulator for Nanopore sequencing, Bioinformatics 34(17), 2018, pp. 2899-2908, 10 pages.

Wick et. al., Performance of neural network basecalling tools for Oxford Nanopore sequencing, dated Feb. 7, 2019, 14 pages.

Ledergerber et. al., Base-calling for next-generation sequencing platforms, Briefings in Bioinformatics vol. 12, No. 5, pp. 489-497, dated Jan. 18, 2011, 9 pages.

Sheikh et. al., Chapter 5 Base-Calling for Bioinformaticians, 2012, 17 pages.

Kriseman et. al., BING: Biomedical informatics pipeline for Next Generation Sequencing, Journal of Biomedical Informatics, vol. 43, 2010, pp. 428-434, 7 pages.

Das et. al., Model-based sequential base calling for Illumina sequencing, IEEE, 2010, 4 pages.

Shamaiah et. al., Base calling error rates in next-generation DNA sequencing, IEEE Statistical Signal Processing Workshop, 2012, 4 pages.

Wolowski, High-quality, high-throughput measurement of protein-DNA binding using HiTS-FLIP, Ludwig Maxmilian University, 2016, 251 pages.

Bravo et. al., Model-Based Quality Assessment and Base-Calling for Second-Generation Sequencing Data, Biometrics, 2009, 10 pages.

Illumina, RTA Theory of Operation, 2009, 8 pages.

Dash et. al., Artificial Intelligence and Evolutionary Computations in Engineering Systems, Advances in Intelligent Systems and Computing, vol. 1056, Springer 2020, 781 pages.

Ahmed, SIGNET: A Neural Network Architecture for Predicting Protein-Protein Interactions, The University of Western Ontario, dated May 7, 2017, 84 pages.

Deepa J, Development of Fully Automated Image Analysis Method for High Density cDNA and array CGH Microarray based genomic studies, Cochin University of Science and Technology, Mar. 2013, 232 pages.

Zhang et. al., Nanopore basecalling from a perspective of instance segmentation, BMC Bioinformatics, 2020, 9 pages.

Kao et. al., naiveBayesCall: An Efficient Model-Based Base-Calling Algorithm for High-Throughput Sequencing, Journal of Computational Biology, dated Mar. 2011, 16 pages.

Wick et. al., Performance of neural network basecalling tools for Oxford Nanopore sequencing, Genome Biology, 2019, 10 pages.

Baek et. al., LncRNAnet: long non-coding RNA identification using deep learning, Bioinformatics, vol. 34 (22), 2018, pp. 3889-3897, 9 pages.

Evans et. al., Estimating Change-Points in Biological Sequences via the Cross-Entropy Method, dated Sep. 20, 2010, 17 pages.

Shen et. al., ParticleCall: A particle filter for base calling in next-generation sequencing systems, BMC Bioinformatics, 2012, 10 pages.

Peresini et. al., Nanopore Base Calling on the Edge, dated Nov. 9, 2020, 15 pages.

Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.

Wang et. al., DeepDNA: a hybrid convolutional and recurrent neural network for compressing human mitochondrial genomes, IEEE International Conference on Bioinformatics and Biomedicine, 2018, 5 pages.

PCT/US2020/024092, International Preliminary Report on Patentability (IPRP), dated Jun. 30, 2021, 30 pages.

PCT/US2020/024091 International Preliminary Report and Patentability (IPRP), dated Jun. 30, 2021, 32 pages.

PCT/US2020/024088 International Preliminary Report on Patentability (IPRP), dated Jun. 30, 2021, 35 pages.

PCT/US2020/024087 International Preliminary Report on Patentability (IPRP), dated Jun. 30, 2021, 26 pages.

PCT/US2021/018917 Internation Search Report and Written Opinion, dated Jul. 1, 2021, 15 pages.

Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].

PCT/US2020/033281, Second Article 34 Amendment Letter in response to Second Written Opinion, dated Jul. 10, 2021, 4 pages.

Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages.

U.S. Appl. No. 16/825,991—Notice of Allowance dated Apr. 19, 2021, 14 pages.

(56) References Cited

OTHER PUBLICATIONS

Arpali et. al., High- throughput screening of large vols. of whole blood using structured illumination and fluoresecent on-chip imaging, Lab on a Chip, United Kingdom, Royal Society of Chemistry, Sep. 12, 2012, vol. 12, pp. 4968-4971.

Liu et. al., 3D Stacked Many Core Architecture for Biological Sequence Analysis Problems, 2017, Int J Parallel Prog, 45:1420-1460.

Wu et. al., FPGA-Based DNA Basecalling Hardware Acceleration, in Proc. IEEE 61st Int. Midwest Symp. Circuits Syst., Aug. 2018, pp. 1098-1101.

Wu et. al., FPGA-Accelerated 3rd Generation DNA Sequencing, in IEEE Transactions on Biomedical Circuits and Systems, vol. 14, Issue 1, Feb. 2020, pp. 65-74.

Prabhakar et. al., Plasticine: A Reconfigurable Architecture for Parallel Patterns, ISCA '17, Jun. 24-28, 2017, Toronto, ON, Canada.

Lin et. al., Network in Network, in Proc. of ICLR, 2014.

Sifre, Rigid-motion Scattering for Image Classification, Ph.D. thesis, 2014.

Sifre et. al., Rotation, Scaling and Deformation Invariant Scattering for Texture Discrimination, in Proc. of CVPR, 2013.

Chollet, Xception: Deep Learning with Depthwise Separable Convolutions, in Proc. of CVPR, 2017. 8 pages.

Zhang et. al., ShuffleNet: An Extremely Efficient Convolutional Neural Network for Mobile Devices, 2017.

He et. al., Deep Residual Learning for Image Recognition, in Proc. of CVPR, 2016.

Xie et. al., Aggregated Residual Transformations for Deep Neural Networks, in Proc. of CVPR, 2017.

Howard et. al., Mobilenets: Efficient Convolutional Neural Networks for Mobile Vision Applications, 2017.

Sandler et. al., MobileNetV2: Inverted Residuals and Linear Bottlenecks, 2018.

Qin et. al., FD-MobileNet: Improved MobileNet with a Fast Downsampling Strategy, 2018.

Chen et. al., Rethinking atrous convolution for semantic image segmentation, 2017.

Huang et. al., Speed/accuracy trade-offs for modern convolutional detectors, 2016.

Oord, Dieleman et. al., WAVENET: A Generative Model for Raw Audio, 2016.

Arik et. al., Deep Voice: Real-time Neural Text-to-Speech, 2017.

Yu et. al., Multi-Scale Context Aggregation by Dilated Convolutions, 2016.

He et. al., Deep Residual Learning for Image Recognition, 2015.

Srivastava et. al., Highway Networks, 2015.

Huang et. al., Densely Connected Convolutional Networks, 2017.

Szegedy et. al., Going Deeper with Convolutions, 2014.

Ioffe et. al., Batch Normalization Accelerating Deep Network Training by Reducing Internal Covariate Shift, 2015.

Wolterink et. al., Dilated Convolutional Neural Networks for Cardiovascular MR Segmentation in Congenital Heart Disease, 2017.

Piqueras, Autoregressive Model Based on a Deep Convolutional Neural Network for Audio Generation, Tampere University of Technology, 2016.

Wu, Introduction to Convolutional Neural Networks, Nanjing University, 2017.

Scikit-image/peak.py at master, Github, retrieved on Jun. 8, 2021, 10 pages, Retrieved from the internet <URL: https://github.com/scikit-image/scikit-image/blob/main/skimage/feature/peak.py>.

3.3.9.11.Watershed and random walker for segmentation, Scipy lecture notes, 2 pages. [retrieved on Jun. 8, 2021] Retrieved from the internet <URL: http:scipy-lectures.org/packages/scikit-image/auto_examples/plot_segmentations.html>.

Mordvintsev et. al., Image Segmentation with Watershed Algorithm, Revision 43532856, 2013, 6 pages. [retrieved on Jun. 8, 2021] Retrieved from the Internet <URL: https://opencv-python-tutroals.readthedocs.io/en/latest/py_tutorials/by_imgproc/py_watershed/py_watershed.html>.

Mzur, Watershed.py, Github, 3 pages. [retrieved on Jun. 8, 2021] Retrieved from the internet <URL: https://github.com/mzur/watershed/blob/master/Watershed.py>.

Thakur et. al., A Survey of Image Segmentation Techniques, International Journal of Research in Computer Applications and Robotics, vol. 2, Issue 4, Apr. 2014, p. 158-165.

Long et. al., Fully Convolutional Networks for Semantic Segmentation, IEEE Transactions on Pattern Analysis and Machine Intelligence, vol. 39, Issue 4, Apr. 1, 2017, 12 pages.

Ronneberger et. al., U-net: Convolutional networks for biomedical image segmentation, in International Conference on Medical Image computing and computer assisted intervention, May 18, 2015, 8 pages.

Xie et. al., Microscopy cell counting and detection with fully convolutional regression networks, Computer methods in biomechanics and biomedical engineering, Imaging and Visualization, 6(3), pp. 283-292, 2018.

Xie, Y., et. al., Beyond classification: structured regression for robust cell detection using convolutional neural network. International conference on medical image computing and computer assisted intervention, Oct. 2015, 12 pages.

Snuverink, Deep Learning for Pixelwise Classification of Hyperspectral Images, Master of Science Thesis, Delft University of Technology, Nov. 23, 2017, 128 pages.

Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b >, 2 pages.

Assem, Predicting periodic and chaotic signals using Wavenets, Master of Science thesis, Delft University of Technology, Aug. 18, 2017, pp. 3-38.

Goodfellow et. al., Convolutional Networks, Deep Learning, MIT Press, 2016.

Illumina, "Indexed Sequencing Overview Guide", Document No. 15057455, v. 5, Mar. 2019.

PCT/US2020/024090 International Preliminary Report on Patentability, dated Apr. 13, 2021, 20 pages.

PCT/US2020/024090 Written Opinion of the International Preliminary Examining Authority, dated Dec. 22, 2020, 11 pages.

PCT/US2020/024090 PCT Direct Letter, filed Mar. 21, 2020, 5 pages.

PCT/US2020/024090 International Search Report, dated Aug. 31, 2020, 8 pages.

PCT/US2020/024090 Article 34 Amendment, dated Dec. 4, 2020, 6 pages.

PCT/US2020/024090 Article 34 Amendment, dated Mar. 18, 2021, 3 pages.

Wan et al. "Multivariate temporal convolutional network: A deep neural networks approach for multivariate time series forecasting." Electronics 8.8 (2019): 876 (Year: 2019).

Xu et al. "UP-CNN: Un-pooling augmented convolutional neural network." Pattern Recognition Letters 119 (2019): 34-40. (Year: 2019).

Zhu, Ligeng, et al. "Sparsely aggregated convolutional networks." Proceedings of the European Conference on Computer Vision (ECCV). 2018. (Year: 2018).

Nagase, Jumpei et al., "Expressive power of skip connection and network architecture", IEICE Technical Report, vol. 118 No. 472, 2019.02.26, pp. 9-15. (Abstract).

Takagi, Jumpei et al., "Efficient Learning for Distillation of DNN by Self Distillation", IEEJ Transactions on Electronic, Information and Systems, vol. 139 No. 12, Dec. 1, 2019, pp. 1509-1516. (Abstract).

* cited by examiner

Figure 1A

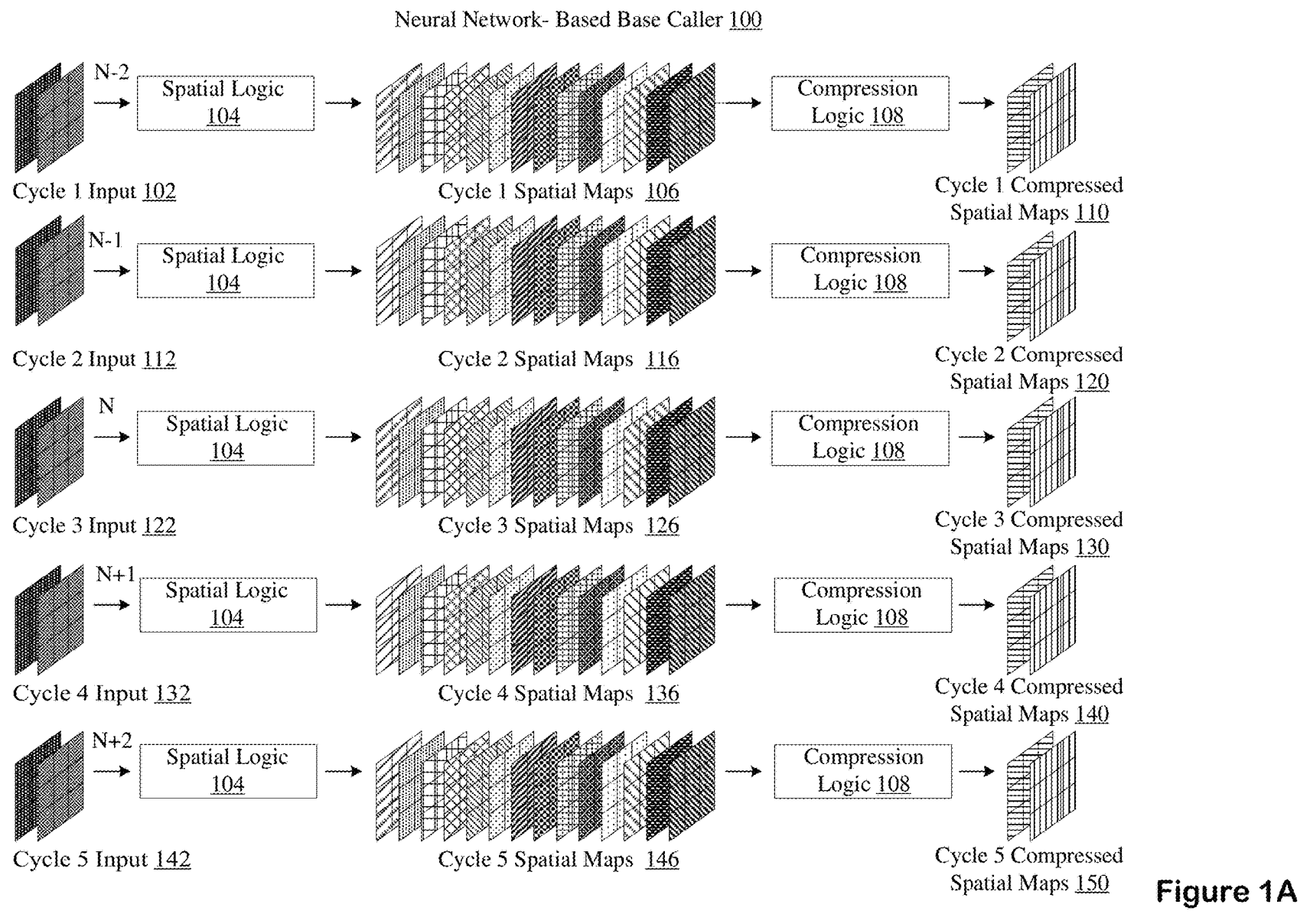

Neural Network- Based Base Caller 100

N-2

Cycle 1 Input 102

Spatial Logic 104

Cycle 1 Spatial Maps 106

Compression Logic 108

Cycle 1 Compressed Spatial Maps 110

N-1

Cycle 2 Input 112

Spatial Logic 104

Cycle 2 Spatial Maps 116

Compression Logic 108

Cycle 2 Compressed Spatial Maps 120

N

Cycle 3 Input 122

Spatial Logic 104

Cycle 3 Spatial Maps 126

Compression Logic 108

Cycle 3 Compressed Spatial Maps 130

N+1

Cycle 4 Input 132

Spatial Logic 104

Cycle 4 Spatial Maps 136

Compression Logic 108

Cycle 4 Compressed Spatial Maps 140

N+2

Cycle 5 Input 142

Spatial Logic 104

Cycle 5 Spatial Maps 146

Compression Logic 108

Cycle 5 Compressed Spatial Maps 150

Output with
1 channel

Channel 1

Channel 0

The kernel applied to the input tensor

Input tensor with 2 channels and a 1x1
convolution kernel

Softmax Function

Figure 1G

Cycle 6 Input 222

N+2

Spatial Logic 104

Cycle 6 Spatial Maps 226

Compression Logic 108

Cycle 6 Compressed Spatial Maps 230

Second Window of Sequencing Cycles

| N-2 | N-1 | N | N+1 | N+2 |
|---|---|---|---|---|
| Cycle 2 | Cycle 3 | Cycle 4 | Cycle 5 | Cycle 6 |

Figure 14:
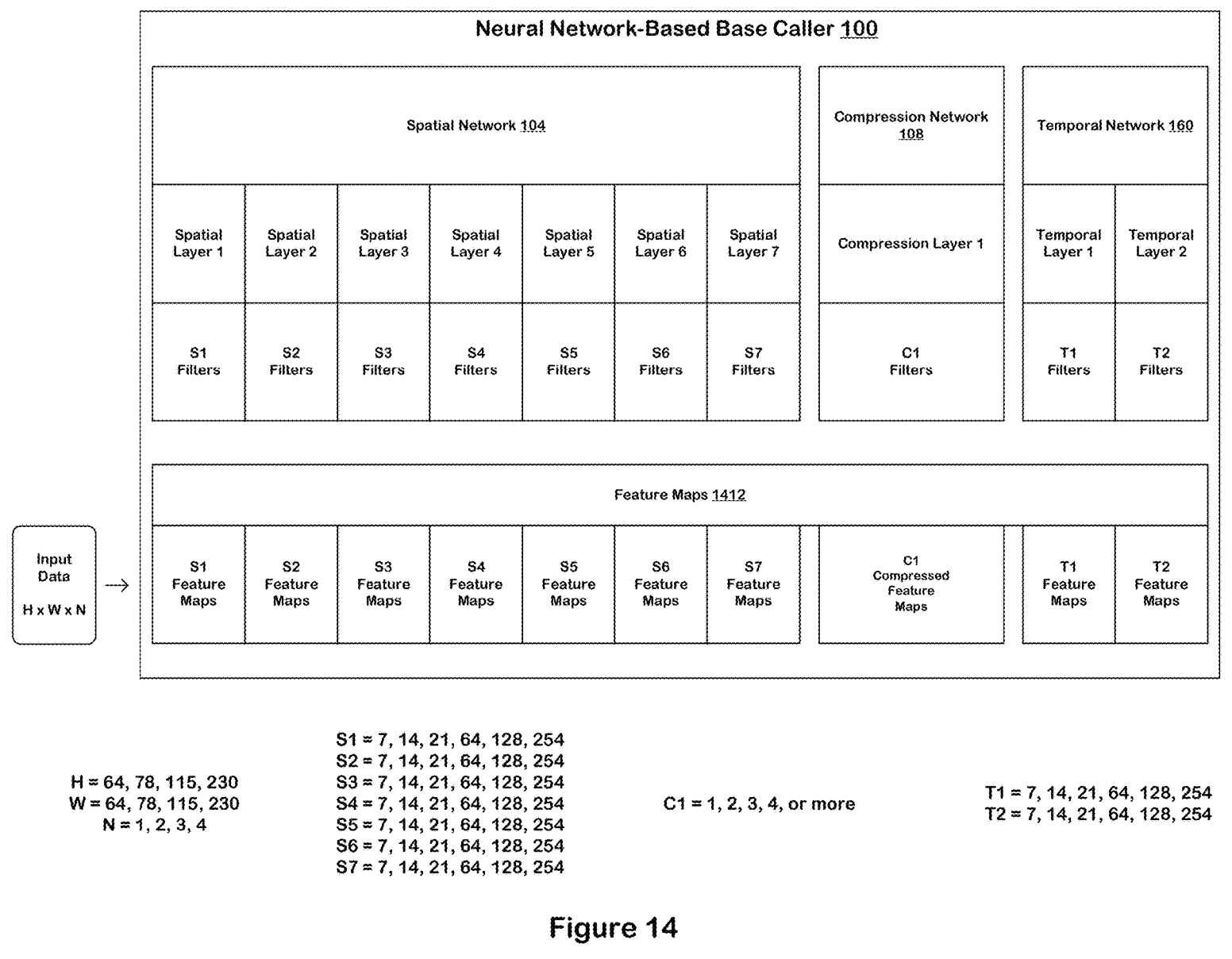

Neural Network-Based Base Caller 100

| Spatial Network 104 | | | | | | | Compression Network 108 | Temporal Network 160 | |
|---|---|---|---|---|---|---|---|---|---|
| Spatial Layer 1 | Spatial Layer 2 | Spatial Layer 3 | Spatial Layer 4 | Spatial Layer 5 | Spatial Layer 6 | Spatial Layer 7 | Compression Layer 1 | Temporal Layer 1 | Temporal Layer 2 |
| S1 Filters | S2 Filters | S3 Filters | S4 Filters | S5 Filters | S6 Filters | S7 Filters | C1 Filters | T1 Filters | T2 Filters |

Feature Maps 1412

| S1 Feature Maps | S2 Feature Maps | S3 Feature Maps | S4 Feature Maps | S5 Feature Maps | S6 Feature Maps | S7 Feature Maps | C1 Compressed Feature Maps | T1 Feature Maps | T2 Feature Maps |
|---|---|---|---|---|---|---|---|---|---|

Input Data
H x W x N

→

H = 64, 78, 115, 230
W = 64, 78, 115, 230
N = 1, 2, 3, 4

S1 = 7, 14, 21, 64, 128, 254
S2 = 7, 14, 21, 64, 128, 254
S3 = 7, 14, 21, 64, 128, 254
S4 = 7, 14, 21, 64, 128, 254
S5 = 7, 14, 21, 64, 128, 254
S6 = 7, 14, 21, 64, 128, 254
S7 = 7, 14, 21, 64, 128, 254

C1 = 1, 2, 3, 4, or more

Figure 15:
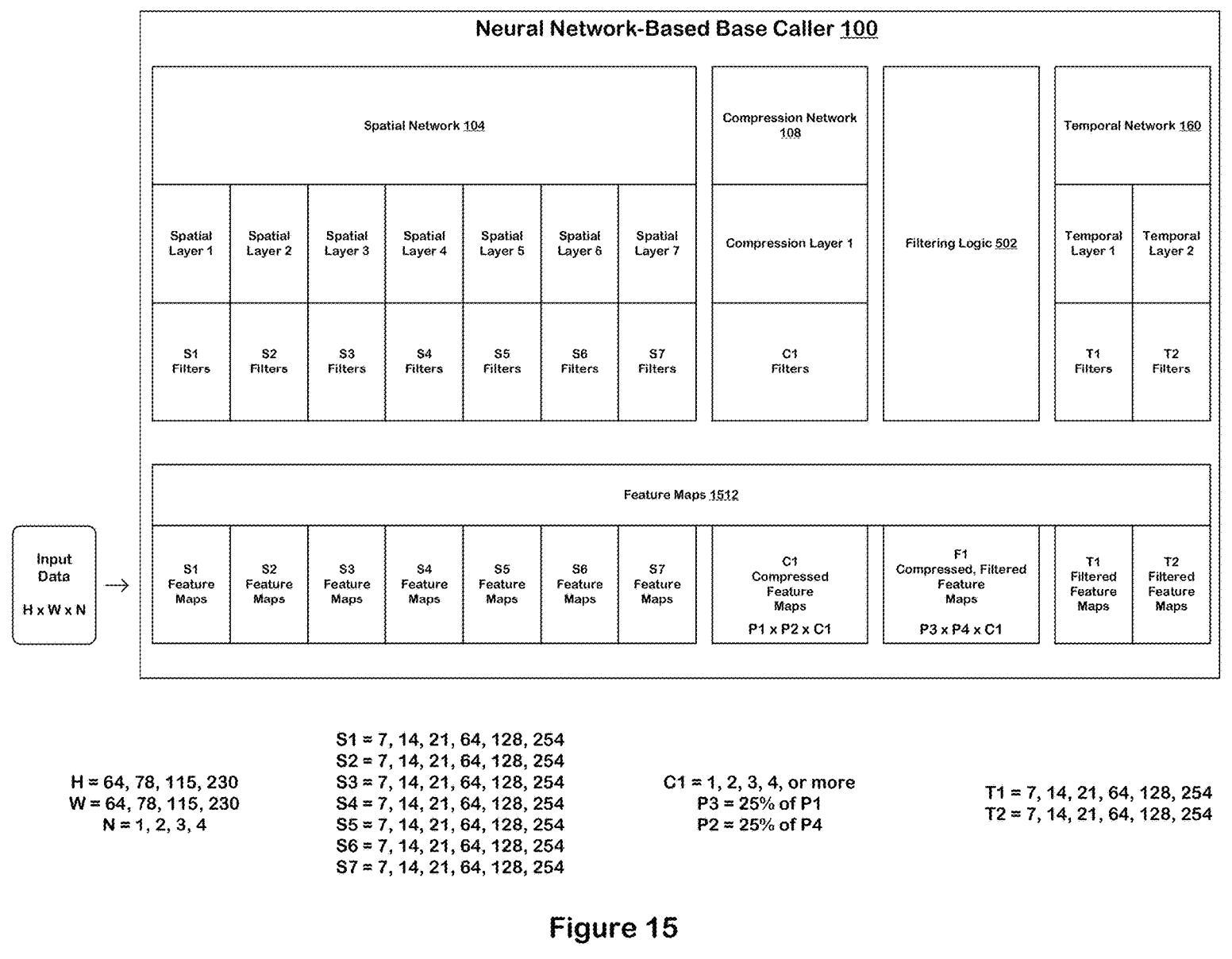

Neural Network-Based Base Caller 100

Spatial Network 104

| Spatial Layer 1 | Spatial Layer 2 | Spatial Layer 3 | Spatial Layer 4 | Spatial Layer 5 | Spatial Layer 6 | Spatial Layer 7 |
|---|---|---|---|---|---|---|
| S1 Filters | S2 Filters | S3 Filters | S4 Filters | S5 Filters | S6 Filters | S7 Filters |

Compression Network 108

| Compression Layer 1 |
|---|
| C1 Filters |

Filtering Logic 502

Temporal Network 160

| Temporal Layer 1 | Temporal Layer 2 |
|---|---|
| T1 Filters | T2 Filters |

Feature Maps 1512

| S1 Feature Maps | S2 Feature Maps | S3 Feature Maps | S4 Feature Maps | S5 Feature Maps | S6 Feature Maps | S7 Feature Maps |
|---|---|---|---|---|---|---|

| C1 Compressed Feature Maps P1 x P2 x C1 |
|---|

| F1 Compressed, Filtered Feature Maps P3 x P4 x C1 |
|---|

| T1 Filtered Feature Maps | T2 Filtered Feature Maps |
|---|---|

Input Data
H x W x N

H = 64, 78, 115, 230
W = 64, 78, 115, 230
N = 1, 2, 3, 4

S1 = 7, 14, 21, 64, 128, 254
S2 = 7, 14, 21, 64, 128, 254
S3 = 7, 14, 21, 64, 128, 254
S4 = 7, 14, 21, 64, 128, 254
S5 = 7, 14, 21, 64, 128, 254
S6 = 7, 14, 21, 64, 128, 254
S7 = 7, 14, 21, 64, 128, 254

C1 = 1, 2, 3, 4, or more
P3 = 25% of P1
P2 = 25% of P4

Figure 17:
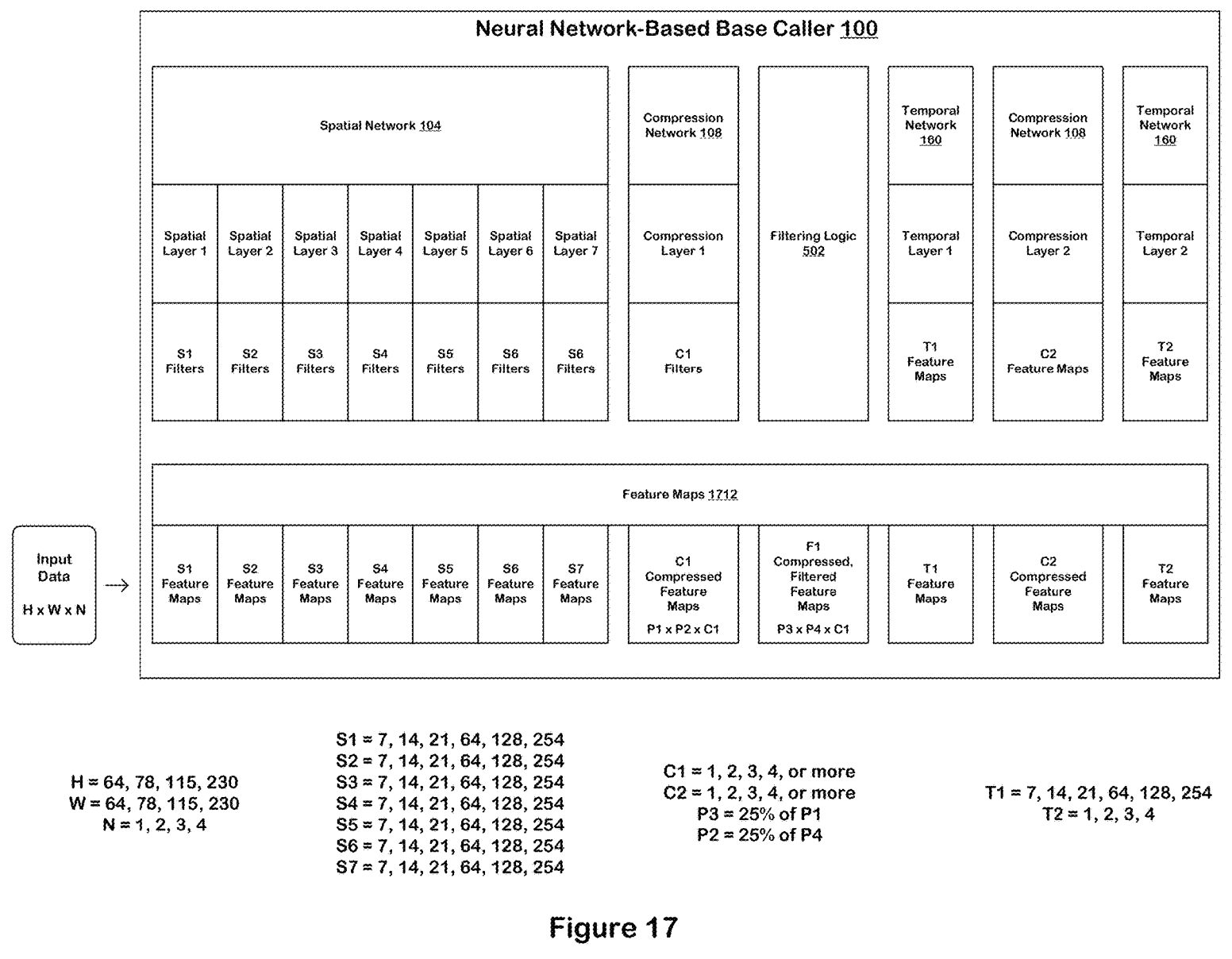

Neural Network-Based Base Caller 100

| Spatial Network 104 | | | | | | | Compression Network 108 | Filtering Logic 502 | Temporal Network 160 | Compression Network 108 | Temporal Network 160 |
|---|---|---|---|---|---|---|---|---|---|---|---|
| Spatial Layer 1 | Spatial Layer 2 | Spatial Layer 3 | Spatial Layer 4 | Spatial Layer 5 | Spatial Layer 6 | Spatial Layer 7 | Compression Layer 1 | | Temporal Layer 1 | Compression Layer 2 | Temporal Layer 2 |
| S1 Filters | S2 Filters | S3 Filters | S4 Filters | S5 Filters | S6 Filters | S6 Filters | C1 Filters | | T1 Feature Maps | C2 Feature Maps | T2 Feature Maps |

Feature Maps 1712

| S1 Feature Maps | S2 Feature Maps | S3 Feature Maps | S4 Feature Maps | S5 Feature Maps | S6 Feature Maps | S7 Feature Maps | C1 Compressed Feature Maps P1 x P2 x C1 | F1 Compressed, Filtered Feature Maps P3 x P4 x C1 | T1 Feature Maps | C2 Compressed Feature Maps | T2 Feature Maps |

Input Data
H x W x N

H = 64, 78, 115, 230
W = 64, 78, 115, 230
N = 1, 2, 3, 4

S1 = 7, 14, 21, 64, 128, 254
S2 = 7, 14, 21, 64, 128, 254
S3 = 7, 14, 21, 64, 128, 254
S4 = 7, 14, 21, 64, 128, 254
S5 = 7, 14, 21, 64, 128, 254
S6 = 7, 14, 21, 64, 128, 254
S7 = 7, 14, 21, 64, 128, 254

C1 = 1, 2, 3, 4, or more
C2 = 1, 2, 3, 4, or more
P3 = 25% of P1
P2 = 25% of P4

Neural Network-Based Base Caller 100

| | RAM usage (GB) | DRAM usage (GB) |
|---|---|---|
| without Compression Logic 108 | 90.81344604 | 0.752478838 |
| with Compression Logic 108 | 44.95265579 | 0.826221764 |

Figure 31

DATA COMPRESSION FOR ARTIFICIAL INTELLIGENCE-BASED BASE CALLING

PRIORITY APPLICATION

This application claims priority to and benefit of U.S. Provisional Patent Application No. 62/979,411, titled "DATA COMPRESSION FOR ARTIFICIAL INTELLIGENCE-BASED BASE CALLING," filed 20 Feb. 2020. The priority application is hereby incorporated by reference for all purposes as if fully set forth herein.

This application claims priority to and benefit of U.S. Provisional Patent Application No. 62/979,399, titled "SQUEEZING LAYER FOR ARTIFICIAL INTELLIGENCE-BASED BASE CALLING," filed 20 Feb. 2020. The priority application is hereby incorporated by reference for all purposes as if fully set forth herein.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolution neural networks for analyzing data.

INCORPORATIONS

The following are incorporated by reference as if fully set forth herein:

U.S. Provisional Patent Application No. 62/979,384, titled "ARTIFICIAL INTELLIGENCE-BASED BASE CALLING OF INDEX SEQUENCES," filed 20 Feb. 2020;

U.S. Provisional Patent Application No. 62/979,414, titled "ARTIFICIAL INTELLIGENCE-BASED MANY-TO-MANY BASE CALLING," filed 20 Feb. 2020;

U.S. Provisional Patent Application No. 62/979,385, titled "KNOWLEDGE DISTILLATION-BASED COMPRESSION OF ARTIFICIAL INTELLIGENCE-BASED BASE CALLER," filed 20 Feb. 2020;

U.S. Provisional Patent Application No. 63/072,032, titled "DETECTING AND FILTERING CLUSTERS BASED ON ARTIFICIAL INTELLIGENCE-PREDICTED BASE CALLS," filed 28 Aug. 2020;

U.S. Provisional Patent Application No. 62/979,412, titled "MULTI-CYCLE CLUSTER BASED REAL TIME ANALYSIS SYSTEM," filed 20 Feb. 2020;

U.S. Nonprovisional patent application Ser. No. 16/825,987, titled "TRAINING DATA GENERATION FOR ARTIFICIAL INTELLIGENCE-BASED SEQUENCING," filed 20 Mar. 2020;

U.S. Nonprovisional patent application Ser. No. 16/825,991 titled "ARTIFICIAL INTELLIGENCE-BASED GENERATION OF SEQUENCING METADATA," filed 20 Mar. 2020;

U.S. Nonprovisional patent application Ser. No. 16/826,126, titled "ARTIFICIAL INTELLIGENCE-BASED BASE CALLING," filed 20 Mar. 2020;

U.S. Nonprovisional patent application Ser. No. 16/826,134, titled "ARTIFICIAL INTELLIGENCE-BASED QUALITY SCORING," filed 20 Mar. 2020; and U.S. Nonprovisional patent application Ser. No. 16/826,168, titled "ARTIFICIAL INTELLIGENCE-BASED SEQUENCING," filed 21 Mar. 2020.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

The rapid improvement in computation capability has made deep convolution neural networks (CNNs) a great success in recent years on many computer vision tasks with significantly improved accuracy. During the inference phase, many applications demand low latency processing of one image with strict power consumption requirement, which reduces the efficiency of graphics processing unit (GPU) and other general-purpose platform, bringing opportunities for specific acceleration hardware, e.g., field programmable gate array (FPGA), by customizing the digital circuit specific for the deep learning algorithm inference. However, deploying CNNs on portable and embedded systems is still challenging due to large data volume, intensive computation, varying algorithm structures, and frequent memory accesses.

As convolution contributes most operations in CNNs, the convolution acceleration scheme significantly affects the efficiency and performance of a hardware CNN accelerator. Convolution involves multiply and accumulate (MAC) operations with four levels of loops that slide along kernel and feature maps. The first loop level computes the MAC of pixels within a kernel window. The second loop level accumulates the sum of products of the MAC across different input feature maps. After finishing the first and second loop levels, a final output pixel is obtained by adding the bias. The third loop level slides the kernel window within an input feature map. The fourth loop level generates different output feature maps.

FPGAs have gained increasing interests and popularity in particular to accelerate the inference tasks, due to their (1) high degree of reconfigurability, (2) faster development time compared to application specific integrated circuits (ASICs) to catch up with the rapid evolving of CNNs, (3) good performance, and (4) superior energy efficiency compared to GPUs. The high performance and efficiency of an FPGA can be realized by synthesizing a circuit that is customized for a specific computation to directly process billions of operations with the customized memory systems. For instance, hundreds to thousands of digital signal processing (DSP) blocks on modern FPGAs support the core convolution operation, e.g., multiplication and addition, with high parallelism. Dedicated data buffers between external on-chip memory and on-chip processing engines (PEs) can be designed to realize the preferred dataflow by configuring tens of Mbyte on-chip block random access memories (BRAM) on the FPGA chip.

Efficient dataflow and hardware architecture of CNN acceleration are desired to minimize data communication while maximizing resource utilization to achieve high performance. An opportunity arises to design methodology and framework to accelerate the inference process of various CNN algorithms on acceleration hardware with high performance, efficiency, and flexibility.

BRIEF DESCRIPTION OF THE DRAWINGS

The patent or application file does not contain any drawings executed in color.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 1A illustrates one implementation of the disclosed compression logic that generates compressed spatial map sets for a first iteration of base calling.

FIG. 1G shows an example softmax function.

FIG. 14 illustrates a first example architecture of the neural network-based base caller disclosed herein.

FIG. 15 illustrates a second example architecture of the neural network-based base caller disclosed herein.

FIG. 16 illustrates a third example architecture of the neural network-based base caller disclosed herein.

FIG. 17 illustrates a fourth example architecture of the neural network-based base caller disclosed herein.

FIG. 31 shows savings in RAM and DRAM usage brought about by the use of the disclosed compression logic.

DETAILED DESCRIPTION

Figure 1B:
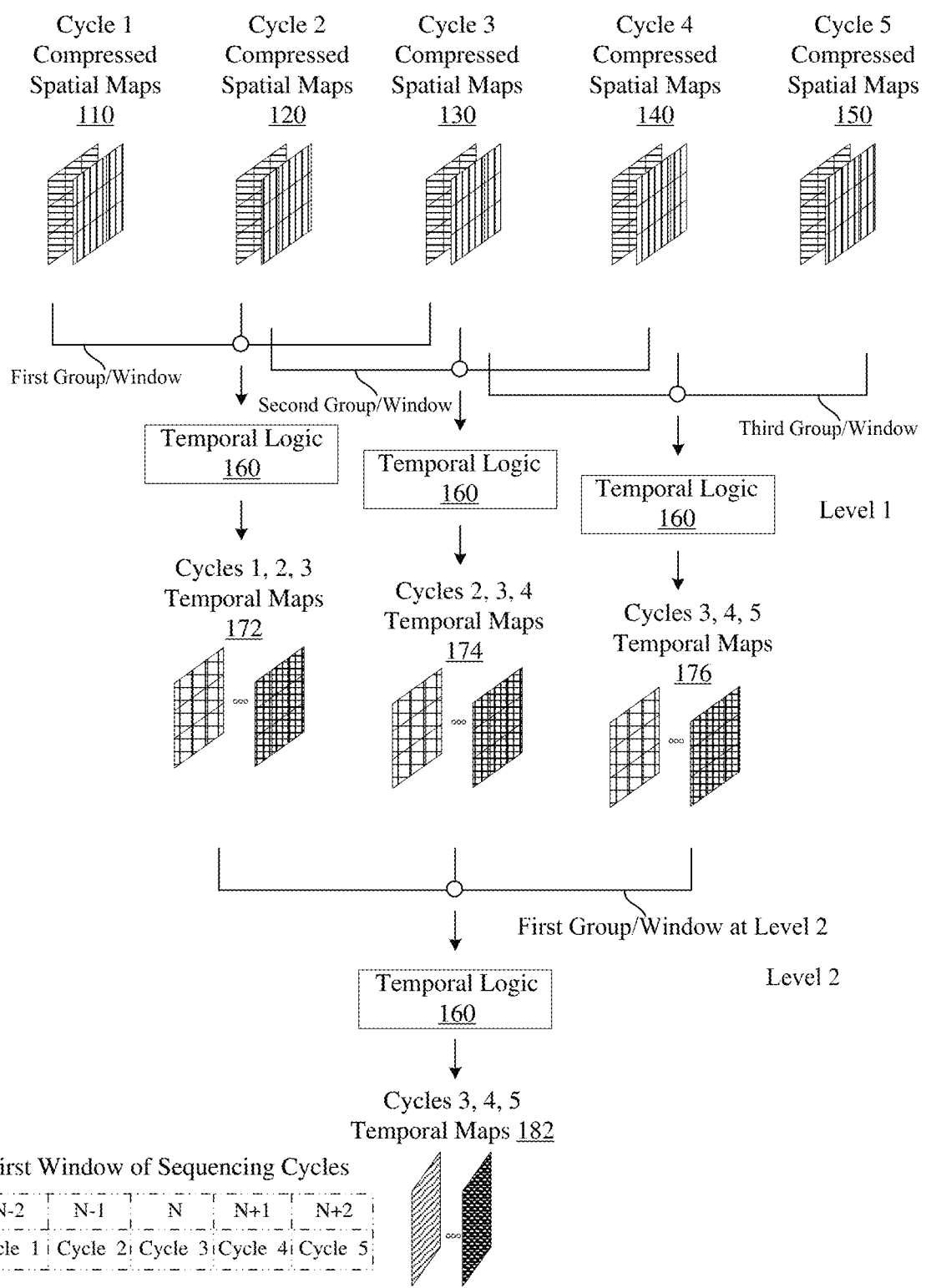
FIG. 1B illustrates one implementation of processing the compressed spatial map sets through the disclosed temporal logic to generate temporal map sets.

The following discussion is presented to enable any person skilled in the art to make and use the technology disclosed and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein.

Sequencing Images

Base calling is the process of determining the nucleotide composition of a sequence. Base calling involves analyzing image data, i.e., sequencing images, produced during a sequencing run (or sequencing reaction) carried out by a sequencing instrument such as Illumina's iSeq, HiSeqX, HiSeq 3000, HiSeq 4000, HiSeq 2500, NovaSeq 6000, NextSeq 550, NextSeq 1000, NextSeq 2000, NextSeqDx, MiSeq, and MiSeqDx.

The following discussion outlines how the sequencing images are generated and what they depict, in accordance with one implementation.

Base calling decodes the intensity data encoded in the sequencing images into nucleotide sequences. In one implementation, the Illumina sequencing platforms employ cyclic reversible termination (CRT) chemistry for base calling. The process relies on growing nascent strands complementary to template strands with fluorescently-labeled nucleotides, while tracking the emitted signal of each newly added nucleotide. The fluorescently-labeled nucleotides have a 3' removable block that anchors a fluorophore signal of the nucleotide type.

Sequencing occurs in repetitive cycles, each comprising three steps: (a) extension of a nascent strand by adding the fluorescently-labeled nucleotide; (b) excitation of the fluorophore using one or more lasers of an optical system of the sequencing instrument and imaging through different filters of the optical system, yielding the sequencing images; and (c) cleavage of the fluorophore and removal of the 3' block in preparation for the next sequencing cycle. Incorporation and imaging cycles are repeated up to a designated number of sequencing cycles, defining the read length. Using this approach, each cycle interrogates a new position along the template strands.

The tremendous power of the Illumina sequencers stems from their ability to simultaneously execute and sense millions or even billions of clusters (also called "analytes") undergoing CRT reactions. A cluster comprises approximately one thousand identical copies of a template strand, though clusters vary in size and shape. The clusters are grown from the template strand, prior to the sequencing run, by bridge amplification or exclusion amplification of the input library. The purpose of the amplification and cluster growth is to increase the intensity of the emitted signal since the imaging device cannot reliably sense fluorophore signal of a single strand. However, the physical distance of the strands within a cluster is small, so the imaging device perceives the cluster of strands as a single spot.

Sequencing occurs in a flow cell (or biosensor)—a small glass slide that holds the input strands. The flow cell is connected to the optical system, which comprises microscopic imaging, excitation lasers, and fluorescence filters. The flow cell comprises multiple chambers called lanes. The lanes are physically separated from each other and may contain different tagged sequencing libraries, distinguishable without sample cross contamination. In some implementations, the flow cell comprises a patterned surface. A "patterned surface" refers to an arrangement of different regions in or on an exposed layer of a solid support.

The imaging device of the sequencing instrument (e.g., a solid-state imager such as a charge-coupled device (CCD) or a complementary metal-oxide-semiconductor (CMOS) sensor) takes snapshots at multiple locations along the lanes in a series of non-overlapping regions called tiles. For example, there can be sixty four or ninety six tiles per lane. A tile holds hundreds of thousands to millions of clusters.

The output of the sequencing run is the sequencing images. Sequencing images depict intensity emissions of the clusters and their surrounding background using a grid (or array) of pixelated units (e.g., pixels, superpixels, subpixels). The intensity emissions are stored as intensity values of the pixelated units. The sequencing images have dimensions w×h of the grid of pixelated units, where w (width) and h (height) are any numbers ranging from 1 and 100,000 (e.g., 115×115, 200×200, 1800×2000, 2200×25000, 2800×3600, 4000×400). In some implementations, w and h are the same. In other implementations, w and h are different. The sequencing images depict intensity emissions generated as a result of nucleotide incorporation in the nucleotide sequences during the sequencing run. The intensity emissions are from associated clusters and their surrounding background.

Neural Network-Based Base Calling

The following discussion focuses on a neural network-based base caller 100 described herein. First, the input to the neural network-based base caller 100 is described, in accordance with one implementation. Then, examples of the structure and form of the neural network-based base caller 100 are provided. Finally, the output of the neural network-based base caller 100 is described, in accordance with one implementation.

A data flow logic provides the sequencing images to the neural network-based base caller 100 for base calling. The neural network-based base caller 100 accesses the sequencing images on a patch-by-patch basis (or a tile-by-tile basis). Each of the patches is a sub-grid (or sub-array) of pixelated units in the grid of pixelated units that forms the sequencing images. The patches have dimensions q×r of the sub-grid of pixelated units, where q (width) and r (height) are any numbers ranging from 1 and 10000 (e.g., 3×3, 5×5, 7×7, 10×10, 15×15, 25×25, 64×64, 78×78, 115×115). In some implementations, q and r are the same. In other implementations, q and r are different. In some implementations, the patches extracted from a sequencing image are of the same size. In other implementations, the patches are of different sizes. In some implementations, the patches can have overlapping pixelated units (e.g., on the edges).

Sequencing produces m sequencing images per sequencing cycle for corresponding m image channels. That is, each of the sequencing images has one or more image (or intensity) channels (analogous to the red, green, blue (RGB) channels of a color image). In one implementation, each image channel corresponds to one of a plurality of filter wavelength bands. In another implementation, each image channel corresponds to one of a plurality of imaging events at a sequencing cycle. In yet another implementation, each image channel corresponds to a combination of illumination with a specific laser and imaging through a specific optical filter. The image patches are tiled (or accessed) from each of the m image channels for a particular sequencing cycle. In different implementations such as 4-, 2-, and 1-channel chemistries, m is 4 or 2. In other implementations, m is 1, 3, or greater than 4.

Consider, for example, that a sequencing run is implemented using two different image channels: a blue channel and a green channel. Then, at each sequencing cycle, the sequencing run produces a blue image and a green image. This way, for a series of k sequencing cycles of the sequencing run, a sequence of k pairs of blue and green images is produced as output and stored as the sequencing images. Accordingly, a sequence of k pairs of blue and green image patches is generated for the patch-level processing by the neural network-based base caller 100.

The input image data to the neural network-based base caller 100 for a single iteration of base calling (or a single instance of forward pass or a single forward traversal) comprises data for a sliding window of multiple sequencing cycles. The sliding window can include, for example, a current sequencing cycle, one or more preceding sequencing cycles, and one or more successive sequencing cycles.

In one implementation, the input image data comprises data for three sequencing cycles, such that data for a current (time t) sequencing cycle to be base called is accompanied with (i) data for a left flanking/context/previous/preceding/prior (time t−1) sequencing cycle and (ii) data for a right flanking/context/next/successive/subsequent (time t+1) sequencing cycle.

In another implementation, the input image data comprises data for five sequencing cycles, such that data for a current (time t) sequencing cycle to be base called is accompanied with (i) data for a first left flanking/context/previous/preceding/prior (time t−1) sequencing cycle, (ii)

data for a second left flanking/context/previous/preceding/prior (time t–2) sequencing cycle, (iii) data for a first right flanking/context/next/successive/subsequent (time t+1), and (iv) data for a second right flanking/context/next/successive/subsequent (time t+2) sequencing cycle.

In yet another implementation, the input image data comprises data for seven sequencing cycles, such that data for a current (time t) sequencing cycle to be base called is accompanied with (i) data for a first left flanking/context/previous/preceding/prior (time t–1) sequencing cycle, (ii) data for a second left flanking/context/previous/preceding/prior (time t–2) sequencing cycle, (iii) data for a third left flanking/context/previous/preceding/prior (time t–3) sequencing cycle, (iv) data for a first right flanking/context/next/successive/subsequent (time t+1), (v) data for a second right flanking/context/next/successive/subsequent (time t+2) sequencing cycle, and (vi) data for a third right flanking/context/next/successive/subsequent (time t+3) sequencing cycle. In other implementations, the input image data comprises data for a single sequencing cycle. In yet other implementations, the input image data comprises data for 10, 15, 20, 30, 58, 75, 92, 130, 168, 175, 209, 225, 230, 275, 318, 325, 330, 525, or 625 sequencing cycles.

The neural network-based base caller 100 processes the image patches through its convolution layers and produces an alternative representation, according to one implementation. The alternative representation is then used by an output layer (e.g., a softmax layer) for generating a base call for either just the current (time t) sequencing cycle or each of the sequencing cycles, i.e., the current (time t) sequencing cycle, the first and second preceding (time t–1, time t–2) sequencing cycles, and the first and second succeeding (time t+1, time t+2) sequencing cycles. The resulting base calls form the sequencing reads.

In one implementation, the neural network-based base caller 100 outputs a base call for a single target cluster for a particular sequencing cycle. In another implementation, the neural network-based base caller 100 outputs a base call for each target cluster in a plurality of target clusters for the particular sequencing cycle. In yet another implementation, the neural network-based base caller 100 outputs a base call for each target cluster in a plurality of target clusters for each sequencing cycle in a plurality of sequencing cycles, thereby producing a base call sequence for each target cluster.

In one implementation, the neural network-based base caller 100 is a multilayer perceptron (MLP). In another implementation, the neural network-based base caller 100 is a feedforward neural network. In yet another implementation, the neural network-based base caller 100 is a fully-connected neural network. In a further implementation, the neural network-based base caller 100 is a fully convolution neural network. In yet further implementation, the neural network-based base caller 100 is a semantic segmentation neural network. In yet another further implementation, the neural network-based base caller 100 is a generative adversarial network (GAN).

In one implementation, the neural network-based base caller 100 is a convolution neural network (CNN) with a plurality of convolution layers. In another implementation, the neural network-based base caller 100 is a recurrent neural network (RNN) such as a long short-term memory network (LSTM), bi-directional LSTM (Bi-LSTM), or a gated recurrent unit (GRU). In yet another implementation, the neural network-based base caller 100 includes both a CNN and an RNN.

In yet other implementations, the neural network-based base caller 100 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The neural network-based base caller 100 can use one or more loss functions such as logistic regression/log loss, multi-class cross-entropy/softmax loss, binary cross-entropy loss, mean-squared error loss, L1 loss, L2 loss, smooth L1 loss, and Huber loss. The neural network-based base caller 100 can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The neural network-based base caller 100 can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The neural network-based base caller 100 is trained using backpropagation-based gradient update techniques. Example gradient descent techniques that can be used for training the neural network-based base caller 100 include stochastic gradient descent, batch gradient descent, and mini-batch gradient descent. Some examples of gradient descent optimization algorithms that can be used to train the neural network-based base caller 100 are Momentum, Nesterov accelerated gradient, Adagrad, Adadelta, RMSprop, Adam, AdaMax, Nadam, and AMSGrad.

In one implementation, the neural network-based base caller 100 uses a specialized architecture to segregate processing of data for different sequencing cycles. The motivation for using the specialized architecture is described first. As discussed above, the neural network-based base caller 100 processes image patches for a current sequencing cycle, one or more preceding sequencing cycles, and one or more successive sequencing cycles. Data for additional sequencing cycles provides sequence-specific context. The neural network-based base caller 100 learns the sequence-specific context during training and base calls them. Furthermore, data for pre and post sequencing cycles provides second order contribution of pre-phasing and phasing signals to the current sequencing cycle.

However, images captured at different sequencing cycles and in different image channels are misaligned and have residual registration error with respect to each other. To account for this misalignment, the specialized architecture comprises spatial convolution layers that do not mix information between sequencing cycles and only mix information within a sequencing cycle.

Spatial convolution layers (or spatial logic) use so-called "segregated convolutions" that operationalize the segregation by independently processing data for each of a plurality of sequencing cycles through a "dedicated, non-shared" sequence of convolutions. The segregated convolutions convolve over data and resulting feature maps of only a given sequencing cycle, i.e., intra-cycle, without convolving over data and resulting feature maps of any other sequencing cycle.

Consider, for example, that the input image data comprises (i) current image patch for a current (time t) sequencing cycle to be base called, (ii) previous image patch for a previous (time t–1) sequencing cycle, and (iii) next image patch for a next (time t+1) sequencing cycle. The specialized architecture then initiates three separate convolution pipelines, namely, a current convolution pipeline, a previous convolution pipeline, and a next convolution pipeline. The current data processing pipeline receives as input the current image patch for the current (time t) sequencing cycle and independently processes it through a plurality of spatial convolution layers to produce a so-called "current spatially convolved representation" as the output of a final spatial convolution layer. The previous convolution pipeline receives as input the previous image patch for the previous (time t–1) sequencing cycle and independently processes it through the plurality of spatial convolution layers to produce a so-called "previous spatially convolved representation" as the output of the final spatial convolution layer. The next convolution pipeline receives as input the next image patch for the next (time t+1) sequencing cycle and independently processes it through the plurality of spatial convolution layers to produce a so-called "next spatially convolved representation" as the output of the final spatial convolution layer.

In some implementations, the current, previous, and next convolution pipelines are executed in parallel. In some implementations, the spatial convolution layers are part of a spatial convolution network (or subnetwork) within the specialized architecture.

The neural network-based base caller 100 further comprises temporal convolution layers (or temporal logic) that mix information between sequencing cycles, i.e., inter-cycles. The temporal convolution layers receive their inputs from the spatial convolution network and operate on the spatially convolved representations produced by the final spatial convolution layer for the respective data processing pipelines.

The inter-cycle operability freedom of the temporal convolution layers emanates from the fact that the misalignment property, which exists in the image data fed as input to the spatial convolution network, is purged out from the spatially convolved representations by the stack, or cascade, of segregated convolutions performed by the sequence of spatial convolution layers.

Temporal convolution layers use so-called "combinatory convolutions" that groupwise convolve over input channels in successive inputs on a sliding window basis. In one implementation, the successive inputs are successive outputs produced by a previous spatial convolution layer or a previous temporal convolution layer.

In some implementations, the temporal convolution layers are part of a temporal convolution network (or subnetwork) within the specialized architecture. The temporal convolution network receives its inputs from the spatial convolution network. In one implementation, a first temporal convolution layer of the temporal convolution network groupwise combines the spatially convolved representations between the sequencing cycles. In another implementation, subsequent temporal convolution layers of the temporal convolution network combine successive outputs of previous temporal convolution layers. The output of the final temporal convolution layer is fed to an output layer that produces an output. The output is used to base call one or more clusters at one or more sequencing cycles.

Additional details about the neural network-based base caller 100 can be found in U.S. Provisional Patent Application No. 62/821,766, titled "ARTIFICIAL INTELLI-GENCE-BASED SEQUENCING,", filed on Mar. 21, 2019, which is incorporated herein by reference.

Compression Network

As discussed above, the specialized architecture of the neural network-based base caller 100 processes sliding windows of image patches for corresponding sequencing cycles. Overlap exists between sequencing cycles of successive sliding windows. This causes the neural network-based base caller 100 to redundantly process image patches for the overlapping sequencing cycles. This in turn results in waste of compute resources. For example, in one implementation, each spatial convolution layer of the neural network-based base caller 100 has nearly 100 million multiplication operations. Then, for a window of five sequencing cycles and a cascade (or sequence) of seven spatial convolution layers, the spatial convolution neural network executes about 620 million multiplication operations. Furthermore, the temporal convolution neural network executes about 10 million multiplication operations.

Since the image data for cycle N–1 in a current sliding window (or a current iteration of base calling) is processed as cycle N in the previous sliding window (or a previous iteration of base calling), an opportunity arises to store the intermediate results of the processing done in the current sliding window and the intermediate results them in subsequent sliding windows, and thereby bypass (or obviate) redundant processing (or reprocessing) of input image data for overlapping sequencing cycles between successive sliding windows.

However, the intermediate results are several terabytes of data that require impractical amount of storage. To overcome this technical problem, the technology disclosed proposes compressing the intermediate results the first time the intermediate results are generated by the neural network-based base caller 100 and repurposing the compressed intermediate results in subsequent sliding windows to avoid redundant computation, and thereby not regenerating (or only-once generating) the intermediate results. In some implementations, the technology disclosed saves about 80% of convolutions in the spatial network of the neural network-based base caller 100. In one implementation, the 80% savings are observed in the spatial convolutions when the compression logic and repurposing of the compressed feature maps in subsequent sequencing cycles is used for an input window of five sequencing cycles (e.g., cycle N, cycle N+1, cycle N–1, cycle N+2, and cycle N–2). In another implementation, 90% savings are observed in the spatial convolutions when the compression logic and repurposing of the compressed feature maps in subsequent sequencing cycles is used for an input window of ten sequencing cycles (e.g., cycle N, cycle N+1, cycle N–1, cycle N+2, cycle N–2, cycle N+3, and cycle N–3). That is, the larger the window size, the bigger the savings from the use of the compression logic and repurposing of the compressed feature maps, and the larger the window size, the better the base calling performance due to incorporation of greater context from additional flanking cycles. So bigger savings for bigger windows improves overall performance for a given compute capability.

The compute efficiency and compact compute footprint brought about by the compression logic facilitates hardware implementation of the neural network-based base caller 100 on resource-constrained processors like Central Processing Units (CPUs), Graphics Processing Units (GPUs), Field Programmable Gate Arrays (FPGAs), Coarse-Grained Reconfigurable Architectures (CGRAs), Application-Specific Integrated Circuits (ASICs), Application Specific Instruction-set Processor (ASIP), and Digital Signal Processors (DSPs).

The compute saved by the compression logic allows for incorporating more convolution operators in the neural network-based base caller 100. Examples include adding more convolution filters in the spatial and temporal convolution layers, increasing the size of the convolution filters, and increasing the number of spatial and temporal convolution layers. Additional convolution operations improve intensity pattern detection and overall base calling accuracy of the neural network-based base caller 100.

The compute saved by the compression logic also allows for expanding the input image data for a subject sliding window to include increased number of sequencing cycles. Expanded sliding windows broaden the base calling context by bringing in surplus image patches from additional flanking sequencing cycles.

Furthermore, any dip in accuracy that may occur due to the use of compressed intermediate results, as opposed to the original intermediate results, is compensated by the incorporation of additional convolution operators and expansion of the sliding windows.

FIG. 1A illustrates one implementation of the disclosed compression logic that generates compressed spatial map sets for a first iteration of base calling. In the illustrated example, a first window of sequencing cycles includes sequencing cycles 1, 2, 3, 4, and 5. Respective images patches 102, 112, 122, 132, and 142 (or per-cycle analyte channel sets) for the respective sequencing cycles 1, 2, 3, 4, and 5 are separately processed through a spatial logic 104 (or spatial network or spatial subnetwork or spatial convolution neural network) to generate respective spatial maps 106, 116, 126, 136, and 146 (or intermediate results or spatial output sets or spatial feature map sets) for the respective sequencing cycles 1, 2, 3, 4, and 5. The spatial convolution network 104 can use 1D, 2D, or 3D convolutions.

The spatial logic 104 includes a sequence (or cascade) of spatial convolution layers. Each spatial convolution layer has a filter bank with a plurality of spatial convolution filters that implement segregated convolutions. Accordingly, each spatial convolution layer produces as output a plurality of spatial feature maps. The number of spatial feature maps produced by a subject spatial convolution layer is a function of the number of spatial convolution filters configured in the subject spatial convolution layer. For example, if the subject spatial convolution layer has fourteen spatial convolution filters, then the subject spatial convolution layer produces fourteen spatial feature maps. From an aggregate perspective, the fourteen spatial feature maps can be considered a spatial feature map volume (or tensor) with fourteen channels (or depth dimension=fourteen).

Furthermore, a next spatial convolution layer that follows the subject spatial convolution layer can also be configured with fourteen spatial convolution filters. In such as case, the next spatial convolution layer processes, as input, the fourteen spatial feature maps generated the subject spatial convolution layer, and itself generates fourteen new spatial feature maps as output. FIG. 1A shows the five spatial feature map sets 106, 116, 126, 136, and 146 generated by a final spatial convolution layer of the spatial network 104 for the respective sequencing cycles 1, 2, 3, 4, and 5. In the illustrated example, each of the five spatial feature map sets 106, 116, 126, 136, and 146 have fourteen feature maps.

Figure 1C:
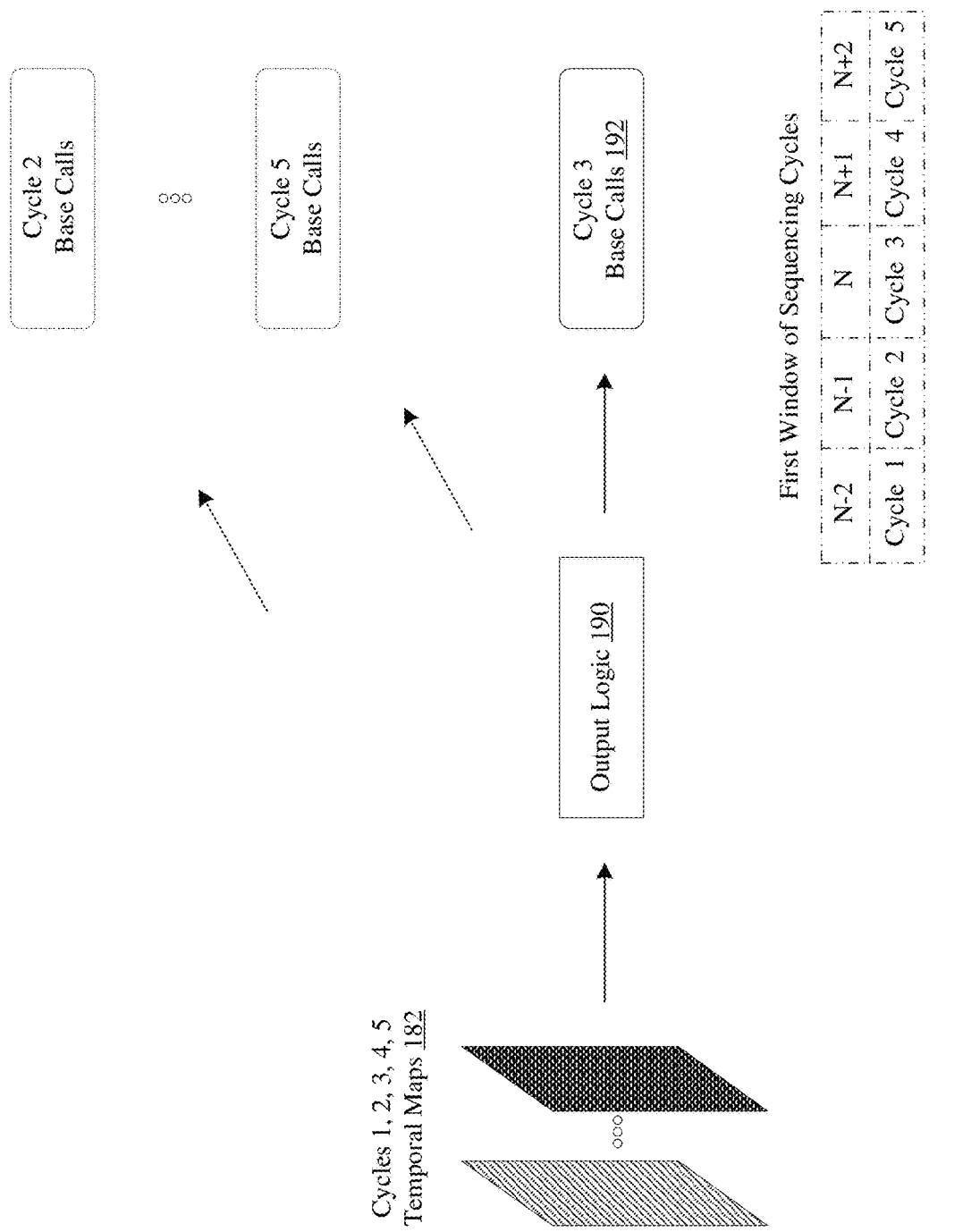
FIG. 1C illustrates one implementation of processing the temporal map sets through the disclosed output logic to generate base call classification data.
Figure 1D:
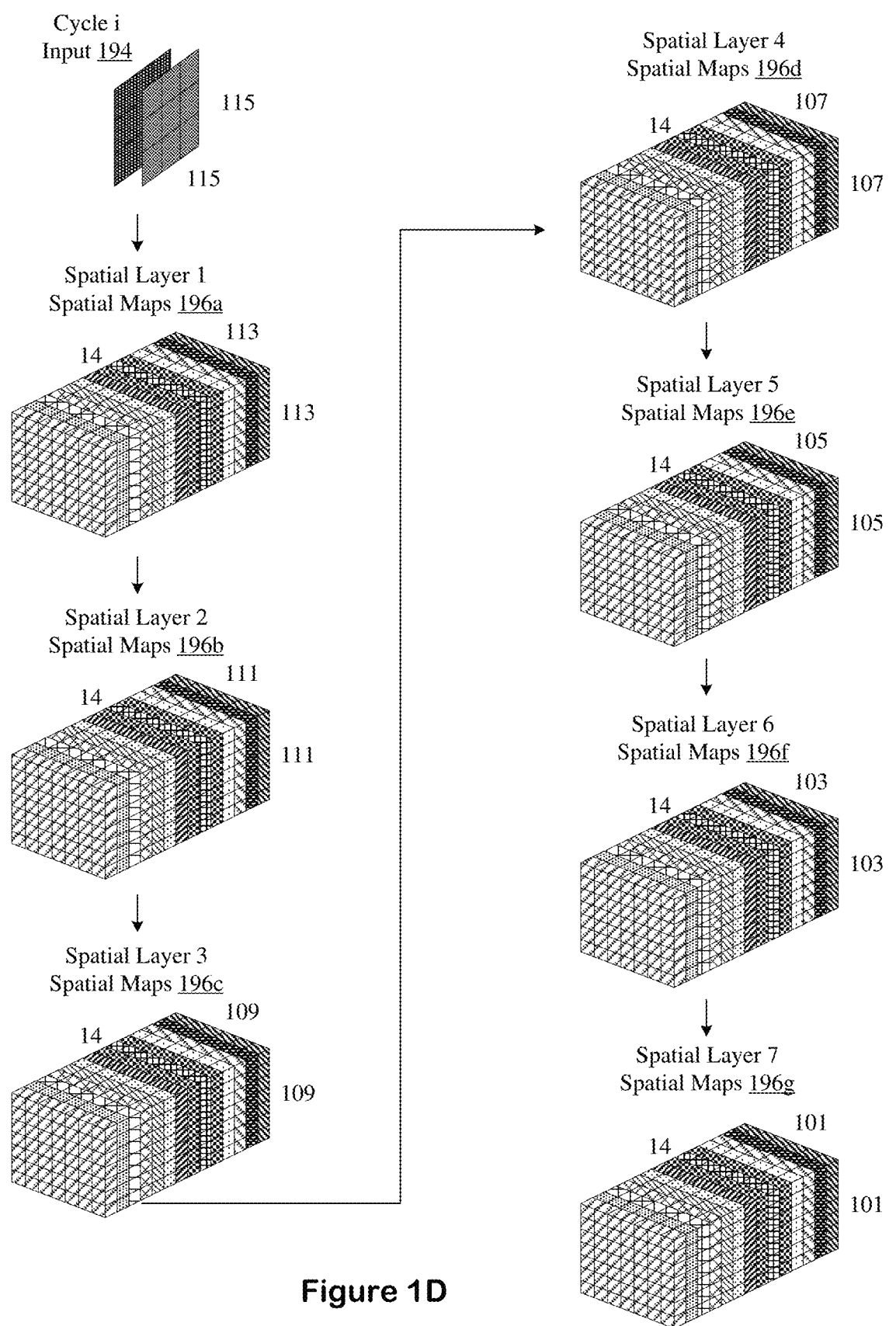
FIG. 1D illustrates an example of a sequence of feature map volumes successively generated by a cascade of spatial convolution layers in response to processing per-cycle image patches for a subject sequencing cycle.

FIG. 1D illustrates a sequence of seven spatial feature map sets 196a, 196b, 196c, 196d, 196e, 196f, and 196g generated by a cascade of seven spatial convolution layers of the spatial network 104. A per-cycle input patch data 194 for a subject sequencing cycle i has a spatial dimensionality of 115×115 and a depth dimensionality of two (due to the two image channels in the original sequencing images). In one implementation, each of the seven spatial convolution layers uses 3×3 convolutions that reduce the spatial dimensionality of successive spatial feature map volumes by two, for example, from 10×10 to 8×8.

The first spatial feature map volume 196a has spatial dimensions 113×113 (i.e., reduced from 115×115 by the 3×3 convolutions of the first spatial convolution layer) and a depth dimension of 14 (i.e., fourteen feature maps or fourteen channels due to fourteen spatial convolution filters in the first spatial convolution layer). The second spatial feature map volume 196b has spatial dimensions 111×111 (i.e., reduced from 113×113 by the 3×3 convolutions of the second spatial convolution layer) and a depth dimension of 14 (i.e., fourteen feature maps or fourteen channels due to fourteen spatial convolution filters in the second spatial convolution layer). The third spatial feature map volume 196c has spatial dimensions 109×109 (i.e., reduced from 111×111 by the 3×3 convolutions of the third spatial convolution layer) and a depth dimension of 14 (i.e., fourteen feature maps or fourteen channels due to fourteen spatial convolution filters in the third spatial convolution layer). The fourth spatial feature map volume 196d has spatial dimensions 107×107 (i.e., reduced from 109×109 by the 3×3 convolutions of the fourth spatial convolution layer) and a depth dimension of 14 (i.e., fourteen feature maps or fourteen channels due to fourteen spatial convolution filters in the fourth spatial convolution layer). The fifth spatial feature map volume 196e has spatial dimensions 105×105 (i.e., reduced from 107×107 by the 3×3 convolutions of the fifth spatial convolution layer) and a depth dimension of 14 (i.e., fourteen feature maps or fourteen channels due to fourteen spatial convolution filters in the fifth spatial convolution layer). The sixth spatial feature map volume 196f has spatial dimensions 103×103 (i.e., reduced from 105×105 by the 3×3 convolutions of the sixth spatial convolution layer) and a depth dimension of 14 (i.e., fourteen feature maps or fourteen channels due to fourteen spatial convolution filters in the sixth spatial convolution layer). The seventh spatial feature map volume 196g has spatial dimensions 101×101 (i.e., reduced from 103×103 by the 3×3 convolutions of the seventh spatial convolution layer) and a depth dimension of 14 (i.e., fourteen feature maps or fourteen channels due to fourteen spatial convolution filters in the seventh spatial convolution layer).

Analogizing to the multi-cycle example illustrated in FIG. 1A, for the five sequencing cycles 1, 2, 3, 4, and 5 and the five per-cycle images patches 102, 112, 122, 132, and 142, the spatial logic 104 separately produces five respective sequences of the seven spatial feature map volumes 196a, 196b, 196c, 196d, 196e, 196f, and 196g, with the spatial maps 106, 116, 126, 136, and 146 in FIG. 1A being equivalent to five separate instances of the final spatial feature map volume 196g in FIG. 1D.

A compression logic 108 (or compression network or compression subnetwork or compression layer or squeezing layer) processes the outputs of the spatial logic 104 and generates a compressed representation of the outputs. In one implementation, the compression network 108 comprises a compression convolution layer that reduces the depth dimensionality of feature maps generated by the spatial network 104.

For example, in FIG. 1A, the depth dimensionality of the spatial maps 106, 116, 126, 136, and 146 is 14 (i.e., fourteen feature maps or fourteen channels per spatial output). The compression network 108 attenuates the spatial maps 106, 116, 126, 136, and 146 into respective compressed spatial map sets 110, 120, 130, 140, and 150 for the respective sequencing cycles 1, 2, 3, 4, and 5. Each of the compressed spatial map sets 110, 120, 130, 140, and 150 has a depth dimensionality of 2 (i.e., two feature maps or two channels per compressed spatial output). In other implementations, the compressed spatial map sets 110, 120, 130, 140, and 150 can have a depth dimensionality of 3 or 4 (i.e., three or fourth feature maps or three or fourth channels per compressed spatial output). In yet other implementations, the compressed spatial map sets 110, 120, 130, 140, and 150 can have a depth dimensionality of 1 (i.e., one feature map or one channel per compressed spatial output). In one implementation, the compression layer 108 does not include an activation function like ReLU. In other implementations, it can include an activation function. In other implementations, the compression logic 108 can configure the corresponding compressed spatial map sets to each have more than four feature maps.

The discussion now turns to how the compression logic 108 generates the compressed outputs.

Figure 1E:
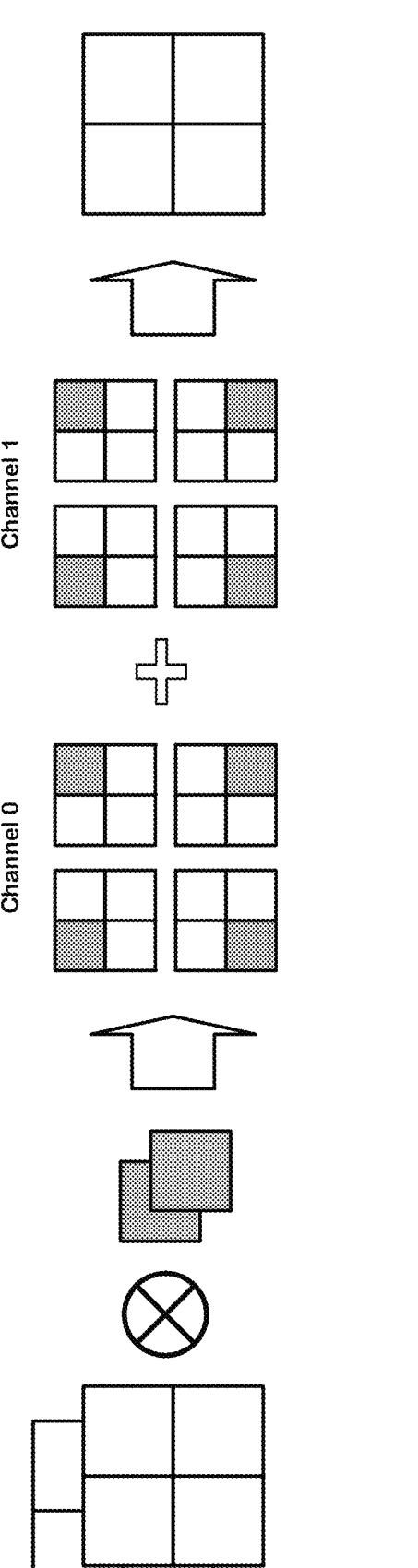
FIG. 1E depicts an example that illustrates how 1×1 convolutions compress feature maps.

In one implementation, the compression logic 108 uses 1×1 convolutions to reduce the number of feature maps (i.e., the depth dimension or the number of channels) while introducing non-linearity. The 1×1 convolutions have a kernel size of 1. The 1×1 convolutions can transform a volume depth into another squeezed or expanded representation without changing the spatial dimensions. A 1×1 convolution operates like a fully connected linear layer across the input channels. This is useful in mapping from feature maps with many channels to fewer feature maps. In FIG. 1E, a single 1×1 convolution is applied to an input tensor with two feature maps. The 1×1 convolution compresses the two-channel input to a single-channel output.

Figure 1F:
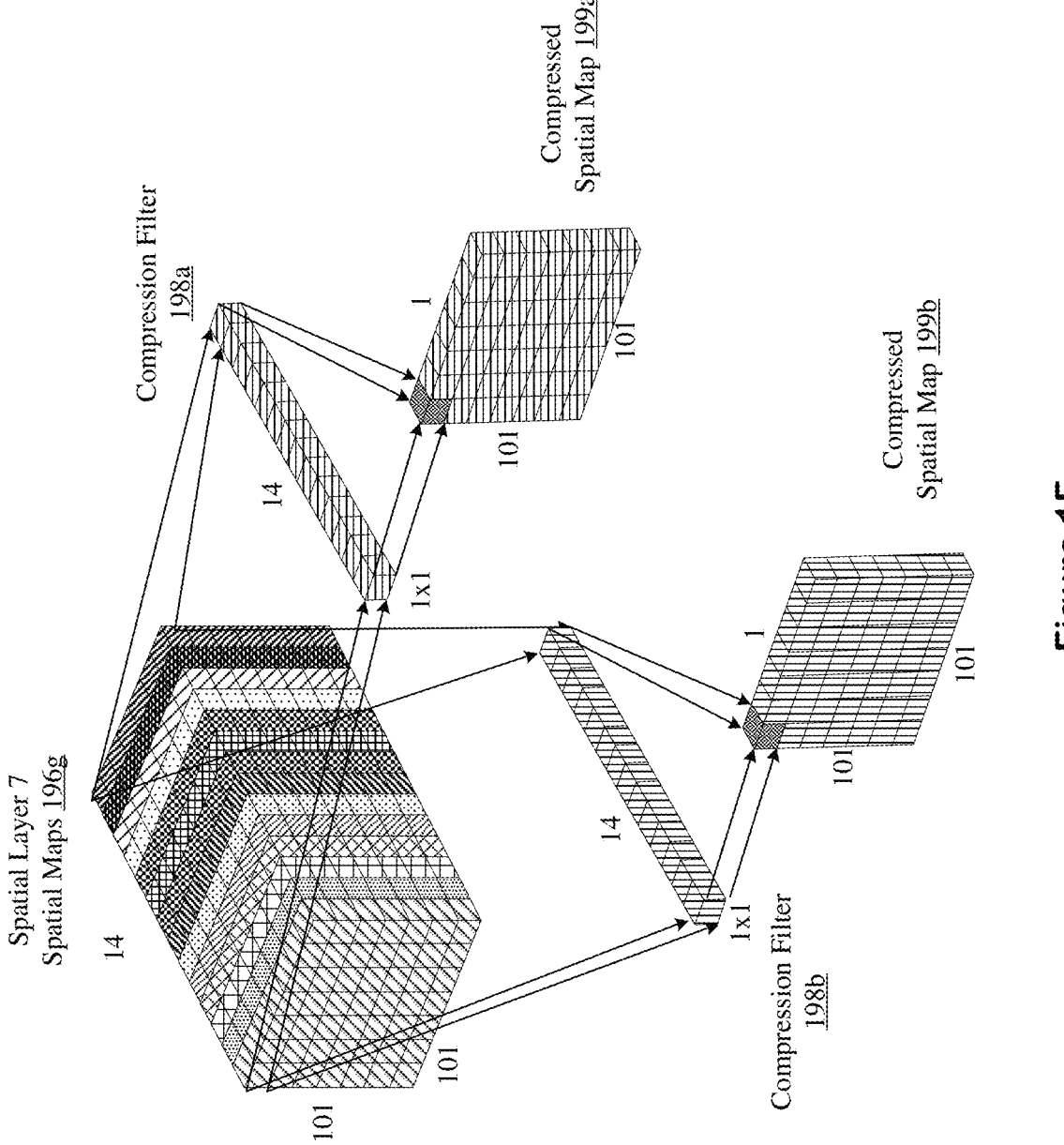
FIG. 1F shows that the compression ratio achieved by the disclosed compression logic is a function of the number of compression filters applied by the disclosed compression logic.

The number of compressed outputs (or compressed feature maps or compressed spatial maps or compressed temporal maps) generated by the compression layer 108 is a function of the number of 1×1 convolution filters (or compression convolution filters or compression filters) configured in the compression layer 108. In FIG. 1F, the compression layer 108 has two 1×1 convolution filters 198a and 198b. The first 1×1 convolution filter 198a processes the spatial feature volume 196g with the fourteen feature maps and generates a first feature map 199a while preserving the spatial dimensionality of 101×101. The second 1×1 convolution filter 198b also processes the spatial feature volume 196g with the fourteen feature maps and generates a second feature map 199b while preserving the spatial dimensionality of 101×101. Accordingly, the compression layer 108 reduces the spatial feature volume 196g with the fourteen feature maps into a compressed output with two spatial feature maps 199a and 199b (i.e., compression ratio=7).

From the timeseries perspective, the sequencing cycle 5 is the center sequencing cycle (N), the sequencing cycles 1 and 2 are the left flanking sequencing cycles (N−1, N−2), and the sequencing cycles 4 and 5 are the left flanking sequencing cycles (N+1, N+2). Accordingly, the center compressed output 130 is generated for the center sequencing cycle (N), the left flanking compressed output 120 is generated for the left flanking sequencing cycle (N−1), the further left flanking compressed output 110 is generated for the further left flanking sequencing cycle (N−2), the right flanking compressed output 140 is generated for the right flanking sequencing cycle (N+1), and the further right flanking compressed output 150 is generated for the further right flanking sequencing cycle (N+2).

From the pipeline perspective, the neural network-based base caller 100 executes five parallel and independent pipelines that respectively process the images patches 102, 112, 122, 132, and 142 through the spatial logic 104 and the compression logic 108 (e.g., as a multi-threaded execution or a multi-clustered execution based on data parallelism). Accordingly, five compressed outputs 110, 120, 130, 140, and 150 are separately, simultaneously, and independently generated by the neural network-based base caller 100.

In some implementations, the compression layer 108 can be considered a final spatial convolution layer of the spatial network 104. In other implementations, the compression network 108 can be considered a separate network inside or outside the specialized architecture of neural network-based base caller 100.

FIG. 1B illustrates one implementation of processing the compressed spatial map sets 110, 120, 130, 140, and 150 through a temporal logic 160 (or temporal network or temporal subnetwork or temporal convolution neural network) of the neural network-based base caller 100. The temporal logic 160 processes groups of successive compressed spatial map sets on a sliding window-basis. For example, in FIG. 1B, the temporal logic 160 processes a first group/window of compressed spatial map sets 110, 120, and 130 for respective sequencing cycles 1, 2, and 3, and generates temporal maps 172 (or temporal map sets or temporal feature maps or temporal feature map sets) as output. The temporal logic 160 processes a second group/window of compressed spatial map sets 120, 130, and 140 for respective sequencing cycles 2, 3, and 4, and generates temporal maps 174 as output. The temporal logic 160 processes a third group/window of compressed spatial map sets 130, 140, and 150 for respective sequencing cycles 3, 4, and 5, and generates temporal maps 176 as output. The temporal convolution network 160 can use 1D, 2D, or 3D convolutions.

The three instances of the temporal logic 160 shown in FIG. 1B represent three filter banks of a first temporal convolution layer of the temporal network 160. The first filter bank applies a first set of temporal convolution filters on the first group of compressed spatial maps 110, 120, and 130 and generates the first set of temporal maps 172. The second filter bank applies a second set of temporal convolution filters on the second group of compressed spatial maps 120, 130, and 140 and generates the second set of temporal maps 174. The third filter bank applies a third set of temporal convolution filters on the third group of compressed spatial maps 130, 140, and 150 and generates the third set of temporal maps 176.

The first, second, and third sets of temporal maps 172, 174, and 176 are processed as a group by the temporal logic 160 to generate temporal maps 182. The fourth instance of the temporal logic 160 shown in FIG. 1B represents a second temporal convolution layer of the temporal network 160 that produces an output for all the sequencing cycles 1, 2, 3, 4, and 5 for which per-cycle image patch pairs were fed as input to the neural network-based base caller 100 in FIG. 1A.

The temporal network 160 has a cascade of temporal convolution layers (e.g., 2, 3, 4, 5, or more temporal convolution layers arranged in a sequence). The cascade of temporal convolution layers process data in a hierarchical form with different levels of grouping. That is, at a given level, a sliding window approach group-wise processes inputs at the given level to generate outputs that are subsequently group-wise processed at a next level in the sliding window fashion.

The temporal convolution layers are configured with temporal convolution filters that implement combinatory convolutions. The combinatory convolutions mix information between feature maps spanning multiple sequencing cycles. The combinatory convolutions combine data between successive sequencing cycles in a subject group/window at a current level in the temporal network 160. For example, the first temporal convolution layer combines the first group of compressed spatial maps 110, 120, and 130 for the first group of sequencing cycles 1, 2, and 3 to generate the first set of temporal maps 172; combines the second group of compressed spatial maps 120, 130, and 140 for the second group of sequencing cycles 2, 3, and 4 to generate the second set of temporal maps 174; and combines the third group of compressed spatial maps 130, 140, and 150 for the third group of sequencing cycles 3, 4, and 5 to generate the third set of temporal maps 176.

The combinatory convolutions also combine data between successive groups of sequencing cycles in a subject group/window at a current level in the temporal network 160. For example, the second temporal convolution layer combines the first, second, and third sets of temporal maps 172, 174, and 176 into the final set of temporal maps 182. At level two, the first, second, and third groups/windows of sequencing cycles from level one are grouped in a first group/window of sequencing cycles 1, 2, 3, 4, and 5.

The combinatory convolutions are configured with as many kernels as the number of inputs to be combined (i.e., the depth column or fibre of the temporal convolution filters is matched with the number of inputs in the subject group/window at the current level). For example, when a temporal convolution layer combines three compressed spatial maps, it uses temporal convolution filters that each have three kernels that perform element-wise multiplication and summation throughout the depth of the three compressed spatial maps.

The final set of temporal maps 182 are produced by a final (or last) temporal convolution layer of the temporal network 160. FIG. 1C illustrates one implementation of processing the final temporal map sets 182 through a disclosed output logic 190 (or output layer or output network or output subnetwork) to generate base call classification data. In one implementation, a plurality of clusters is base called simultaneously for one or more sequencing cycles. In the example illustrated in FIG. 1C, base calls 192 are generated for many clusters only for the center sequencing cycle 3. In other implementations, the technology disclosed causes the output logic 190 to generate, for a given window of input, base calls not only for the center sequencing cycle but also for the flanking sequencing cycles (as indicated by optional dotted lines), in accordance with one implementation. For example, in one implementation, the technology disclosed simultaneously generates base calls for cycle N, cycle N+1, cycle N−1, cycle N+2, cycle N−2, and so on for a given input window. That is, a single forward propagation/traversal/base calling iteration of the neural network-based base caller 102 generates base calls for multiple sequencing cycles in the input window of sequencing cycles, which is referred to herein as "many-to-many base calling."

Examples of the output layer 190 include a softmax function, a log-softmax function, an ensemble output average function, a multi-layer perceptron uncertainty function, a Bayes Gaussian distribution function, and a cluster intensity function. In one implementation, the output layer 190 produces a per-cluster, per-cycle probability quadruple for each cluster and for each sequencing cycle.

The following discussion focuses on the per-cluster, per-cycle probability quadruples using the softmax function as an example. We first explain the softmax function and then the per-cluster, per-cycle probability quadruples.

Softmax function is a preferred function for multi-class classification. The softmax function calculates the probabilities of each target class over all possible target classes. The output range of the softmax function is between zero and one and the sum of all the probabilities is equal to one. The softmax function computes the exponential of the given input value and the sum of exponential values of all the input values. The ratio of the exponential of the input value and the sum of exponential values is the output of the softmax function, referred to herein as "exponential normalization."

Formally, training a so-called softmax classifier is regression to a class probability, rather than a true classifier as it does not return the class but rather a confidence prediction of each class's probability. The softmax function takes a class of values and converts them to probabilities that sum to one. The softmax function squashes a n-dimensional vector of arbitrary real values to n-dimensional vector of real values within the range zero to one. Thus, using the softmax function ensures that the output is a valid, exponentially normalized probability mass function (nonnegative and summing to one).

Intuitively, the softmax function is a "soft" version of the maximum function. The term "soft" derives from the fact that the softmax function is continuous and differentiable. Instead of selecting one maximal element, it breaks the vector into parts of a whole with the maximal input element getting a proportionally larger value, and the other getting a less proportion of the value. The property of outputting a probability distribution makes the softmax function suitable for probabilistic interpretation in classification tasks.

Let us consider z as a vector of inputs to the softmax layer. The softmax layer units are the number of nodes in the softmax layer and therefore, the length of the z vector is the number of units in the softmax layer (if we have ten output units, then there are ten z elements).

For an n-dimensional vector $Z=[z_1, z_2, \ldots z_n]$, the softmax function uses exponential normalization (exp) to produce another n-dimensional vector p(Z) with normalized values in the range [0, 1] and that add to unity:

$$Z = \begin{bmatrix} z_1 \\ z_2 \\ \vdots \\ z_n \end{bmatrix} \text{ and, } p(Z) \rightarrow \begin{bmatrix} p_1 \\ p_2 \\ \vdots \\ p_n \end{bmatrix}$$

$$p_j = \frac{\exp^{z_j}}{\sum_{k=1}^{n} \exp^{z_k}} \forall\, j \in 1, 2, \ldots, n$$

Figure 1G:
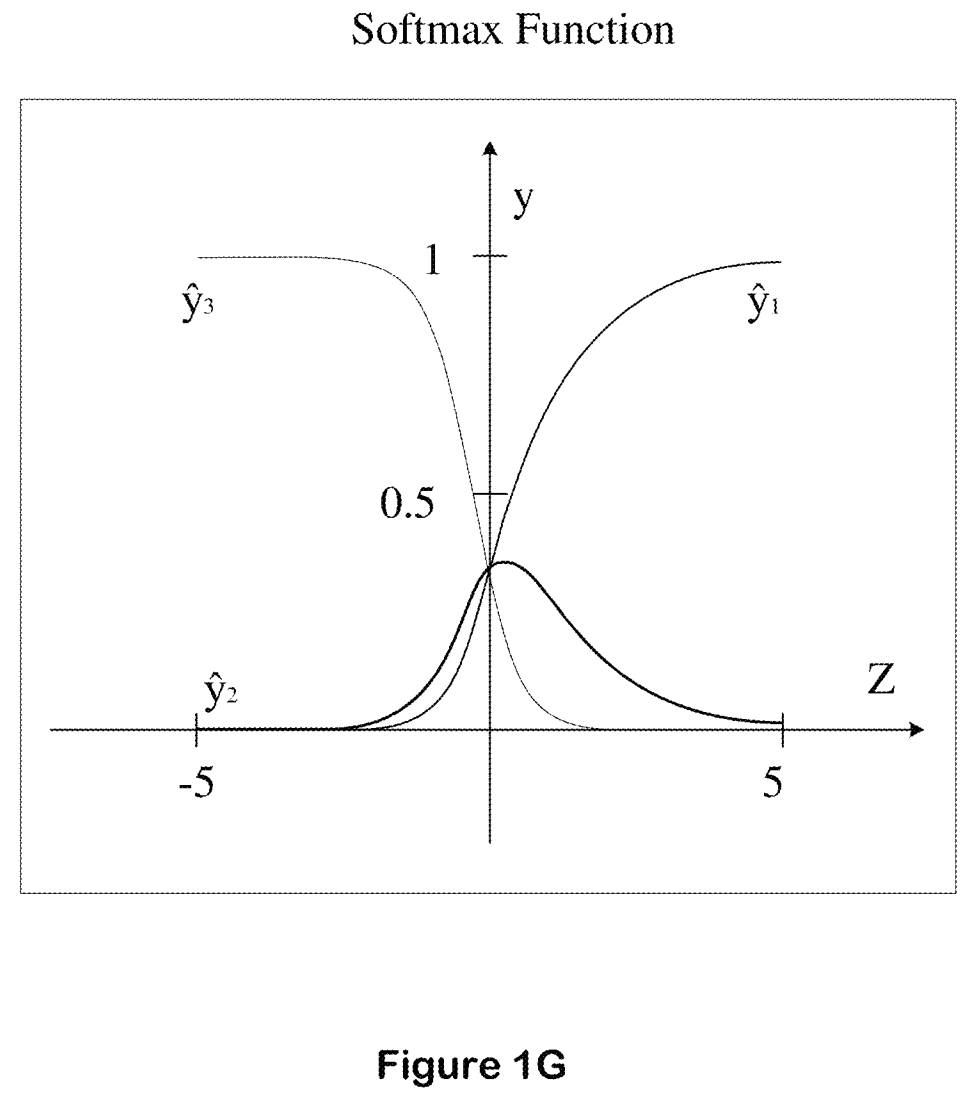

FIG. 1G shows an example softmax function. Softmax function is applied to three classes as $$z \mapsto softmax\left(\left[z; \frac{z}{10}; -2z\right]\right).$$

Note that the three outputs always sum to one. They thus define a discrete probability mass function.

Figure 1H:
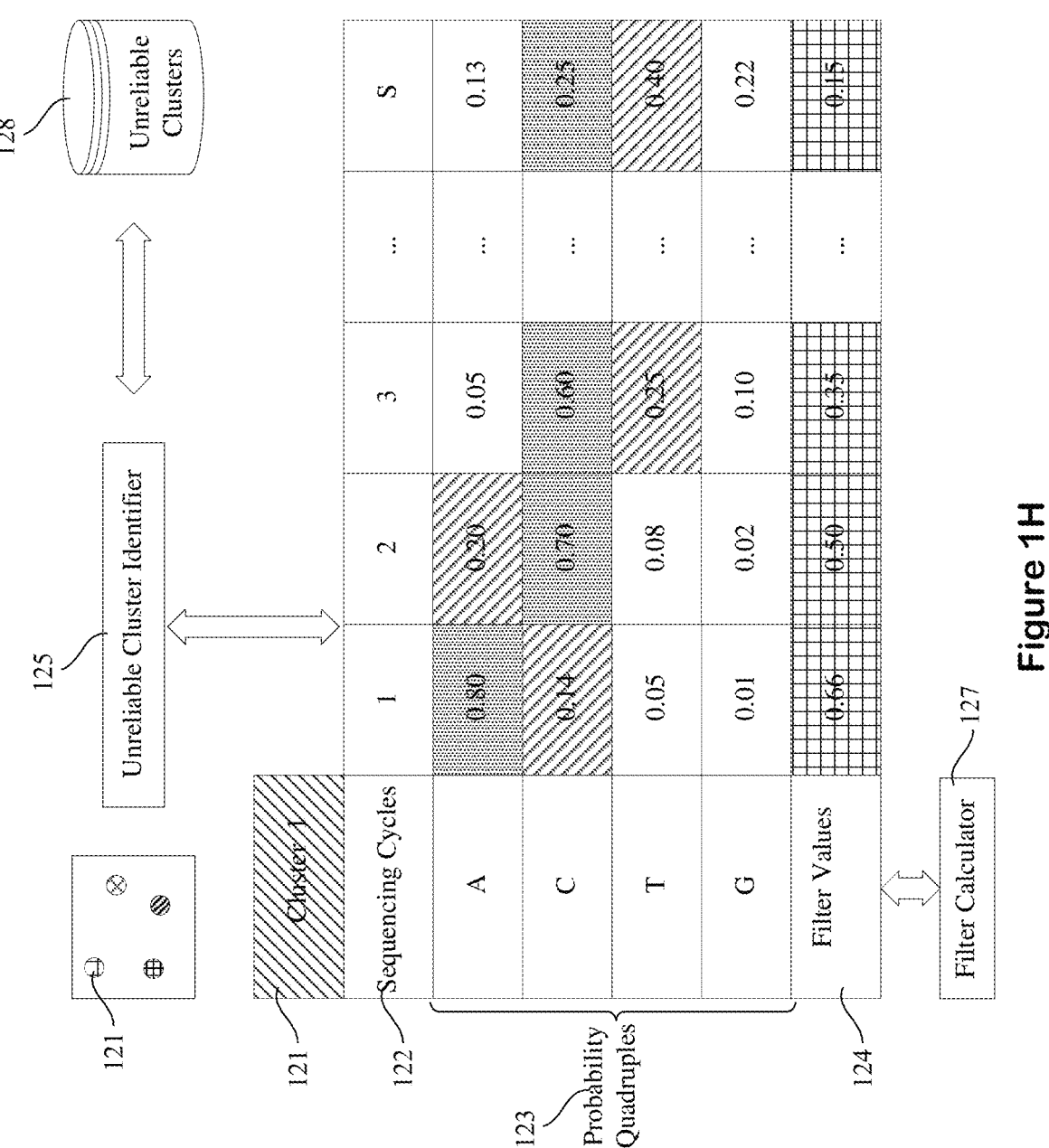
FIG. 1H depicts example per-cluster, per-cycle probability quadruples produced by the technology disclosed.

A particular per-cluster, per-cycle probability quadruple identifies probabilities of a base incorporated in a particular cluster at a particular sequencing cycle being A, C, T, and G. When the output layer of the neural network-based base caller 100 uses a softmax function, the probabilities in the per-cluster, per-cycle probability quadruple are exponentially normalized classification scores that sum to unity. FIG. 1H depicts example per-cluster, per-cycle probability quadruples 123 produced by the softmax function for cluster 1 (121, shown in brown color) and for sequencing cycles 1 through S (122), respectively. In other words, the first subset of sequencing cycles includes S sequencing cycles.

The unreliable cluster identifier 125 identifies unreliable clusters based on generating filter values from the per-cluster, per-cycle probability quadruple. In this application, the per-cluster, per-cycle probability quadruples are also referred to as base call classification scores or normalized base call classification scores or initial base call classification scores or normalized initial base call classification scores or initial base calls.

A filter calculator 127 determines a filter value for each per-cluster, per-cycle probability quadruple based on the probabilities it identifies, thereby generating a sequence of filter values for each cluster. The sequence of filter values is stored as filter values 124.

The filter value for a per-cluster, per-cycle probability quadruple is determined based on a calculation involving one or more of the probabilities. In one implementation, the calculation used by the filter calculator 127 is subtraction. For example, in the implementation illustrated in FIG. 1H, the filter value for the per-cluster, per-cycle probability quadruple is determined by subtracting a second highest one of the probabilities (shown in blue color) from a highest one of the probabilities (shown in magenta color).

In another implementation, the calculation used by the filter calculator 116 is division. For example, the filter value for the per-cluster, per-cycle probability quadruple is determined as a ratio of the highest one of the probabilities (shown in magenta color) to the second highest one of the probabilities (shown in blue color). In yet another implementation, the calculation used by the filter calculator 127 is addition. In yet further implementation, the calculation used by the filter calculator 127 is multiplication.

In one implementation, the filter calculator 127 generates the filter values 124 using a filtering function. In one example, the filtering function is a chastity filter that defines chastity as a ratio of a brightest base intensity divided by a sum of the brightest base intensity and a second brightest base intensity. In another example, the filtering function is at least one of a maximum log probability function, a minimum squared error function, average signal-to-noise ratio (SNR), and a minimum absolute error function.

The unreliable cluster identifier 125 uses the filter values 124 to identify some clusters in the plurality of clusters as unreliable clusters 128. Data identifying the unreliable clusters 128 can be in computer readable format or medium. The unreliable clusters can be identified by instrument ID, the run number on the instrument, the flow cell ID, the lane number, the tile number, the X coordinate of the cluster, the Y coordinate of the cluster, and unique molecular identifiers (UMIs). The unreliable cluster identifier 125 identifies those clusters in the plurality of clusters as unreliable clusters whose sequences of filter values contain "G" number of filter values below a threshold "H." In one implementation, the "G" ranges from 1 to 5. In another implementation, the "H" ranges from 0.5 to 0.99. In one implementation, the unreliable clusters 128 identify those pixels that correspond to (i.e., depict intensity emissions of) the unreliable clusters.

Such pixels are filtered out by a filtering logic 502, as describe later in this application.

Unreliable clusters are low-quality clusters that emit an amount of desired signal which is insignificant compared to background signal. The signal to noise ratio for unreliable clusters is substantially low, for example, less than 1. In some implementations, unreliable clusters may not produce any amount of a desired signal. In other implementations, unreliable clusters may produce a very low amount of signal relative to background. In one implementation, the signal is an optical signal and is intended to include, for example, fluorescent, luminescent, scatter, or absorption signals. Signal level refers to an amount or quantity of detected energy or coded information that has a desired or predefined characteristic. For example, an optical signal can be quantified by one or more of intensity, wavelength, energy, frequency, power luminance or the like. Other signals can be quantified according to characteristics such as voltage, current, electric field strength, magnetic field strength, frequency, power, temperature, etc. Absence of signal in unreliable clusters is understood to be a signal level of zero or a signal level that is not meaningfully distinguished from noise.

There are many potential reasons for poor quality signals of unreliable clusters. If there has been a polymerase chain reaction (PCR) error in colony amplification such that a sizable proportion of the ~1000 molecules in an unreliable cluster contains a different base at a certain position, then one may observe a signal for two bases—this is interpreted as a sign of poor quality and referred to as phase error. Phase error occurs when individual molecules in an unreliable cluster do not incorporate a nucleotide in some cycle (e.g., because of incomplete remove of the 3' terminators, termed phasing) and then lag behind the other molecules, or when an individual molecule incorporates more than one nucleotide in a single cycle (e.g., because of incorporation of nucleotides without effective 3'-blocking, termed prephasing). This results in the loss of synchrony in the readout of the sequence copies. The proportion of sequences in unreliable clusters that are affected by phasing and pre-phasing increases with cycle number, which is a major reason why the quality of reads tends to decline at high cycle numbers.

Unreliable clusters also result from fading. Fading is an exponential decay in signal intensity of unreliable clusters as a function of cycle number. As the sequencing run progress, the strands in unreliable clusters are washed excessively, exposed to laser emissions that create reactive species, and subject to harsh environmental conditions. All of these lead to a gradual loss of fragments in unreliable clusters, decreasing their signal intensity.

Unreliable clusters also result from underdeveloped colonies, i.e., small cluster sizes of unreliable clusters that produce empty or partially filled wells on a patterned flow cell. That is, in some implementations, the unreliable clusters are indicative of empty, polyclonal, and dim wells on the patterned flow cell. Unreliable clusters also result from overlapping colonies caused by unexclusive amplification. Unreliable clusters also result from under-illumination or uneven-illumination, for example, due to being located on the edges of a flow cell. Unreliable clusters also result from impurities on the flow cell that obfuscate emitted signal. Unreliable clusters also include polyclonal clusters when multiple clusters are deposited in the same well.

The first window of sequencing cycles includes sequencing cycles 1, 2, 3, 4, and 5, and the first iteration of base calling produces base calls 192 for the center sequencing cycle 3. The second window of sequencing cycles includes sequencing cycles 2, 3, 4, 5, and 6 and a second iteration of base calling produces base calls 292 for the center sequencing cycle 4. Accordingly, sequencing cycles 2, 3, 4, and 5 are the overlapping sequencing cycles between the first and second windows or between the second and third iterations of base calling.

The disclosed base calling systems and techniques store, in memory (e.g., on-chip DRM, on-chip SRAM or BRAM, off-chip DRAM), the compressed spatial map sets 120, 130, 140, and 150 generated during the first iteration of base calling for the respective sequencing cycles 2, 3, 4, and 5. During the second iteration of base calling, the disclosed base calling systems and techniques do not reprocess the respective input image patches 112, 122, 132, and 142 for the overlapping cycles 2, 3, 4, and 5 through the spatial network 104. Instead, during the second iteration of base calling, the disclosed base calling systems and techniques reuse the previously generated compressed spatial map sets 120, 130, 140, and 150 in lieu of the respective input image patches 112, 122, 132, and 142.

The compression logic is further configured to require the compressed spatial map sets 120, 130, 140, and 150 and the respective input image patches 112, 122, 132, and 142 to have the same number of per-cycle feature maps/channels. This ensures that the compressed spatial map sets 120, 130, 140, and 150 are lossless representatives of the respective input image patches 112, 122, 132, and 142. That is, if the respective input image patches 112, 122, 132, and 142 each have two feature maps/channels, then the compression logic 108 configures the compressed spatial map sets 120, 130, 140, and 150 to also have two feature maps/channels. Similarly, if the respective input image patches 112, 122, 132, and 142 each have three feature maps/channels, then the compression logic 108 configures the compressed spatial map sets 120, 130, 140, and 150 to also have three feature maps/channels. In the same vein, if the respective input image patches 112, 122, 132, and 142 each have four feature maps/channels, then the compression logic 108 configures the compressed spatial map sets 120, 130, 140, and 150 to also have four feature maps/channels.

Figure 2A:
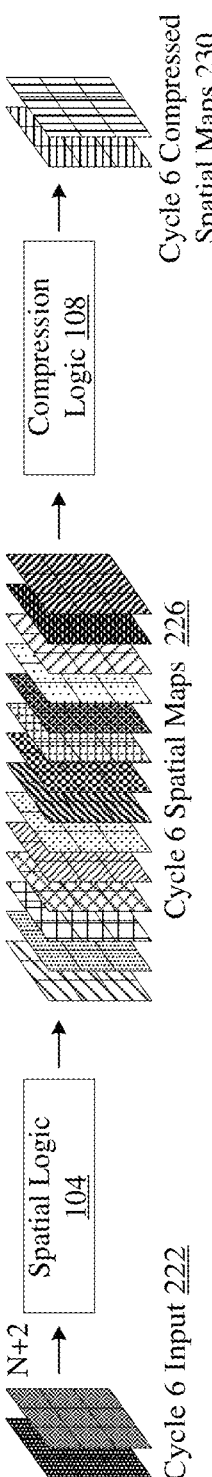
FIG. 2A shows that, during a second iteration of base calling, spatial maps and corresponding compressed spatial maps are generated only for the non-overlapping sequencing cycle 6.

FIG. 2A shows that, during the second iteration of base calling, spatial maps 226 and corresponding compressed spatial maps 230 are generated only for the non-overlapping sequencing cycle 6 by processing input image data 222 through the spatial logic 104 and the compression logic 108. Accordingly, the input image patches 112, 122, 132, and 142 for the overlapping cycles 2, 3, 4, and 5 (highlighted with grey fill in the legend) are not reprocessed to avoid redundant convolutions.

Figure 2B:
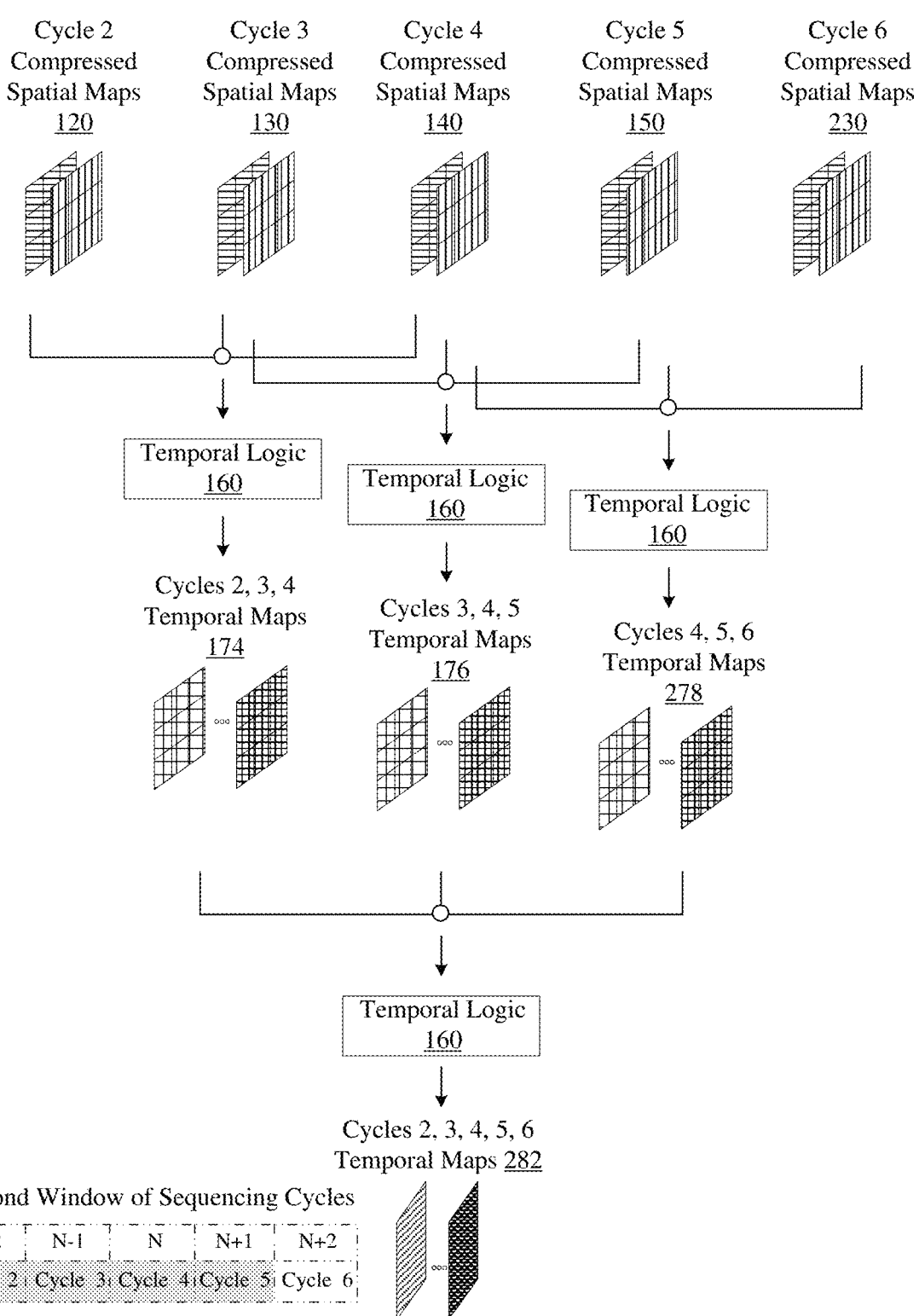
FIG. 2B shows that the compressed spatial map sets generated during the first iteration of base calling are used in conjunction with a compressed spatial map set generated during the second iteration of base calling to generate base calls for the center sequencing cycle 4.
Figure 2C:
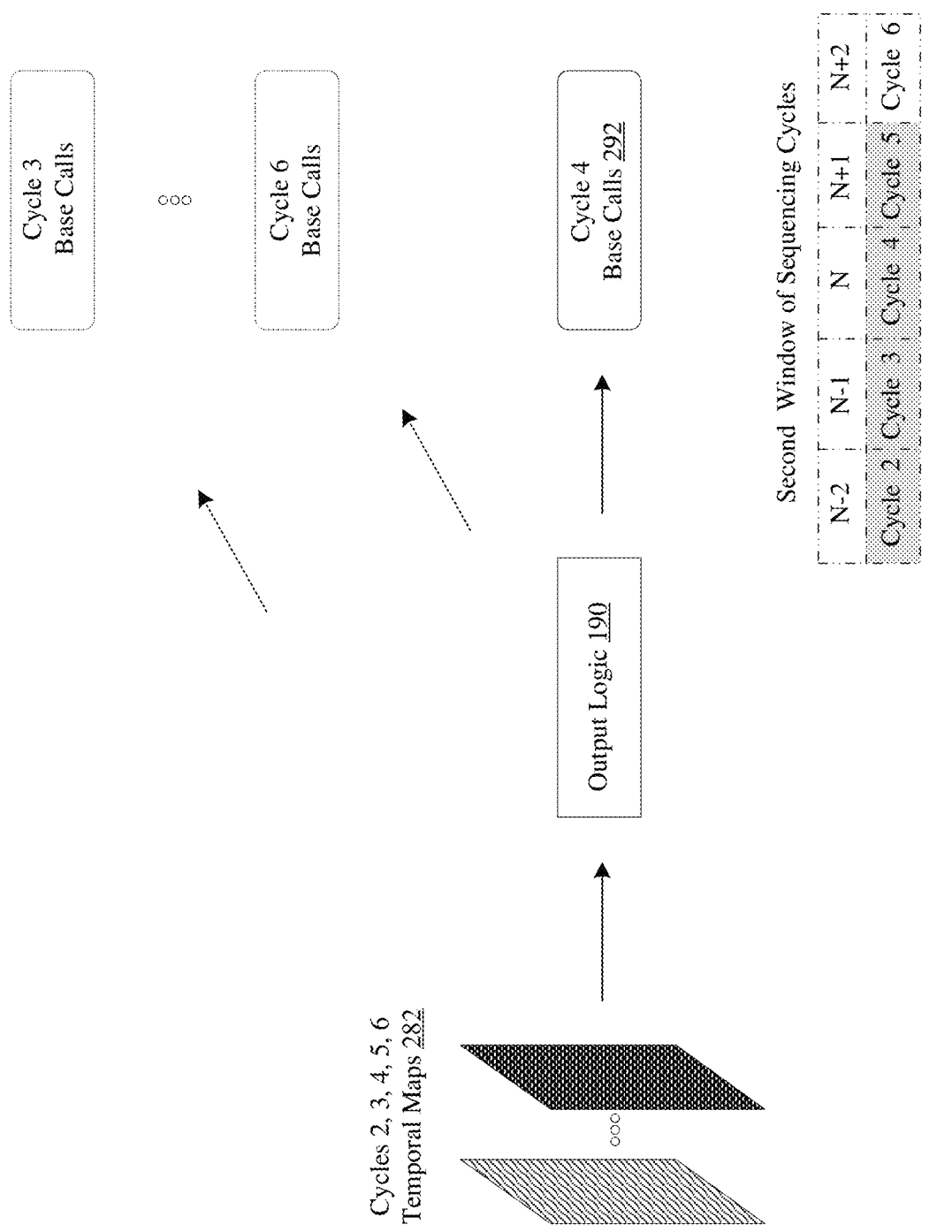
FIG. 2C shows that the output layer processes a final temporal map set generated during the second iteration of base calling and produces the base calls for the center sequencing cycle 4.

FIG. 2B shows that the compressed spatial map sets 120, 130, 140, and 150 generated during the first iteration of base calling are used in conjunction with the compressed spatial map set 230 generated during the second iteration of base calling to generate the base calls 292 for the center sequencing cycle 4. In FIG. 2B, temporal map sets 174, 176, and 278 are generated by the first temporal convolution layer of the temporal network 160 in a manner similar to the one discussed above with respect to FIG. 1B. Temporal map set 282 is generated by the second and last temporal convolution layer of the temporal network 160 in a manner similar to the one discussed above with respect to FIG. 1B. FIG. 2C shows that the output layer 190 processes the final temporal map set 282 generated during the second iteration of base calling and produces the base calls 292 for the center sequencing cycle 4.

The third window of sequencing cycles includes sequencing cycles 3, 4, 5, 6, and 7 and a third iteration of base calling produces base calls 392 for the center sequencing cycle 5.

Accordingly, sequencing cycles 3, 4, 5, and 6 are the overlapping sequencing cycles between the second and third windows or between the second and third iterations of base calling.

The disclosed base calling systems and techniques store, in memory (e.g., on-chip DRM, on-chip SRAM or BRAM, off-chip DRAM), the compressed spatial map sets 130, 140, and 150 generated during the first iteration of base calling for the respective sequencing cycles 3, 4, and 5 and the compressed spatial map set 230 generated during the second iteration of base calling for the sequencing cycle 6. During the third iteration of base calling, the disclosed base calling systems and techniques do not reprocess the respective input image patches 122, 132, 142, and 222 for the overlapping cycles 3, 4, 5, and 6 through the spatial network 104. Instead, during the third iteration of base calling, the disclosed base calling systems and techniques reuse the previously generated compressed spatial map sets 130, 140, 150, and 230 in lieu of the respective input image patches 122, 132, 142, and 222.

Figure 3A:
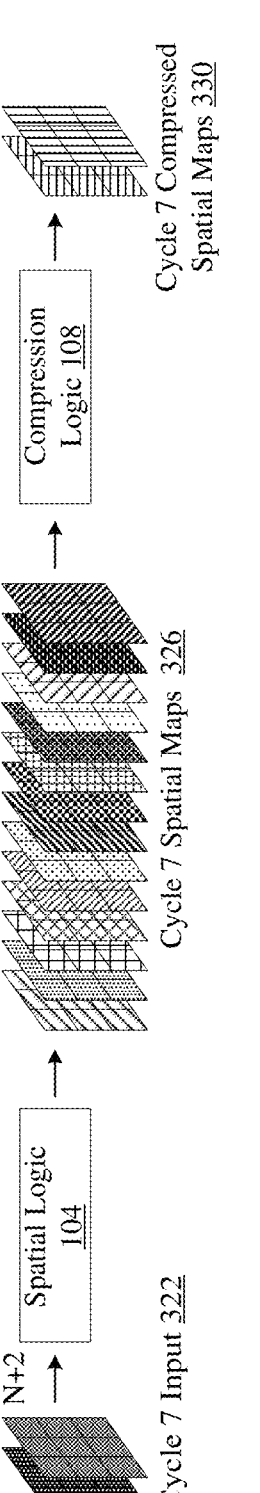
FIG. 3A shows that, during a third iteration of base calling, spatial maps and corresponding compressed spatial maps are generated only for the non-overlapping sequencing cycle 7.

FIG. 3A shows that, during the third iteration of base calling, spatial maps 326 and corresponding compressed spatial maps 330 are generated only for the non-overlapping sequencing cycle 7 by processing input image data 322 through the spatial logic 104 and the compression logic 108. Accordingly, the input image patches 122, 132, 142, and 222 for the overlapping cycles 3, 4, 5, and 6 (highlighted with grey fill in the legend) are not reprocessed to avoid redundant convolutions.

Figure 3B:
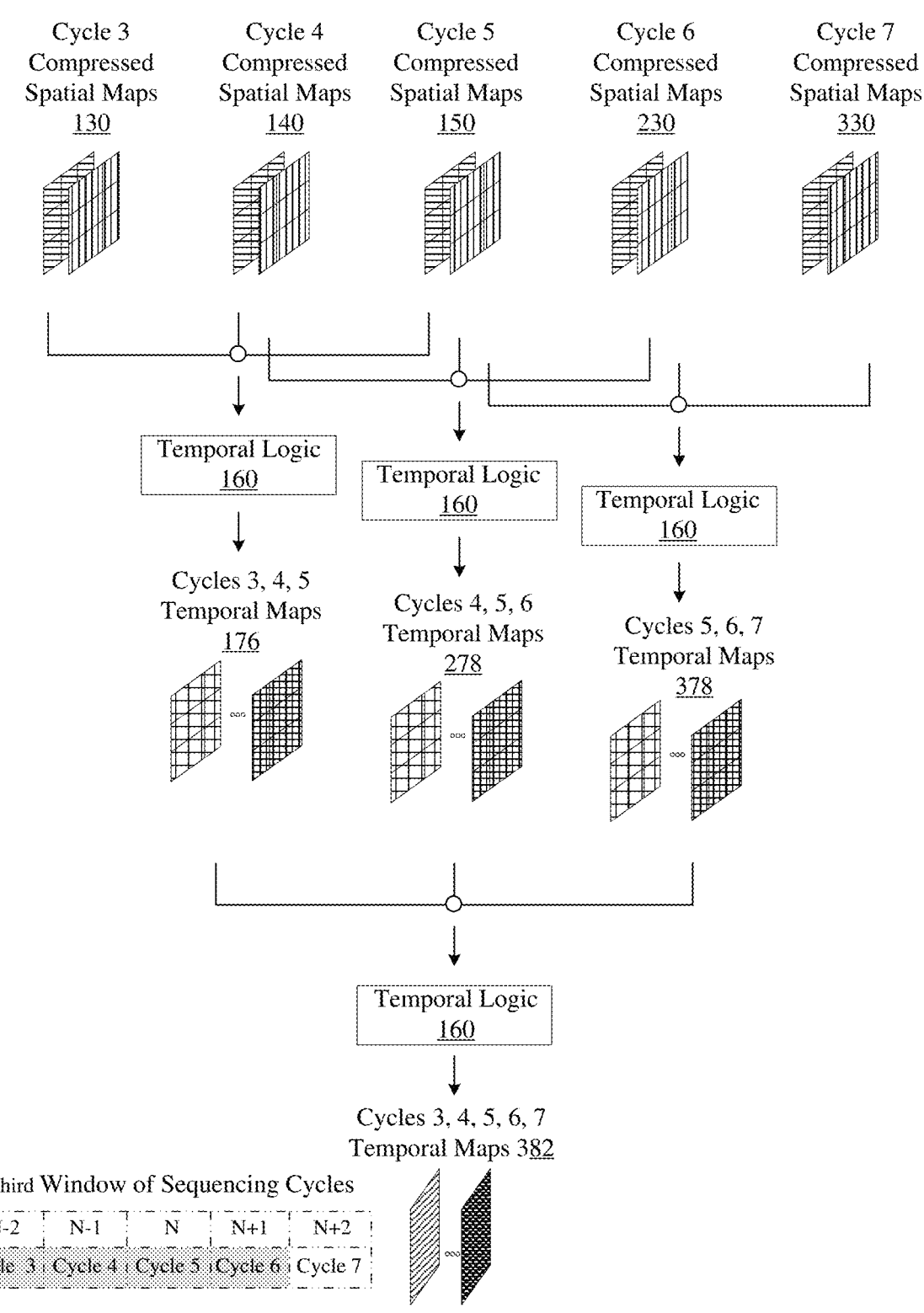
FIG. 3B shows that the compressed spatial map sets generated during the first and second iterations of base calling are used in conjunction with a compressed spatial map set generated during the third iteration of base calling to generate base calls for the center sequencing cycle 5.
Figure 3C:
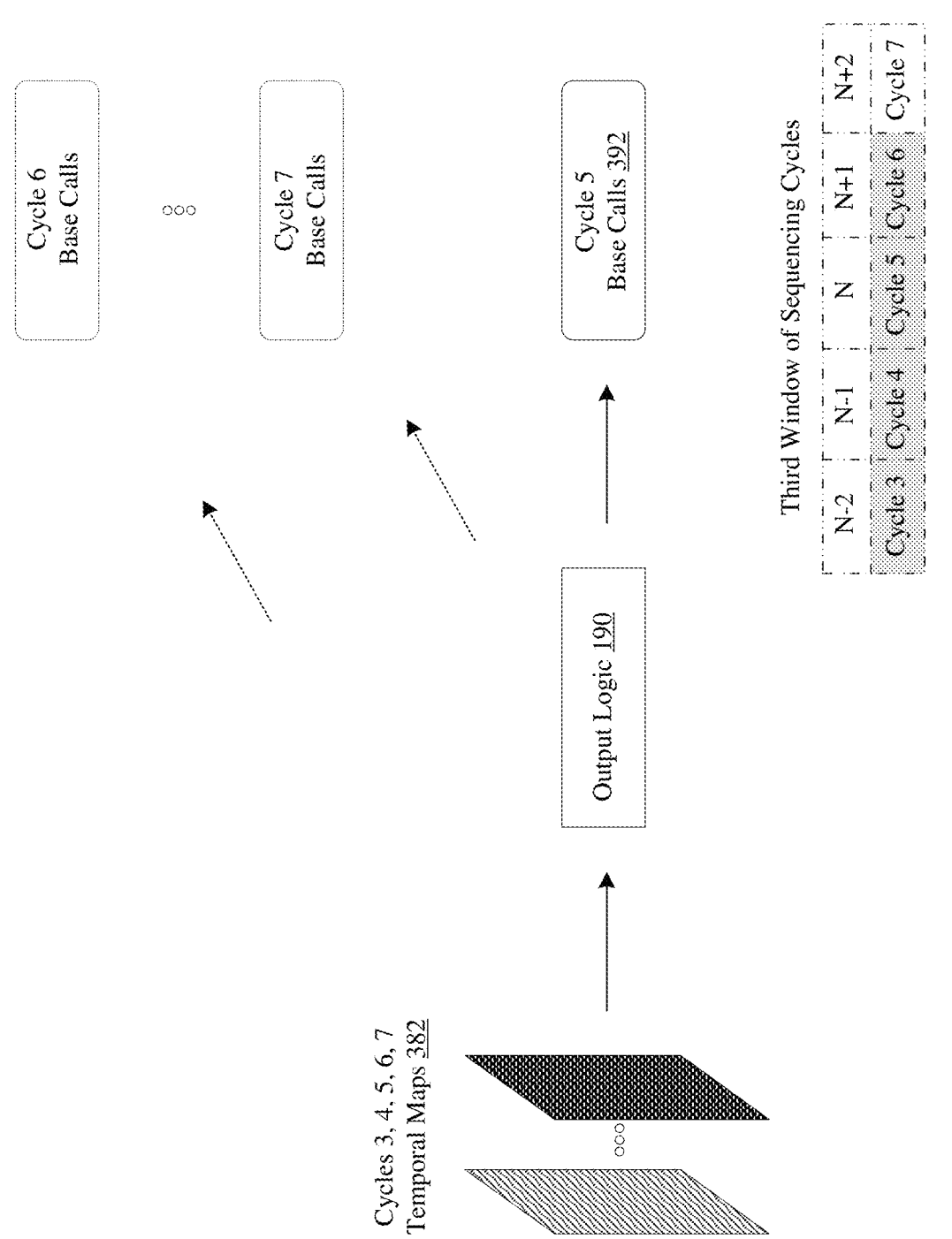
FIG. 3C shows that the output layer processes a final temporal map set generated during the third iteration of base calling and produces the base calls for the center sequencing cycle 5.

FIG. 3B shows that the compressed spatial map sets 130, 140, 150, and 230 generated during the first and second iterations of base calling are used in conjunction with the compressed spatial map set 330 generated during the third iteration of base calling to generate the base calls 392 for the center sequencing cycle 5. In FIG. 3B, temporal map sets 176, 278, and 378 are generated by the first temporal convolution layer of the temporal network 160 in a manner similar to the one discussed above with respect to FIG. 1B. Temporal map set 382 is generated by the second and last temporal convolution layer of the temporal network 160 in a manner similar to the one discussed above with respect to FIG. 1B. FIG. 3C shows that the output layer 190 processes the final temporal map set 382 generated during the third iteration of base calling and produces the base calls 392 for the center sequencing cycle 5.

Figure 4A:
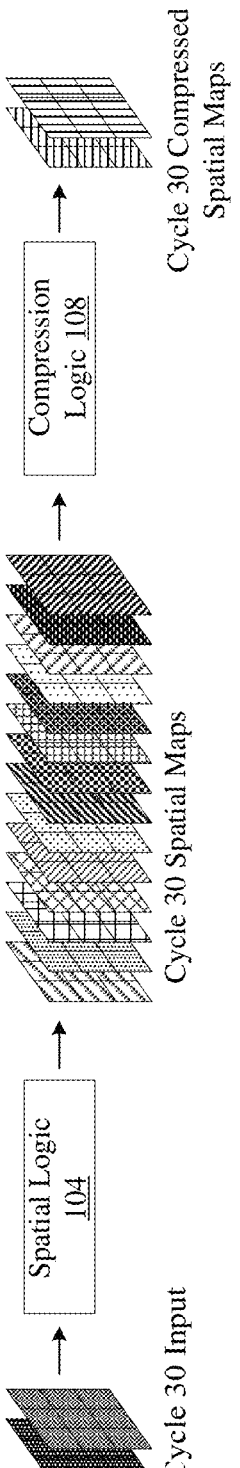
FIG. 4A shows a fourteenth iteration of base calling for base calling a center sequencing cycle 16.
Figure 4B:
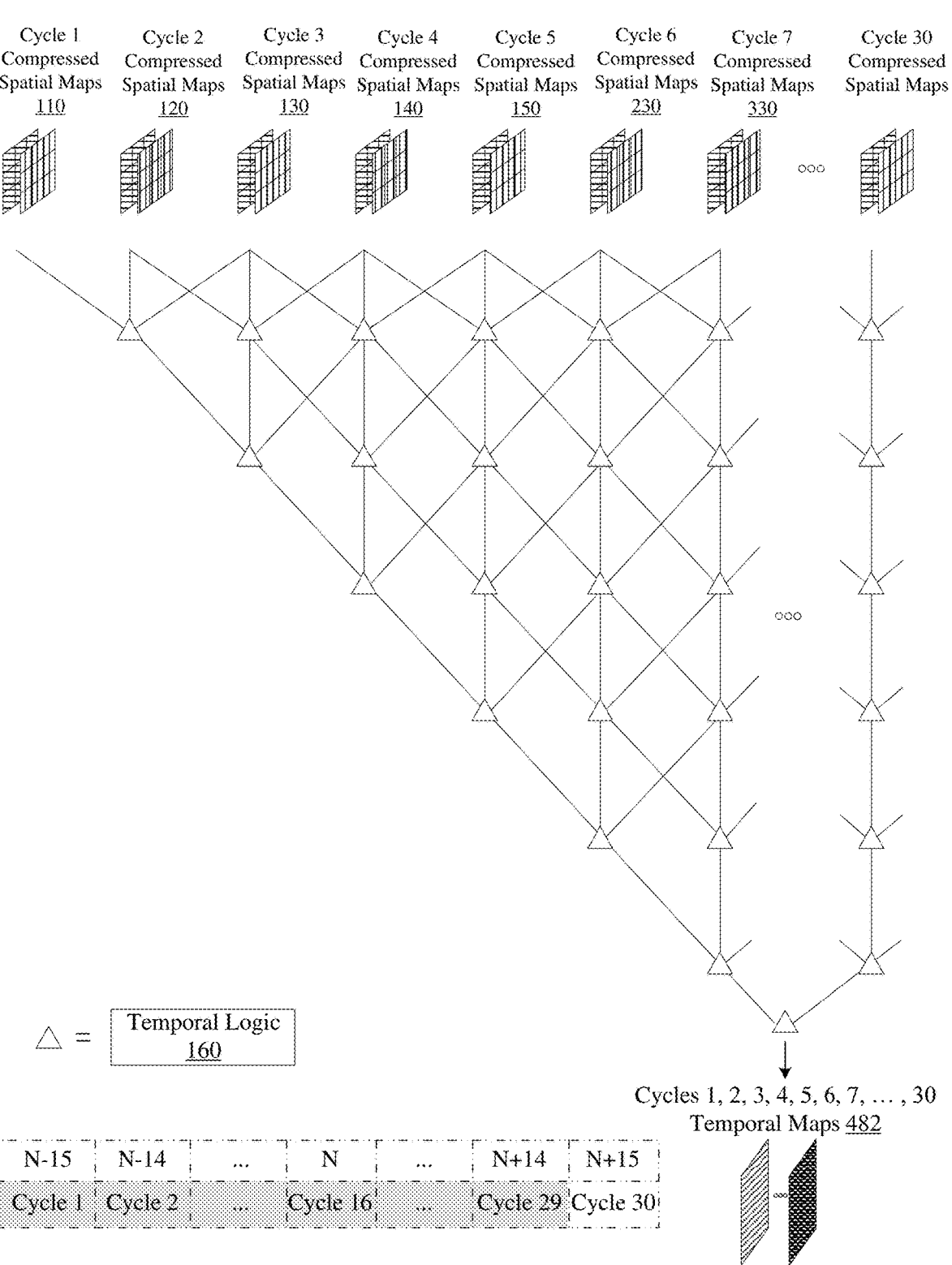
FIG. 4B shows that compressed spatial maps previously generated for sequencing cycles 1 to 29 are used to generate a final temporal map set for base calling the center sequencing cycle 16.
Figure 4C:
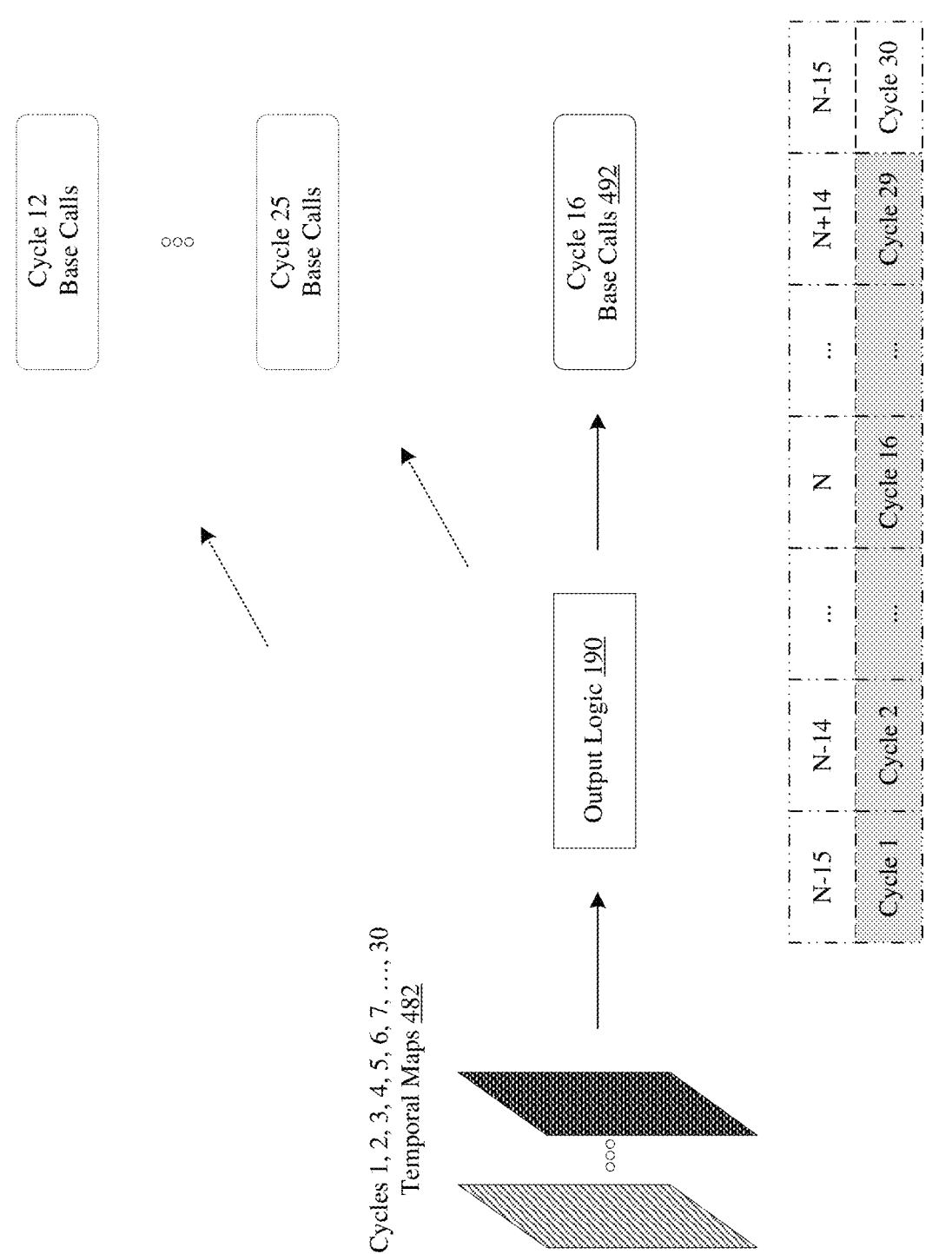
FIG. 4C shows that the output layer processes the final temporal map set generated during the fourteenth iteration of base calling and produces base calls for the center sequencing cycle 16.

A compressed spatial map set once generated for a given sequencing cycle can be reused for base calling any subsequent sequencing cycle. FIG. 4A shows a fourteenth iteration of base calling for base calling a center sequencing cycle 16. FIG. 4B shows that compressed spatial maps previously generated for sequencing cycles 1 to 29 are used to generate a final temporal map set 482 for base calling the center sequencing cycle 16. FIG. 4C shows that the output layer 190 processes the final temporal map set 482 generated during the fourteenth iteration of base calling and produces base calls 492 for the center sequencing cycle 16.

Figure 5A:
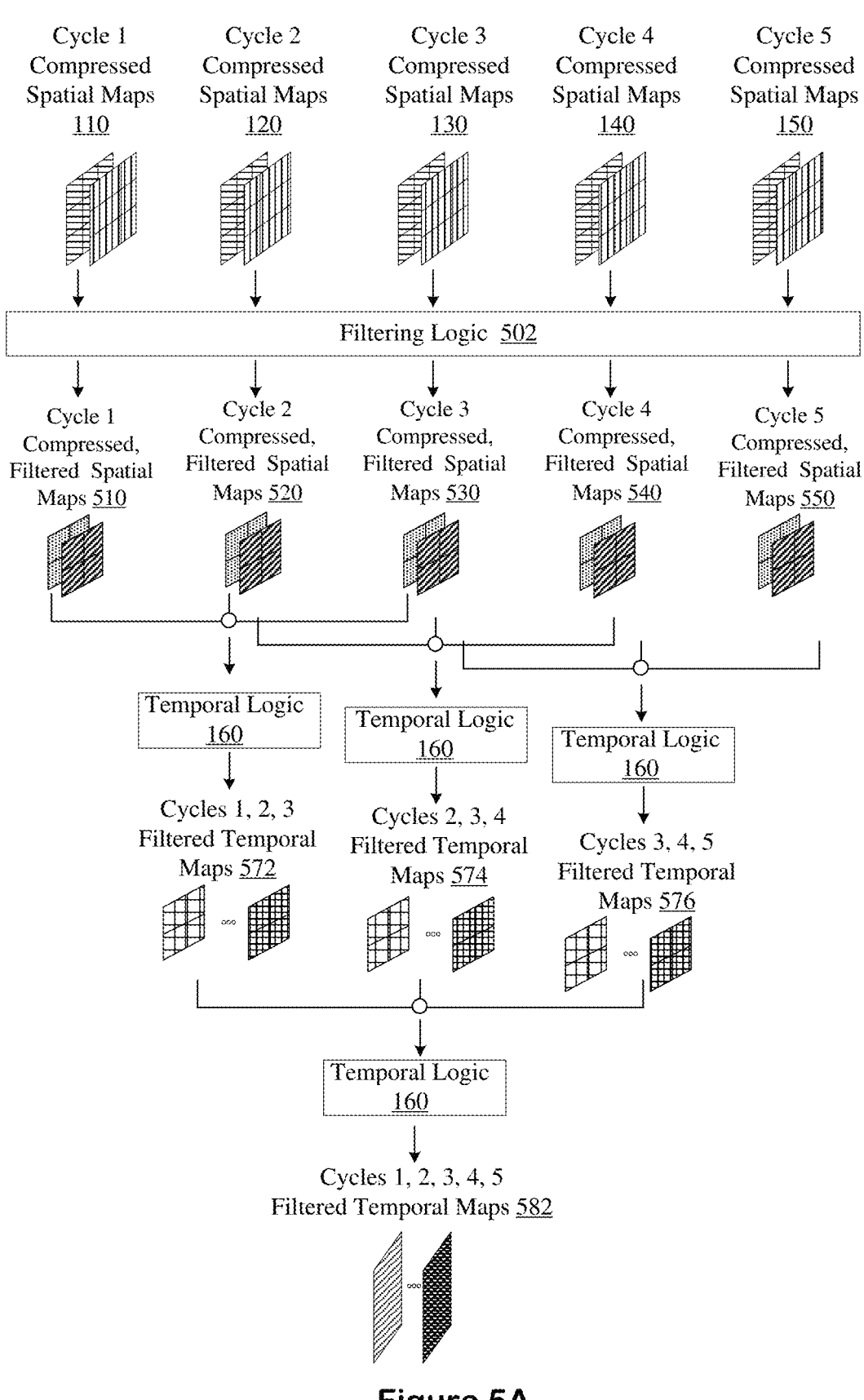
FIG. 5A illustrates one implementation of filtering the compressed spatial map sets for the respective sequencing cycles 1, 2, 3, 4, and 5 using filtering logic to generate respective compressed, filtered spatial maps during the first iteration of base calling.

FIG. 5A illustrates one implementation of filtering the compressed spatial map sets 110, 120, 130, 140, and 150 using filtering logic 502 to generate respective compressed, filtered spatial maps 510, 520, 530, 540, and 550 (depicting only reliable clusters) for the respective sequencing cycles 1, 2, 3, 4, and 5 during the first iteration of base calling. As discussed above, the unreliable clusters data 128 identifies those portions (e.g., pixels) of the spatial maps and the compressed spatial maps that correspond to the unreliable clusters. Such pixels can be identified, for example, based on location coordinates of the unreliable clusters.

The filtering logic 502 uses the data 128 identifying the unreliable clusters to filter out (or discard or remove) those pixels from the compressed spatial map sets 110, 120, 130, 140, and 150 that correspond to (i.e., depict intensity emissions of) the unreliable clusters. In some implementations, this results in 75% of pixels being discarded from the compressed spatial map sets, and thereby prevents many unproductive convolutions.

Figure 5B:
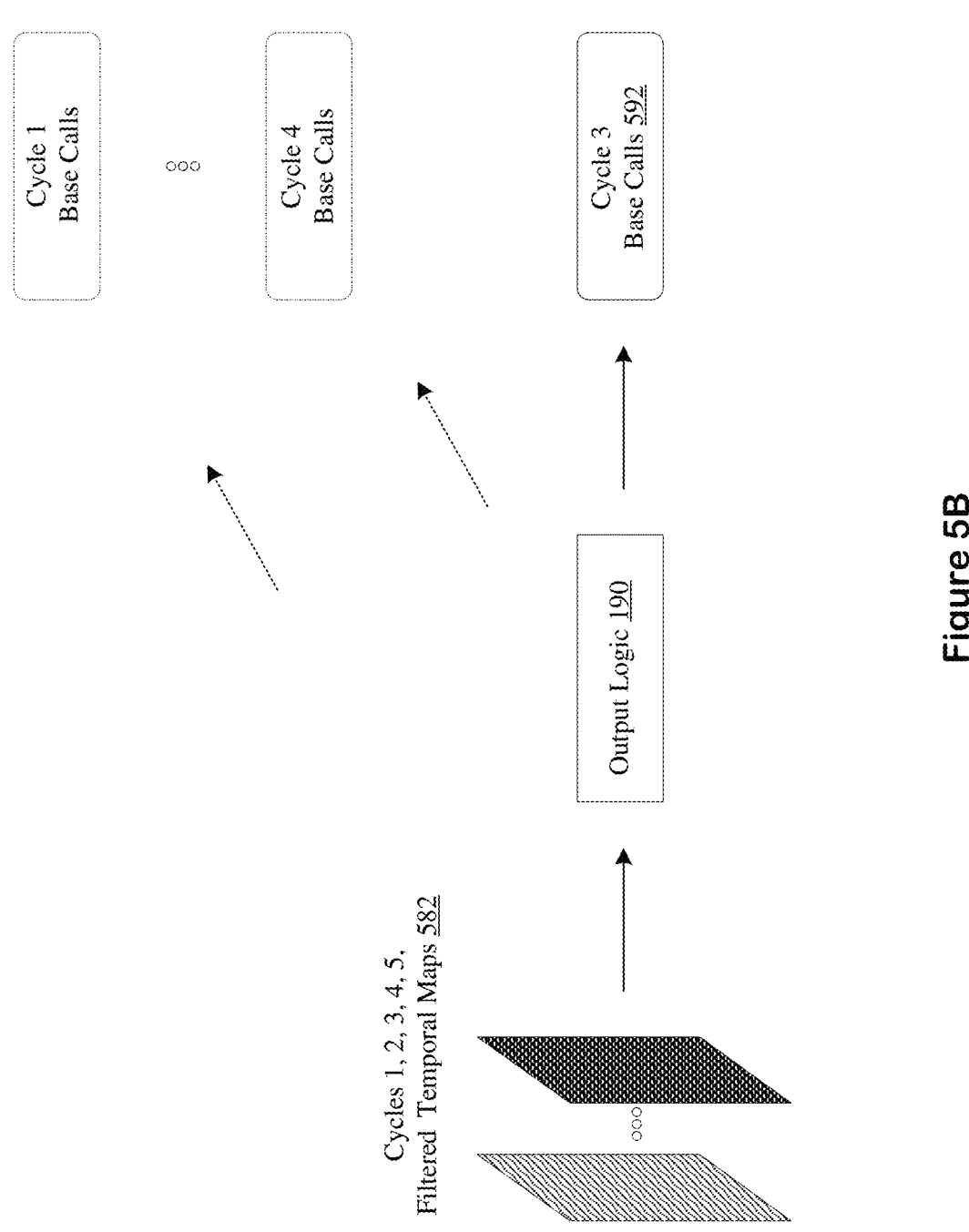
FIG. 5B shows that the output layer processes the final filtered temporal map set generated during the first iteration of base calling and produces base calls for the center sequencing cycle 3.

In FIG. 5A, filtered temporal map sets 572, 574, and 576 (depicting only reliable clusters) are generated from the compressed, filtered spatial maps 510, 520, 530, 540, and 550 for base calling the center sequencing cycle 3. The filtered temporal map sets 572, 574, and 576 (depicting only reliable clusters) are generated by the first temporal convolution layer of the temporal network 160 in a manner similar to the one discussed above with respect to FIG. 1B. Filtered temporal map set 582 (depicting only reliable clusters) is generated by the second and last temporal convolution layer of the temporal network 160 in a manner similar to the one discussed above with respect to FIG. 1B. FIG. 5B shows that the output layer 190 processes the final filtered temporal map set 582 generated during the first iteration of base calling and produces base calls 592 for the center sequencing cycle 3.

Figure 6A:
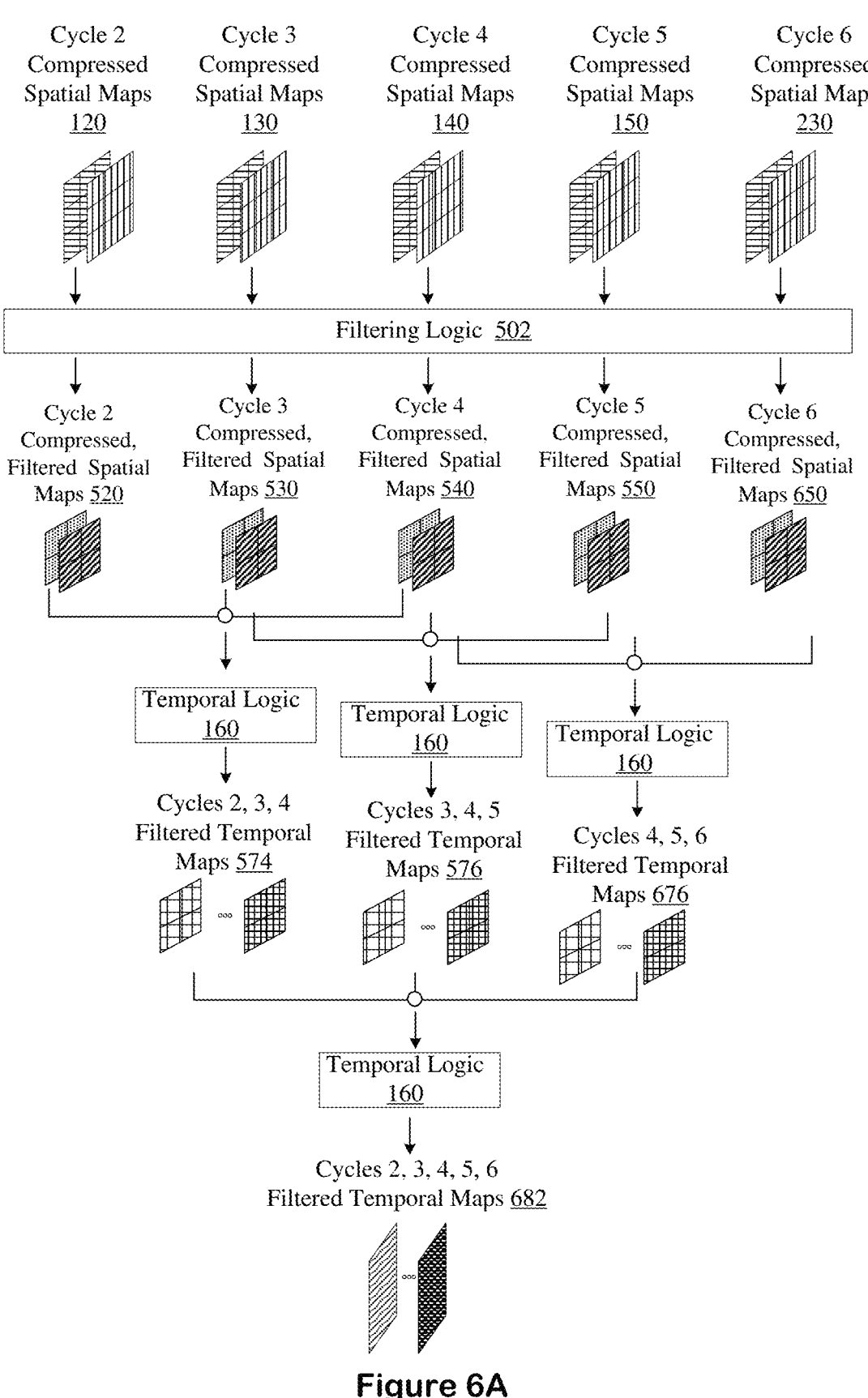
FIG. 6A illustrates one implementation of filtering the compressed spatial map sets for the respective sequencing cycles 2, 3, 4, 5, and 6 using the filtering logic to generate respective compressed, filtered spatial maps during the second iteration of base calling.

FIG. 6A illustrates one implementation of filtering the compressed spatial map sets 120, 130, 140, 150, and 230 using the filtering logic 502 to generate respective compressed, filtered spatial maps 520, 530, 540, 550, and 650 (depicting only reliable clusters) for the respective sequencing cycles 2, 3, 4, 5, and 6 during the second iteration of base calling. The filtering logic 502 uses the data 128 identifying the unreliable clusters to filter out (or discard or remove) those pixels from the compressed spatial map sets 120, 130, 140, 150, and 230 that correspond to (i.e., depict intensity emissions of) the unreliable clusters.

Figure 6B:
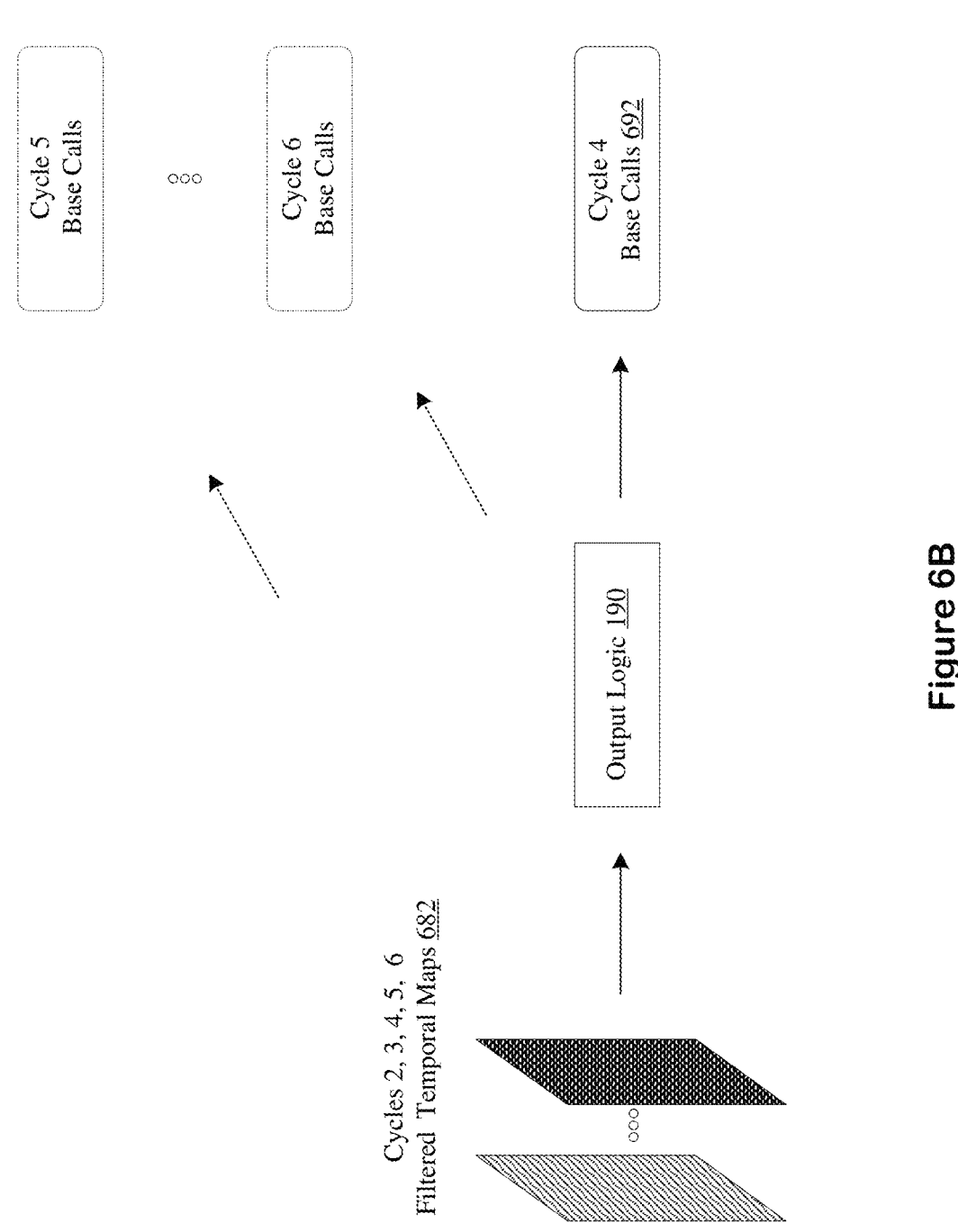
FIG. 6B shows that the output layer processes the final filtered temporal map set generated during the second iteration of base calling and produces base calls for the center sequencing cycle 4.

In FIG. 6A, filtered temporal map sets 574, 576, and 676 (depicting only reliable clusters) are generated from the compressed, filtered spatial maps 520, 530, 540, 550, and 650 for base calling the center sequencing cycle 4. The filtered temporal map sets 574, 576, and 676 (depicting only reliable clusters) are generated by the first temporal convolution layer of the temporal network 160 in a manner similar to the one discussed above with respect to FIG. 1B. Filtered temporal map set 682 (depicting only reliable clusters) is generated by the second and last temporal convolution layer of the temporal network 160 in a manner similar to the one discussed above with respect to FIG. 1B. FIG. 6B shows that the output layer 190 processes the final filtered temporal map set 682 generated during the second iteration of base calling and produces base calls 692 for the center sequencing cycle 4.

Figure 7A:
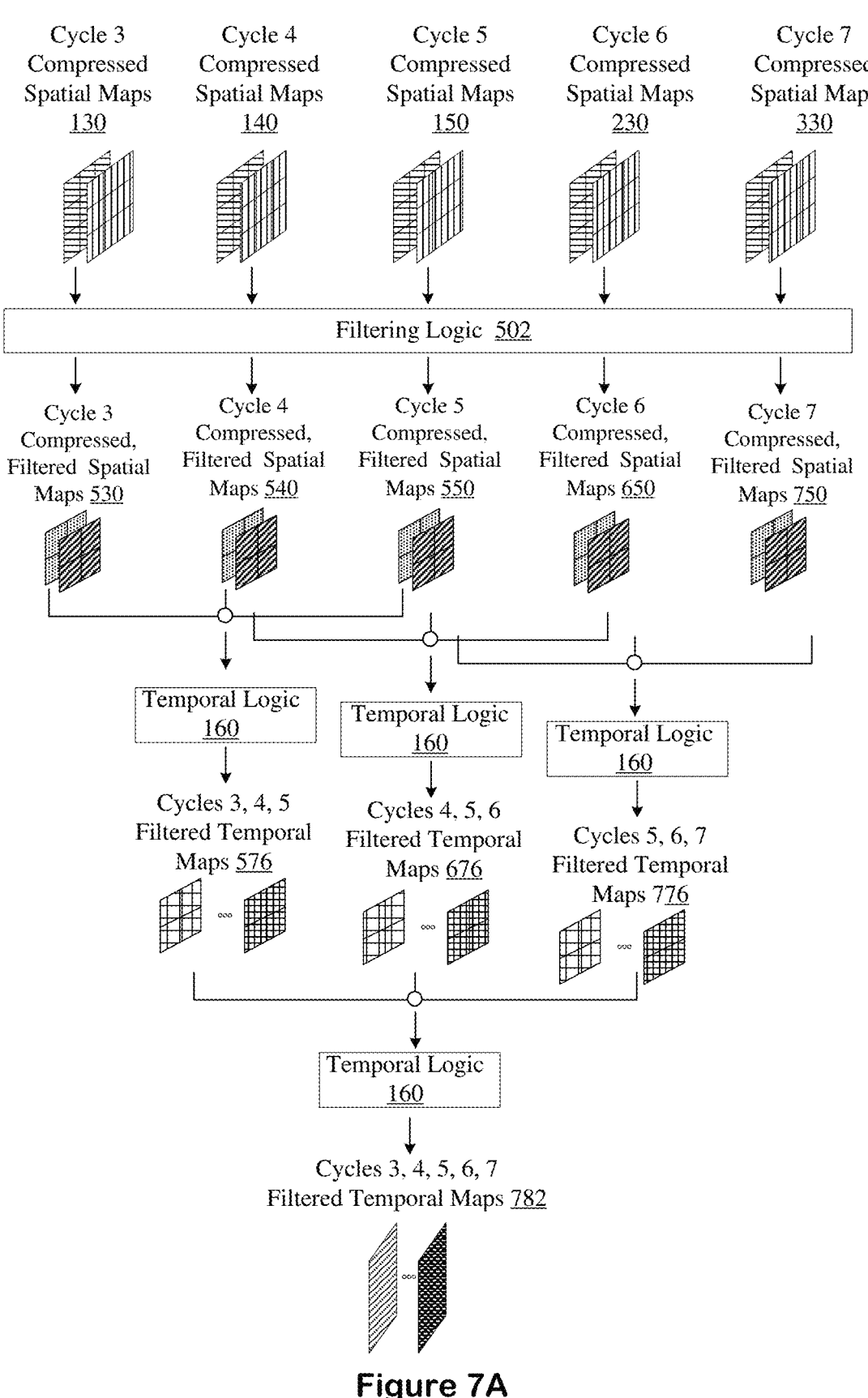
FIG. 7A illustrates one implementation of filtering the compressed spatial map sets for the respective sequencing cycles 3, 4, 5, 6 and 7 using the filtering logic to generate respective compressed, filtered spatial maps during the third iteration of base calling.

FIG. 7A illustrates one implementation of filtering the compressed spatial map sets 130, 140, 150, 230, and 330 using the filtering logic 502 to generate respective compressed, filtered spatial maps 530, 540, 550, 650, and 750 (depicting only reliable clusters) for the respective sequencing cycles 3, 4, 5, 6 and 7 during the third iteration of base calling. The filtering logic 502 uses the data 128 identifying the unreliable clusters to filter out (or discard or remove) those pixels from the compressed spatial map sets 130, 140, 150, 230, and 330 that correspond to (i.e., depict intensity emissions of) the unreliable clusters.

Figure 7B:
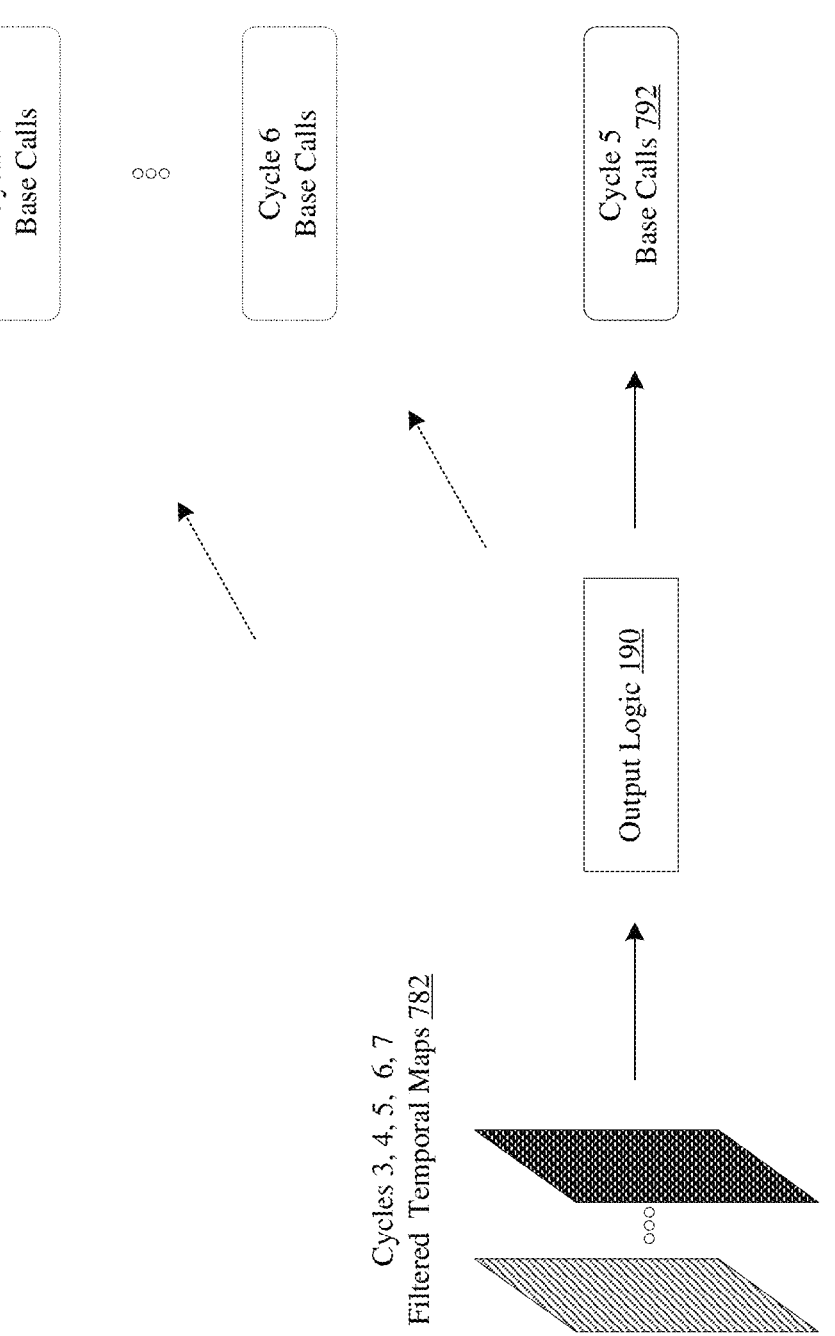
FIG. 7B shows that the output layer processes the final filtered temporal map set generated during the third iteration of base calling and produces base calls for the center sequencing cycle 5.

In FIG. 7A, filtered temporal map sets 576, 676, and 776 (depicting only reliable clusters) are generated from the compressed, filtered spatial maps 530, 540, 550, 650, 750 for base calling the center sequencing cycle 5. The filtered temporal map sets 576, 676, and 776 (depicting only reliable clusters) are generated by the first temporal convolution layer of the temporal network 160 in a manner similar to the one discussed above with respect to FIG. 1B. Filtered temporal map set 782 (depicting only reliable clusters) is generated by the second and last temporal convolution layer of the temporal network 160 in a manner similar to the one discussed above with respect to FIG. 1B. FIG. 7B shows that the output layer 190 processes the final filtered temporal map set 782 generated during the third iteration of base calling and produces base calls 792 for the center sequencing cycle 5.

In other implementations, the compression logic 108 can configure the corresponding compressed temporal map sets to each have more than four feature maps.

The compression logic 108 discussed above with respect to the spatial feature maps applies equivalently to compression of temporal feature maps generated by the temporal logic 160. The reusing of once generated compressed spatial feature maps in subsequent sequencing cycles also applies equivalently to reusing of once generated compressed temporal feature maps in subsequent sequencing cycles.

In some implementations, reusing the compressed temporal feature maps results in two orders of efficiency and compute savings over reusing the compressed spatial feature maps because the compressed temporal feature maps are generated from the compressed spatial feature maps at a later stage of the processing pipeline. Repurposing the intermediate results from a further processing engine (i.e., the temporal network 160) increases the number of earlier processing steps that can be skipped. That is, reusing the compressed spatial feature maps eliminates redundant processing of the original image data through the spatial network 104 but can include redundantly processing of the compressed spatial feature maps through the temporal network 160. In contrast, reusing the compressed temporal feature maps eliminates both—the redundant processing of original image data through the spatial network 104 and the redundant processing of the compressed spatial feature maps through the temporal network 160.

Figure 8A:
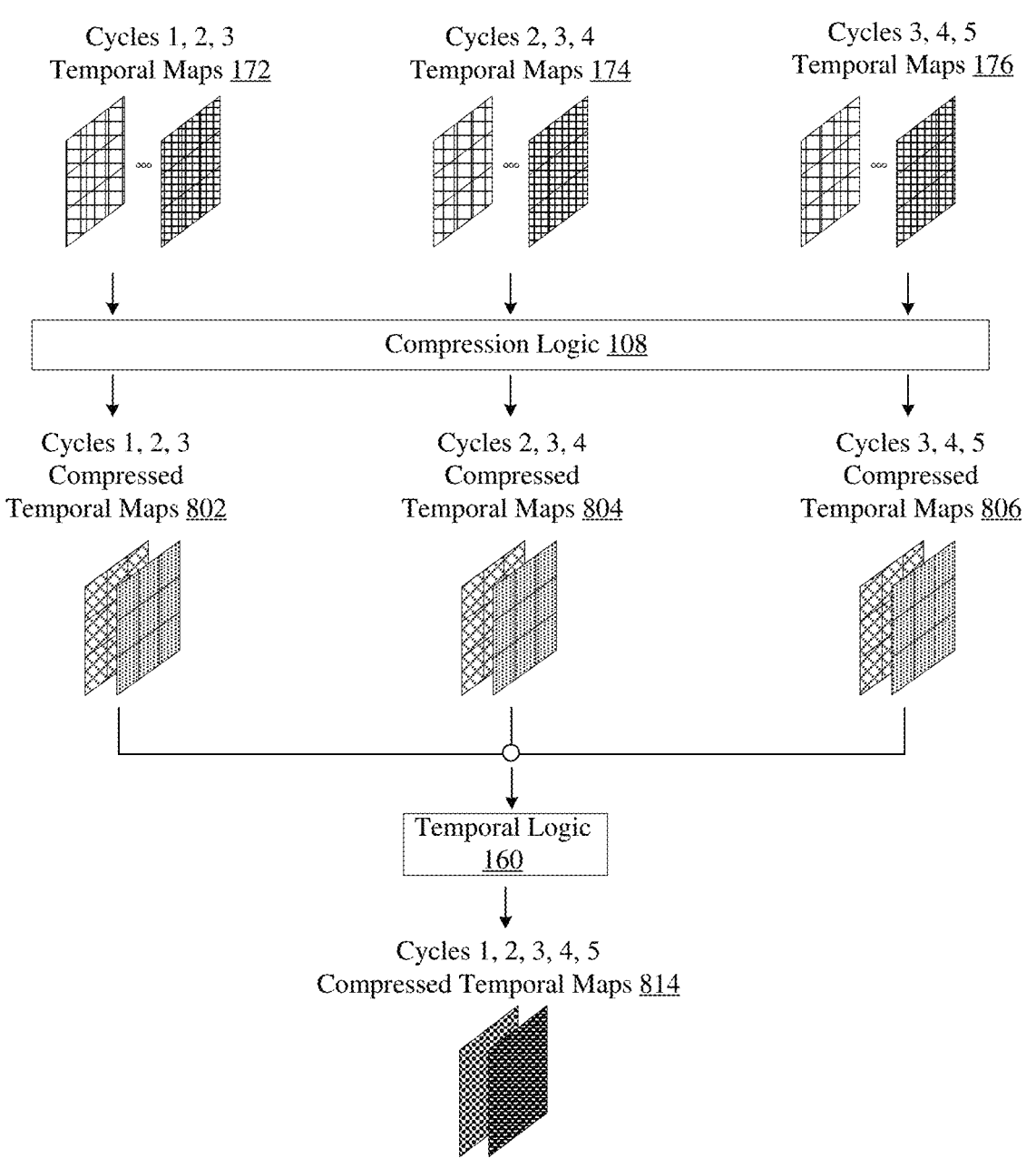
FIG. 8A shows one implementation of processing the sets of temporal feature maps generated during the first iteration of base calling through the compression logic to generate respective sets of compressed temporal feature maps.
Figure 8B:
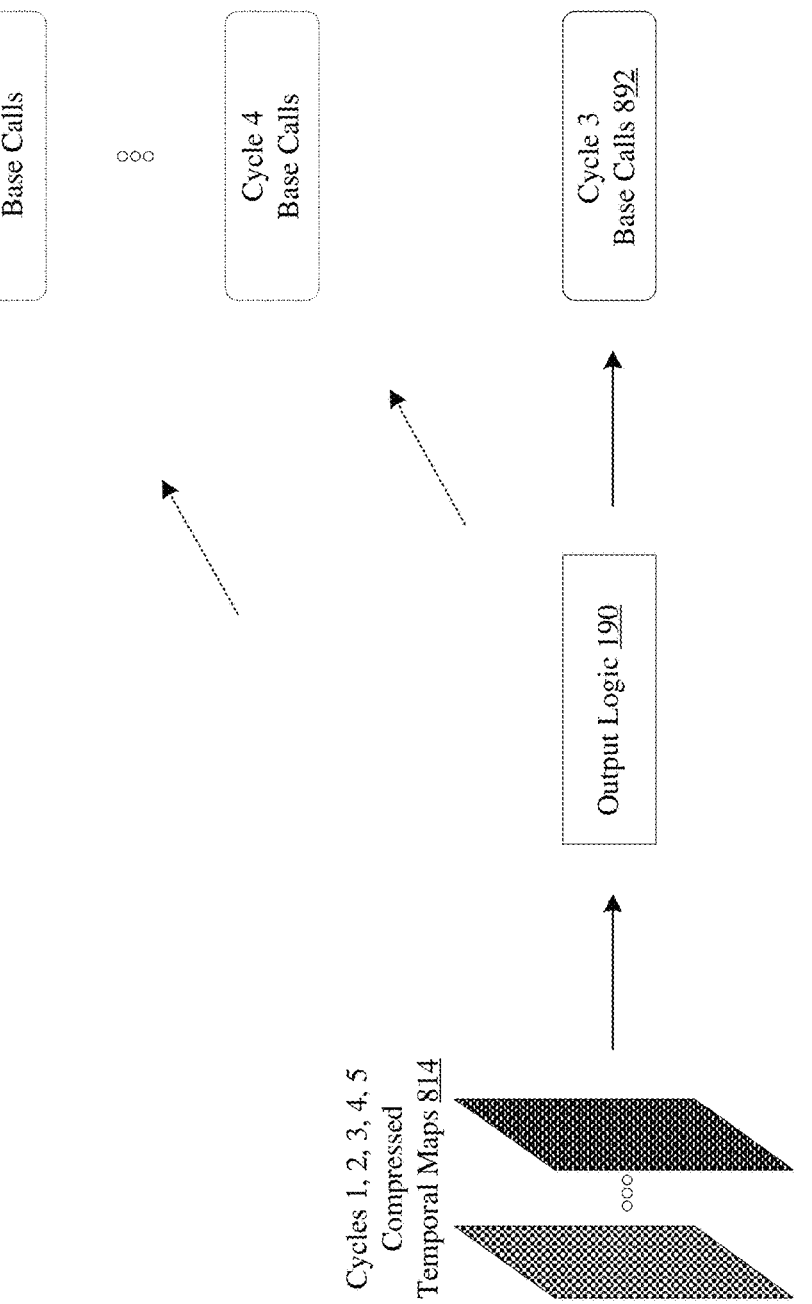
FIG. 8B shows that the output layer processes a final compressed temporal map set generated during the first iteration of base calling and produces base calls for the center sequencing cycle 3.

FIG. 8A shows one implementation of processing the sets of temporal feature maps 172, 174, and 176 generated during the first iteration of base calling through the compression logic 108 to generate respective sets of compressed temporal feature maps 802, 804, and 806. The compressed temporal feature map sets 802, 804, and 806 are generated by the compression logic 108 in a manner similar to the one discussed above with respect to FIGS. 1E and 1F. That is, for example, if the first temporal feature map set 172 has, for example, twenty-one feature maps (or channels or depth=21), then the compression logic 108 can configure the corresponding compressed temporal feature map set 802 to have one, two, three, four, or feature maps. The sets of compressed temporal feature maps 802, 804, and 806 are processed by the second temporal convolution layer of the temporal network 160 in a manner similar to the one discussed above with respect to FIG. 1B to generate a final compressed temporal feature map set 814. FIG. 8B shows that the output layer 190 processes the final compressed temporal feature map set 814 generated during the first iteration of base calling and produces base calls 892 for the center sequencing cycle 3.

Figure 9A:
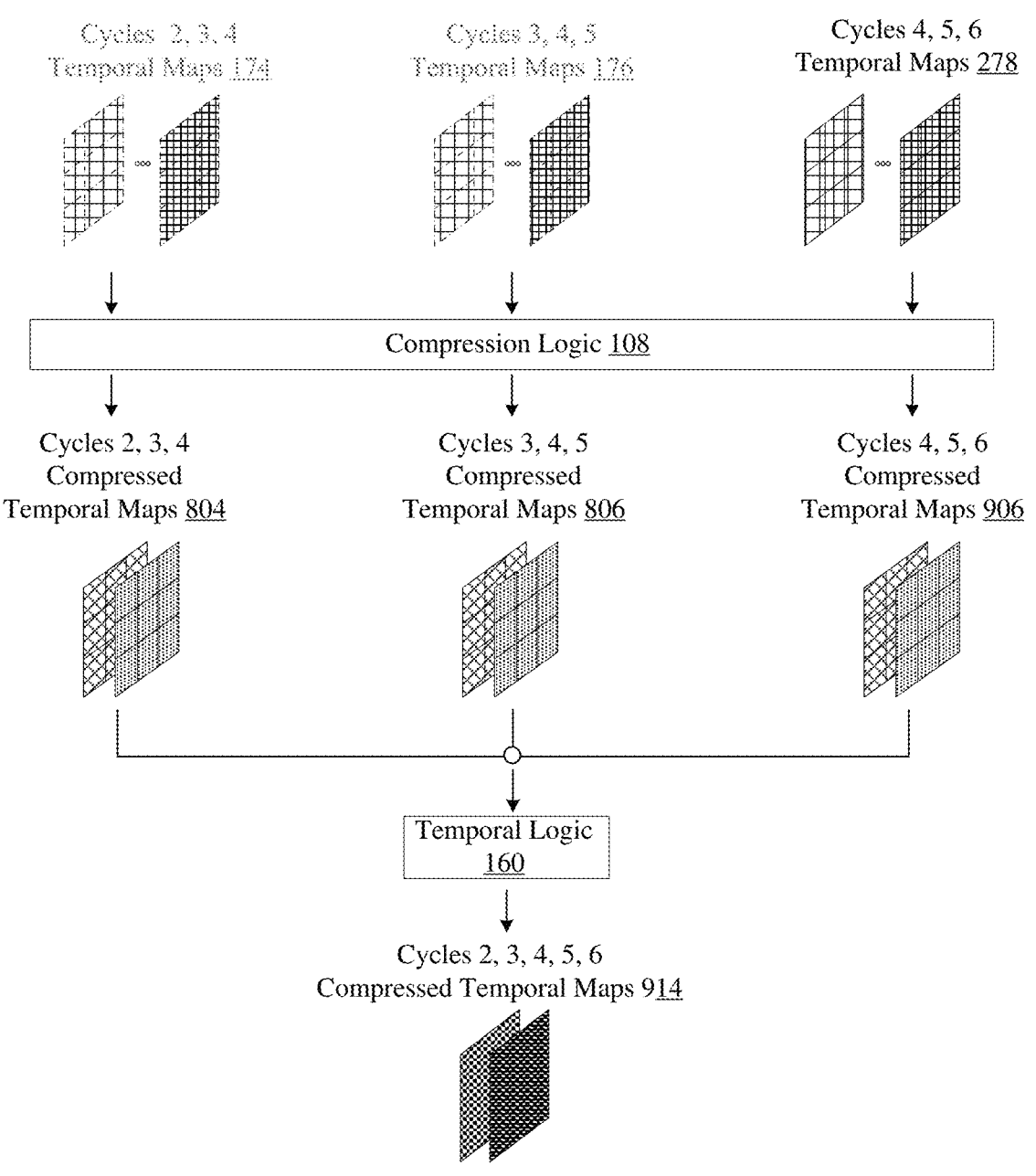
FIG. 9A shows that the compressed temporal map sets generated during the first base calling iteration are used in conjunction with a compressed temporal map set generated during the second iteration of base calling to generate base calls for the center sequencing cycle 4.

FIG. 9A shows one implementation of reusing, in the second base calling iteration, those compressed temporal maps that were generated in the first base calling iteration. That is, the first and second sets of compressed temporal maps 804 and 806 were generated in FIG. 8A for the first base calling iteration and are now repurposed in the second base calling iteration shown in FIGS. 9A and 9B.

Note that the first and second sets of compressed temporal maps 804 and 806 were generated in FIG. 8A from the first and second sets of temporal maps 172 and 174. Further note that the first and second sets of temporal maps 172 and 174 were generated in FIG. 1B from the compressed spatial maps 110, 120, 130, and 140, which in turn were generated in FIG. 1A from the respective spatial maps 106, 116, 126, and 136, which in turn were generated in FIG. 1A from the respective image patches 102, 112, 122, and 132.

Unlike FIGS. 1B, 2B, and 3B that redundantly generate overlapping temporal maps 172, 174, and 176, in FIG. 9A, the overlapping temporal maps 174 and 176 (depicted in FIG. 9A with dotted lines and ghost text) are not redundantly generated from FIG. 8A (the first base calling iteration) to FIG. 9A (the second base calling iteration). This occurs because the compression logic 108 is incorporated into the temporal network 160 to generate the first and second sets of compressed temporal maps 804 and 806 in the first base calling iteration, which replace the overlapping temporal maps 174 and 176 in the second base calling iteration. The compressed temporal maps can be stored in memory (e.g., on-chip DRM, on-chip SRAM or BRAM, off-chip DRAM).

Figure 9B:
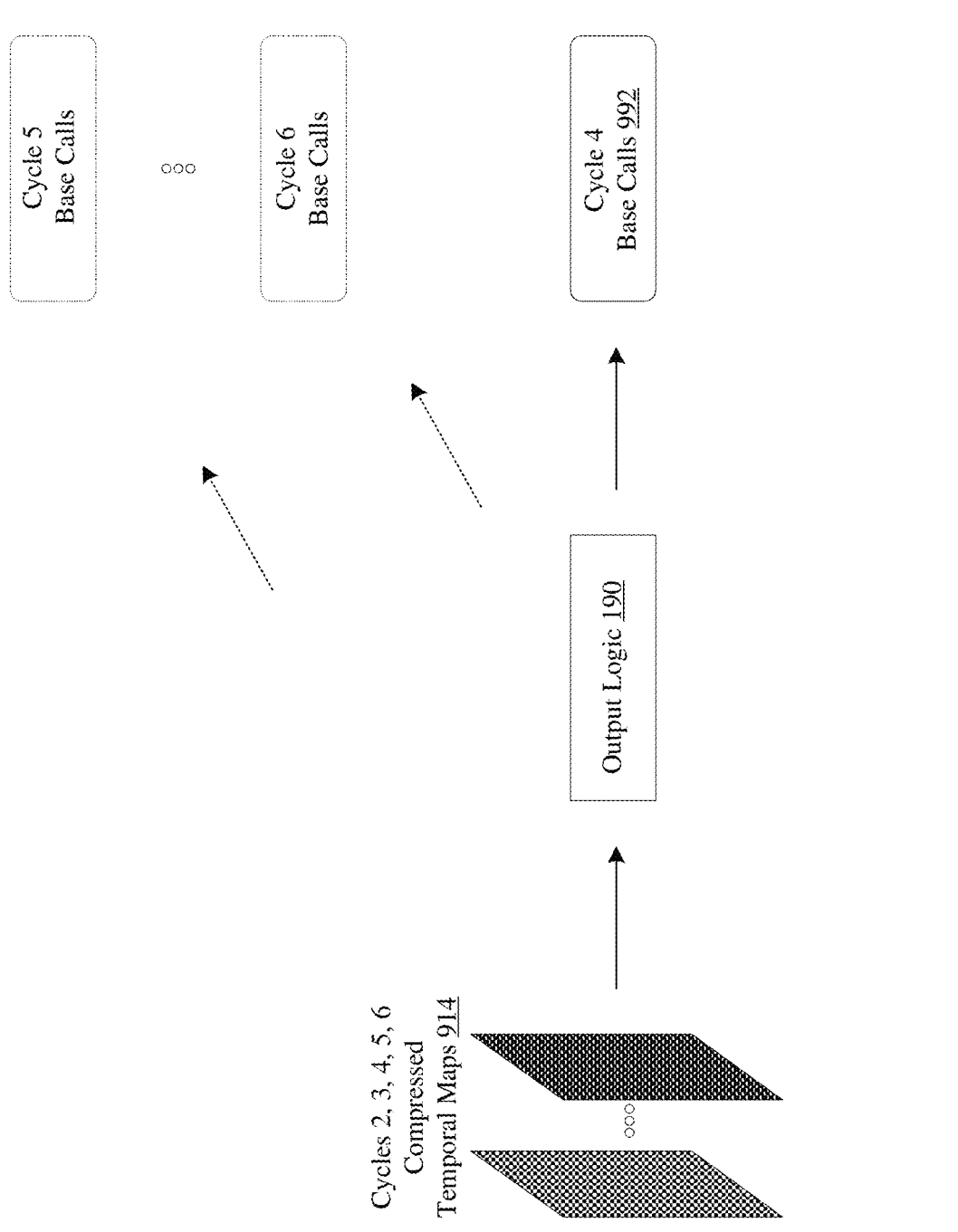
FIG. 9B shows that the output layer processes a final compressed temporal map set generated during the second iteration of base calling and produces base calls for the center sequencing cycle 4.

FIG. 9A also shows processing the non-overlapping temporal maps 278 (i.e., non-overlapping between the first and second base calling iterations) through the compression logic 108 to generate compressed temporal maps 906. The compressed temporal map sets 804, 806, and 906 are processed by the second temporal convolution layer of the temporal network 160 in a manner similar to the one discussed above with respect to FIG. 1B to generate a final compressed temporal feature map set 914. FIG. 9B shows that the output layer 190 processes the final compressed temporal feature map set 914 generated during the second iteration of base calling and produces base calls 992 for the center sequencing cycle 4.

Figure 10A:
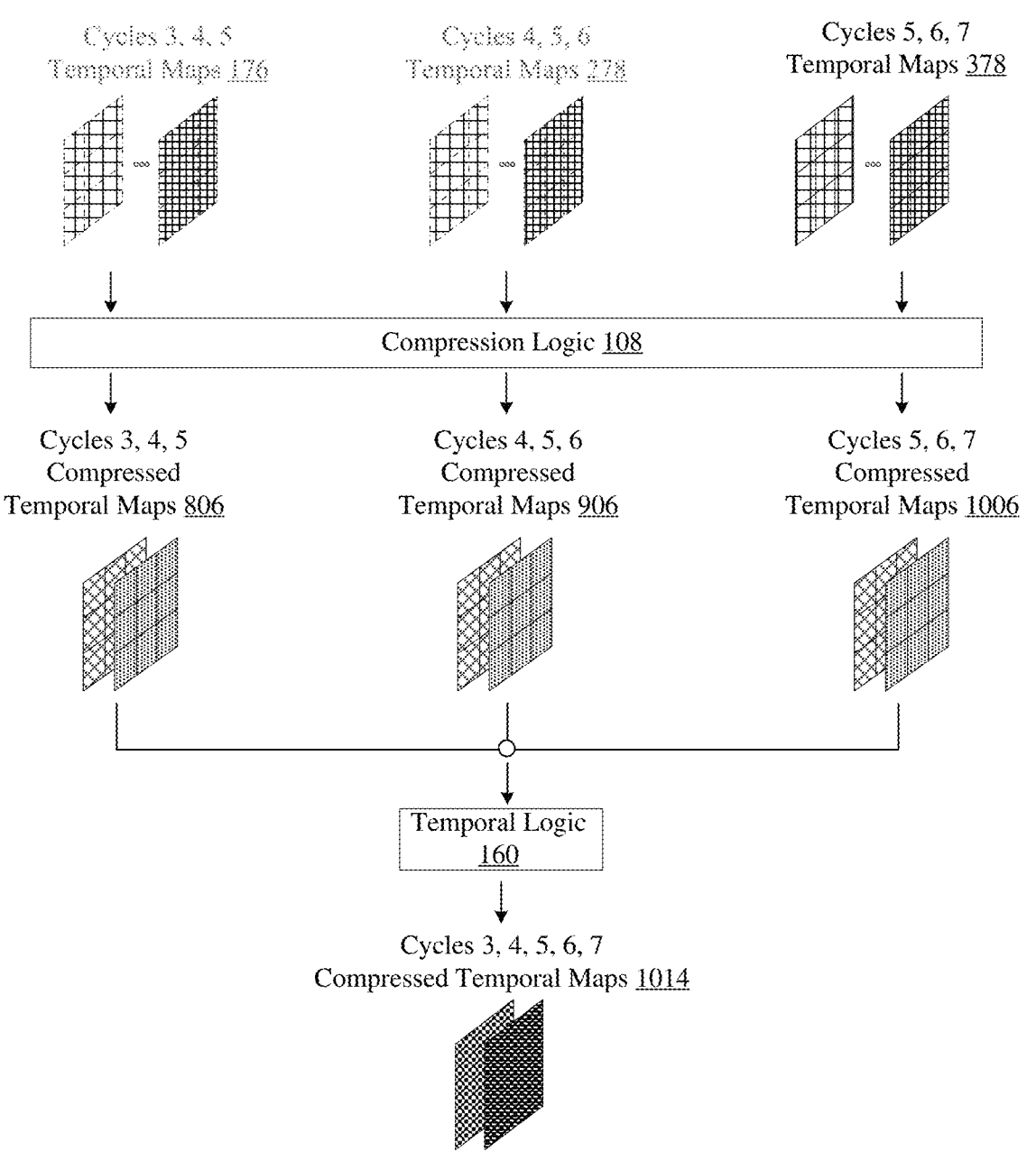
FIG. 10A shows that the compressed temporal map sets generated during the first and second base calling iterations are used in conjunction with a compressed temporal map set generated during the third iteration of base calling to generate base calls for the center sequencing cycle 5.

Unlike FIGS. 1B, 2B, and 3B that redundantly generate overlapping temporal maps 174, 176, and 278, in FIG. 10A, the overlapping temporal maps 176 and 278 (depicted in FIG. 10A with dotted lines and ghost text) are not redundantly generated from FIG. 9A (the second base calling iteration) to FIG. 10A (the third base calling iteration). This occurs because the compression logic 108 is incorporated into the temporal network 160 to generate the first and second sets of compressed temporal maps 806 and 906 in the first and second base calling iterations, which replace the overlapping temporal maps 176 and 278 in the third base calling iteration. The compressed temporal maps can be stored in memory (e.g., on-chip DRM, on-chip SRAM or BRAM, off-chip DRAM).

Figure 10B:
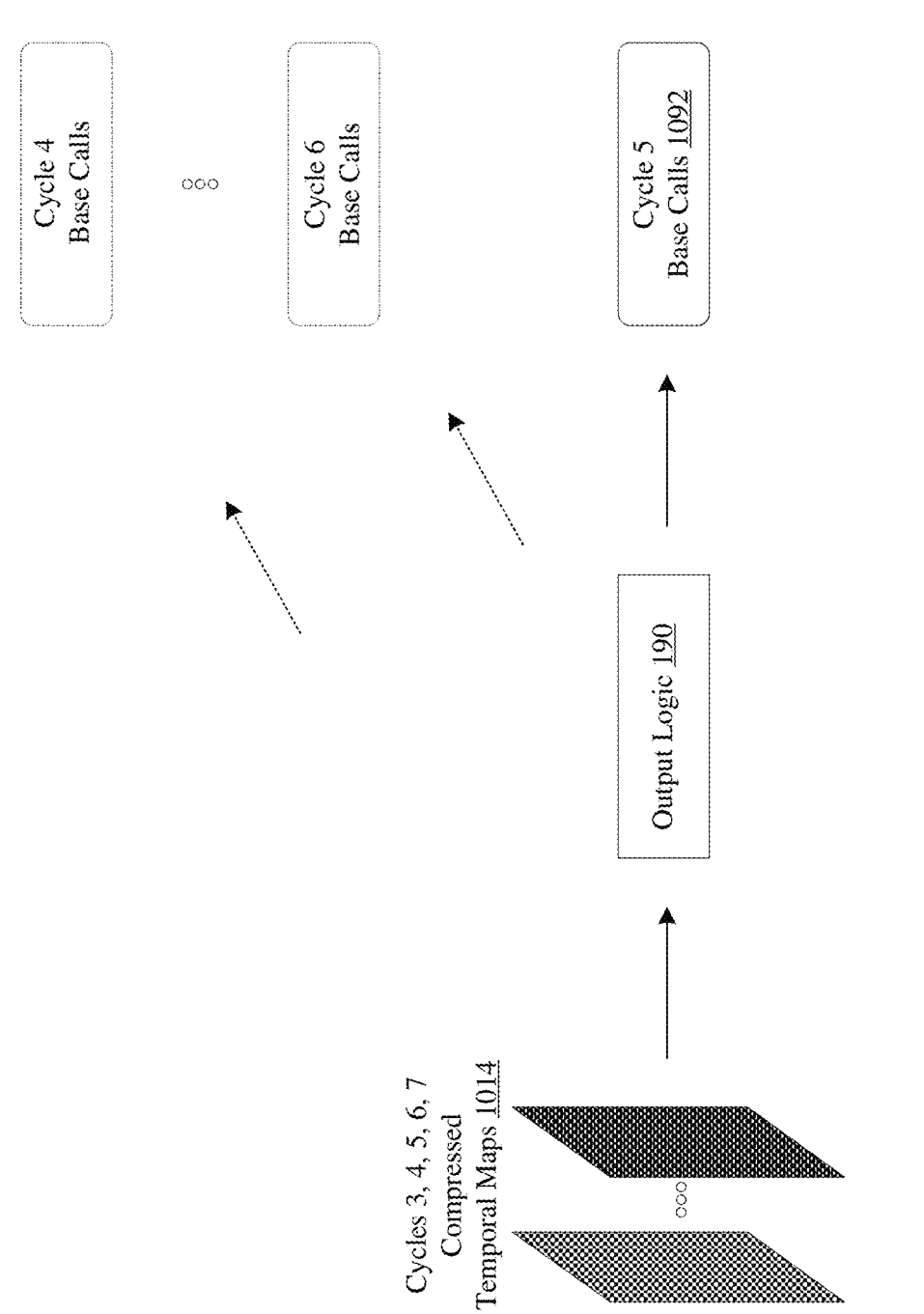
FIG. 10B shows that the output layer processes a final compressed temporal map set generated during the third iteration of base calling and produces base calls for the center sequencing cycle 5.

FIG. 10A also shows processing the non-overlapping temporal maps 378 (i.e., non-overlapping between the second and third base calling iterations) through the compression logic 108 to generate compressed temporal maps 1006. The compressed temporal map sets 806, 906, and 1006 are processed by the second temporal convolution layer of the temporal network 160 in a manner similar to the one discussed above with respect to FIG. 1B to generate a final compressed temporal feature map set 1014. FIG. 10B shows that the output layer 190 processes the final compressed temporal feature map set 1014 generated during the third iteration of base calling and produces base calls 1092 for the center sequencing cycle 5.

Figure 11A:
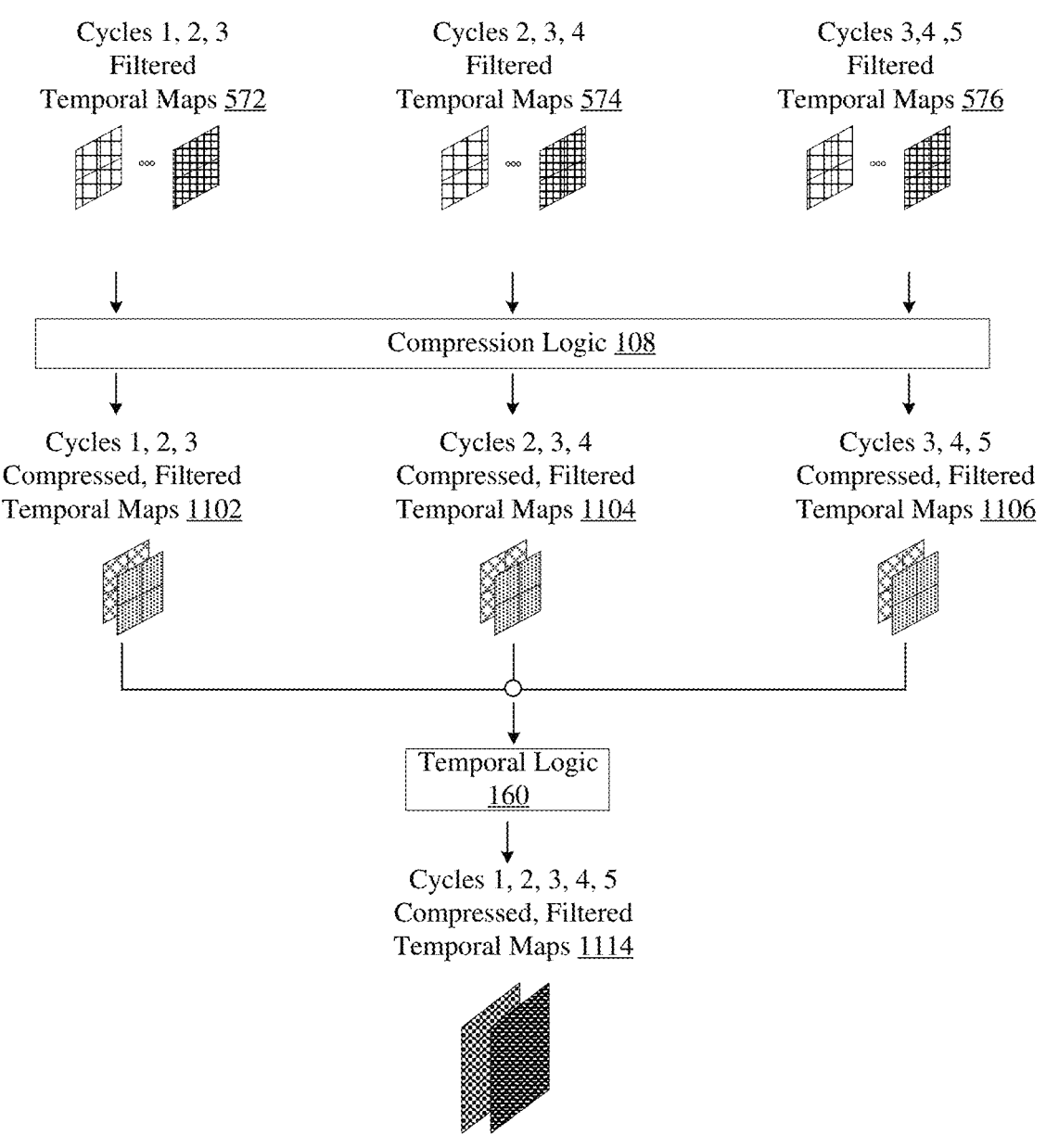
FIG. 11A shows one implementation of processing the sets of filtered temporal feature maps generated during the first iteration of base calling through the compression logic to generate respective sets of compressed, filtered temporal feature maps.
Figure 11B:
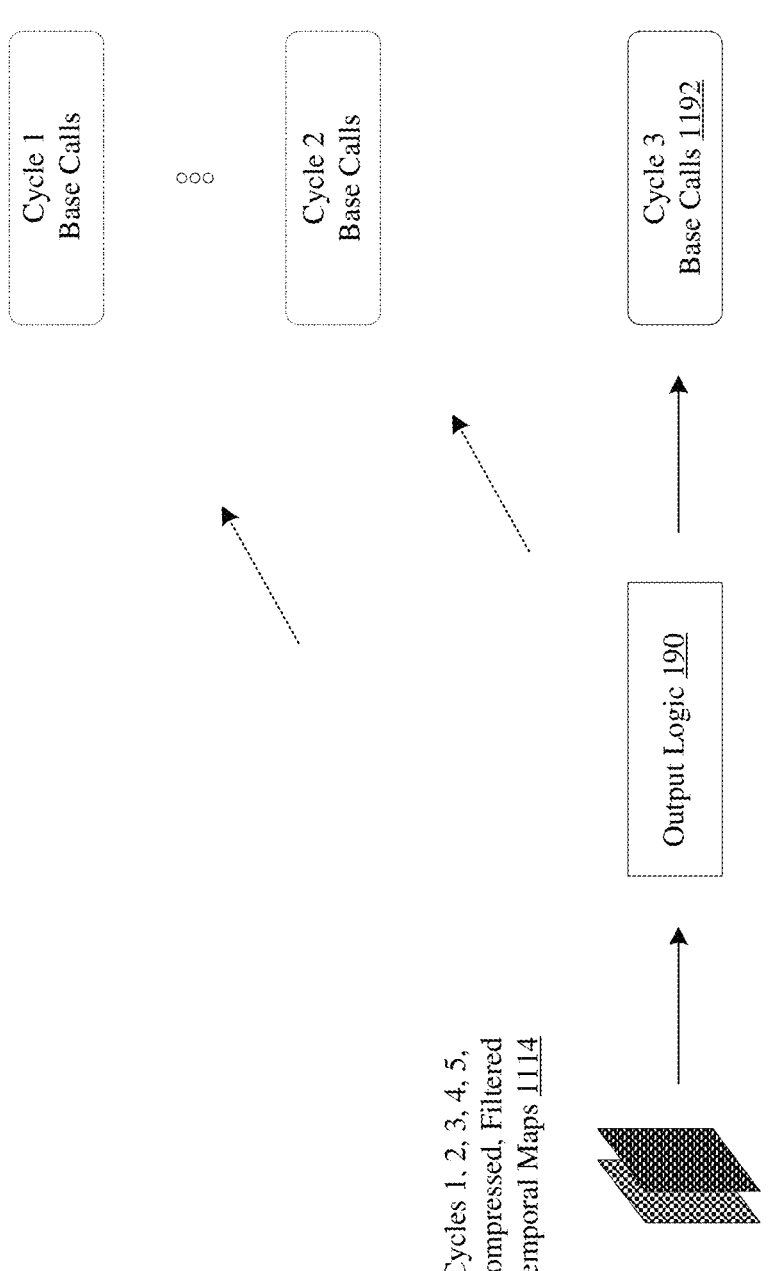
FIG. 11B shows that the output layer processes a final compressed, filtered temporal map set generated during the first iteration of base calling and produces base calls for the center sequencing cycle 3.

FIG. 11A shows one implementation of processing the sets of filtered temporal feature maps 572, 574, and 576 generated during the first iteration of base calling through the compression logic 108 to generate respective sets of compressed, filtered temporal feature maps 1102, 1104, and 1306. The compressed, filtered temporal feature map sets 1102, 1104, and 1106 (depicting only reliable clusters) are generated by the compression logic 108 in a manner similar to the one discussed above with respect to FIGS. 1E and 1F. That is, for example, if the first filtered temporal feature map set 572 has, for example, twenty-one feature maps (or channels or depth=21), then the compression logic 108 can configure the corresponding compressed, filtered temporal feature map set 1102 to have one, two, three, or four feature maps. The sets of compressed, filtered temporal feature maps 1102, 1104, and 1106 are processed by the second filtered temporal convolution layer of the filtered temporal network 160 in a manner similar to the one discussed above with respect to FIG. 1B to generate a final compressed, filtered temporal feature map set 1114. FIG. 8B shows that the output layer 190 processes the final compressed, filtered temporal feature map set 1114 generated during the first iteration of base calling and produces base calls 1192 for the center sequencing cycle 3.

In other implementations, the compression logic 108 can configure the corresponding compressed feature map sets to each have more than four feature maps.

Figure 12A:
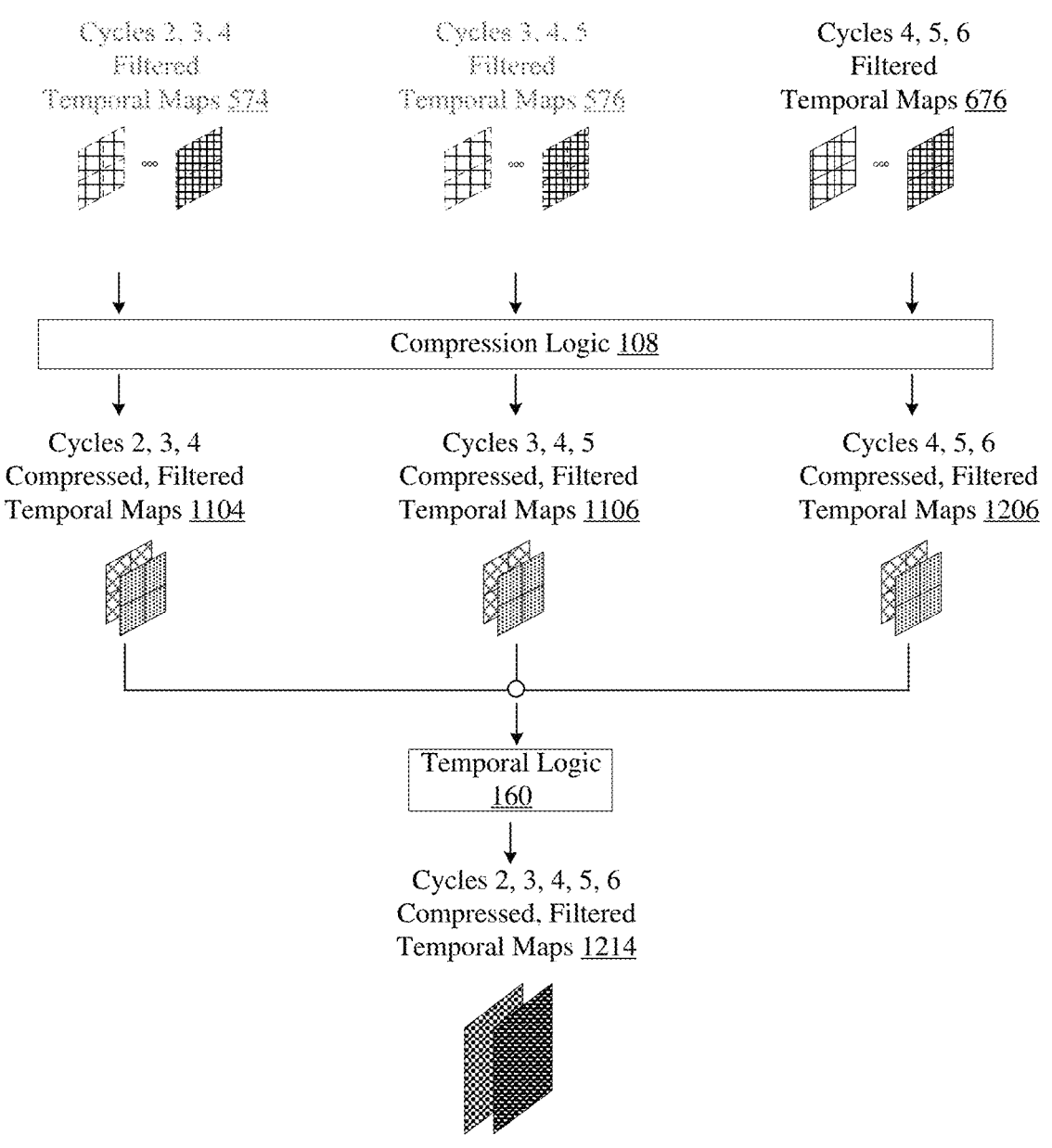
FIG. 12A shows that the compressed, filtered temporal map sets generated during the first base calling iteration are used in conjunction with a compressed, filtered temporal map set generated during the second iteration of base calling to generate base calls for the center sequencing cycle 4.

FIG. 12A shows one implementation of reusing, in the second base calling iteration, those compressed, filtered temporal maps that were generated in the first base calling iteration. That is, the first and second sets of compressed, filtered temporal maps 1104 and 1106 were generated in FIG. 11A for the first base calling iteration and are now repurposed in the second base calling iteration shown in FIGS. 12A and 2B.

Note that the first and second sets of compressed, filtered temporal maps 1104 and 1106 were generated in FIG. 11A from the first and second sets of filtered temporal maps 572 and 574. Further note that the first and second sets of filtered temporal maps 572 and 574 were generated in FIG. 5A from the compressed, filtered spatial maps 510, 520, 530, and 540, which in turn were generated in FIG. 5A from the respective compressed spatial maps 110, 120, 130, and 140, which in turn were generated in FIG. 1A from the respective spatial maps 106, 116, 126, and 136, which in turn were generated in FIG. 1A from the respective image patches 102, 112, 122, and 132.

Unlike FIGS. 5A, 6A, and 7A that redundantly generate overlapping filtered temporal maps 572, 574, and 576, in FIG. 12A, the overlapping filtered temporal maps 574 and 576 (depicted in FIG. 12A with dotted lines and ghost text) are not redundantly generated from FIG. 11A (the first base calling iteration) to FIG. 12A (the second base calling iteration). This occurs because the compression logic 108 is incorporated into the filtered temporal network 160 to generate the first and second sets of compressed, filtered temporal maps 1104 and 1106 in the first base calling iteration, which replace the overlapping filtered temporal maps 574 and 576 in the second base calling iteration. The compressed, filtered temporal maps can be stored in memory (e.g., on-chip DRM, on-chip SRAM or BRAM, off-chip DRAM).

Figure 12B:
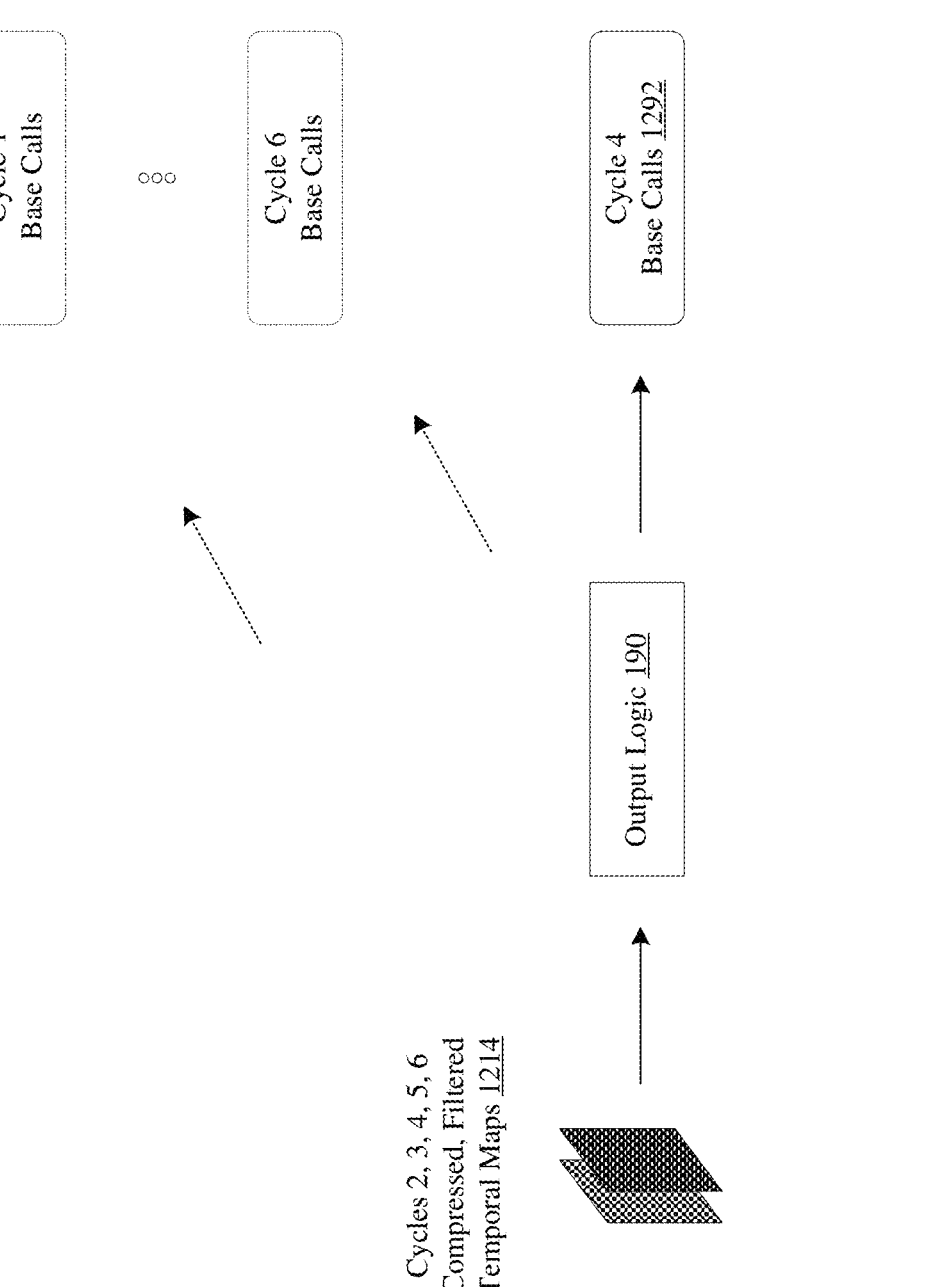
FIG. 12B shows that the output layer processes a final compressed, filtered temporal map set generated during the second iteration of base calling and produces base calls for the center sequencing cycle 4.

FIG. 12A also shows processing the non-overlapping filtered temporal maps 676 (i.e., non-overlapping between the first and second base calling iterations) through the compression logic 108 to generate compressed, filtered temporal maps 1206 (depicting only reliable clusters). The compressed, filtered temporal map sets 1104, 1106, and 1206 are processed by the second filtered temporal convolution layer of the filtered temporal network 160 in a manner similar to the one discussed above with respect to FIG. 1B to generate a final compressed, filtered temporal feature map set 1214. FIG. 12B shows that the output layer 190 processes the final compressed, filtered temporal feature map set 1214 generated during the second iteration of base calling and produces base calls 1292 for the center sequencing cycle 4.

Figure 13A:
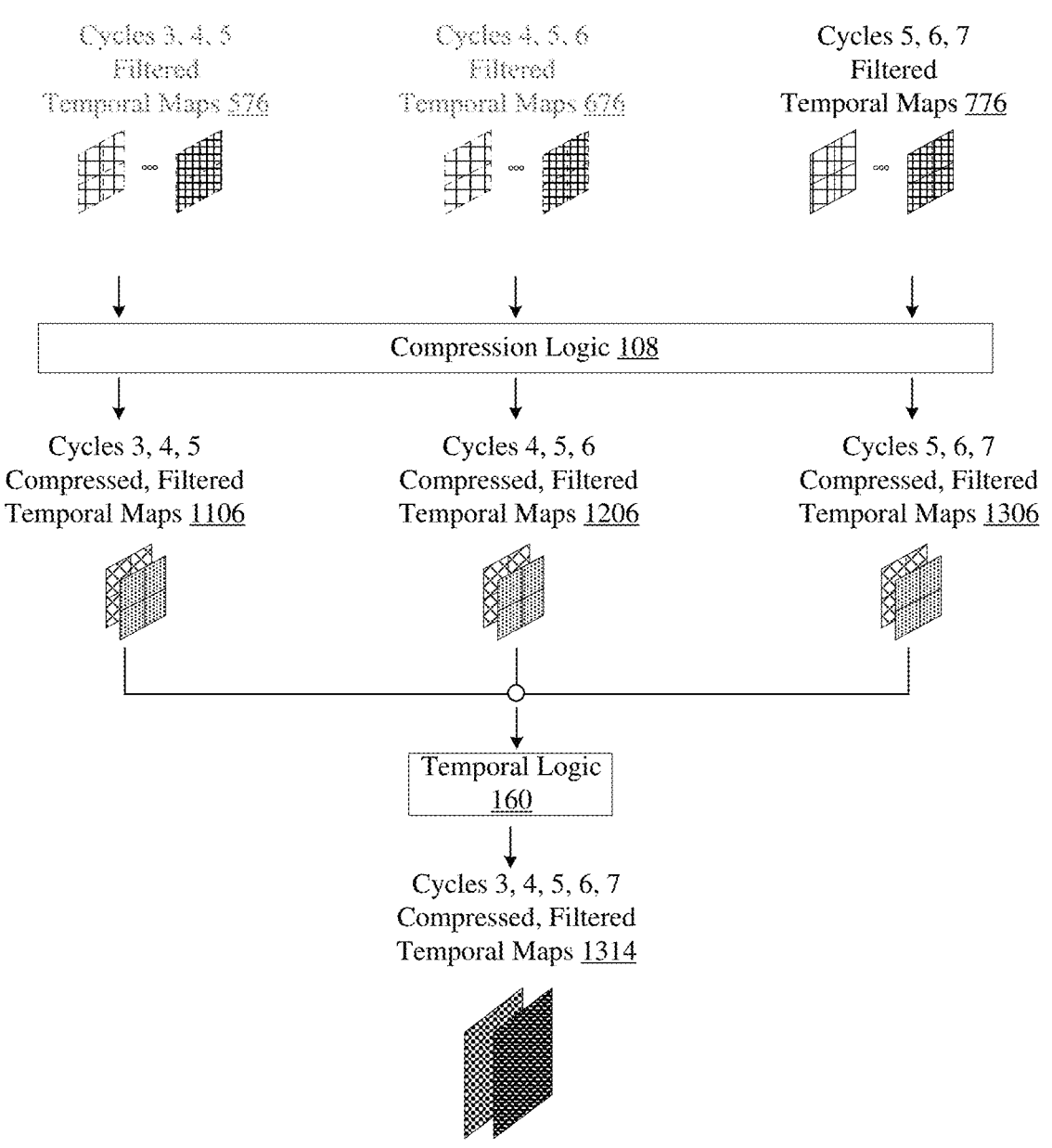
FIG. 13A shows that the compressed, filtered temporal map sets generated during the first and second base calling iterations are used in conjunction with a compressed, filtered temporal map set generated during the third iteration of base calling to generate base calls for the center sequencing cycle 5.

Unlike FIGS. 5A, 6A, and 7A that redundantly generate overlapping filtered temporal maps 574, 576, and 676, in FIG. 13A, the overlapping filtered temporal maps 576 and 676 (depicted in FIG. 13A with dotted lines and ghost text) are not redundantly generated from FIG. 12A (the second base calling iteration) to FIG. 13A (the third base calling iteration). This occurs because the compression logic 108 is incorporated into the filtered temporal network 160 to generate the first and second sets of compressed, filtered temporal maps 1106 and 1206 in the first and second base calling iterations, which replace the overlapping filtered temporal maps 576 and 676 in the third base calling iteration. The compressed, filtered temporal maps can be stored in memory (e.g., on-chip DRM, on-chip SRAM or BRAM, off-chip DRAM).

Figure 13B:
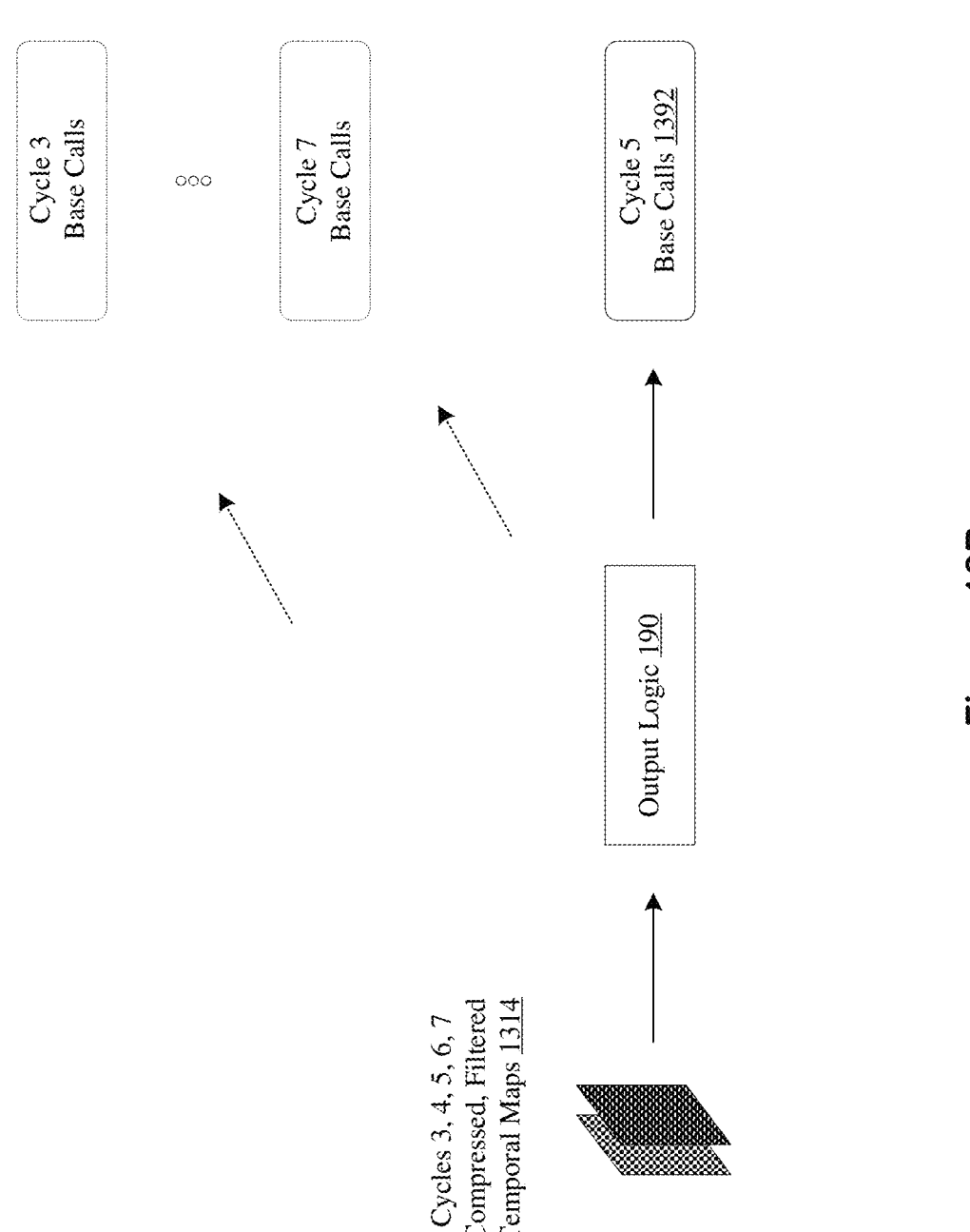
FIG. 13B shows that the output layer processes a final compressed, filtered temporal map set generated during the third iteration of base calling and produces base calls for the center sequencing cycle 5.

FIG. 13A also shows processing the non-overlapping filtered temporal maps 776 (i.e., non-overlapping between the second and third base calling iterations) through the compression logic 108 to generate compressed, filtered temporal maps 1306 (depicting only reliable clusters). The compressed, filtered temporal map sets 1106, 1206, and 1306 are processed by the second filtered temporal convolution layer of the filtered temporal network 160 in a manner similar to the one discussed above with respect to FIG. 1B to generate a final compressed, filtered temporal feature map set 1314. FIG. 13B shows that the output layer 190 processes the final compressed, filtered temporal feature map set 1314 generated during the third iteration of base calling and produces base calls 1392 for the center sequencing cycle 5.

FIG. 14 illustrates a first example architecture of the neural network-based base caller 100. In the illustrated implementation, the neural network-based base caller 100 comprises the spatial network 104, the compression network 108, and the temporal network 160. The spatial network 104 comprises seven spatial convolution layers. The compression network 108 comprises a compression layer. The temporal network 160 comprises two temporal convolution layers.

Each of the seven spatial convolution layers can have a same number of convolution filters or can have a different number of convolution filters. The first spatial convolution layer can have S1 number of filters, where S1 can be, for example, 7, 14, 21, 64, 128, or 254. The second spatial convolution layer can have S2 number of filters, where S2 can be, for example, 7, 14, 21, 64, 128, or 254. The third spatial convolution layer can have S3 number of filters, where S3 can be, for example, 7, 14, 21, 64, 128, or 254. The fourth spatial convolution layer can have S4 number of filters, where S4 can be, for example, 7, 14, 21, 64, 128, or 254. The fifth spatial convolution layer can have S5 number of filters, where S5 can be, for example, 7, 14, 21, 64, 128, or 254. The sixth spatial convolution layer can have S6 number of filters, where S6 can be, for example, 7, 14, 21, 64, 128, or 254. The seventh spatial convolution layer can have S7 number of filters, where S7 can be, for example, 7, 14, 21, 64, 128, or 254.

The compression layer can have C1 number of filters, where C1 can be, for example, 1, 2, 3, 4, or more.

Each of the two temporal convolution layers can have a same number of convolution filters or can have a different number of convolution filters. The first temporal convolution layer can have T1 number of filters, where T1 can be, for example, 7, 14, 21, 64, 128, or 254. The second temporal convolution layer can have T2 number of filters, where T2 can be, for example, 7, 14, 21, 64, 128, or 254. FIG. 14 also shows feature maps 1412 generated by each of the layers of the neural network-based base caller 100.

FIG. 15 illustrates a second example architecture of the neural network-based base caller 100. FIG. 15 shows the filtering logic 502 as part of the neural network-based base caller 100. In other implementations, the filtering logic 502 is not part of the neural network-based base caller 100. The compressed feature maps C1 have a spatial dimensionality of P1×P2. The filtering logic 502 filters out those pixels in the compressed feature maps C1 that correspond to unreliable clusters, and generates compressed, filtered feature maps F1 with the spatial dimensionality of P3×P4. The compressed, filtered feature maps F1 depict only reliable clusters. In one implementation, the filtering logic 502 discards 75% of the pixels in the compressed feature maps C1 and therefore P3 is 25% of P1 and P4 is 25% of P2. FIG. 15 also shows feature maps 1512 generated by each of the layers of the neural network-based base caller 100.

Figure 16:
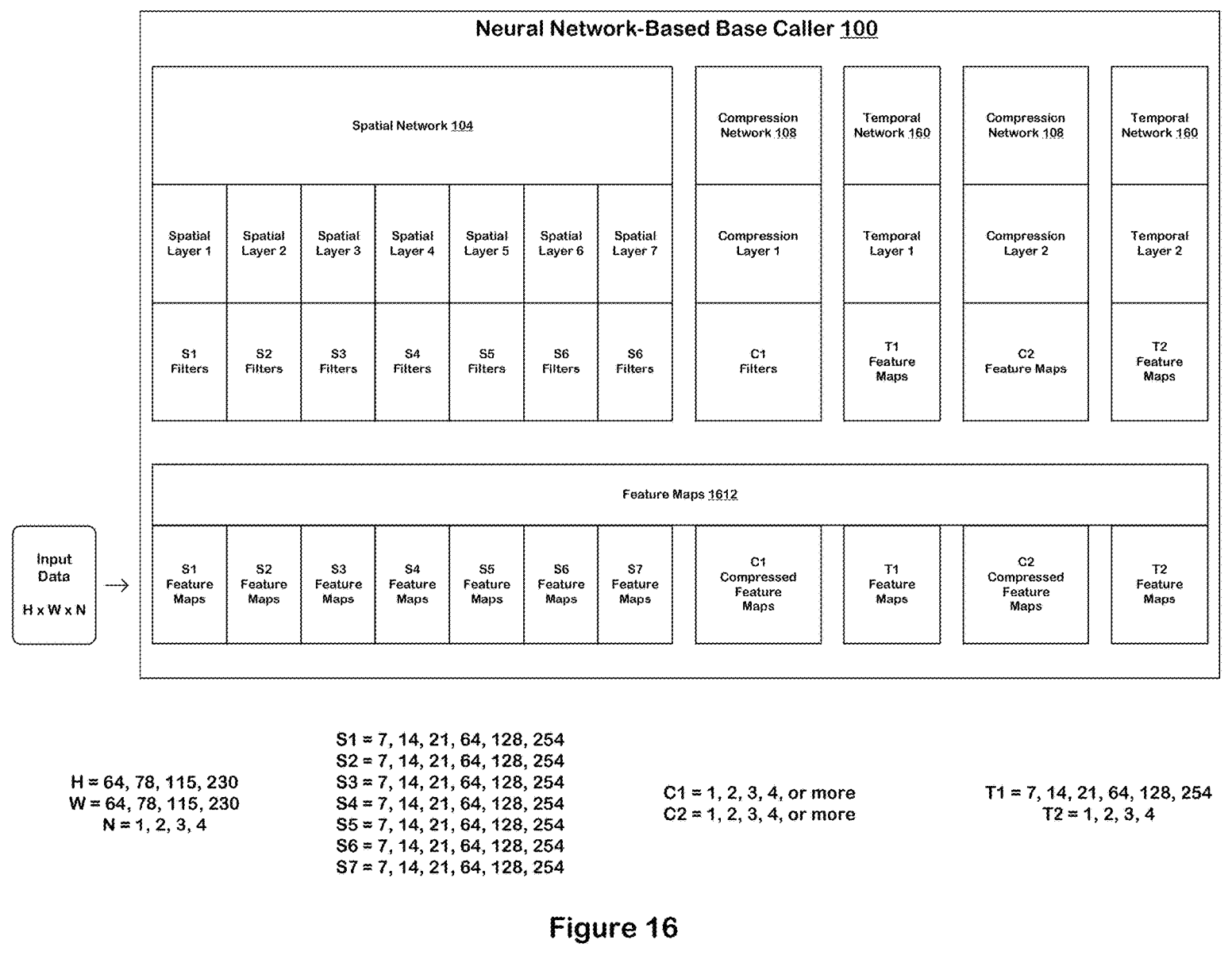

FIG. 16 illustrates a third example architecture of the neural network-based base caller 100. FIG. 16 shows that the compression network 108 is used to compress outputs of the spatial network 104 as well as the temporal network 160. FIG. 16 also shows feature maps 1612 generated by each of the layers of the neural network-based base caller 100.

FIG. 17 illustrates a fourth example architecture of the neural network-based base caller 100. FIG. 17 shows that the filtering logic 502 is applied to the compressed outputs of the spatial network 104 to generate compressed and filtered temporal outputs from the temporal network 160. FIG. 17 also shows feature maps 1712 generated by each of the layers of the neural network-based base caller 100.

Figure 18:
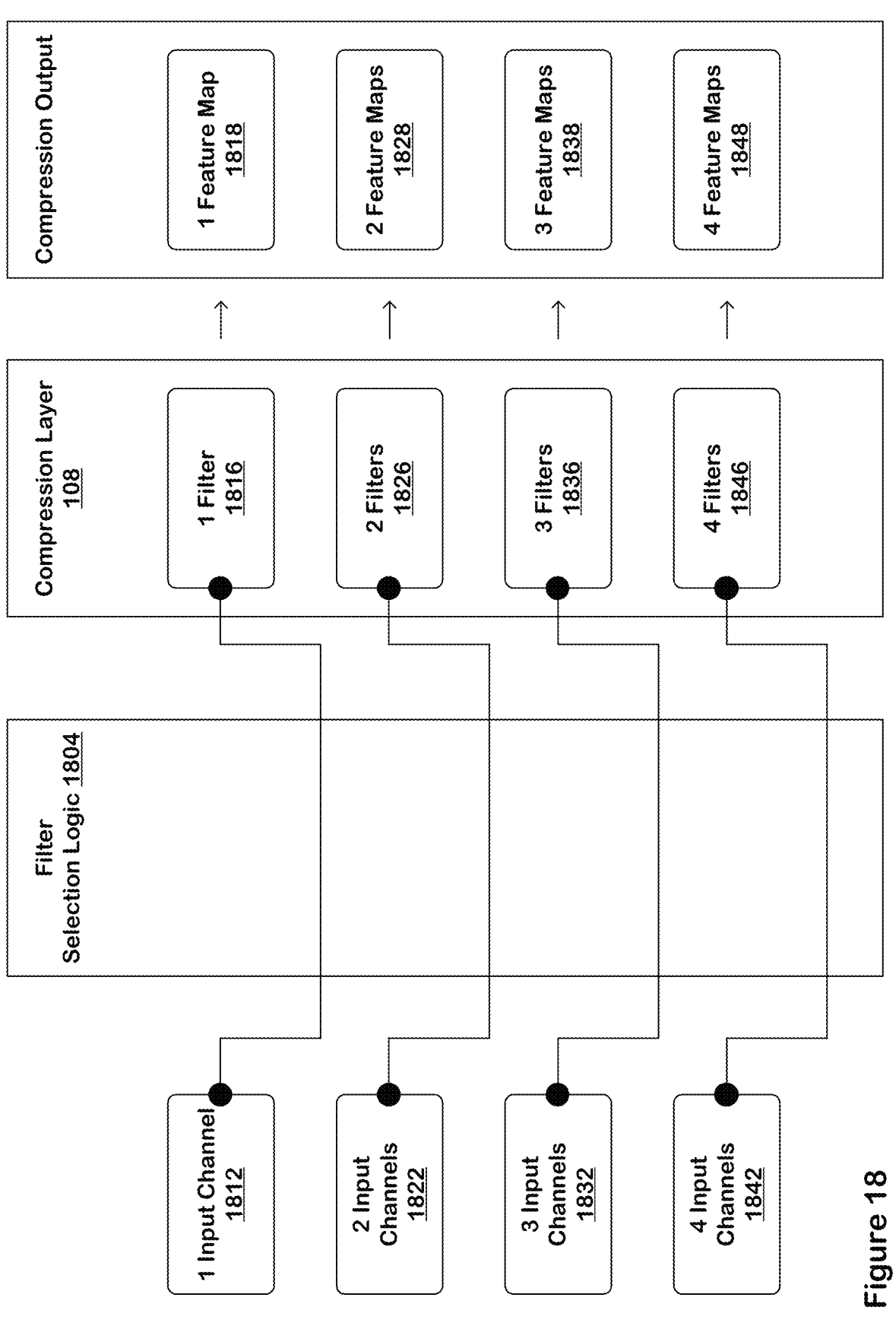
FIG. 18 shows one implementation of a filter configuration logic that configures a count (or numerosity) of convolution filters in the compression layer in dependence upon a number of channels in the input data.

FIG. 18 shows one implementation of a filter configuration logic 1804 that configures a count (or numerosity) of convolution filters in the compression layer 108 in dependence upon a number of channels in the input data. This allows the compressed feature maps to be lossless representatives of the input data. In some implementations, the input data can be overwritten in memory with the corresponding compressed representation for reuse in subsequent sequencing cycles.

In one implementation, for input data that contains only one channel 1812 in each per-cycle input (e.g., only one image channel), the filter configuration logic 1804 configures the compression layer 108 with only one convolution filter 1816 that generates only one compressed feature map 1818 per-sequencing cycle. In another implementation, for input data that contains two channels 1822 in each per-cycle input (e.g., two image channels like blue and green image channels in the sequencing images corresponding to blue and green lasers), the filter configuration logic 1804 configures the compression layer 108 with two convolution filters 1826 that generate two compressed feature maps 1828 per-sequencing cycle. In yet another implementation, for input data that contains three channels 1832 in each per-cycle input (e.g., three image channels), the filter configuration logic 1804 configures the compression layer 108 with three convolution filters 1836 that generate three compressed feature maps 1838 per-sequencing cycle. In yet further implementation, for input data that contains four channels 1842 in each per-cycle input (e.g., four image channels like A, C, T, and G channels in the sequencing images corresponding to the nucleotides A, C, T, and G), the filter configuration logic 1804 configures the compression layer 108 with four convolution filters 1846 that generate four compressed feature maps 1848 per-sequencing cycle. In other implementations, the compression logic 108 can configure the corresponding compressed feature map sets to each have more than four feature maps, and therefore select more than four filters for the compression layer 108.

Figure 19A:
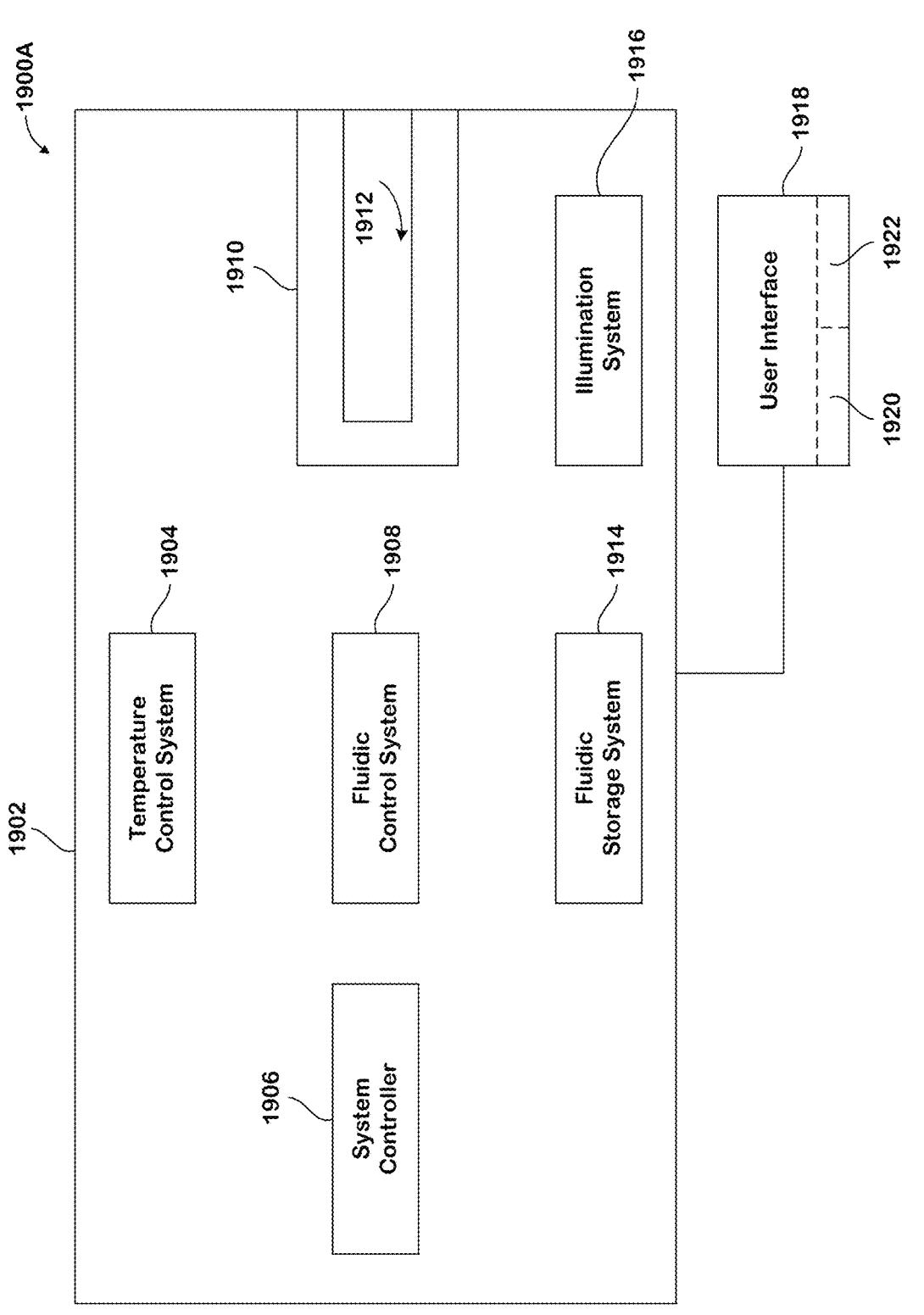
FIGS. 19A and 19B depict one implementation of a sequencing system. The sequencing system comprises a configurable processor.
Figure 19B:
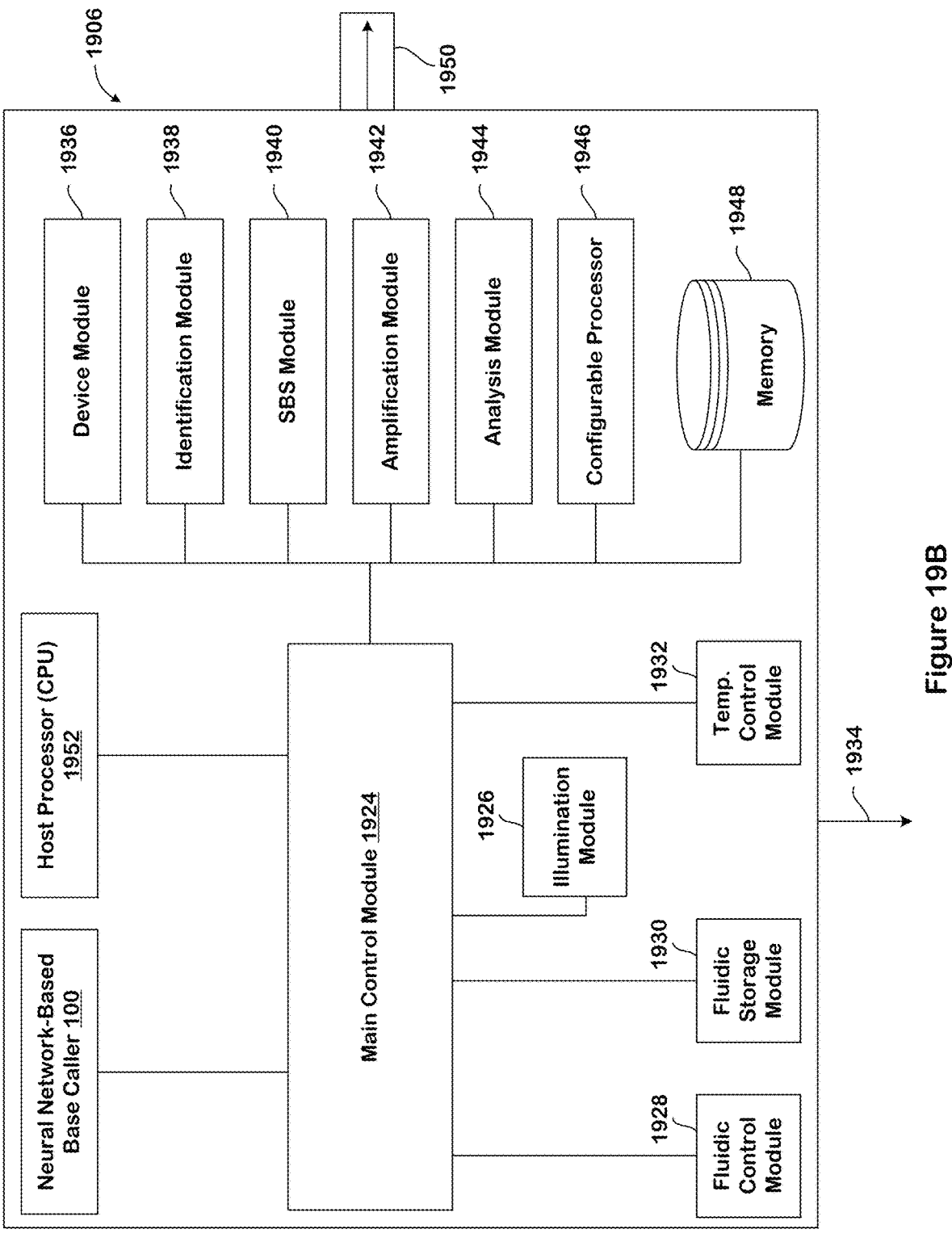

FIGS. 19A and 19B depict one implementation of a sequencing system 1900A. The sequencing system 1900A comprises a configurable processor 1946. The configurable processor 1946 implements the base calling techniques disclosed herein. The sequencing system is also referred to as a "sequencer."

The sequencing system 1900A can operate to obtain any information or data that relates to at least one of a biological or chemical substance. In some implementations, the sequencing system 1900A is a workstation that may be similar to a bench-top device or desktop computer. For example, a majority (or all) of the systems and components for conducting the desired reactions can be within a common housing 1902.

In particular implementations, the sequencing system 1900A is a nucleic acid sequencing system configured for various applications, including but not limited to de novo sequencing, resequencing of whole genomes or target genomic regions, and metagenomics. The sequencer may also be used for DNA or RNA analysis. In some implementations, the sequencing system 1900A may also be configured to generate reaction sites in a biosensor. For example, the sequencing system 1900A may be configured to receive a sample and generate surface attached clusters of clonally amplified nucleic acids derived from the sample. Each cluster may constitute or be part of a reaction site in the biosensor.

The exemplary sequencing system 1900A may include a system receptacle or interface 1910 that is configured to interact with a biosensor 1912 to perform desired reactions within the biosensor 1912. In the following description with respect to FIG. 19A, the biosensor 1912 is loaded into the system receptacle 1910. However, it is understood that a cartridge that includes the biosensor 1912 may be inserted into the system receptacle 1910 and in some states the cartridge can be removed temporarily or permanently. As described above, the cartridge may include, among other things, fluidic control and fluidic storage components.

In particular implementations, the sequencing system 1900A is configured to perform a large number of parallel reactions within the biosensor 1912. The biosensor 1912 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 1912 may include a solid-state imaging device (e.g., CCD or CMOS imager) and a flow cell mounted thereto. The flow cell may include one or more flow channels that receive a solution from the sequencing system 1900A and direct the solution toward the reaction sites. Optionally, the biosensor 1912 can be configured to engage a thermal element for transferring thermal energy into or out of the flow channel.

The sequencing system 1900A may include various components, assemblies, and systems (or sub-systems) that interact with each other to perform a predetermined method or assay protocol for biological or chemical analysis. For example, the sequencing system 1900A includes a system controller 1906 that may communicate with the various components, assemblies, and sub-systems of the sequencing system 1900A and also the biosensor 1912. For example, in addition to the system receptacle 1910, the sequencing system 1900A may also include a fluidic control system 1908 to control the flow of fluid throughout a fluid network of the sequencing system 1900A and the biosensor 1912; a fluid storage system 1914 that is configured to hold all fluids (e.g., gas or liquids) that may be used by the bioassay system; a temperature control system 1904 that may regulate the temperature of the fluid in the fluid network, the fluid storage system 1914, and/or the biosensor 1912; and an illumination system 1916 that is configured to illuminate the biosensor 1912. As described above, if a cartridge having the biosensor 1912 is loaded into the system receptacle 1910, the cartridge may also include fluidic control and fluidic storage components.

Also shown, the sequencing system 1900A may include a user interface 1918 that interacts with the user. For example, the user interface 1918 may include a display 1920 to display or request information from a user and a user input device 1922 to receive user inputs. In some implementations, the display 1920 and the user input device 1922 are the same device. For example, the user interface 1918 may include a touch-sensitive display configured to detect the presence of an individual's touch and also identify a location of the touch on the display. However, other user input devices 1922 may be used, such as a mouse, touchpad, keyboard, keypad, handheld scanner, voice-recognition system, motion-recognition system, and the like. As will be discussed in greater detail below, the sequencing system 1900A may communicate with various components, including the biosensor 1912 (e.g., in the form of a cartridge), to perform the desired reactions. The sequencing system 1900A may also be configured to analyze data obtained from the biosensor to provide a user with desired information.

The system controller 1906 may include any processor-based or microprocessor-based system, including systems using microcontrollers, reduced instruction set computers (RISC), application specific integrated circuits (ASICs), field programmable gate array (FPGAs), coarse-grained reconfigurable architectures (CGRAs), logic circuits, and any other circuit or processor capable of executing functions described herein. The above examples are exemplary only, and are thus not intended to limit in any way the definition and/or meaning of the term system controller. In the exemplary implementation, the system controller 1906 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the sequencing system 1900A.

The set of instructions may include various commands that instruct the sequencing system 1900A or biosensor 1912 to perform specific operations such as the methods and processes of the various implementations described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the sequencing system 1900A, processed in response to user inputs, or processed in response to a request made by another processing machine (e.g., a remote request through a communication link). In the illustrated implementation, the system controller 1906 includes an analysis module 1944. In other implementations, system controller 1906 does not include the analysis module 1944 and instead has access to the analysis module 1944 (e.g., the analysis module 1944 may be separately hosted on cloud).

The system controller 1906 may be connected to the biosensor 1912 and the other components of the sequencing system 1900A via communication links. The system controller 1906 may also be communicatively connected to off-site systems or servers. The communication links may be hardwired, corded, or wireless. The system controller 1906 may receive user inputs or commands, from the user interface 1918 and the user input device 1922.

The fluidic control system 1908 includes a fluid network and is configured to direct and regulate the flow of one or more fluids through the fluid network. The fluid network may be in fluid communication with the biosensor 1912 and the fluid storage system 1914. For example, select fluids may be drawn from the fluid storage system 1914 and directed to the biosensor 1912 in a controlled manner, or the fluids may be drawn from the biosensor 1912 and directed toward, for example, a waste reservoir in the fluid storage system 1914. Although not shown, the fluidic control system 1908 may include flow sensors that detect a flow rate or pressure of the fluids within the fluid network. The sensors may communicate with the system controller 1906.

The temperature control system 1904 is configured to regulate the temperature of fluids at different regions of the fluid network, the fluid storage system 1914, and/or the biosensor 1912. For example, the temperature control system 1904 may include a thermocycler that interfaces with the biosensor 1912 and controls the temperature of the fluid that flows along the reaction sites in the biosensor 1912. The temperature control system 1904 may also regulate the temperature of solid elements or components of the sequencing system 1900A or the biosensor 1912. Although not shown, the temperature control system 1904 may include sensors to detect the temperature of the fluid or other components. The sensors may communicate with the system controller 1906.

The fluid storage system 1914 is in fluid communication with the biosensor 1912 and may store various reaction components or reactants that are used to conduct the desired reactions therein. The fluid storage system 1914 may also store fluids for washing or cleaning the fluid network and biosensor 1912 and for diluting the reactants. For example, the fluid storage system 1914 may include various reservoirs to store samples, reagents, enzymes, other biomolecules, buffer solutions, aqueous, and non-polar solutions, and the like. Furthermore, the fluid storage system 1914 may also include waste reservoirs for receiving waste products from the biosensor 1912. In implementations that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 1916 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In implementations that use an illumination system, the illumination system 1916 may be configured to direct an excitation light to reaction sites. As one example, fluorophores may be excited by green wavelengths of light, as such the wavelength of the excitation light may be approximately 1932 nm. In one implementation, the illumination system 1916 is configured to produce illumination that is parallel to a surface normal of a surface of the biosensor 1912. In another implementation, the illumination system 1916 is configured to produce illumination that is off-angle relative to the surface normal of the surface of the biosensor 1912. In yet another implementation, the illumination system 1916 is configured to produce illumination that has plural angles, including some parallel illumination and some off-angle illumination.

The system receptacle or interface 1910 is configured to engage the biosensor 1912 in at least one of a mechanical, electrical, and fluidic manner. The system receptacle 1910 may hold the biosensor 1912 in a desired orientation to facilitate the flow of fluid through the biosensor 1912. The system receptacle 1910 may also include electrical contacts that are configured to engage the biosensor 1912 so that the sequencing system 1900A may communicate with the biosensor 1912 and/or provide power to the biosensor 1912. Furthermore, the system receptacle 1910 may include fluidic ports (e.g., nozzles) that are configured to engage the biosensor 1912. In some implementations, the biosensor 1912 is removably coupled to the system receptacle 1910 in a mechanical manner, in an electrical manner, and also in a fluidic manner.

In addition, the sequencing system 1900A may communicate remotely with other systems or networks or with other bioassay systems 1900A. Detection data obtained by the bioassay system(s) 1900A may be stored in a remote database.

FIG. 19B is a block diagram of a system controller 1906 that can be used in the system of FIG. 19A. In one implementation, the system controller 1906 includes one or more processors or modules that can communicate with one another. Each of the processors or modules may include an algorithm (e.g., instructions stored on a tangible and/or non-transitory computer readable storage medium) or sub-algorithms to perform particular processes. The system controller 1906 is illustrated conceptually as a collection of modules, but may be implemented utilizing any combination of dedicated hardware boards, DSPs, processors, etc. Alternatively, the system controller 1906 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 1950 may transmit information (e.g., commands) to or receive information (e.g., data) from the biosensor 1912 (FIG. 19A) and/or the sub-systems 1908, 1914, 1904 (FIG. 19A). In implementations, the communication port 1950 may output a plurality of sequences of pixel signals. A communication link 1934 may receive user input from the user interface 1918 (FIG. 19A) and transmit data or information to the user interface 1918. Data from the biosensor 1912 or sub-systems 1908, 1914, 1904 may be processed by the system controller 1906 in real-time during a bioassay session. Additionally or alternatively, data may be stored temporarily in a system memory during a bioassay session and processed in slower than real-time or off-line operation.

As shown in FIG. 19B, the system controller 1906 may include a plurality of modules 1926-1948 that communicate with a main control module 1924, along with a central processing unit (CPU) 1952. The main control module 1924 may communicate with the user interface 1918 (FIG. 19A). Although the modules 1926-1948 are shown as communicating directly with the main control module 1924, the modules 1926-1948 may also communicate directly with each other, the user interface 1918, and the biosensor 1912. Also, the modules 1926-1948 may communicate with the main control module 1924 through the other modules.

The plurality of modules 1926-1948 include system modules 1928-1932, 1926 that communicate with the sub-systems 1908, 1914, 1904, and 1916, respectively. The fluidic control module 1928 may communicate with the fluidic control system 1908 to control the valves and flow sensors of the fluid network for controlling the flow of one or more fluids through the fluid network. The fluid storage module 1930 may notify the user when fluids are low or when the waste reservoir is at or near capacity. The fluid storage module 1930 may also communicate with the temperature control module 1932 so that the fluids may be stored at a desired temperature. The illumination module 1926 may communicate with the illumination system 1916 to illuminate the reaction sites at designated times during a protocol, such as after the desired reactions (e.g., binding events) have occurred. In some implementations, the illumination module 1926 may communicate with the illumination system 1916 to illuminate the reaction sites at designated angles.

The plurality of modules 1926-1948 may also include a device module 1936 that communicates with the biosensor 1912 and an identification module 1938 that determines identification information relating to the biosensor 1912. The device module 1936 may, for example, communicate with the system receptacle 1910 to confirm that the biosensor has established an electrical and fluidic connection with the sequencing system 1900A. The identification module 1938 may receive signals that identify the biosensor 1912. The identification module 1938 may use the identity of the biosensor 1912 to provide other information to the user. For example, the identification module 1938 may determine and then display a lot number, a date of manufacture, or a protocol that is recommended to be run with the biosensor 1912.

The plurality of modules 1926-1948 also includes an analysis module 1944 (also called signal processing module or signal processor) that receives and analyzes the signal data (e.g., image data) from the biosensor 1912. Analysis module 1944 includes memory (e.g., RAM or Flash) to store detection/image data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 1918 to display desired information to the user. In some implementations, the signal data may be processed by the solid-state imager (e.g., CMOS image sensor) before the analysis module 1944 receives the signal data.

The analysis module 1944 is configured to obtain image data from the light detectors at each of a plurality of sequencing cycles. The image data is derived from the emission signals detected by the light detectors and process the image data for each of the plurality of sequencing cycles through the neural network-based base caller 100 and produce a base call for at least some of the analytes at each of the plurality of sequencing cycle. The light detectors can be part of one or more over-head cameras (e.g., Illumina's GAIIx's CCD camera taking images of the clusters on the biosensor 1912 from the top), or can be part of the biosensor 1912 itself (e.g., Illumina's iSeq's CMOS image sensors underlying the clusters on the biosensor 1912 and taking images of the clusters from the bottom).

The output of the light detectors is the sequencing images, each depicting intensity emissions of the clusters and their surrounding background. The sequencing images depict intensity emissions generated as a result of nucleotide incorporation in the sequences during the sequencing. The intensity emissions are from associated analytes and their surrounding background. The sequencing images are stored in memory 1948.

Protocol modules 1940 and 1942 communicate with the main control module 1924 to control the operation of the sub-systems 1908, 1914, and 1904 when conducting predetermined assay protocols. The protocol modules 1940 and 1942 may include sets of instructions for instructing the sequencing system 1900A to perform specific operations pursuant to predetermined protocols. As shown, the protocol module may be a sequencing-by-synthesis (SBS) module 1940 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g., as catalyzed by a polymerase enzyme) or ligation (e.g., catalyzed by a ligase enzyme). In a particular polymerase-based SBS implementation, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 1916 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for implementations that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 4196:193-199 (20019); WO 04/0119497; U.S. Pat. No. 7,0197,026; WO 91/066719; WO 07/123744; U.S. Pat. Nos. 7,329,492; 7,211,414; 7,3119,019; 7,4019,2191, and US 20019/01470190192, each of which is incorporated herein by reference.

For the nucleotide delivery step of an SBS cycle, either a single type of nucleotide can be delivered at a time, or multiple different nucleotide types (e.g., A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one implementation, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some implementations, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in US Pat. App. Ser. Nos. 61/19319,294 and 61/619,19719, which are incorporated herein by reference in their entireties. U.S. application Ser. No. 13/624,200, which was filed on Sep. 21, 2012, is also incorporated by reference in its entirety.

The plurality of protocol modules may also include a sample-preparation (or generation) module 1942 that is configured to issue commands to the fluidic control system 1908 and the temperature control system 1904 for amplifying a product within the biosensor 1912. For example, the biosensor 1912 may be engaged to the sequencing system 1900A. The amplification module 1942 may issue instructions to the fluidic control system 1908 to deliver necessary amplification components to reaction chambers within the biosensor 1912. In other implementations, the reaction sites may already contain some components for amplification, such as the template DNA and/or primers. After delivering the amplification components to the reaction chambers, the amplification module 1942 may instruct the temperature control system 1904 to cycle through different temperature stages according to known amplification protocols. In some implementations, the amplification and/or nucleotide incorporation is performed isothermally.

The SBS module 1940 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module 1940 may instruct the fluidic control system 1908 to direct a flow of reagent and enzyme solutions through the biosensor 1912. Exemplary reversible terminator-based SBS methods which can be utilized with the apparatus and methods set forth herein are described in US Patent Application Publication No. 2007/01667019 A1, US Patent Application Publication No. 2006/01196*3901 A1, U.S. Pat. No. 7,0197, 026, US Patent Application Publication No. 2006/0240439 A1, US Patent Application Publication No. 2006/ 021914714709 A1, PCT Publication No. WO 019/0619514, US Patent Application Publication No. 20019/014700900 A1, PCT Publication No. WO 06/019B199 and PCT Publication No. WO 07/014702191, each of which is incorporated herein by reference in its entirety. Exemplary reagents for reversible terminator-based SBS are described in U.S. Pat. Nos. 7,1941,444; 7,0197,026; 7,414,14716; 7,427,673; 7,1966,1937; 7,1992,4319 and WO 07/14193193619, each of which is incorporated herein by reference in its entirety.

In some implementations, the amplification and SBS modules may operate in a single assay protocol where, for example, template nucleic acid is amplified and subsequently sequenced within the same cartridge.

The sequencing system 1900A may also allow the user to reconfigure an assay protocol. For example, the sequencing system 1900A may offer options to the user through the user interface 1918 for modifying the determined protocol. For example, if it is determined that the biosensor 1912 is to be used for amplification, the sequencing system 1900A may request a temperature for the annealing cycle. Furthermore, the sequencing system 1900A may issue warnings to a user if a user has provided user inputs that are generally not acceptable for the selected assay protocol.

In implementations, the biosensor 1912 includes millions of sensors (or pixels), each of which generates a plurality of sequences of pixel signals over successive base calling cycles. The analysis module 1944 detects the plurality of sequences of pixel signals and attributes them to corresponding sensors (or pixels) in accordance to the row-wise and/or column-wise location of the sensors on an array of sensors.

Figure 19C:
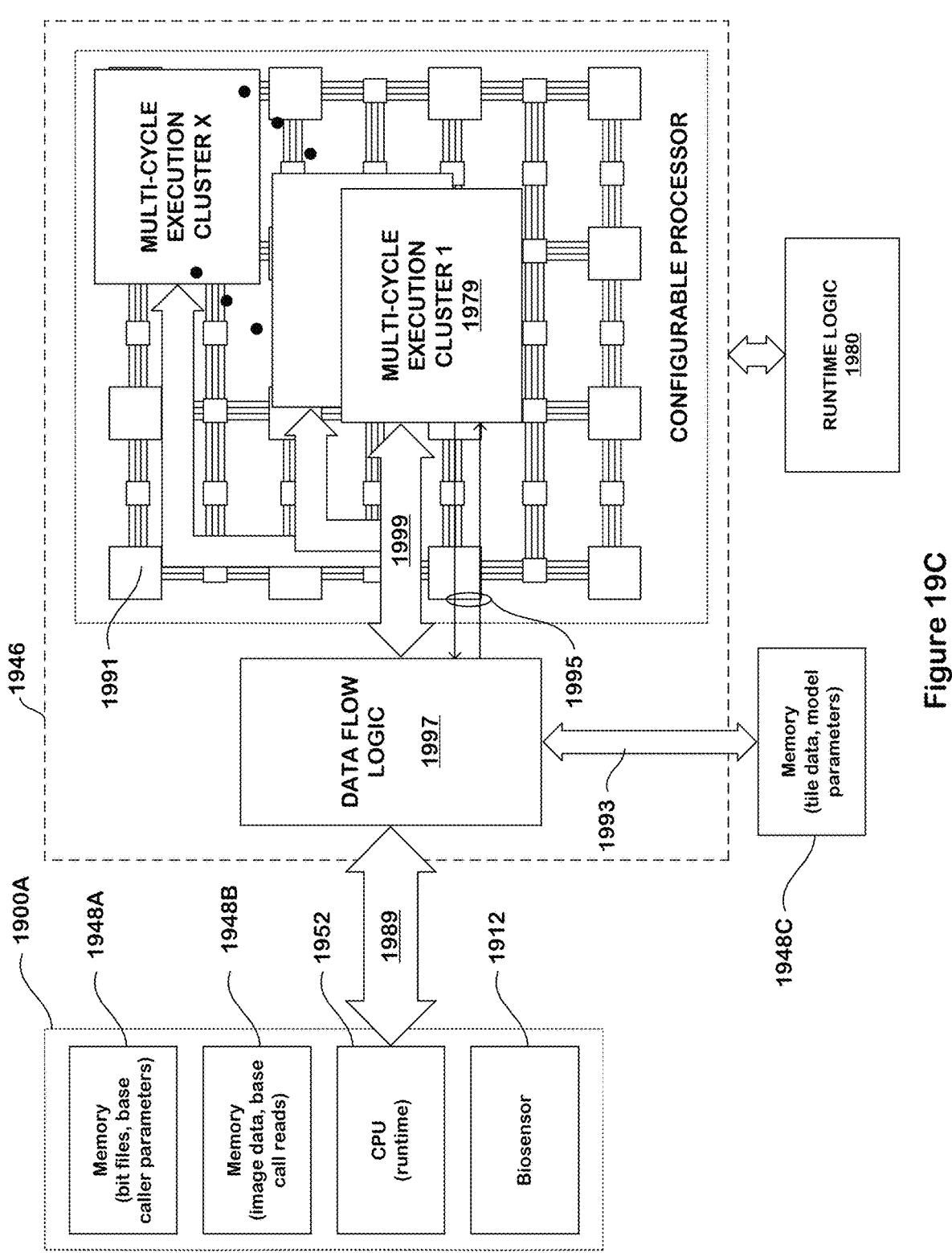
FIG. 19C is a simplified block diagram of a system for analysis of sensor data from the sequencing system, such as base call sensor outputs.

FIG. 19C is a simplified block diagram of a system for analysis of sensor data from the sequencing system 1900A, such as base call sensor outputs. In the example of FIG. 19C, the system includes the configurable processor 1946. The configurable processor 1946 can execute a base caller (e.g., the neural network-based base caller 100) in coordination with a runtime program/logic 1980 executed by the central processing unit (CPU) 1952 (i.e., a host processor). The sequencing system 1900A comprises the biosensor 1912 and flow cells. The flow cells can comprise one or more tiles in which clusters of genetic material are exposed to a sequence of analyte flows used to cause reactions in the clusters to identify the bases in the genetic material. The sensors sense the reactions for each cycle of the sequence in each tile of the flow cell to provide tile data. Genetic sequencing is a data intensive operation, which translates base call sensor data into sequences of base calls for each cluster of genetic material sensed in during a base call operation.

The system in this example includes the CPU 1952, which executes a runtime program/logic 1980 to coordinate the base call operations, memory 1948B to store sequences of arrays of tile data, base call reads produced by the base calling operation, and other information used in the base call operations. Also, in this illustration the system includes memory 1948A to store a configuration file (or files), such as FPGA bit files, and model parameters for the neural networks used to configure and reconfigure the configurable processor 1946, and execute the neural networks. The sequencing system 1900A can include a program for configuring a configurable processor and in some implementations a reconfigurable processor to execute the neural networks.

The sequencing system 1900A is coupled by a bus 1989 to the configurable processor 1946. The bus 1989 can be implemented using a high throughput technology, such as in one example bus technology compatible with the PCIe standards (Peripheral Component Interconnect Express) currently maintained and developed by the PCI-SIG (PCI Special Interest Group). Also in this example, a memory 1948C is coupled to the configurable processor 1946 by bus 1993. The memory 1948C can be on-board memory, disposed on a circuit board with the configurable processor 1946. The memory 1948C is used for high speed access by the configurable processor 1946 of working data used in the base call operation. The bus 1993 can also be implemented using a high throughput technology, such as bus technology compatible with the PCIe standards.

Configurable processors, including field programmable gate arrays FPGAs, coarse grained reconfigurable arrays CGRAs, and other configurable and reconfigurable devices, can be configured to implement a variety of functions more efficiently or faster than might be achieved using a general purpose processor executing a computer program. Configuration of configurable processors involves compiling a functional description to produce a configuration file, referred to sometimes as a bitstream or bit file, and distributing the configuration file to the configurable elements on the processor. The configuration file defines the logic functions to be executed by the configurable processor, by configuring the circuit to set data flow patterns, use of distributed memory and other on-chip memory resources, lookup table contents, operations of configurable logic blocks and configurable execution units like multiply-and-accumulate units, configurable interconnects and other elements of the configurable array. A configurable processor is reconfigurable if the configuration file may be changed in the field, by changing the loaded configuration file. For example, the configuration file may be stored in volatile SRAM elements, in non-volatile read-write memory elements, and in combinations of the same, distributed among the array of configurable elements on the configurable or reconfigurable processor. A variety of commercially available configurable processors are suitable for use in a base calling operation as described herein. Examples include Google's Tensor Processing Unit (TPU)™, rackmount solutions like GX4 Rackmount Series™, GX9 Rackmount Series™ NVIDIA DGX-1™, Microsoft' Stratix V FPGA™, Graphcore's Intelligent Processor Unit (IPU)™, Qualcomm's Zeroth Platform™ with Snapdragon processors™, NVIDIA's Volta™ NVIDIA's DRIVE PX™, NVIDIA's JETSON TX1/TX2 MODULE™, Intel's Nirvana™ Movidius VPU™, Fujitsu DPI™, ARM's DynamicIQ™, IBM TrueNorth™, Lambda GPU Server with Testa V100s™, Xilinx Alveo™ U200, Xilinx Alveo™ U2190, Xilinx Alveo™ U280, Intel/Altera Stratix™ GX2800, Intel/Altera Stratix™ GX2800, and Intel Stratix™ GX10M. In some examples, a host CPU can be implemented on the same integrated circuit as the configurable processor.

Implementations described herein implement the neural network-based base caller 100 using the configurable processor 1946. The configuration file for the configurable processor 1946 can be implemented by specifying the logic functions to be executed using a high level description language HDL or a register transfer level RTL language specification. The specification can be compiled using the resources designed for the selected configurable processor to generate the configuration file. The same or similar specification can be compiled for the purposes of generating a design for an application-specific integrated circuit which may not be a configurable processor.

Alternatives for the configurable processor configurable processor 1946, in all implementations described herein, therefore include a configured processor comprising an application specific ASIC or special purpose integrated circuit or set of integrated circuits, or a system-on-a-chip SOC device, or a graphics processing unit (GPU) processor or a coarse-grained reconfigurable architecture (CGRA) processor, configured to execute a neural network based base call operation as described herein.

In general, configurable processors and configured processors described herein, as configured to execute runs of a neural network, are referred to herein as neural network processors.

The configurable processor 1946 is configured in this example by a configuration file loaded using a program executed by the CPU 1952, or by other sources, which configures the array of configurable elements 1991 (e.g., configuration logic blocks (CLB) such as look up tables (LUTs), flip-flops, compute processing units (PMUs), and compute memory units (CMUs), configurable I/O blocks, programmable interconnects), on the configurable processor to execute the base call function. In this example, the configuration includes data flow logic 1997 which is coupled to the buses 1989 and 1993 and executes functions for distributing data and control parameters among the elements used in the base call operation.

Also, the configurable processor 1946 is configured with data flow logic 1997 to execute the neural network-based base caller 100. The logic 1997 comprises multi-cycle execution clusters (e.g., 1979) which, in this example, includes execution cluster 1 through execution cluster X. The number of multi-cycle execution clusters can be selected according to a trade-off involving the desired throughput of the operation, and the available resources on the configurable processor 1946.

The multi-cycle execution clusters are coupled to the data flow logic 1997 by data flow paths 1999 implemented using configurable interconnect and memory resources on the configurable processor 1946. Also, the multi-cycle execution clusters are coupled to the data flow logic 1997 by control paths 1995 implemented using configurable interconnect and memory resources for example on the configurable processor 1946, which provide control signals indicating available execution clusters, readiness to provide input units for execution of a run of the neural network-based base caller 100 to the available execution clusters, readiness to provide trained parameters for the neural network-based base caller 100, readiness to provide output patches of base call classification data, and other control data used for execution of the neural network-based base caller 100.

The configurable processor 1946 is configured to execute runs of the neural network-based base caller 100 using trained parameters to produce classification data for the sensing cycles of the base calling operation. A run of the neural network-based base caller 100 is executed to produce classification data for a subject sensing cycle of the base calling operation. A run of the neural network-based base caller 100 operates on a sequence including a number N of arrays of tile data from respective sensing cycles of N sensing cycles, where the N sensing cycles provide sensor data for different base call operations for one base position per operation in time sequence in the examples described herein. Optionally, some of the N sensing cycles can be out of sequence if needed according to a particular neural network model being executed. The number N can be any number greater than one. In some examples described herein, sensing cycles of the N sensing cycles represent a set of sensing cycles for at least one sensing cycle preceding the subject sensing cycle and at least one sensing cycle following the subject cycle in time sequence. Examples are described herein in which the number N is an integer equal to or greater than five.

The data flow logic 1997 is configured to move tile data and at least some trained parameters of the model parameters from the memory 1948A to the configurable processor 1946 for runs of the neural network-based base caller 100, using input units for a given run including tile data for spatially aligned patches of the N arrays. The input units can be moved by direct memory access operations in one DMA operation, or in smaller units moved during available time slots in coordination with the execution of the neural network deployed.

Tile data for a sensing cycle as described herein can comprise an array of sensor data having one or more features. For example, the sensor data can comprise two images which are analyzed to identify one of four bases at a base position in a genetic sequence of DNA, RNA, or other genetic material. The tile data can also include metadata about the images and the sensors. For example, in implementations of the base calling operation, the tile data can comprise information about alignment of the images with the clusters such as distance from center information indicating the distance of each pixel in the array of sensor data from the center of a cluster of genetic material on the tile.

During execution of the neural network-based base caller 100 as described below, tile data can also include data produced during execution of the neural network-based base caller 100, referred to as intermediate data, which can be reused rather than recomputed during a run of the neural network-based base caller 100. For example, during execution of the neural network-based base caller 100, the data flow logic 1997 can write intermediate data to the memory 1948A in place of the sensor data for a given patch of an array of tile data. Implementations like this are described in more detail below.

As illustrated, a system is described for analysis of base call sensor output, comprising memory (e.g., 1948A) accessible by the runtime program/logic 1980 storing tile data including sensor data for a tile from sensing cycles of a base calling operation. Also, the system includes a neural network processor, such as configurable processor 1946 having access to the memory. The neural network processor is configured to execute runs of a neural network using trained parameters to produce classification data for sensing cycles. As described herein, a run of the neural network is operating on a sequence of N arrays of tile data from respective sensing cycles of N sensing cycles, including a subject cycle, to produce the classification data for the subject cycle. The data flow logic 1997 is provided to move tile data and the trained parameters from the memory to the neural network processor for runs of the neural network using input units including data for spatially aligned patches of the N arrays from respective sensing cycles of N sensing cycles.

Also, a system is described in which the neural network processor has access to the memory, and includes a plurality of execution clusters, the execution clusters in the plurality of execution clusters configured to execute a neural network. The data flow logic 1997 has access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

Figure 20A:
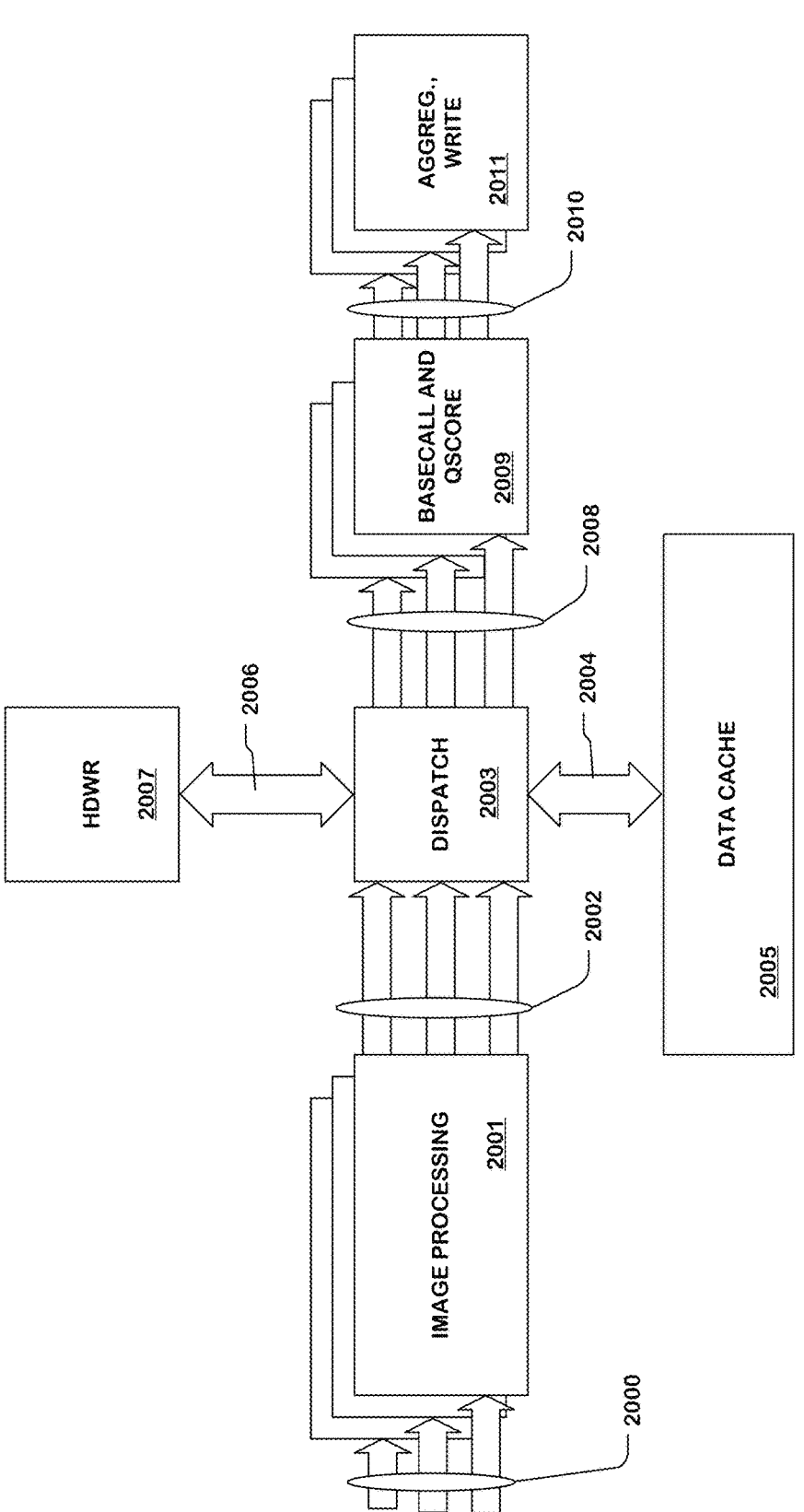
FIG. 20A is a simplified diagram showing aspects of the base calling operation, including functions of a runtime program executed by a host processor.

FIG. 20A is a simplified diagram showing aspects of the base calling operation, including functions of a runtime program (e.g., the runtime logic 1980) executed by a host processor. In this diagram, the output of image sensors from a flow cell are provided on lines 2000 to image processing threads 2001, which can perform processes on images such as alignment and arrangement in an array of sensor data for the individual tiles and resampling of images, and can be used by processes which calculate a tile cluster mask for each tile in the flow cell, which identifies pixels in the array of sensor data that correspond to clusters of genetic material on the corresponding tile of the flow cell. The outputs of the image processing threads 2001 are provided on lines 2002 to a dispatch logic 2003 in the CPU which routes the arrays of tile data to a data cache 2005 (e.g., SSD storage) on a high-speed bus 2004, or on high-speed bus 2006 to the neural network processor hardware 2007, such as the configurable processor 1946 of FIG. 19C, according to the state of the base calling operation. The processed and transformed images can be stored on the data cache 2005 for sensing cycles that were previously used. The hardware 2007 returns classification data output by the neural network to the dispatch logic 2003, which passes the information to the data cache 2005, or on lines 2008 to threads 2009 that perform base call and quality score computations using the classification data, and can arrange the data in standard formats for base call reads. The outputs of the threads 2009 that perform base calling and quality score computations are provided on lines 2010 to threads 2011 that aggregate the base call reads, perform other operations such as data compression, and write the resulting base call outputs to specified destinations for utilization by the customers.

In some implementations, the host can include threads (not shown) that perform final processing of the output of the hardware 2007 in support of the neural network. For example, the hardware 2007 can provide outputs of classification data from a final layer of the multi-cluster neural network. The host processor can execute an output activation function, such as a softmax function, over the classification data to configure the data for use by the base call and quality score threads 2002. Also, the host processor can execute input operations (not shown), such as batch normalization of the tile data prior to input to the hardware 2007.

Figure 20B:
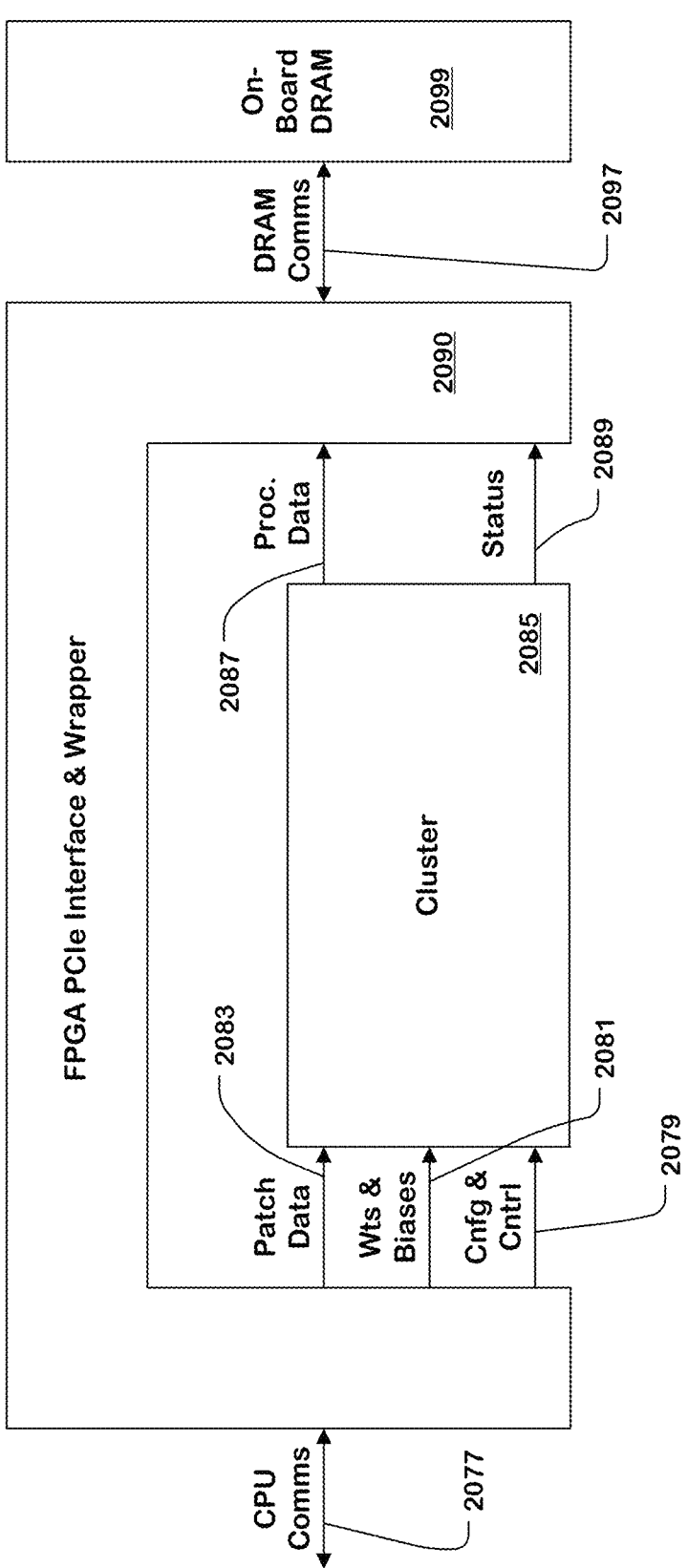
FIG. 20B is a simplified diagram of a configuration of a configurable processor.

FIG. 20B is a simplified diagram of a configuration of a configurable processor 1946 such as that of FIG. 19C. In FIG. 20B, the configurable processor 1946 comprises an FPGA with a plurality of high speed PCIe interfaces. The FPGA is configured with a wrapper 2090 which comprises the data flow logic 1997 described with reference to FIG. 19C. The wrapper 2090 manages the interface and coordination with a runtime program in the CPU across the CPU communication link 2077 and manages communication with the on-board DRAM 2099 (e.g., memory 1448A) via DRAM communication link 2097. The data flow logic 1997 in the wrapper 2090 provides patch data retrieved by traversing the arrays of tile data on the on-board DRAM 2099 for the number N cycles to a cluster 2085, and retrieves process data 2087 from the cluster 2085 for delivery back to the on-board DRAM 2099. The wrapper 2090 also manages transfer of data between the on-board DRAM 2099 and host memory, for both the input arrays of tile data, and for the output patches of classification data. The wrapper transfers patch data on line 2083 to the allocated cluster 2085. The wrapper provides trained parameters, such as weights and biases on line 2081 to the cluster 2085 retrieved from the on-board DRAM 2099. The wrapper provides configuration and control data on line 2079 to the cluster 2085 provided from, or generated in response to, the runtime program on the host via the CPU communication link 2077. The cluster can also provide status signals on line 2089 to the wrapper 2090, which are used in cooperation with control signals from the host to manage traversal of the arrays of tile data to provide spatially aligned patch data, and to execute the multi-cycle neural network over the patch data using the resources of the cluster 2085.

As mentioned above, there can be multiple clusters on a single configurable processor managed by the wrapper 2090 configured for executing on corresponding ones of multiple patches of the tile data. Each cluster can be configured to provide classification data for base calls in a subject sensing cycle using the tile data of multiple sensing cycles described herein.

In examples of the system, model data, including kernel data like filter weights and biases can be sent from the host CPU to the configurable processor, so that the model can be updated as a function of cycle number. A base calling operation can comprise, for a representative example, on the order of hundreds of sensing cycles. Base calling operation can include paired end reads in some implementations. For example, the model trained parameters may be updated once every 20 cycles (or other number of cycles), or according to update patterns implemented for particular systems and neural network models. In some implementations including paired end reads in which a sequence for a given string in a genetic cluster on a tile includes a first part extending from a first end down (or up) the string, and a second part extending from a second end up (or down) the string, the trained parameters can be updated on the transition from the first part to the second part.

In some examples, image data for multiple cycles of sensing data for a tile can be sent from the CPU to the wrapper 2090. The wrapper 2090 can optionally do some pre-processing and transformation of the sensing data and write the information to the on-board DRAM 2099. The input tile data for each sensing cycle can include arrays of sensor data including on the order of 4000×3000 pixels per sensing cycle per tile or more, with two features representing colors of two images of the tile, and one or two bytes per feature per pixel. For an implementation in which the number N is three sensing cycles to be used in each run of the multi-cycle neural network, the array of tile data for each run of the multi-cycle neural network can consume on the order of hundreds of megabytes per tile. In some implementations of the system, the tile data also includes an array of distance-from-cluster center (DFC) data, stored once per tile, or other type of metadata about the sensor data and the tiles.

In operation, when a multi-cycle cluster is available, the wrapper allocates a patch to the cluster. The wrapper fetches a next patch of tile data in the traversal of the tile and sends it to the allocated cluster along with appropriate control and configuration information. The cluster can be configured with enough memory on the configurable processor to hold a patch of data including patches from multiple cycles in some systems, that is being worked on in place, and a patch of data that is to be worked on when the current patch of processing is finished using a ping-pong buffer technique or raster scanning technique in various implementations.

When an allocated cluster completes its run of the neural network for the current patch and produces an output patch, it will signal the wrapper. The wrapper will read the output patch from the allocated cluster, or alternatively the allocated cluster will push the data out to the wrapper. Then the wrapper will assemble output patches for the processed tile in the DRAM 2099. When the processing of the entire tile has been completed, and the output patches of data transferred to the DRAM, the wrapper sends the processed output array for the tile back to the host/CPU in a specified format. In some implementations, the on-board DRAM 2099 is managed by memory management logic in the wrapper 2090. The runtime program can control the sequencing operations to complete analysis of all the arrays of tile data for all the cycles in the run in a continuous flow to provide real time analysis.

Figure 21:
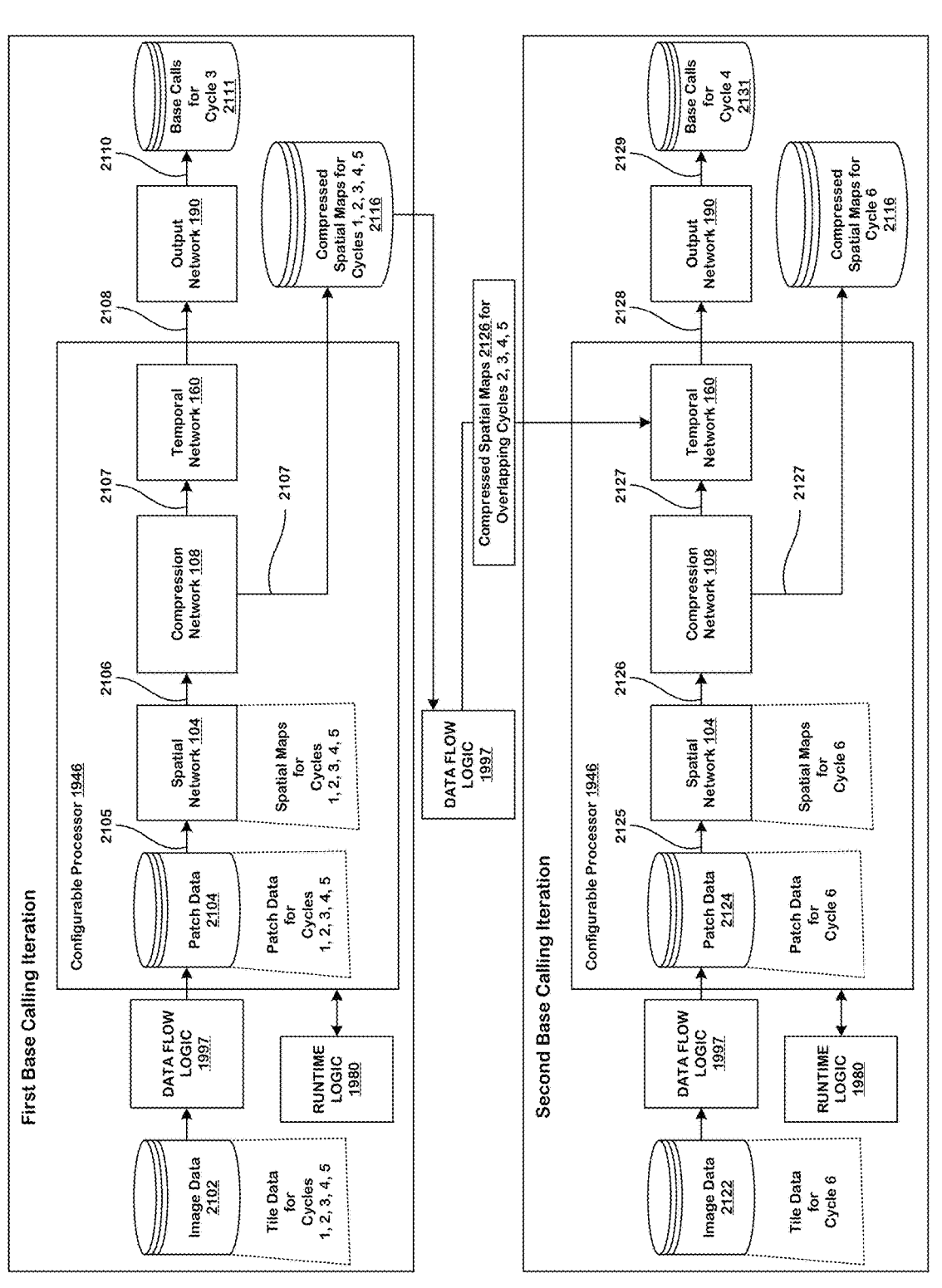
FIG. 21 illustrates another implementation of the disclosed data flow logic making compressed spatial maps, generated during the first base calling iteration, available during the second base calling iteration from off-chip memory (e.g., off-chip DRAM, host RAM, host high bandwidth memory (HBM)).

FIG. 21 illustrates another implementation of the disclosed data flow logic making compressed spatial maps, generated during the first base calling iteration, available during the second base calling iteration from off-chip memory 2116 (e.g., off-chip DRAM, host RAM, host high bandwidth memory (HBM)).

In one implementation, a host memory (e.g., memory 1948B) attached to a host processor (e.g., CPU 1952) is configured to receive a progression of sequencing images 2102 as a sequencing run progresses. A configurable processor (e.g., configurable processor 1946) has an array of processing units. Processing units in the array of processing units are configured to execute the neural network-based base caller 100 to produce base call predictions. The data flow logic 1997 has access to the host memory, the host processor, and the configurable processor. For the first base calling iteration, the data flow logic 1997 loads sequencing images for sequencing cycles in the first window of sequencing cycles (e.g., the sequencing cycles 1 to 5 in FIG. 1A) on the configurable processor from the host memory.

The runtime logic 1980 is configured to cause the processing units of the configurable processor to execute the spatial network 104 of the neural network-based base caller 100 on the sequencing images 2102 on a cycle-by-cycle basis and generate spatial feature map sets 2106 for each of the sequencing cycles in the first window of sequencing cycles. In one implementation, the runtime logic 1980 executes, in parallel, multiple processing clusters of the neural network-based base caller 100 on patches 2104 tiled from the sequencing images 2102. The multiple processing clusters apply the spatial network 104 on the patches 2104 on a patch-by-patch basis 2105.

The runtime logic 1980 is configured to cause the processing units of the configurable processor to execute the compression network 108 of the neural network-based base caller 100 on the spatial feature map sets 2106 on the cycle-by-cycle basis and generate compressed spatial feature map sets 2107, and process the compressed spatial feature maps sets 2107 through the temporal network 160 and the output network 190 to produce base call predications 2111 for one or more sequencing cycles in the first window of sequencing cycles. The temporal network 160 generates the temporal feature maps 2108. The output network 190 generates base call classification scores 2110 (e.g., unnormalized base-wise scores). In one implementation, the compressed spatial feature map sets 2107 are stored on the off-chip memory 2116.

In one implementation, the data flow logic 1997 is configured to move the compressed spatial feature map sets 2107 to the host memory 2116 and overwrite corresponding ones of the sequencing images 2102 with the compressed spatial feature map sets 2107. In other implementations, corresponding ones of the patches 2104 are replaced by the compressed spatial feature map sets 2107.

For the second base calling iteration and for the second window of sequencing cycles (e.g., the sequencing cycles 2 to 6 in FIG. 2A) that shares one or more overlapping sequencing cycles (e.g., the sequencing cycles 2-5) with the first window of sequencing cycle, and has at least one non-overlapping sequencing cycle (e.g., the sequencing cycle 6), the data flow logic 1997 is configured to load, on the configurable processor from the host memory, compressed spatial feature map sets 2126 for the overlapping sequencing cycles, and sequencing images 2122 (or patches 2124) for the non-overlapping sequencing cycle.

The runtime logic 1980 is configured to cause the processing units of the configurable processor to execute the spatial network 104 on the sequencing images 2122 for the non-overlapping sequencing cycle and generate a spatial feature map set 2126 for the non-overlapping sequencing cycle. In one implementation, the multiple processing clusters apply the spatial network 104 on the patches 2124 on a patch-by-patch basis 2125.

The runtime logic 1980 is configured to cause the processing units of the configurable processor to execute the compression network 108 on the spatial feature map set 2126 and generate a compressed spatial feature map set 2127 for the non-overlapping sequencing cycle, and process the compressed spatial feature maps sets 2126 for the overlapping sequencing cycles and the compressed spatial feature map set 2127 for the non-overlapping sequencing cycle through the temporal network 160 and the output network 190 to produce base call predications 2131 for one or more sequencing cycles in the second window of sequencing cycles. The temporal network 160 generates the temporal feature maps 2128. The output network 190 generates base call classification scores 2129 (e.g., unnormalized base-wise scores). In one implementation, the compressed spatial feature map set 2127 is stored on the off-chip memory 2116.

Figure 22:
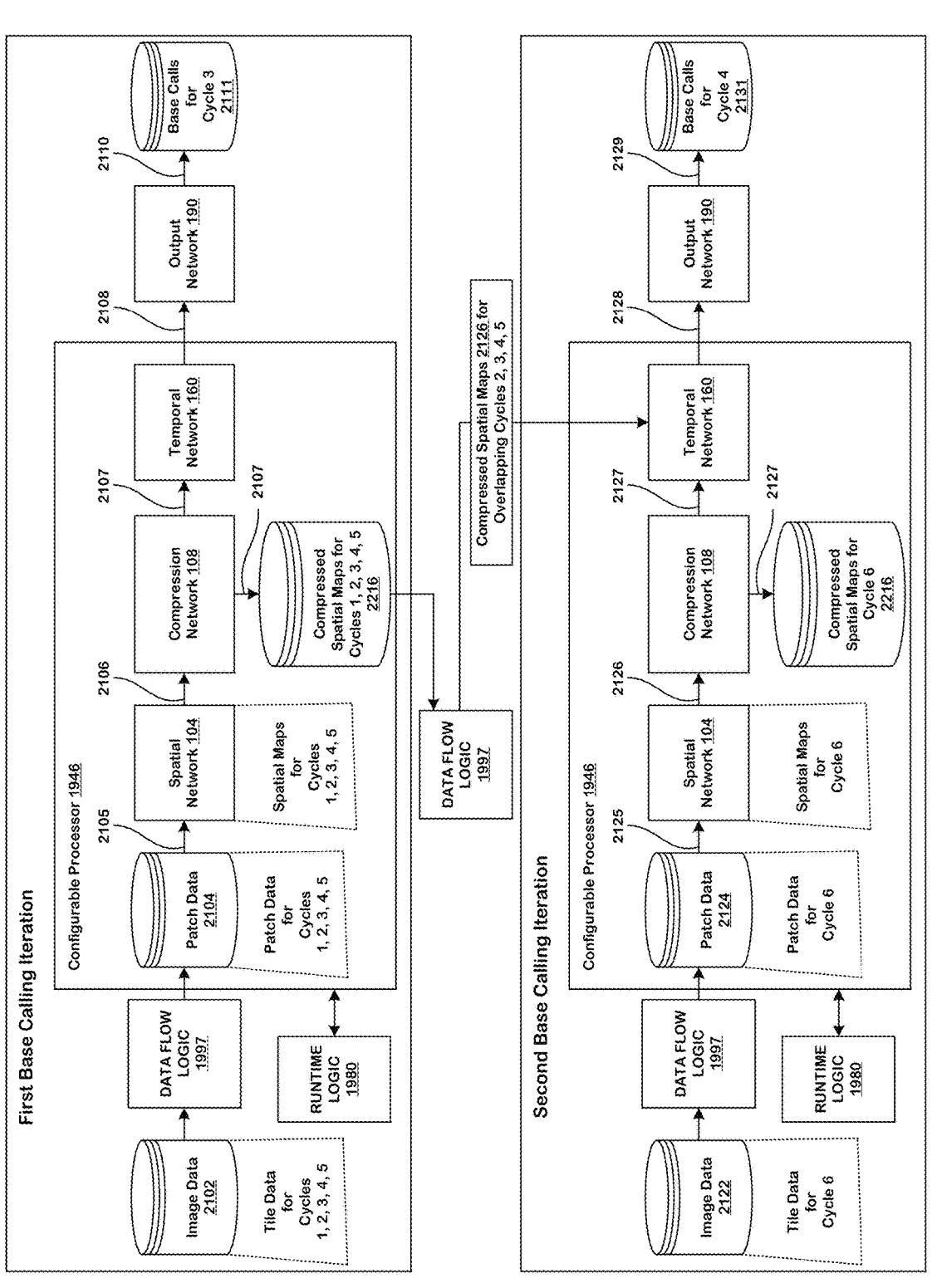
FIG. 22 illustrates one implementation of a disclosed data flow logic making compressed spatial maps, generated during the first base calling iteration, available during the second base calling iteration from on-chip memory (e.g., on-chip DRAM, on-chip SRAM, on-chip BRAM, DRAM attached to the processor via an interconnect).

FIG. 22 illustrates one implementation of a disclosed data flow logic making compressed spatial maps, generated during the first base calling iteration, available during the second base calling iteration from on-chip memory 2216 (e.g., processor memory like on-chip DRAM, on-chip SRAM, on-chip BRAM, DRAM attached to the processor via an interconnect). In FIG. 22, the compressed spatial feature maps sets 2107 and the compressed spatial feature map set 2127 are stored on the on-chip memory 2216. Also in FIG. 22, the data flow logic 1997 is configured to load, on the configurable processor from the on-chip memory 2216, the compressed spatial feature map sets 2126 for the overlapping sequencing cycles.

Split Architecture

Figure 23:
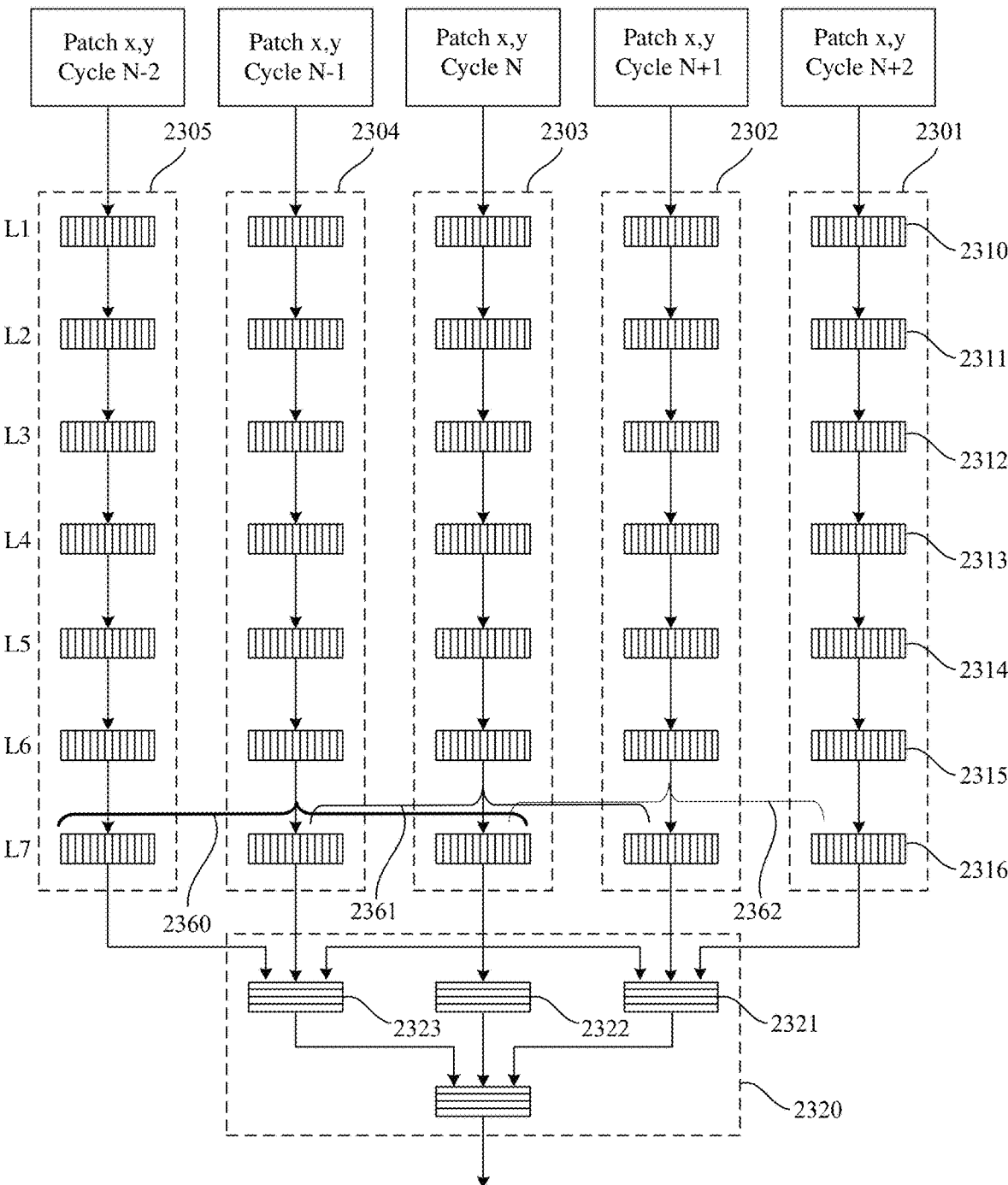
FIG. 23 illustrates one implementation of a so-called split architecture of the disclosed neural network-based base caller.

FIG. 23 illustrates one implementation of a so-called split architecture of the neural network-based base caller 100. As discussed above, the spatial convolution network 104 is configured to process a window of per-cycle sequencing image sets for a series of sequencing cycles (cycles N+2, N+1, N, N−1, and N−2) of a sequencing run on a cycle-by-cycle basis by separately convolving respective per-cycle sequencing image sets in the window of per-cycle sequencing image sets through respective sequences 2301, 2302, 2303, 2304, and 2405 of spatial convolution layers to generate respective per-cycle spatial feature map sets for respective sequencing cycles in the series of sequencing cycles. For example, each of the five sequences 2301, 2302, 2303, 2304, and 2405 of spatial convolution layers has seven spatial convolution layers (i.e., layers L1 to L7 in FIG. 23).

The respective sequences 2301, 2302, 2303, 2304, and 2405 of spatial convolution layers have respective sequences of spatial convolution filter banks (e.g., the sequence comprising spatial convolution filter banks 2310, 2311, 2312, 2313, 2314, 2315, and 2316 for the sequence 2301 of spatial convolution layers). In one implementation, trained coefficients (or weights) of spatial convolution filters in spatial convolution filter banks of the respective sequences of spatial convolution filter banks vary between sequences of spatial convolution layers in the respective sequences of spatial convolution layers.

For example, the spatial convolution layer sequences 2301, 2302, 2303, 2304, and 2405 are configured with convolution filters with different trained coefficients. In another example, the convolution filters in corresponding level spatial convolution layers have different trained coefficients (e.g., convolution filter banks 2382, 2383, 2384, 2385, and 2312 in the respective third spatial convolution layers of the five sequences 2301, 2302, 2303, 2304, and 2405 of spatial convolution layers).

The temporal convolution network 160 is configured to process the per-cycle spatial feature map sets on a groupwise basis by convolving on respective overlapping groups (e.g., groups 2360, 2361, and 2362) of per-cycle spatial feature map sets in the per-cycle spatial feature map sets using respective temporal convolution filter banks 2321, 2322, and 2323 of a first temporal convolution layer 2320 to generate respective per-group temporal feature map sets for the respective overlapping groups of per-cycle spatial feature map sets. In one implementation, trained coefficients (or weights) of temporal convolution filters in the respective temporal convolution filter banks vary between temporal convolution filter banks 2321, 2322, and 2323 in the respective temporal convolution filter banks.

Skip Architecture

Figure 24A:
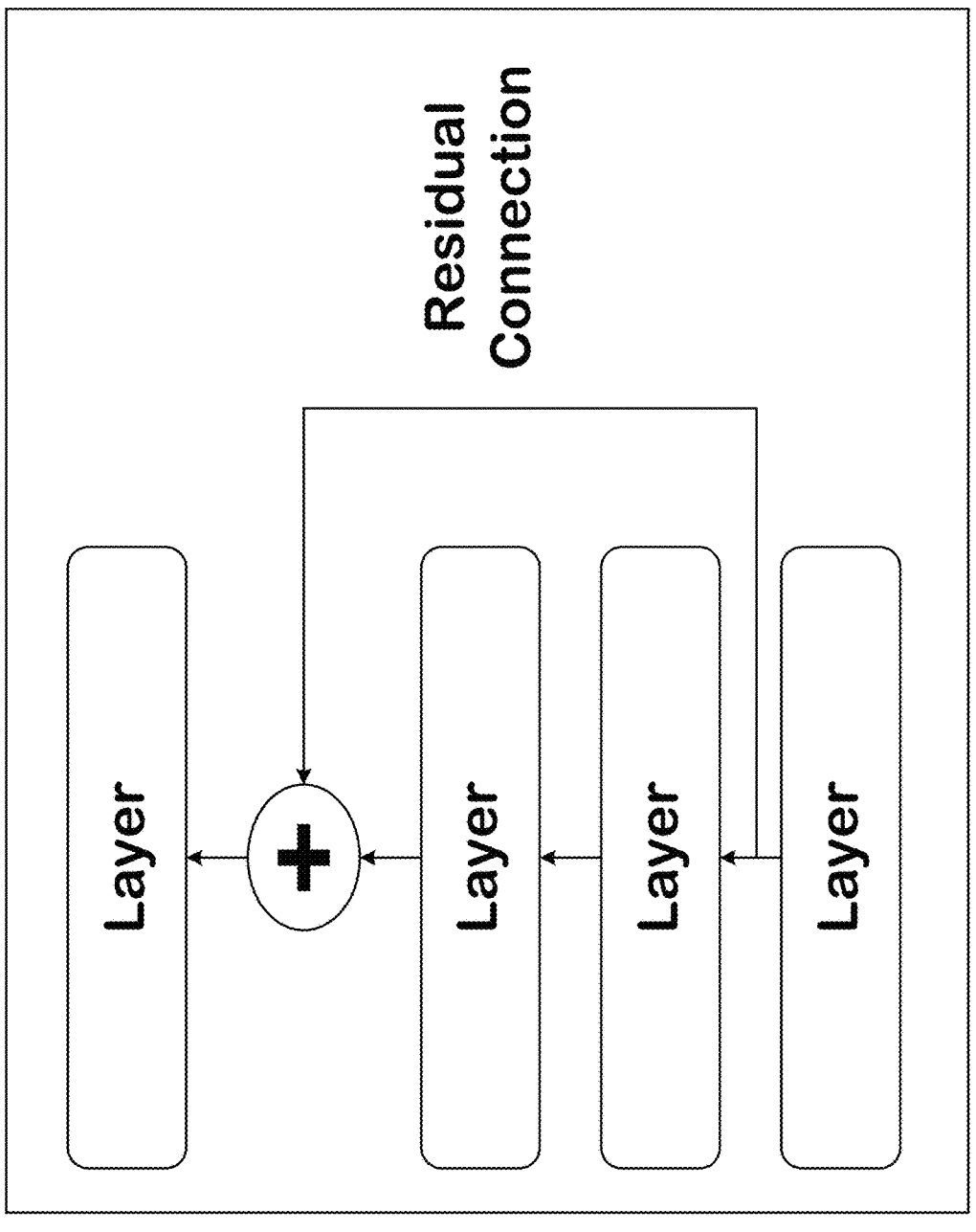
FIG. 24A depicts a residual connection that reinjects prior information downstream via feature-map addition.

FIG. 24A depicts a residual (or skip) connection that reinjects prior information downstream via feature-map addition. A residual connection comprises reinjecting previous representations into the downstream flow of data by adding a past output tensor to a later output tensor, which helps prevent information loss along the data processing flow. Residual connections tackle two common problems that plague any large-scale deep learning model: vanishing gradients and representational bottlenecks.

A residual connection comprises making the output of an earlier layer available as input to a later layer, effectively creating a shortcut in a sequential network. Rather than being concatenated to the later activation, the earlier output is summed with the later activation, which assumes that both activations are the same size. If they are of different sizes, a linear transformation to reshape the earlier activation into the target shape can be used.

Figure 24B:
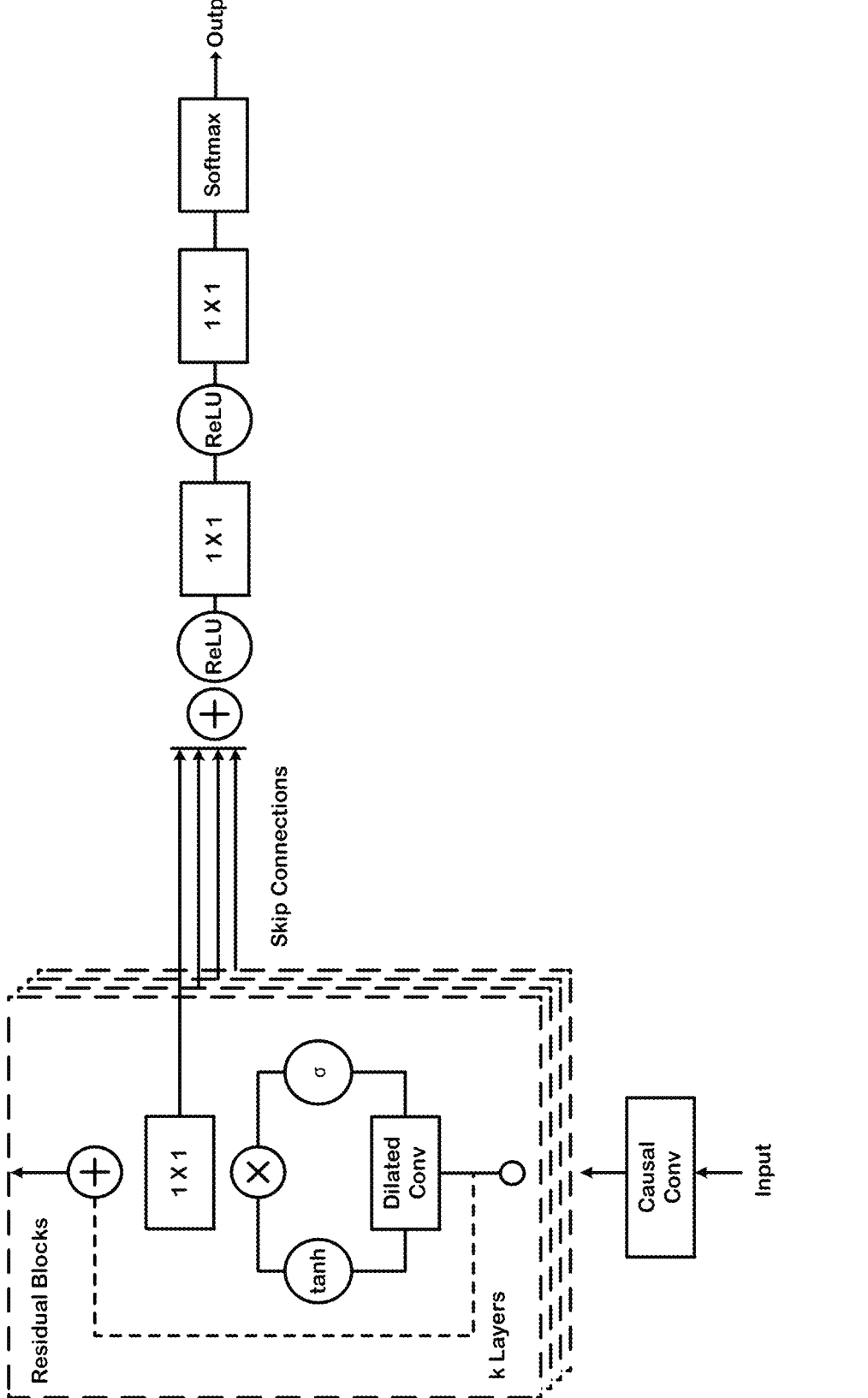
FIG. 24B depicts one implementation of residual blocks and skip connections.

FIG. 24B depicts one implementation of residual blocks and skip connections. A residual network stacks a number of residual units to alleviate the degradation of training accuracy. Residual blocks make use of special additive skip connections to combat vanishing gradients in deep neural networks. At the beginning of a residual block, the data flow is separated into two streams: the first carries the unchanged input of the block, while the second applies weights and non-linearities. At the end of the block, the two streams are merged using an element-wise sum. The main advantage of such constructs is to allow the gradient to flow through the network more easily.

Configured with a residual network, in some implementations, the neural network-based base caller 100 is easily trained and improved accuracy can be achieved for image classification and object detection. The neural network-based base caller 100 connects the output of the $l^{th}$ layer as input to the $(l+1)^{th}$ layer, which gives rise to the following layer transition: $x_l=H_l(x_{l-1})$. Residual blocks add a skip connection that bypasses the non-linear transformations with an identify function: $x_l=H_l(x_{l-1})+x_{l-1}$. An advantage of residual blocks is that the gradient can flow directly through the identity function from later layers to the earlier layers (e.g., spatial, and temporal convolution layers). The identity function and the output of $H_l$ are combined by summation (addition).

Figure 24C:
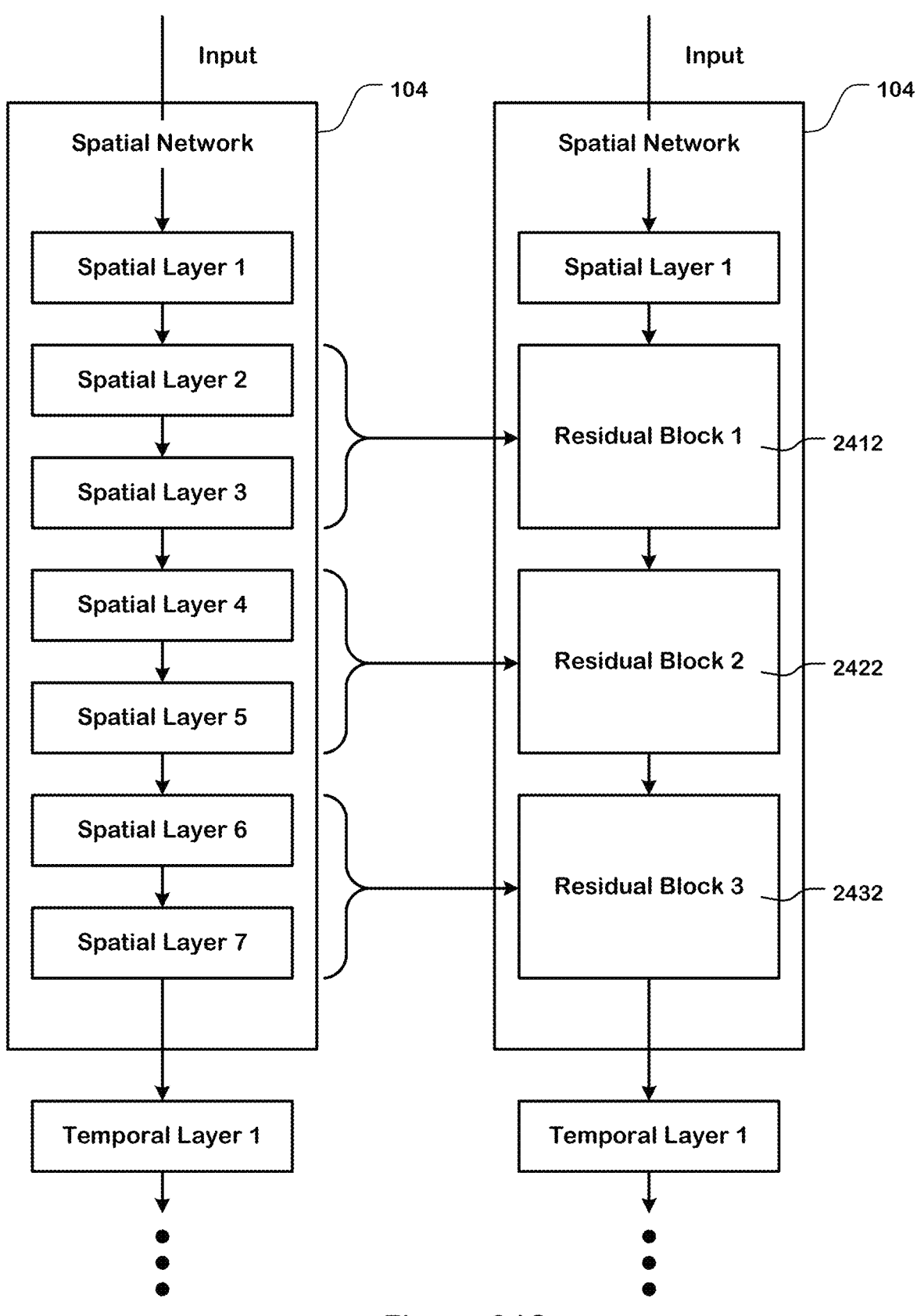
FIG. 24C shows a residual architecture of the neural network-based base caller in which the spatial convolution layers are grouped into residual blocks with skip connections.

FIG. 24C shows a residual architecture of the neural network-based base caller 100 in which the spatial convolution layers are grouped into residual blocks with skip connections. In other implementations, the temporal convolution layers of the neural network-based base caller 100 are grouped into residual blocks with skip connections.

In the implementation illustrated in FIG. 24C, the second and third spatial convolution layers are grouped into a first residual block 2412; the fourth and fifth spatial convolution layers are grouped into a second residual block 2422; and the sixth and seventh spatial convolution layers are grouped into a third residual block 2432.

Figure 25A:
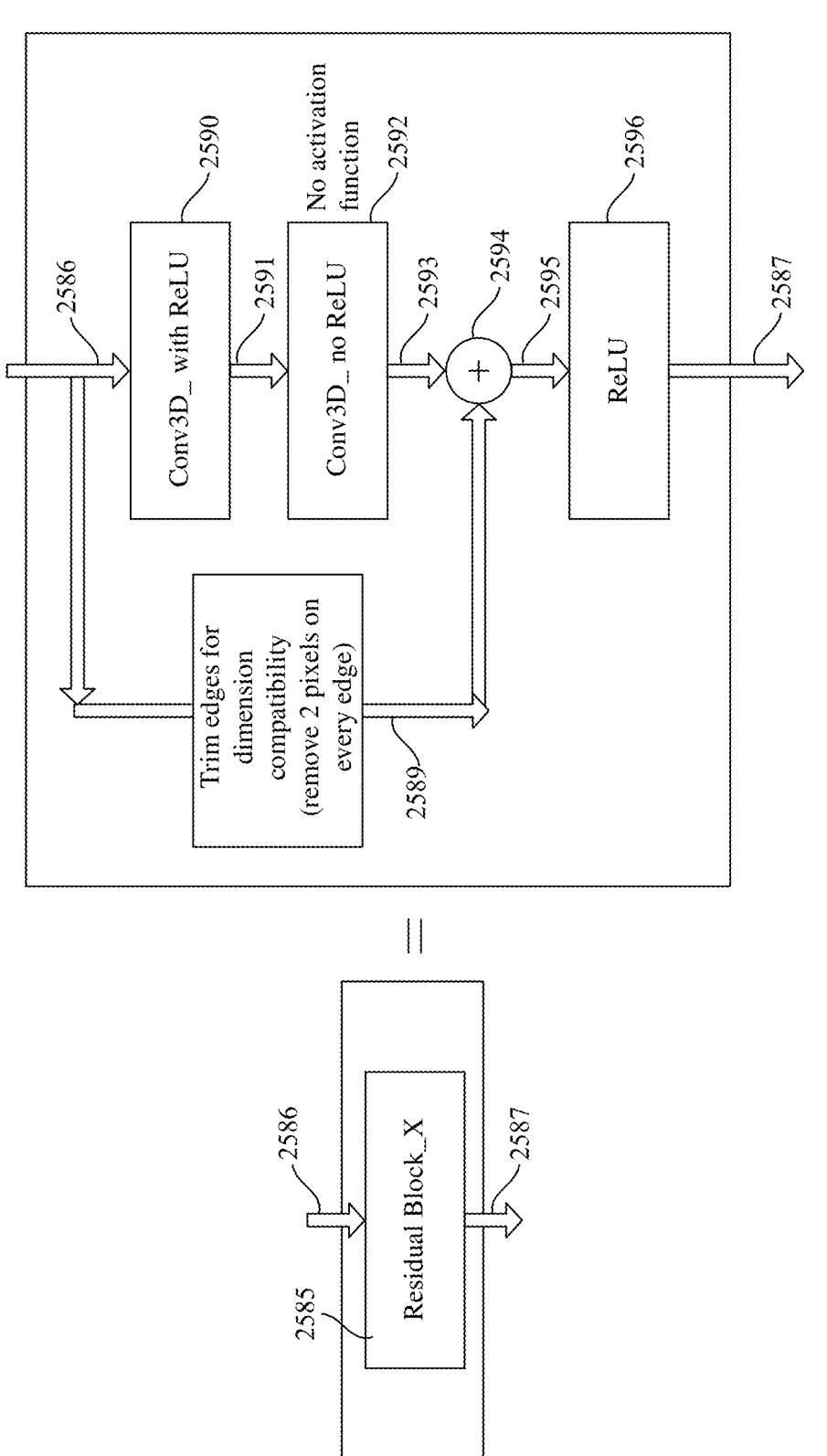
FIG. 25A shows details of a disclosed bus network of the neural network-based base caller described herein.

FIG. 25A shows details of a bus network of the neural network-based base caller 100. In one implementation, a given residual block 2585 of the bus network comprises a set of spatial convolution layers 2590 and 2592. A first spatial convolution layer 2590 in the set of spatial convolution layers receives as input a preceding output 2586 generated by a preceding spatial convolution layer not part of the given residual block 2585 (e.g., a zero spatial convolution layer preceding the first spatial convolution layer 2590 in the spatial network 104). The first spatial convolution layer 2590 processes the preceding output 2586 and generates a first output 2591. A second spatial convolution layer 2592 in the set of spatial convolution layers, which succeeds the first spatial convolution layer 2590, receives the first output 2591, processes the first output 2591 and generates a second output 2593. In one implementation, the first spatial convolution layer 2590 has a non-linear activation function like ReLU that generates the first output 2591. In another implementation, the second spatial convolution layer 2592 lacks the non-linear activation function.

A skip connection 2589 provides the preceding output 2586 to a summer 2594. The summer 2594 also receives the second output 2593 from the second spatial convolution layer 2592. The summer 2594 combines the preceding output 2586 and the second output 2593 and generates a summed output 2595. The summed output 2595 is further processed through a non-linear activation like ReLU 2596 to generate a final summed output 2587. The final summed output 2587 is then fed as input to a succeeding residual block, in some implementations. In some implementations, the preceding output 2586 is modified to be dimensionality-compatible with the second output 2593. For example, edges of feature maps in the preceding output 2586 are trimmed to produce feature maps that have the same spatial dimensionality as the feature maps in the second output 2593.

Figure 25B:
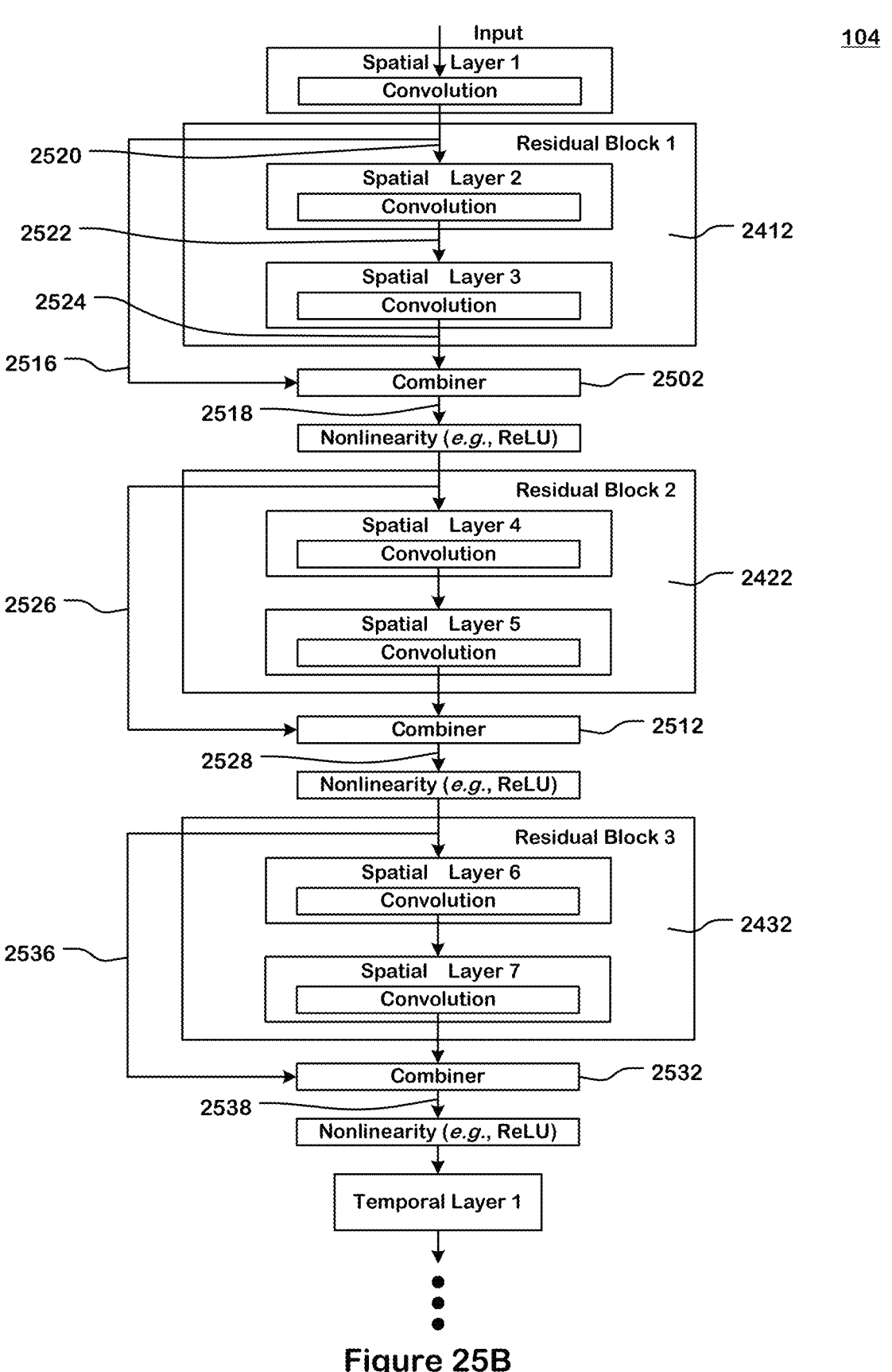
FIG. 25B shows an example operation of the disclosed bus network.

FIG. 25B shows an example operation of the disclosed bus network. In one implementation, the bus network is configured to form buses (e.g., 2516, 2526, 2536, 2602, 2604, 2702, and 2712) between spatial convolution layers within the respective sequences of spatial convolution layers. The buses are configured to cause respective per-cycle spatial feature map sets generated by two or more spatial convolution layers in a particular sequence of spatial convolution layer for a particular sequencing cycle to combine into a combined per-cycle spatial feature map set, and provide the combined per-cycle spatial feature map set as input to another spatial convolution layer in the particular sequence of spatial convolution layer.

For example, consider the first residual block 2412. Here, the two or more spatial convolution layers include a first spatial convolution layer and a third spatial convolution layer. The first spatial convolution layer generates a first per-cycle spatial feature map set 2520. The first spatial convolution layer provides the first per-cycle spatial feature map set 2520 as input to a second spatial convolution layer. The second spatial convolution layer processes the first per-cycle spatial feature map set 2520 and generates a second per-cycle spatial feature map set 2522. The second spatial convolution layer provides the second per-cycle spatial feature map set 2522 as input to the third spatial convolution layer. The third spatial convolution layer processes the second per-cycle spatial feature map set 2522 and generates a third per-cycle spatial feature map set 2524. The buses (e.g., the skip bus 2519) are further configured to cause the first spatial feature map set 2520 and the third per-cycle spatial feature map set 2524 to combine (e.g., summed or concatenated by a combiner 2502) into the combined per-cycle spatial feature map set 2518. Then, the another spatial convolution layer is a fourth spatial convolution layer that immediately succeeds the third spatial convolution layer in the particular sequence of spatial convolution layer. The fourth spatial convolution layer processes the combined per-cycle spatial feature map set 2518 as input. The same notion analogously applies to the second and third residual blocks 2422 and 2432, where 2526 and 2536 are the skip buses like the skip buses 2516, and cause the respective combiners 2512 and 2532 to generate the respective combined per-cycle spatial feature map sets 2528 and 2538.

Figure 25C:
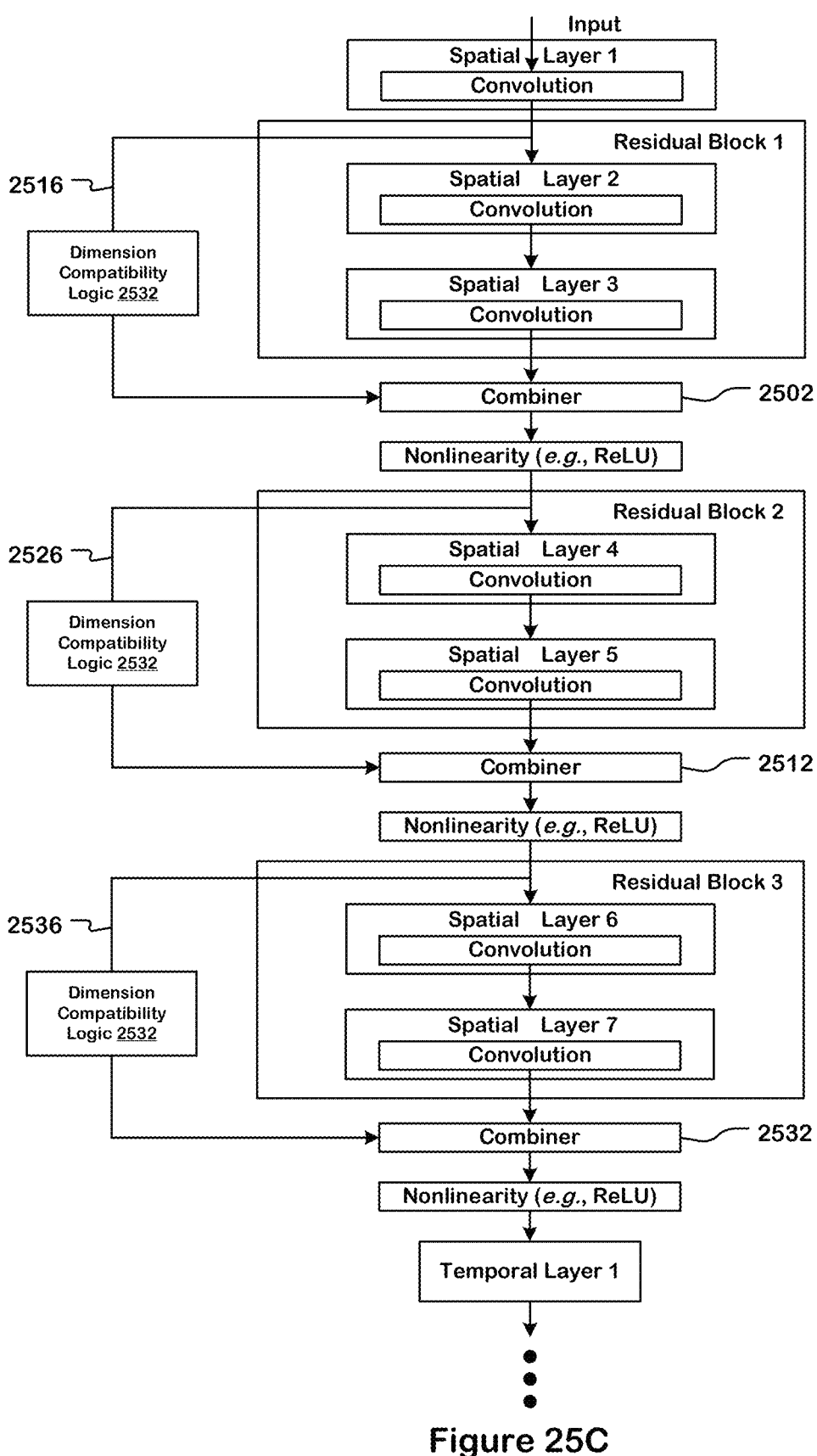
FIG. 25C shows one implementation of a dimension compatibility logic of the disclosed bus network.

FIG. 25C shows one implementation of a dimension compatibility logic 2532 that ensures that, prior to the combination, the incoming feature maps supplied by the skip buses are modified (e.g., trimmed) to have the same spatial dimensionality as the receiving feature maps with which the incoming feature maps are combined by the combiners of the bus network.

Figure 26:
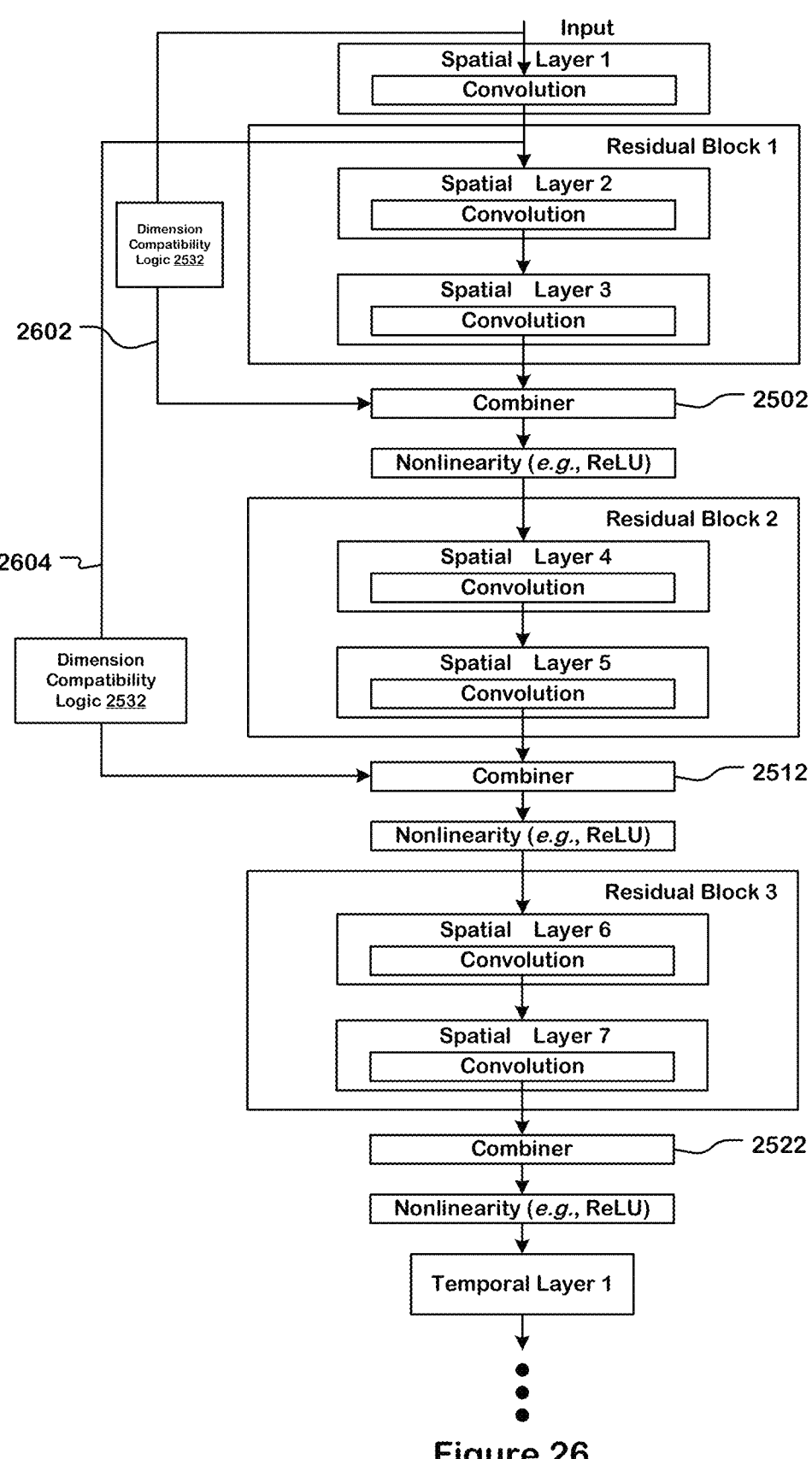
FIG. 26 shows another example of the disclosed bus network.

FIG. 26 shows another example of the disclosed bus network in which a skip bus 2602 combines the first spatial convolution layer's output with the output of the first residual block. FIG. 26 also shows that a skip bus 2604 can also causes feature maps to be combined across residual blocks and across non-successive layers (e.g., from layers 1 and 5) to be generate a combined representation that can be processed by another layer (e.g., to layer 6).

Figure 27:
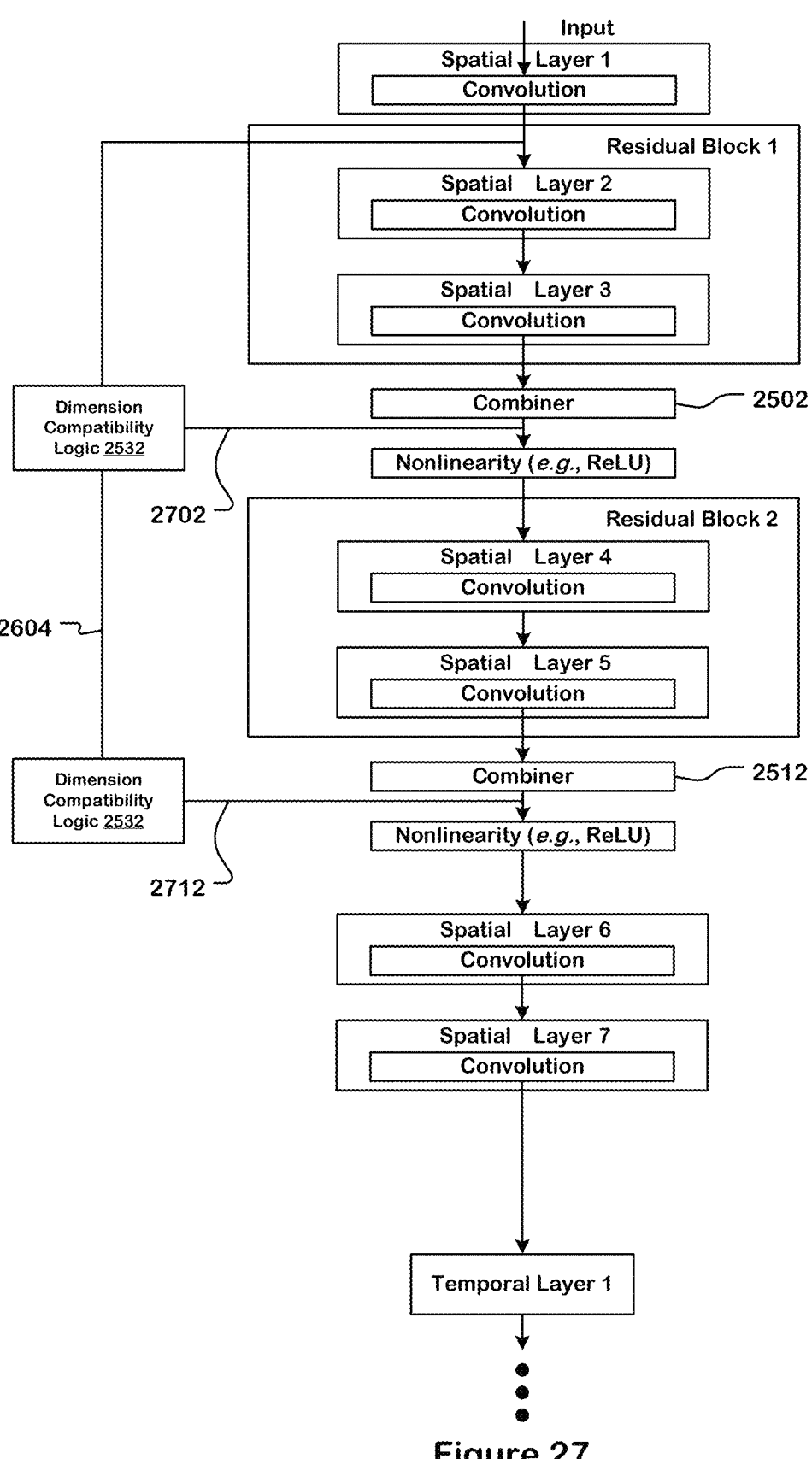
FIG. 27 shows yet another example of the disclosed bus network.

FIG. 27 shows yet another example of the disclosed bus network in which inputs and combined representations from multiple successive and/or non-successive layers (e.g., from layer 1, combiner 2502, and combiner 2512) can be combined by example skip buses 2702, 2604, and 2712 to generate a combined representation that can be processed by another layer (e.g., to layer 6).

Figure 28:
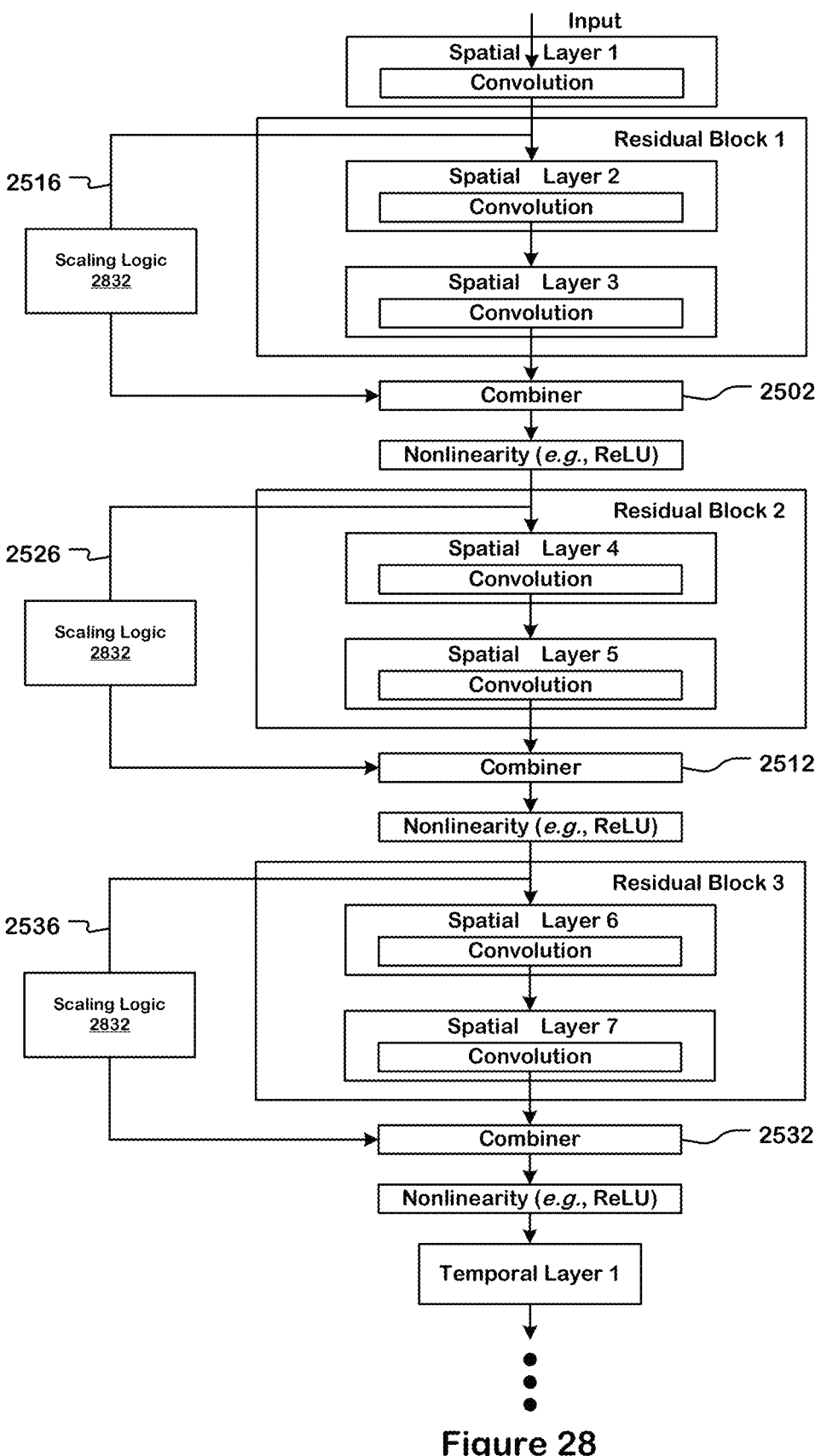
FIG. 28 shows one implementation of a scaling logic of the disclosed bus network.

FIG. 28 shows one implementation of a scaling logic 2832 that scales the incoming feature maps supplied by the skip buses before combining them with the receiving feature maps with which they are combined by the combiners of the bus network. The values used by the scaling logic 2832 can range, for example, anywhere between 0 and 1, including 0 and 1. The scaling logic can be used, for example, to attenuate or amplify the strength/magnitude/value (e.g., feature values (e.g., floating point values) of the incoming feature maps.)

Figure 29:
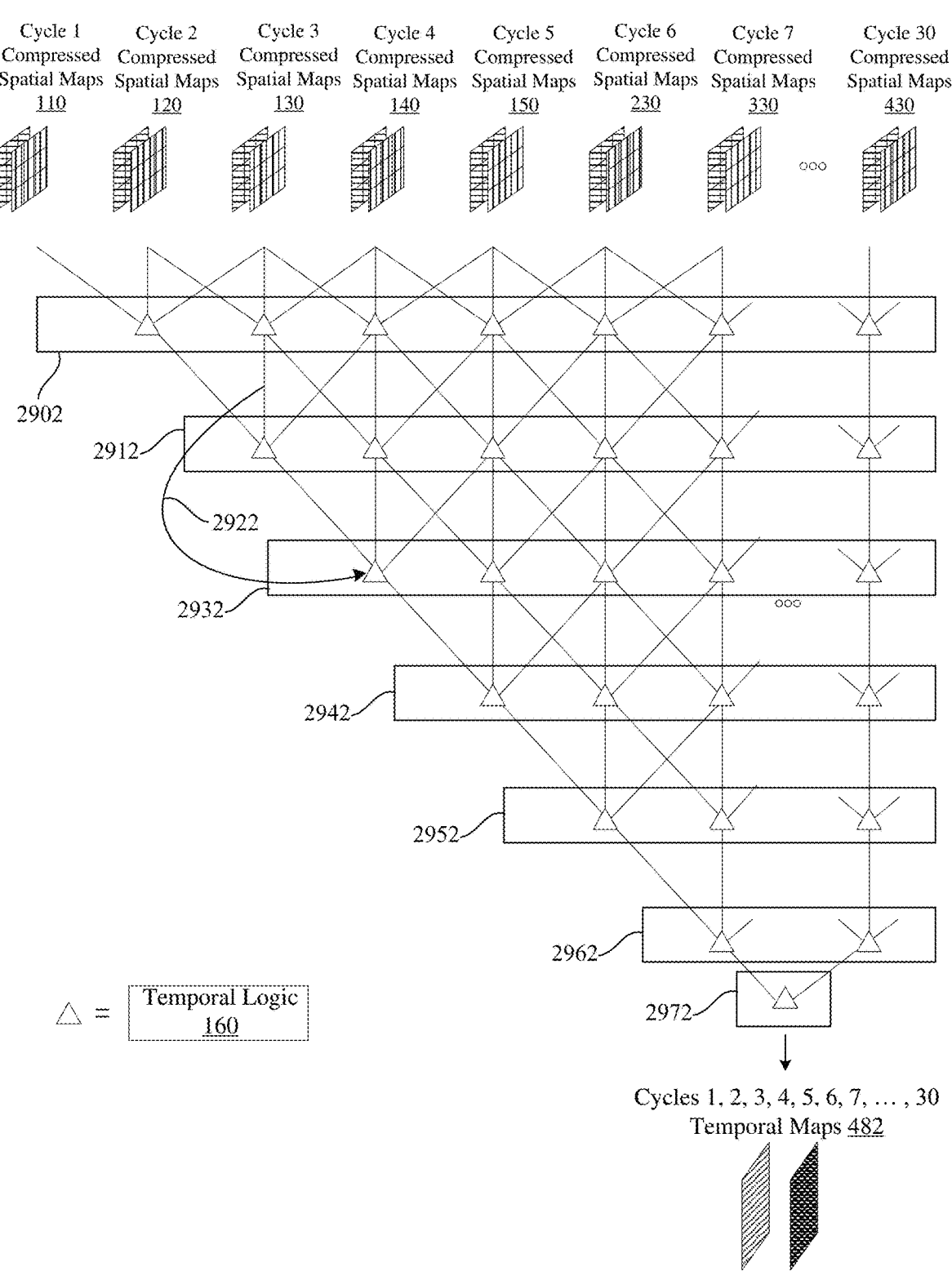
FIG. 29 shows one implementation of skip connections between temporal convolution layers of the temporal network.

FIG. 29 shows one implementation of skip connections between temporal convolution layers 2902, 2912, 2922, 2932, 2942, 2952, 2962, and 2972 of the temporal network 160. For example, a skip connection 2922 supplies temporal feature maps from the first temporal convolution layer 2902 to the third temporal convolution layer 2932.

Figure 30:
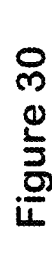
FIG. 30 compares base calling performance by the network network-based base caller configured with the compression logic (sqz2 base caller) against the network network-based base caller without the compression logic and against Illumina's non-neural network-based base caller Real-Time Analysis (RTA) software.

FIG. 30 compares base calling performance by the network network-based base caller 100 configured with the compression logic 108 (sqz2 base caller) against the network network-based base caller 100 without the compression logic 108 (used as baseline neural network models) and against Illumina's non-neural network-based base caller Real-Time Analysis (RTA) software) (use as a baseline traditional image processing model). As seen in the chart in FIG. 30, the sqz2 base caller (purple fitted line) has a lower base calling error percentage ("Error %" on Y-axis) than the RTA base caller (black fitted line) and the two instances of the network network-based base caller 100 without the compression logic 108 (red and cyan fitted lines).

FIG. 31 shows savings in RAM and DRAM usage brought about by the use of the disclosed compression logic 108.

Figure 32:
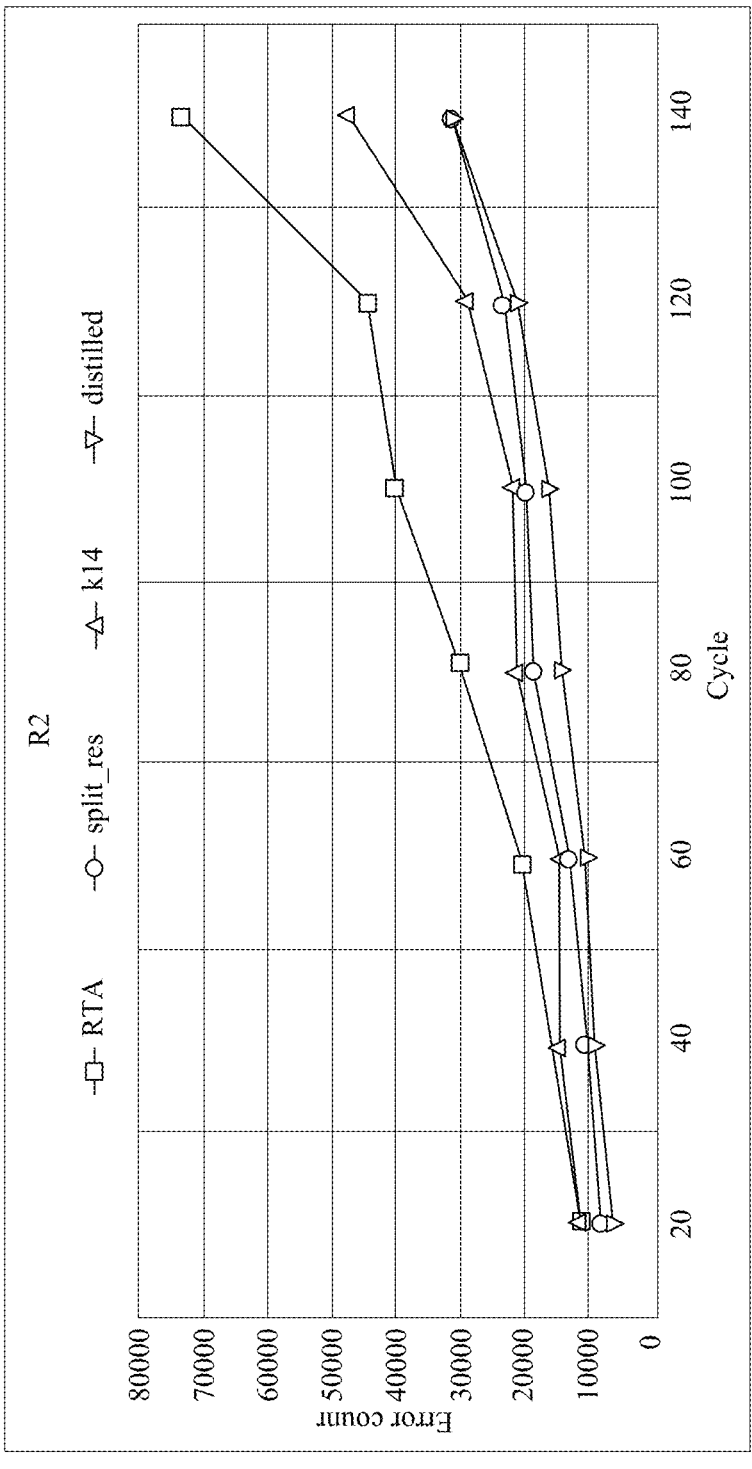
FIG. 32 compares base calling performance by the network network-based base caller configured with the split and skip architectures (split_res) against the RTA base caller and another version of the network network-based base caller without the split and skip architectures (distilled).

FIG. 32 compares base calling performance by the network network-based base caller 100 configured with the split and skip architectures (split_res) against the RTA base caller and another version of the network network-based base caller 100 without the split and skip architectures (distilled). As seen in the chart in FIG. 32, the split_res base caller (orange fitted line) has a lower base calling error percentage ("Error Count" on Y-axis) than the RTA base caller (blue fitted line).

"Logic" (e.g., data flow logic), as used herein, can be implemented in the form of a computer product including a non-transitory computer readable storage medium with computer usable program code for performing the method steps described herein. The "logic" can be implemented in the form of an apparatus including a memory and at least one processor that is coupled to the memory and operative to perform exemplary method steps. The "logic" can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media). In one implementation, the logic implements a data processing function. The logic can be a general purpose, single core or multicore, processor with a computer program specifying the function, a digital signal processor with a computer program, configurable logic such as an FPGA with a configuration file, a special purpose circuit such as a state machine, or any combination of these. Also, a computer program product can embody the computer program and configuration file portions of the logic.

Figure 33:
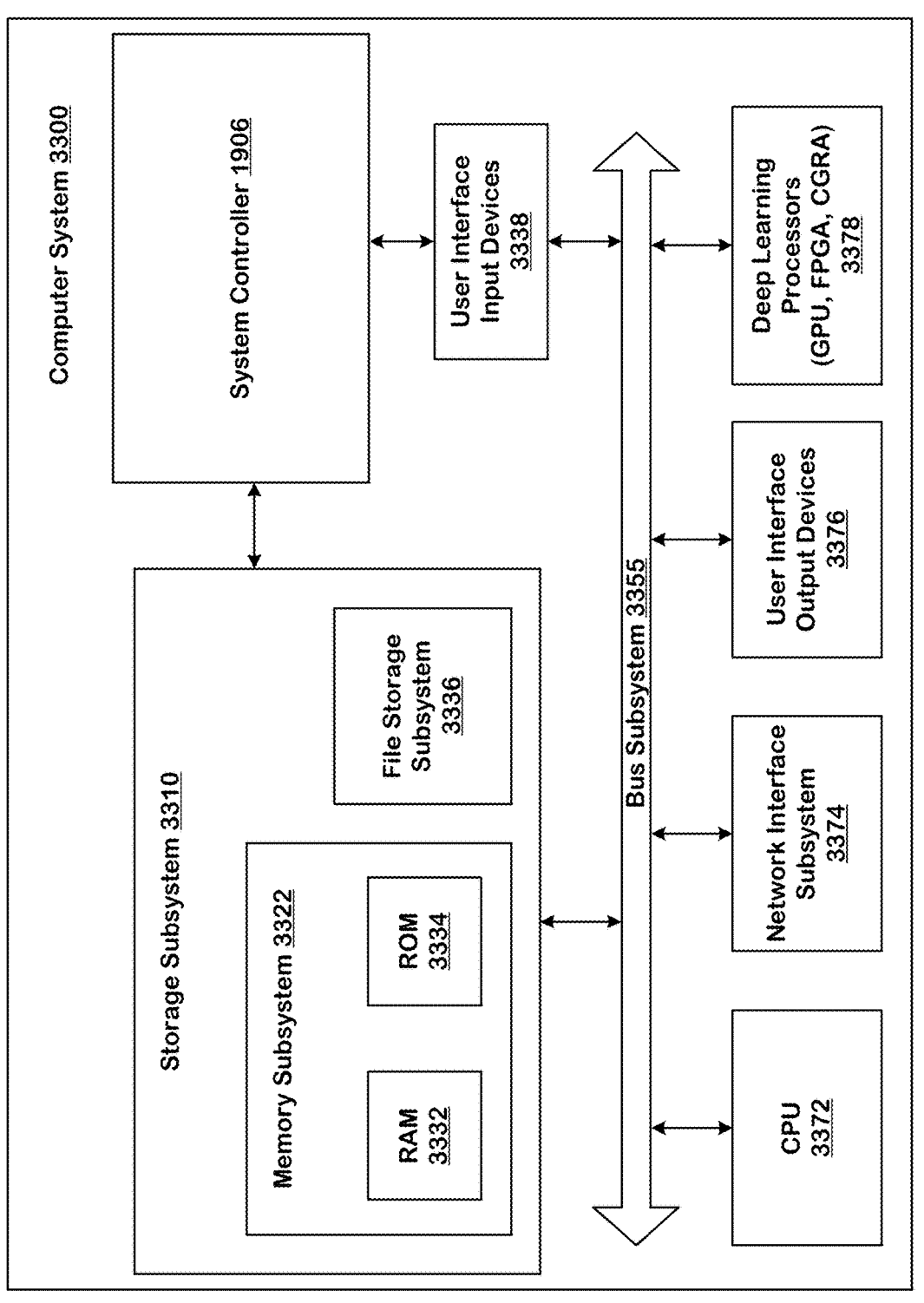
FIG. 33 is a computer system that can be used to implement the technology disclosed.

FIG. 33 is a computer system 3300 that can be used by the sequencing system 1900A to implement the base calling techniques disclosed herein. Computer system 3300 includes at least one central processing unit (CPU) 3372 that communicates with a number of peripheral devices via bus subsystem 3355. These peripheral devices can include a storage subsystem 3358 including, for example, memory devices and a file storage subsystem 3336, user interface input devices 3338, user interface output devices 3376, and a network interface subsystem 3374. The input and output devices allow user interaction with computer system 3300. Network interface subsystem 3374 provides an interface to outside networks, including an interface to corresponding interface devices in other computer systems.

In one implementation, the system controller 1906 is communicably linked to the storage subsystem 3310 and the user interface input devices 3338.

User interface input devices 3338 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 3300.

User interface output devices 3376 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 3300 to the user or to another machine or computer system.

Storage subsystem 3358 stores programming and data constructs that provide the functionality of some or all of the modules and methods described herein. These software modules are generally executed by deep learning processors 3378.

Deep learning processors 3378 can be graphics processing units (GPUs), field-programmable gate arrays (FPGAs), application-specific integrated circuits (ASICs), and/or coarse-grained reconfigurable architectures (CGRAs). Deep learning processors 3378 can be hosted by a deep learning cloud platform such as Google Cloud Platform™, Xilinx™, and Cirrascale™. Examples of deep learning processors 3378 include Google's Tensor Processing Unit (TPU)™, rackmount solutions like GX4 Rackmount Series™, GX33 Rackmount Series™ NVIDIA DGX-1™, Microsoft' Stratix V FPGA™, Graphcore's Intelligent Processor Unit (IPU)™, Qualcomm's Zeroth Platform™ with Snapdragon processors™, NVIDIA's Volta™ NVIDIA's DRIVE PX™, NVIDIA's JETSON TX1/TX2 MODULE™, Intel's Nirvana™ Movidius VPU™, Fujitsu DPI™, ARM's DynamicIQ™, IBM TrueNorth™, Lambda GPU Server with Testa V100s™, SambaNova's Reconfigurable Dataflow Unit (RDU)™, and others.

Memory subsystem 3322 used in the storage subsystem 3358 can include a number of memories including a main random access memory (RAM) 3332 for storage of instructions and data during program execution and a read only memory (ROM) 3334 in which fixed instructions are stored. A file storage subsystem 3336 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 3336 in the storage subsystem 3358, or in other machines accessible by the processor.

Bus subsystem 3355 provides a mechanism for letting the various components and subsystems of computer system 3300 communicate with each other as intended. Although bus subsystem 3355 is shown schematically as a single bus, alternative implementations of the bus subsystem can use multiple buses.

Computer system 3300 itself can be of varying types including a personal computer, a portable computer, a workstation, a computer terminal, a network computer, a television, a mainframe, a server farm, a widely-distributed set of loosely networked computers, or any other data processing system or user device. Due to the ever changing nature of computers and networks, the description of computer system 3300 depicted in FIG. 33 is intended only as a specific example for purposes of illustrating the preferred implementations of the present invention. Many other configurations of computer system 3300 are possible having more or less components than the computer system depicted in FIG. 33.

CLAUSES

We disclose the following clauses:
Compression (Squeeze)
1. An artificial intelligence-based method of base calling, the method including:
accessing a series of per-cycle analyte channel sets generated for sequencing cycles of a sequencing run;
processing, through a spatial network of a neural network-based base caller, a first window of per-cycle analyte channel sets in the series for a first window of sequencing cycles of the sequencing run, and generating respective sequences of spatial output sets for respective sequencing cycles in the first window of sequencing cycles;
processing, through a compression network of the neural network-based base caller, respective final spatial output sets in the respective sequences of spatial output sets, and generating respective compressed spatial output sets for the respective sequencing cycles in the first window of sequencing cycles; and
generating, based on the respective compressed spatial output sets, base call predictions for one or more sequencing cycles in the first window of sequencing cycles.
2. The artificial intelligence-based method of clause 1, wherein the respective final spatial output sets have M channels (feature maps), wherein the respective compressed spatial output sets have N channels (feature maps), and wherein M>N.
3. The artificial intelligence-based method of clause 1, further including:
for a second window of sequencing cycles of the sequencing run that shares, with the first window of sequencing cycles, one or more overlapping sequencing cycles for which the spatial network previously generated spatial output sets, and at least one non-overlapping sequencing cycle for which the spatial network is yet to generate a spatial output set,
processing, through the spatial network, a per-cycle analyte channel set only for the non-overlapping sequencing cycle, and generating a sequence of spatial output sets for the non-overlapping sequencing cycle, thereby bypassing reprocessing, through the spatial network, respective per-cycle analyte channel sets for the overlapping sequencing cycles;
processing, through the compression network, a final spatial output set in the sequence of spatial output sets, and generating a compressed spatial output set for the non-overlapping sequencing cycle, wherein the final spatial output has M channels (feature maps), wherein the compressed spatial output has N channels (feature maps), and wherein M>N; and
generating, based on respective compressed spatial output sets for the overlapping sequencing cycles previously generated for the first window of sequencing cycles and on the compressed spatial output set, base call predictions for one or more sequencing cycles in the second window of sequencing cycles, thereby substituting the respective compressed spatial output sets for the overlapping sequencing cycles for the respective per-cycle analyte channel sets for the overlapping sequencing cycles.
4. The artificial intelligence-based method of clause 3, further including:
for a third window of sequencing cycles of the sequencing run that shares, with the first and second windows of sequencing cycles, one or more overlapping sequencing cycles for which the spatial network previously generated spatial output sets, and at least one non-overlapping sequencing cycle for which the spatial network is yet to generate a spatial output set,
processing, through the spatial network, a per-cycle analyte channel set only for the non-overlapping sequencing cycle, and generating a sequence of spatial output sets for the non-overlapping sequencing cycle, thereby bypassing reprocessing, through the spatial network, respective per-cycle analyte channel sets for the overlapping sequencing cycles;

processing, through the compression network, a final spatial output set in the sequence of spatial output sets, and generating a compressed spatial output set for the non-overlapping sequencing cycle, wherein the final spatial output has M channels (feature maps), wherein the compressed spatial output has N channels (feature maps), and wherein M>N; and generating, based on respective compressed spatial output sets for the overlapping sequencing cycles previously generated for the first and second windows of sequencing cycles and on the compressed spatial output set, base call predictions for one or more sequencing cycles in the third window of sequencing cycles, thereby substituting the respective compressed spatial output sets for the overlapping sequencing cycles for the respective per-cycle analyte channel sets for the overlapping sequencing cycles.

5. The artificial intelligence-based method of clause 1, wherein each per-cycle analyte channel set in the series depicts intensities registered in response to nucleotide incorporation in analytes at a corresponding sequencing cycle in the sequencing run.

6. The artificial intelligence-based method of clause 5, wherein the spatial network has a sequence of spatial convolution layers that separately processes each per-cycle analyte channel set in a particular window of per-cycle analyte channel sets in the series for a particular window of sequencing cycles of the sequencing run, and produce a sequence of spatial output sets for each sequencing cycle in the particular window of sequencing cycles, including beginning with a first spatial convolution layer that combines intensities only within a per-cycle analyte channel set of a subject sequencing cycle and not between per-cycle analyte channel sets of different sequencing cycles in the particular window of sequencing cycles, and continuing with successive spatial convolution layers that combine spatial outputs of preceding spatial convolution layers only within a subject sequencing cycle and not between the different sequencing cycles in the particular window of sequencing cycles.

7. The artificial intelligence-based method of clause 6, wherein respective spatial convolution layers in the sequence of spatial convolution layers have different counts of convolution filters, wherein a final spatial convolution layer in the sequence of spatial convolution layers has M convolution filters, and wherein M is an integer greater than four.

8. The artificial intelligence-based method of clause 7, wherein respective spatial convolution layers in the sequence of spatial convolution layers have a same count of convolution filters, wherein the same count is M, and wherein M is an integer greater than four.

9. The artificial intelligence-based method of clause 8, wherein the convolution filters in the spatial network use two-dimensional (2D) convolutions.

10. The artificial intelligence-based method of clause 8, wherein the convolution filters in the spatial network use three-dimensional (3D) convolutions.

11. The artificial intelligence-based method of clause 6, wherein the neural network-based base caller has a temporal network, wherein the temporal network has a sequence of temporal convolution layers that group-wise processes respective compressed spatial output sets for windows of successive sequencing cycles in the particular window of sequencing cycles, and produces a sequence of temporal output sets for the particular window of sequencing cycles, including beginning with a first temporal convolution layer that combines compressed spatial output sets between the different sequencing cycles in the particular window of sequencing cycles, and continuing with successive temporal convolution layers that combine successive temporal outputs of preceding temporal convolution layers.

12. The artificial intelligence-based method of clause 11, further including:

for the first window of sequencing cycles, processing, through a first temporal convolution layer in the sequence of temporal convolution layers of the temporal network, the respective compressed spatial output sets for windows of successive sequencing cycles in the first window of sequencing cycles, and generating a plurality of temporal output sets for the first window of sequencing cycles;

processing, through the compression network, the plurality of temporal output sets, and generating respective compressed temporal output sets for respective temporal output sets in the plurality of temporal output sets, wherein the respective temporal output sets have M channels (feature maps), wherein the respective compressed temporal output sets have N channels (feature maps), and wherein M>N;

processing, through a final temporal convolution layer in the sequence of temporal convolution layers of the temporal network, the respective compressed temporal output sets, and generating a final temporal output set for the first window of sequencing cycles; and generating, based on the final temporal output set, the base call predictions for one or more sequencing cycles in the first window of sequencing cycles, wherein an output layer processes the final temporal output set and produces a final output for the first window of sequencing cycles, wherein the base call predictions are generated based on the final output.

13. The artificial intelligence-based method of clause 12, further including:

for the second window of sequencing cycles that shares, with the first window of sequencing cycles, one or more overlapping windows of successive sequencing cycles for which the first temporal convolution layer previously generated temporal output sets, and at least one non-overlapping window of successive sequencing cycles for which the first temporal convolution layer is yet to generate a temporal output set, processing, through the first temporal convolution layer, respective compressed spatial output sets only for respective sequencing cycles in the non-overlapping window of successive sequencing cycles, and generating a temporal output set for the non-overlapping window of successive sequencing cycles, thereby bypassing reprocessing through the first temporal convolution layer respective compressed spatial output sets for respective sequencing cycles in the overlapping windows of successive sequencing cycles;

processing, through the compression network, the temporal output set, and generating a compressed temporal output set for the non-overlapping window of successive sequencing cycles, wherein the temporal output set has M channels (feature maps), wherein the compressed temporal output has N channels (feature maps), and wherein M>N; processing, through the final temporal convolution layer, respective compressed temporal output sets for the overlapping windows of successive sequencing cycles previously generated for the first window of sequencing cycles and on the compressed temporal output set, and generating a final temporal output set for the second window of sequencing cycles, thereby substituting the respective compressed temporal output sets for the overlapping windows of successive sequencing cycles for the respective per-cycle analyte channel sets for the overlapping windows of successive sequencing cycles; and generating, based on the final temporal output set, the base call predictions for one or more sequencing cycles in the second window of sequencing cycles, wherein an output layer processes the final temporal output set and produces a final output for the second window of sequencing cycles, wherein the base call predictions are generated based on the final output.

14. The artificial intelligence-based method of clause 13, further including:

for the third window of sequencing cycles that shares, with the first and second windows of sequencing cycles, one or more overlapping windows of successive sequencing cycles for which the first temporal convolution layer previously generated temporal output sets, and at least one non-overlapping window of successive sequencing cycles for which the first temporal convolution layer is yet to generate a temporal output set, processing, through the first temporal convolution layer, respective compressed spatial output sets only for respective sequencing cycles in the non-overlapping window of successive sequencing cycles, and generating a temporal output set for the non-overlapping window of successive sequencing cycles, thereby bypassing reprocessing, through the first temporal convolution layer, respective compressed spatial output sets for respective sequencing cycles in the overlapping windows of successive sequencing cycles;

processing, through the compression network, the temporal output set, and generating a compressed temporal output set for the non-overlapping window of successive sequencing cycles, wherein the temporal output set has M channels (feature maps), wherein the compressed temporal output has N channels (feature maps), and wherein M>N; and processing, through the final temporal convolution layer, respective compressed temporal output sets for the overlapping windows of successive sequencing cycles previously generated for the first and second windows of sequencing cycles and on the compressed temporal output set, and generating a final temporal output set for the third window of sequencing cycles, thereby substituting the respective compressed temporal output sets for the overlapping windows of successive sequencing cycles for the respective per-cycle analyte channel sets for the overlapping windows of successive sequencing cycles; and generating, based on the final temporal output set, the base call predictions for one or more sequencing cycles in the third window of sequencing cycles, wherein an output layer processes the final temporal output set and produces a final output for the third window of sequencing cycles, wherein the base call predictions are generated based on the final output.

15. The artificial intelligence-based method of clause 11, wherein respective temporal convolution layers in the sequence of temporal convolution layers of the temporal network have different counts of convolution filters, wherein the first temporal convolution layer has M convolution filters, and wherein M is an integer greater than four.

16. The artificial intelligence-based method of clause 11, wherein respective temporal convolution layers in the sequence of temporal convolution layers of the temporal network have a same count of convolution filters, wherein the same count is M, and wherein M is an integer greater than four.

17. The artificial intelligence-based method of clause 16, wherein the convolution filters in the temporal network use one-dimensional (1D) convolutions.

18. The artificial intelligence-based method of clause 1, wherein the compression network uses 1×1 convolutions to control a number of compressed spatial outputs in a compressed spatial output set, wherein the compression network has N convolution filters, and wherein N is an integer equal to or less than four.

19. The artificial intelligence-based method of clause 1, further including using data identifying unreliable analytes to remove portions of compressed spatial outputs in a compressed spatial output set corresponding to the unreliable analytes, and generating a compressed, filtered spatial output set to substitute the compressed spatial output set and generate base call predictions only for those analytes that are not the unreliable analytes.

20. The artificial intelligence-based method of clause 19, further including processing through the temporal network compressed, filtered spatial output sets instead of corresponding compressed spatial output sets.

21. The artificial intelligence-based method of clause 20, further including generating compressed temporal output sets from the compressed, filtered spatial output sets.

22. The artificial intelligence-based method of clause 19, wherein the data identifying the unreliable analytes identifies pixels that depict intensities of the unreliable clusters.

23. The artificial intelligence-based method of clause 19, wherein the data identifying the unreliable analytes identifies pixels that do not depict any intensities.

24. The artificial intelligence-based method of clause 20, wherein the compressed spatial output sets have four to nine times as many total pixels as the corresponding compressed, filtered spatial output sets.

25. The artificial intelligence-based method of clause 24, wherein the compressed, filtered spatial output sets cause the temporal network to operate on 75% fewer pixels, and thereby reduce compute operations, memory access, and memory occupancy for the temporal network by 75%.

26. The artificial intelligence-based method of clause 5, wherein bypassing reprocessing through the spatial network reduces compute operations, memory access, and memory occupancy for the temporal network by 80%.

27. The artificial intelligence-based method of clause 14, wherein bypassing reprocessing through the temporal network reduces compute operations, memory access, and memory occupancy for the temporal network.

28. The artificial intelligence-based method of clause 27, further including reallocating compute resources made available by the compression network to addition of supplemental convolution filters in the spatial network and the temporal network.

29. The artificial intelligence-based method of clause 27, further including reallocating compute resources made available by the compression network to addition of supplemental per-cycle analyte channel sets in each window of per-cycle analyte channel sets used to generate base call predictions for a particular sequence cycle.

30. The artificial intelligence-based method of clause 27, further including reallocating compute resources made available by the compression network to addition of supplemental spatial convolution layers in the spatial network.

31. The artificial intelligence-based method of clause 27, further including reallocating compute resources made available by the compression network to addition of supplemental temporal convolution layers in the temporal network.

32. The artificial intelligence-based method of clause 1, further including using one or more compressed spatial output sets generated for one or more preceding windows of sequence cycles in conjunction with one or more compressed spatial output sets generated for a current window of sequence cycles to generate base call predictions for one or more sequencing cycles in the current window of sequencing cycles.

33. The artificial intelligence-based method of clause 1, further including using one or more compressed spatial output sets generated for one or more succeeding windows of sequence cycles in conjunction with one or more compressed spatial output sets generated for a current window of sequence cycles to generate base call predictions for one or more sequencing cycles in the current window of sequencing cycles.

34. The artificial intelligence-based method of clause 1, further including using one or more compressed temporal output sets generated for one or more preceding windows of sequence cycles in conjunction with one or more compressed temporal output sets generated for a current window of sequence cycles to generate base call predictions for one or more sequencing cycles in the current window of sequencing cycles.

35. The artificial intelligence-based method of clause 1, further including using one or more compressed temporal output sets generated for one or more succeeding windows of sequence cycles in conjunction with one or more compressed temporal output sets generated for a current window of sequence cycles to generate base call predictions for one or more sequencing cycles in the current window of sequencing cycles.

36. The artificial intelligence-based method of clause 1, wherein a per-cycle analyte channel set encodes analyte data for analytes sequenced during the sequencing run.

37. The artificial intelligence-based method of clause 36, wherein the analyte data is image data that identifies intensity emissions collected from the analytes.

38. The artificial intelligence-based method of clause 37, wherein the image data has a plurality of image channels (images).

39. The artificial intelligence-based method of clause 38, wherein an image channel (image) is generated by a combination of (i) illumination with a specific laser and (ii) imaging through a specific optical filter.

40. The artificial intelligence-based method of clause 36, wherein the analyte data is electrical current and/or voltage data detected based on analyte activity.

41. The artificial intelligence-based method of clause 36, wherein the analyte data is pH scale data detected based on analyte activity.

42. The artificial intelligence-based method of clause 1, wherein a number of channels in each per-cycle analyte channel set in the series determines a number of convolution filters in the compression network and therefore a number of channels in compressed spatial output sets and compressed temporal output sets.

43. The artificial intelligence-based method of clause 1, wherein the compressed spatial output sets, the compressed, filter spatial output sets, and the compressed temporal output sets are stored in a quantized form.

44. A system, comprising:
   host memory attached to a host processor and configured to receive a progression of sequencing images as a sequencing run progresses;
   a configurable processor having an array of processing units, processing units in the array of processing units configured to execute a neural network-based base caller to produce base call predictions;
   data flow logic having access to the host memory, the host processor, and the configurable processor, and configured to load sequencing images for sequencing cycles in a first window of sequencing cycles on the configurable processor from the host memory;
   runtime logic configured to cause the processing units to execute a spatial network of the neural network-based base caller on the sequencing images for the sequencing cycles in the first window of sequencing cycles on a cycle-by-cycle basis and generate spatial feature map sets for each of the sequencing cycles in the first window of sequencing cycles;
   the runtime logic configured to cause the processing units to execute a compression network of the neural network-based base caller on the spatial feature map sets on the cycle-by-cycle basis and generate compressed spatial feature map sets, and process the compressed spatial feature maps sets through a temporal network and an output network to produce base call predications for one or more sequencing cycles in the first window of sequencing cycles;
   the data flow logic configured to move the compressed spatial feature map sets to the host memory and overwrite the sequencing images with the compressed spatial feature map sets;
   for a second window of sequencing cycles that shares one or more overlapping sequencing cycles with the first window of sequencing cycles, and has at least one non-overlapping sequencing cycle, the data flow logic configured to load, on the configurable processor from the host memory, compressed spatial feature map sets for the overlapping sequencing cycles, and sequencing images for the non-overlapping sequencing cycle;

the runtime logic configured to cause the processing units to execute the spatial network on the sequencing images for the non-overlapping sequencing cycle and generate a spatial feature map set for the non-overlapping sequencing cycle; and the runtime logic configured to cause the processing units to execute the compression network on the spatial feature map set and generate a compressed spatial feature map set for the non-overlapping sequencing cycle, and process the compressed spatial feature maps sets for the overlapping sequencing cycles and the compressed spatial feature map set for the non-overlapping sequencing cycle through the temporal network and the output network to produce base call predications for one or more sequencing cycles in the second window of sequencing cycles.

45. A system, comprising:

host memory attached to a host processor and configured to receive a progression of sequencing images as a sequencing run progresses;

a configurable processor having an array of processing units attached to processor memory, processing units in the array of processing units configured to execute a neural network-based base caller to produce base call predictions;

data flow logic having access to the host memory, the host processor, the configurable processor, and the processor memory, and configured to load sequencing images for sequencing cycles in a first window of sequencing cycles on the configurable processor from the host memory;

runtime logic configured to cause the processing units to execute a spatial network of the neural network-based base caller on the sequencing images for the sequencing cycles in the first window of sequencing cycles on a cycle-by-cycle basis and generate spatial feature map sets for each of the sequencing cycles in the first window of sequencing cycles;

the runtime logic configured to cause the processing units to execute a compression network of the neural network-based base caller on the spatial feature map sets on the cycle-by-cycle basis and generate compressed spatial feature map sets, and process the compressed spatial feature maps sets through a temporal network and an output network to produce base call predications for one or more sequencing cycles in the first window of sequencing cycles;

the data flow logic configured to move the compressed spatial feature map sets to the processor memory;

for a second window of sequencing cycles that shares one or more overlapping sequencing cycles with the first window of sequencing cycles, and has at least one non-overlapping sequencing cycle, the data flow logic configured to load, on the configurable processor from the processor memory, compressed spatial feature map sets for the overlapping sequencing cycles, and, load from the host memory, sequencing images for the non-overlapping sequencing cycle;

the runtime logic configured to cause the processing units to execute the spatial network on the sequencing images for the non-overlapping sequencing cycle and generate a spatial feature map set for the non-overlapping sequencing cycle; and the runtime logic configured to cause the processing units to execute the compression network on the spatial feature map set and generate a compressed spatial feature map set for the non-overlapping sequencing cycle, and process the compressed spatial feature maps sets for the overlapping sequencing cycles and the compressed spatial feature map set for the non-overlapping sequencing cycle through the temporal network and the output network to produce base call predications for one or more sequencing cycles in the second window of sequencing cycles.

46. A system, comprising:

neural network logic configured to execute a first traversal of a neural network graph to independently process respective inputs in a first set of inputs through a first processing logic and generate respective alternative representations of the respective inputs in the first set of inputs without mixing information between the respective inputs in the first set of inputs, and produce outputs for the first traversal based on the respective alternative representations of the respective inputs in the first set of inputs;

the neural network logic configured to execute a second traversal of the neural network graph to independently process respective inputs in a second set of inputs through the first processing logic and generate respective alternative representations of the respective inputs in the second set of inputs without mixing information between the respective inputs in the second set of inputs, and produce outputs for the second traversal based on the respective alternative representations of the respective inputs in the second set of inputs, wherein the first and second set of inputs have one or more overlapping inputs and at least one non-overlapping input;

runtime logic configured with the neural network logic to execute the first traversal to generate the respective alternative representations of the respective inputs in the first set of inputs, to store the respective alternative representations of the respective inputs in the first set of inputs in memory in a compressed form, and to produce the outputs for the first traversal based on the compressed form of the respective alternative representations of the respective inputs in the first set of inputs; and the runtime logic configured to execute the second traversal to process only the non-overlapping input through the first processing logic and generate an alternative representation of the non-overlapping input, to store the alternative representation of the non-overlapping input in memory in the compressed form, to retrieve the compressed form of respective alternative representations of the overlapping inputs generated in the first traversal to compensate for bypassing redundant generation of the respective alternative representations of the overlapping inputs in the second traversal, and to produce the outputs for the second traversal based on the compressed form of the respective alternative representations of the overlapping inputs and the compressed form of the alternative representation of the non-overlapping input.

47. The system of clause 46, wherein the memory is on-chip memory.

48. The system of clause 46, wherein the memory is off-chip memory.

49. The system of clause 46, wherein a number of channels in the compressed form corresponds to a number of channels in the inputs in the first and second set of inputs.

50. An artificial intelligence-based method of base calling, the method including:

accessing a series of per-cycle analyte channel sets generated for sequencing cycles of a sequencing run, wherein a subject per-cycle analyte channel set encodes analyte data detected for analytes at a subject sequencing cycle of the sequencing run;

processing the subject per-cycle analyte channel set through a first processing module of a neural network and producing an intermediate representation of the subject per-cycle analyte channel set with M feature maps;

processing the intermediate representation through a second processing module of the neural network and producing a reduced intermediate representation of the subject per-cycle analyte channel set with N feature maps, where M>N; and using the reduced intermediate representation of the subject per-cycle analyte channel set to generate base call predictions for the analytes at the subject sequencing cycle and/or at other sequencing cycles of the sequencing run.

51. The artificial intelligence-based method of clause 50, wherein the first processing module is a convolution layer with M convolution filters.

52. The artificial intelligence-based method of clause 50, wherein the second processing module is a convolution layer with N convolution filters.

53. An artificial intelligence-based method of base calling, the method including:

processing a progression of per-cycle analyte channel sets generated for sequencing cycles of a sequencing run through a neural network-based base caller on a sliding window basis such that successive sliding windows have overlapping sequencing cycles, including:

for a current window of the sequencing cycles that comprises one or more preceding sequencing cycles, a center sequencing cycle, and one or more succeeding sequencing cycles:

generating a spatial intermediate representation and a compressed intermediate representation for each of the preceding sequencing cycles, the center sequencing cycle, and the succeeding sequencing cycles based on applying the neural network-based base caller on the current window of the per-cycle analyte channel sets, wherein the spatial intermediate representation has M channels, the compressed intermediate representation has N channels, and M>N; and base calling at least the center sequencing cycle based on the compressed intermediate representations generated for the preceding sequencing cycles, the center sequencing cycle, and the succeeding sequencing cycles; and using the compressed intermediate representations generated for the preceding sequencing cycles, the center sequencing cycle, and the succeeding sequencing cycles to base call at least at a center sequencing cycle in a next window of the sequencing cycles.

54. An artificial intelligence-based system for base calling, the system comprising:

a host processor;

memory accessible by the host processor storing analyte data for sequencing cycles of a sequencing run; and a configurable processor having access to the memory, the configurable processor including:

a plurality of execution clusters, the execution clusters in the plurality of execution clusters configured to execute a neural network; and data flow logic having access to the memory and to the execution clusters in the plurality of execution clusters, configured to provide the analyte data to available execution clusters in the plurality of execution clusters, cause the execution clusters to apply the analyte data to the neural network to generate intermediate representations and compressed intermediate representations of the analyte data for use in a current base calling step, and to feed back the compressed intermediate representations to the memory for use in a future base calling step as a replacement of the analyte data, wherein an intermediate representation as M channels, a compressed intermediate representation has N channels, and M>N.

55. A system, comprising:

runtime logic configured to execute a first iteration of a base caller to process an input and generate intermediate representations of the input;

compression logic configured to process the intermediate representations and generate compressed intermediate representations of the input; and the runtime logic configured to use the compressed intermediate representations in lieu of the input in a subsequent iteration of the base caller.

56. A system, comprising:

runtime logic configured to execute a first iteration of a base caller to process an input and generate intermediate representations of the input;

compression logic configured to process the intermediate representations and generate compressed intermediate representations, wherein the compressed intermediate representations are configured to have as many channels as the input; and the runtime logic configured to use the compressed intermediate representations in lieu of the input in a subsequent iteration of the base caller.

57. The system of clause 56, wherein the channels correspond to feature maps.

58. The system of clause 56, wherein the channels correspond to a depth dimension.

59. The system of clause 56, wherein the channels correspond to spatial dimensions.

Split

1. A system, comprising:

a spatial convolution network configured to process a window of per-cycle sequencing image sets for a series of sequencing cycles of a sequencing run on a cycle-by-cycle basis by separately convolving respective per-cycle sequencing image sets in the window of per-cycle sequencing image sets through respective sequences of spatial convolution layers to generate respective per-cycle spatial feature map sets for respective sequencing cycles in the series of sequencing cycles;

wherein the respective sequences of spatial convolution layers have respective sequences of spatial convolution filter banks, wherein trained coefficients of spatial convolution filters in spatial convolution filter banks of the respective sequences of spatial convolution filter banks vary between sequences of spatial convolution layers in the respective sequences of spatial convolution layers;

a temporal convolution network configured to process the per-cycle spatial feature map sets on a groupwise basis by convolving on respective overlapping groups of per-cycle spatial feature map sets in the per-cycle spatial feature map sets using respective temporal convolution filter banks of a first temporal convolution layer to generate respective per-group temporal feature map sets for the respective overlapping groups of per-cycle spatial feature map sets; and wherein trained coefficients of temporal convolution filters in the respective temporal convolution filter banks vary between temporal convolution filter banks in the respective temporal convolution filter banks.

2. The system of clause 1, wherein the spatial convolution filters use intra-cycle segregated convolutions.

3. The system of clause 1, wherein the temporal convolution filters use inter-cycle combinatory convolutions.

4. The system of clause 1, further configured to comprise a compression network that separately convolves the respective per-cycle spatial feature map sets through respective compression convolution layers to generate respective per-cycle compressed spatial feature map sets for the respective sequencing cycles.

5. The system of clause 4, wherein trained coefficients of compression convolution filters in the respective compression convolution layers vary between compression convolution layers in the respective compression convolution layers.

6. The system of clause 5, wherein the temporal convolution network is further configured to process the per-group temporal feature map sets on the groupwise basis by convolving on respective overlapping groups of per-group temporal feature map sets in the per-group temporal feature map sets using respective temporal convolution filter banks of a second temporal convolution layer to generate respective further per-group temporal feature map sets for the respective overlapping groups of per-group temporal feature map sets.

7. The system of clause 6, further configured to comprise an output network that processes a final temporal feature map set generated by a final temporal convolution layer to generate a final output.

8. The system of clause 7, further configured to produce base call predications for one or more sequencing cycles in the series of sequencing cycles based on the final output.

9. A system, comprising:

a spatial convolution network configured to process a window of per-cycle sequencing image sets for a series of sequencing cycles of a sequencing run on a cycle-by-cycle basis by separately convolving respective per-cycle sequencing image sets in the window of per-cycle sequencing image sets through respective sequences of spatial convolution layers to generate respective per-cycle spatial feature map sets for respective sequencing cycles in the series of sequencing cycles;

a temporal convolution network configured to process the per-cycle spatial feature map sets on a groupwise basis by convolving on respective overlapping groups of per-cycle spatial feature map sets in the per-cycle spatial feature map sets using respective temporal convolution filter banks to generate respective per-group temporal feature map sets for the respective overlapping groups of per-cycle spatial feature map sets; and wherein trained coefficients of temporal convolution filters in the respective temporal convolution filter banks vary between temporal convolution filter banks in the respective temporal convolution filter banks.

10. The system of clause 9, wherein the respective sequences of spatial convolution layers have respective sequences of spatial convolution filter banks, wherein trained coefficients of spatial convolution filters in spatial convolution filter banks of the respective sequences of spatial convolution filter banks are shared between sequences of spatial convolution layers in the respective sequences of spatial convolution layers.

11. The system of clause 9, further configured to comprise a compression network that separately convolves the respective per-cycle spatial feature map sets through respective compression convolution layers to generate respective per-cycle compressed spatial feature map sets for the respective sequencing cycles, wherein trained coefficients of compression convolution filters in the respective compression convolution layers vary between compression convolution layers in the respective compression convolution layers.

12. An artificial intelligence-based method of base calling, the method including:

processing, through spatial convolution network, a window of per-cycle sequencing image sets for a series of sequencing cycles of a sequencing run on a cycle-by-cycle basis by separately convolving respective per-cycle sequencing image sets in the window of per-cycle sequencing image sets through respective sequences of spatial convolution layers, and generating respective per-cycle spatial feature map sets for respective sequencing cycles in the series of sequencing cycles;

wherein the respective sequences of spatial convolution layers have respective sequences of spatial convolution filter banks, wherein trained coefficients of spatial convolution filters in spatial convolution filter banks of the respective sequences of spatial convolution filter banks vary between sequences of spatial convolution layers in the respective sequences of spatial convolution layers;

processing, through a temporal convolution network, the per-cycle spatial feature map sets on a groupwise basis by convolving on respective overlapping groups of per-cycle spatial feature map sets in the per-cycle spatial feature map sets using respective temporal convolution filter banks of a first temporal convolution layer, and generating respective per-group temporal feature map sets for the respective overlapping groups of per-cycle spatial feature map sets; and wherein trained coefficients of temporal convolution filters in the respective temporal convolution filter banks vary between temporal convolution filter banks in the respective temporal convolution filter banks.

13. The artificial intelligence-based method of clause 12, further including separately convolving the respective per-cycle spatial feature map sets through respective compression convolution layers of a compression network and generating respective per-cycle compressed spatial feature map sets for the respective sequencing cycles.

14. The artificial intelligence-based method of clause 13, wherein trained coefficients of compression convolution filters in the respective compression convolution layers vary between compression convolution layers in the respective compression convolution layers.

15. The artificial intelligence-based method of clause 14, further including processing, through the temporal convolution network, the per-group temporal feature map sets on the groupwise basis by convolving on respective overlapping groups of per-group temporal feature map sets in the per-group temporal feature map sets using respective temporal convolution filter banks of a second temporal convolution layer, and generating respective further per-group temporal feature map sets for the respective overlapping groups of per-group temporal feature map sets.

16. The artificial intelligence-based method of clause 15, further including processing, through an output network, a final temporal feature map set generated by a final temporal convolution layer, and generating a final output.

17. The artificial intelligence-based method of clause 16, further including producing base call predications for one or more sequencing cycles in the series of sequencing cycles based on the final output.

18. An artificial intelligence-based method of base calling, the method including:

processing, through spatial convolution network, a window of per-cycle sequencing image sets for a series of sequencing cycles of a sequencing run on a cycle-by-cycle basis by separately convolving respective per-cycle sequencing image sets in the window of per-cycle sequencing image sets through respective sequences of spatial convolution layers, and generating respective per-cycle spatial feature map sets for respective sequencing cycles in the series of sequencing cycles;

processing, through a temporal convolution network, the per-cycle spatial feature map sets on a groupwise basis by convolving on respective overlapping groups of per-cycle spatial feature map sets in the per-cycle spatial feature map sets using respective temporal convolution filter banks of a first temporal convolution layer, and generating respective per-group temporal feature map sets for the respective overlapping groups of per-cycle spatial feature map sets; and wherein trained coefficients of temporal convolution filters in the respective temporal convolution filter banks vary between temporal convolution filter banks in the respective temporal convolution filter banks.

19. The artificial intelligence-based method of clause 18, wherein the respective sequences of spatial convolution layers have respective sequences of spatial convolution filter banks, wherein trained coefficients of spatial convolution filters in spatial convolution filter banks of the respective sequences of spatial convolution filter banks are shared between sequences of spatial convolution layers in the respective sequences of spatial convolution layers.

20. The artificial intelligence-based method of clause 18, further including separately convolving the respective per-cycle spatial feature map sets through respective compression convolution layers of a compression network and generating respective per-cycle compressed spatial feature map sets for the respective sequencing cycles, wherein trained coefficients of compression convolution filters in the respective compression convolution layers vary between compression convolution layers in the respective compression convolution layers.

21. A system, comprising:

a spatial convolution network configured to apply respective sequences of spatial convolution layers to respective per-cycle sequencing images in a window of per-cycle sequencing images; and wherein the respective sequences of spatial convolution layers have respective sequences of spatial convolution filter banks that differ from one sequence of spatial convolution layers to another sequence of spatial convolution layers.

22. A system, comprising:

a temporal convolution network configured with a first temporal convolution layer configured to apply respective sets of temporal convolution filters to respective sliding windows of spatial feature maps; and wherein the respective sets of temporal convolution filters in the first temporal convolution layer have temporal convolution filters that differ from one set of temporal convolution filters to another set of temporal convolution filters.

23. The system of clause 22, wherein the temporal convolution network is configured with a second temporal convolution layer that succeeds the first temporal convolution layer, wherein the second convolution layer is configured to apply respective sets of temporal convolution filters to respective sliding windows of temporal feature maps, and wherein the respective sets of temporal convolution filters in the second temporal convolution layer have temporal convolution filters that differ from one set of temporal convolution filters to another set of temporal convolution filters.

Skip

1. A system, comprising:

a spatial convolution network configured to process a window of per-cycle sequencing image sets for a series of sequencing cycles of a sequencing run on a cycle-by-cycle basis by separately processing respective per-cycle sequencing image sets in the window of per-cycle sequencing image sets through respective spatial processing pipelines, the respective spatial processing pipelines configured to convolve the respective per-cycle sequencing image sets through respective sequences of spatial convolution layers to generate respective per-cycle spatial feature map sets for respective sequencing cycles in the series of sequencing cycles; and a bus network, connected to the spatial convolution network, and configured to form buses between spatial convolution layers within the respective sequences of spatial convolution layers, the buses configured to cause respective per-cycle spatial feature map sets generated by two or more spatial convolution layers in a particular sequence of spatial convolution layer for a particular sequencing cycle to combine into a combined per-cycle spatial feature map set, and provide the combined per-cycle spatial feature map set as input to another spatial convolution layer in the particular sequence of spatial convolution layer.

2. The system of clause 1, wherein the two or more spatial convolution layers include a first spatial convolution layer and a third spatial convolution layer, wherein the first spatial convolution layer generates a first per-cycle spatial feature map set, wherein the first spatial convolution layer provides the first per-cycle spatial feature map set as input to a second spatial convolution layer, wherein the second spatial convolution layer processes the first per-cycle spatial feature map set and generates a second per-cycle spatial feature map set, wherein the second spatial convolution layer provides the second per-cycle spatial feature map set as input to the third spatial convolution layer, and wherein the third spatial convolution layer processes the second per-cycle spatial feature map set and generates a third per-cycle spatial feature map set.

3. The system of clause 2, wherein the buses are further configured to cause the first spatial feature map set and the third per-cycle spatial feature map set to combine into the combined per-cycle spatial feature map set.

4. The system of clause 3, wherein the another spatial convolution layer is a fourth spatial convolution layer that immediately succeeds the third spatial convolution layer in the particular sequence of spatial convolution layer, wherein the fourth spatial convolution layer processes the combined per-cycle spatial feature map set as input.

5. The system of clause 2, wherein the two or more spatial convolution layers include the first spatial convolution layer and a seventh spatial convolution layer, wherein the third spatial convolution layer provides the third per-cycle spatial feature map set as input to a fourth spatial convolution layer, wherein the fourth spatial convolution layer processes the third per-cycle spatial feature map set and generates a fourth per-cycle spatial feature map set, wherein the fourth spatial convolution layer provides the fourth per-cycle spatial feature map set as input to a fifth spatial convolution layer, and wherein the fifth spatial convolution layer processes the fourth per-cycle spatial feature map set and generates a fifth per-cycle spatial feature map set.

6. The system of clause 5, wherein the buses are further configured to cause the first spatial feature map set and the fifth spatial feature map set to combine into the combined per-cycle spatial feature map set.

7. The system of clause 6, wherein the another spatial convolution layer is a sixth spatial convolution layer that immediately succeeds the fifth spatial convolution layer in the particular sequence of spatial convolution layer, wherein the sixth spatial convolution layer processes the combined per-cycle spatial feature map set as input.

8. The system of clause 5, wherein the two or more spatial convolution layers include the first spatial convolution layer, the third spatial convolution layer, and the fifth spatial convolution layer, and wherein the buses are further configured to cause the first per-cycle spatial feature map set, the third per-cycle spatial feature map set, and the fifth per-cycle spatial feature map set to combine into the combined per-cycle spatial feature map set.

9. The system of clause 8, wherein the another spatial convolution layer is the sixth spatial convolution layer that processes the combined per-cycle spatial feature map set as input.

10. The system of clause 1, wherein the buses are further configured to cause a per-cycle sequencing image set for the particular sequencing cycle, provided as input to the first spatial convolution layer, and the third per-cycle spatial feature map set to combine into the combined per-cycle spatial feature map set.

11. The system of clause 10, wherein the another spatial convolution layer is the fourth spatial convolution layer that processes the combined per-cycle spatial feature map set as input.

12. The system of clause 1, wherein the bus network is further configured to include dimensionality compatibility logic configured to modify spatial and depth dimensionality of an incoming per-cycle spatial feature map set that is combined with a receiving per-cycle spatial feature map set to generate the combined per-cycle spatial feature map set.

13. The system of clause 12, wherein the dimensionality compatibility logic is a dimensionality reduction operation, including convolution, pooling, or averaging.

14. The system of clause 12, wherein the bus network is further configured to include scaling logic configured to scale feature values of the incoming per-cycle spatial feature map set that is combined with the receiving per-cycle spatial feature map set to generate the combined per-cycle spatial feature map set.

15. The system of clause 1, further configured to comprise a temporal convolution network configured to process the per-cycle spatial feature map sets on a groupwise basis by convolving on respective overlapping groups of per-cycle spatial feature map sets in the per-cycle spatial feature map sets using respective temporal convolution filter banks of a first temporal convolution layer to generate respective per-group temporal feature map sets for the respective overlapping groups of per-cycle spatial feature map sets.

16. The system of clause 15, further configured to comprise the bus network, connected to the temporal convolution network, and configured to form buses between temporal convolution layers within the respective sequences of temporal convolution layers, the buses configured to cause respective per-cycle temporal feature map sets generated by two or more temporal convolution layers in a particular sequence of temporal convolution layer for a particular sequencing cycle to combine into a combined per-cycle temporal feature map set, and provide the combined per-cycle temporal feature map set as input to another temporal convolution layer in the particular sequence of temporal convolution layer.

17. An artificial intelligence-based method, including:
    processing, through a spatial convolution network, a window of per-cycle sequencing image sets for a series of sequencing cycles of a sequencing run on a cycle-by-cycle basis by separately processing respective per-cycle sequencing image sets in the window of per-cycle sequencing image sets through respective spatial processing pipelines, including convolving the respective per-cycle sequencing image sets through respective sequences of spatial convolution layers to generate respective per-cycle spatial feature map sets for respective sequencing cycles in the series of sequencing cycles; and combining respective per-cycle spatial feature map sets generated by two or more spatial convolution layers in a particular sequence of spatial convolution layer for a particular sequencing cycle into a combined per-cycle spatial feature map set, and providing the combined per-cycle spatial feature map set as input to another spatial convolution layer in the particular sequence of spatial convolution layer.

18. The artificial intelligence-based method of clause 17, wherein the two or more spatial convolution layers include a first spatial convolution layer and a third spatial convolution layer, wherein the first spatial convolution layer generates a first per-cycle spatial feature map set, wherein the first spatial convolution layer provides the first per-cycle spatial feature map set as input to a second spatial convolution layer, wherein the second spatial convolution layer processes the first per-cycle spatial feature map set and generates a second per-cycle spatial feature map set, wherein the second spatial convolution layer provides the second per-cycle spatial feature map set as input to the third spatial convolution layer, and wherein the third spatial convolution layer processes the second per-cycle spatial feature map set and generates a third per-cycle spatial feature map set.

19. The artificial intelligence-based method of clause 18, wherein the buses are further configured to cause the first spatial feature map set and the third per-cycle spatial feature map set to combine into the combined per-cycle spatial feature map set.

20. The artificial intelligence-based method of clause 19, wherein the another spatial convolution layer is a fourth spatial convolution layer that immediately succeeds the third spatial convolution layer in the particular sequence of spatial convolution layer, wherein the fourth spatial convolution layer processes the combined per-cycle spatial feature map set as input.

Other implementations of the method described above can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

What is claimed is:

1. An artificial intelligence-based method of base calling, the method including:

accessing a series of per-cycle analyte channel sets generated for sequencing cycles of a sequencing run;

processing, through a spatial network of a neural network-based base caller, a first window of per-cycle analyte channel sets in the series for a first window of sequencing cycles of the sequencing run, and generating respective sequences of spatial output sets for respective sequencing cycles in the first window of sequencing cycles;

processing, through a compression network of the neural network-based base caller, respective final spatial output sets in the respective sequences of spatial output sets by applying a number of convolution filters based on a number of channels in the per-cycle analyte channel sets, and generating respective compressed spatial output sets for the respective sequencing cycles in the first window of sequencing cycles;

storing, in memory, the respective compressed spatial output sets for the respective sequencing cycles; and generating, based on the respective compressed spatial output sets stored in memory, base call predictions for one or more sequencing cycles in the first window of sequencing cycles.

2. The artificial intelligence-based method of claim 1, wherein the channels correspond to at least a filter wavelength, an imaging event, or illumination of a specific laser through a specific optical filter utilized during the sequencing run.

3. The artificial intelligence-based method of claim 1, further including:

for a second window of sequencing cycles of the sequencing run that shares, with the first window of sequencing cycles, one or more overlapping sequencing cycles for which the spatial network previously generated spatial output sets, and at least one non-overlapping sequencing cycle, processing, through the spatial network, a per-cycle analyte channel set only for the at least one non-overlapping sequencing cycle, and generating a sequence of spatial output sets for the at least one non-overlapping sequencing cycle;

processing, through the compression network, a final spatial output set in the sequence of spatial output sets, and generating a compressed spatial output set for the at least one non-overlapping sequencing cycle, wherein the final spatial output set has M channels, wherein the compressed spatial output set has N channels, and wherein M>N; and generating, based on respective compressed spatial output sets for the overlapping sequencing cycles previously generated for the first window of sequencing cycles and on the compressed spatial output set for the at least one non-overlapping sequencing cycle, base call predictions for one or more sequencing cycles in the second window of sequencing cycles.

4. The artificial intelligence-based method of claim 3, further including:

for a third window of sequencing cycles of the sequencing run that shares, with the first and second windows of sequencing cycles, one or more overlapping sequencing cycles for which the spatial network previously generated spatial output sets, and at least one non-overlapping sequencing cycle for the third window, processing, through the spatial network, a per-cycle analyte channel set only for the at least one non-overlapping sequencing cycle for the third window, and generating a sequence of spatial output sets for the at least one non-overlapping sequencing cycle for the third window;

processing, through the compression network, a final spatial output set in the sequence of spatial output sets, and generating a compressed spatial output set for the at least one non-overlapping sequencing cycle for the third window, wherein the final spatial output set has M channels, wherein the compressed spatial output set has N channels, and wherein M>N; and generating, based on respective compressed spatial output sets for the overlapping sequencing cycles previously generated for the first and second windows of sequencing cycles and on the compressed spatial output set for the at least one non-overlapping sequencing cycle of the third window, base call predictions for one or more sequencing cycles in the third window of sequencing cycles.

5. The artificial intelligence-based method of claim 1, wherein each per-cycle analyte channel set in the series depicts intensities registered in response to nucleotide incorporation in analytes at a corresponding sequencing cycle in the sequencing run.

6. The artificial intelligence-based method of claim 5, wherein the spatial network has a sequence of spatial convolution layers that separately processes each per-cycle analyte channel set in a particular window of per-cycle analyte channel sets in the series for a particular window of sequencing cycles of the sequencing run, and produces a sequence of spatial output sets for each sequencing cycle in the particular window of sequencing cycles, including beginning with a first spatial convolution layer that combines intensities only within a per-cycle analyte channel set of a subject sequencing cycle and not between per-cycle analyte channel sets of different sequencing cycles in the particular window of sequencing cycles, and continuing with successive spatial convolution layers that combine spatial outputs of preceding spatial convolution layers only within a subject sequencing cycle and not between the different sequencing cycles in the particular window of sequencing cycles.

7. The artificial intelligence-based method of claim 6, wherein the neural network-based base caller has a temporal network, wherein the temporal network has a sequence of temporal convolution layers that groupwise processes respective compressed spatial output sets for windows of successive sequencing cycles in the particular window of sequencing cycles, and produces a sequence of temporal output sets for the particular window of sequencing cycles, including beginning with a first temporal convolution layer that combines compressed spatial output sets between the different sequencing cycles in the particular window of sequencing cycles, and continuing with successive temporal convolution layers that combine successive temporal outputs of preceding temporal convolution layers.

8. The artificial intelligence-based method of claim 7, further including:

for the first window of sequencing cycles, processing, through a first temporal convolution layer in the sequence of temporal convolution layers of the temporal network, respective compressed spatial output sets for windows of successive sequencing cycles in the first window of sequencing cycles, and generating a plurality of temporal output sets for the first window of sequencing cycles;

processing, through the compression network, the plurality of temporal output sets, and generating respective compressed temporal output sets for respective temporal output sets in the plurality of temporal output sets, wherein the respective temporal output sets have M channels, wherein the respective compressed temporal output sets have N channels, and wherein M>N;

processing, through a final temporal convolution layer in the sequence of temporal convolution layers of the temporal network, the respective compressed temporal output sets, and generating a final temporal output set for the first window of sequencing cycles; and generating, based on the final temporal output set, the base call predictions for one or more sequencing cycles in the first window of sequencing cycles, wherein an output layer processes the final temporal output set and produces a final output for the first window of sequencing cycles, wherein the base call predictions are generated based on the final output.

9. The artificial intelligence-based method of claim 8, further including:

for a second window of sequencing cycles that shares, with the first window of sequencing cycles, one or more overlapping windows of successive sequencing cycles for which the first temporal convolution layer previously generated temporal output sets, and at least one non-overlapping window of successive sequencing cycles for which the first temporal convolution layer is yet to generate a temporal output set, processing, through the first temporal convolution layer, respective compressed spatial output sets only for respective sequencing cycles in the at least one non-overlapping window of successive sequencing cycles, and generating a temporal output set for the at least one non-overlapping window of successive sequencing cycles;

processing, through the compression network, the temporal output set, and generating a compressed temporal output set for the at least one non-overlapping window of successive sequencing cycles, wherein the temporal output set has M channels, wherein the compressed temporal output set has N channels, and wherein M>N;

processing, through the final temporal convolution layer, respective compressed temporal output sets for the overlapping windows of successive sequencing cycles previously generated for the first window of sequencing cycles and on the compressed temporal output set, and generating a final temporal output set for the second window of sequencing cycles; and generating, based on the final temporal output set for the second window of sequencing cycles, base call predictions for one or more sequencing cycles in the second window of sequencing cycles, wherein an output layer processes the final temporal output set for the second window of sequencing cycles and produces a final output for the second window of sequencing cycles, wherein the base call predictions are generated based on the final output for the second window of sequencing cycles.

10. The artificial intelligence-based method of claim 9, further including:

for a third window of sequencing cycles that shares, with the first and second windows of sequencing cycles, one or more overlapping windows of successive sequencing cycles for which the first temporal convolution layer previously generated temporal output sets, and at least one non-overlapping window of successive sequencing cycles for the third window, processing, through the first temporal convolution layer, respective compressed spatial output sets only for respective sequencing cycles in the at least one non-overlapping window of successive sequencing cycles for the third window, and generating a temporal output set for the at least one non-overlapping window of successive sequencing cycles for the third window;

processing, through the compression network, the temporal output set for the at least one non-overlapping window of successive sequencing cycles for the third window, and generating a compressed temporal output set for the at least one non-overlapping window of successive sequencing cycles for the third window, wherein the temporal output set has M channels, wherein the compressed temporal output set has N channels, and wherein M>N; and processing, through the final temporal convolution layer, respective compressed temporal output sets for the overlapping windows of successive sequencing cycles previously generated for the first and second windows of sequencing cycles and on the compressed temporal output set for the at least one non-overlapping window of successive sequencing cycles for the third window, and generating a final temporal output set for the third window of sequencing cycles; and generating, based on the final temporal output set for the third window of sequencing cycles, base call predictions for one or more sequencing cycles in the third window of sequencing cycles, wherein an output layer processes the final temporal output set for the third window of sequencing cycles and produces a final output for the third window of sequencing cycles, wherein the base call predictions are generated based on the final output for the third window of sequencing cycles.

11. The artificial intelligence-based method of claim 1, wherein the spatial network has a sequence of spatial convolution layers having convolution filters that use two-dimensional (2D) convolutions.

12. The artificial intelligence-based method of claim 1, wherein the neural network-based base caller has a temporal network comprising convolution filters that use one-dimensional (1D) convolutions.

13. The artificial intelligence-based method of claim 1, wherein the compression network uses 1×1 convolutions to control a number of compressed spatial outputs in a compressed spatial output set, wherein the compression network has N convolution filters, and wherein N is an integer equal to or less than four.

14. The artificial intelligence-based method of claim 1, further including using data identifying unreliable analytes to remove portions of compressed spatial outputs in a compressed spatial output set corresponding to the unreliable analytes, and generating a compressed, filtered spatial output set to substitute the compressed spatial output set and generate base call predictions only for those analytes that are not the unreliable analytes.

15. The artificial intelligence-based method of claim 14, further including processing through a temporal network compressed, filtered spatial output sets instead of corresponding compressed spatial output sets.

16. The artificial intelligence-based method of claim 15, wherein the compressed spatial output sets have four to nine times as many total pixels as the corresponding compressed, filtered spatial output sets.

17. The artificial intelligence-based method of claim 14, wherein the data identifying the unreliable analytes identifies pixels that depict intensities of unreliable clusters.

18. The artificial intelligence-based method of claim 1, further comprising:

generating, based on the respective compressed spatial output sets, base call predictions for one or more sequencing cycles in the first window of sequencing cycles.

19. A system, comprising:

at least one processor; and a non-transitory computer readable medium comprising instructions that, when executed by the at least one processor, cause the system to:

execute a first iteration of a base caller to process an input and generate intermediate representations of the input for a sliding window of sequencing cycles;

process, utilizing compression logic, the intermediate representations by applying a number of convolution filters based on a number of channels in the input and generate compressed intermediate representations of the input;

store, in memory, the compressed intermediate representations of the input; and use the compressed intermediate representations in lieu of the input in a subsequent iteration of the base caller.

20. The system of claim 19, wherein channels from the number of channels correspond to at least a filter wavelength, an imaging event, or illumination of a specific laser through a specific optical filter utilized during a sequencing run.

*  *  *  *  *